US011339184B2

(12) United States Patent
Brady et al.

(10) Patent No.: US 11,339,184 B2
(45) Date of Patent: May 24, 2022

(54) ANTIBACTERIAL COMPOUNDS, COMPOSITIONS THEREOF, AND METHODS USING SAME

(71) Applicant: The Rockefeller University, New York, NY (US)

(72) Inventors: Sean F. Brady, New York, NY (US); James Peek, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 16/936,900

(22) Filed: Jul. 23, 2020

(65) Prior Publication Data

US 2021/0024562 A1    Jan. 28, 2021

Related U.S. Application Data

(60) Provisional application No. 62/877,417, filed on Jul. 23, 2019, provisional application No. 63/050,288, filed on Jul. 10, 2020.

(51) Int. Cl.
*C07H 9/04* (2006.01)
*A61P 31/06* (2006.01)

(52) U.S. Cl.
CPC .............. *C07H 9/04* (2013.01); *A61P 31/06* (2018.01)

(58) Field of Classification Search
None
See application file for complete search history.

(56) References Cited

U.S. PATENT DOCUMENTS

| 5,786,350 | A | 7/1998 | Occelli |
| 2005/0261262 | A1 | 11/2005 | Ma |
| 2014/0356376 | A1 | 12/2014 | Brown |
| 2018/0021450 | A1 | 1/2018 | Brown |

FOREIGN PATENT DOCUMENTS

| WO | 2019147753 | 8/2019 | |
| WO | WO-2020021252 A1 * | 1/2020 | ......... A61K 31/4025 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
"4-[1-[(7S,9E,11S,12R,13S,14R,15R,16S,17R,18S,19E,21Z)-11-[[(3Ar,4R,6R,7aS)-4-methyl-4,6,7,7a-tetrahydro-3aH-[1,3]dioxolo[4,5-c]pyran-6-yl]oxy]-13-acetyloxy-2,15,17-trihydroxy-3,7,12,14,16,22-hexamethyl-6,23,27,29-tetraoxo-8,30-dioxa-24-azatetracyclo[23.3.1.14,7.05,28]triaconta-1(28),2,4,9,19,21,25-heptaen-18-yl]ethoxy]-3,3-dimethyl-4-oxobutanoic acid | C50H63NO19", PubChem Compound, (Dec. 18, 2015), Database accession No. CID 101617059, URL: NCBI, XP055629974.
Altschul et al., 1990, "Basic Local Alignment Search Tool", Journal of Molecular Biology, 215:403-410.
Aristoff PA et al., 2010, "Rifamycins—obstacles and opportunities", Tuberculosis (Edinb), 90:94-118.
Artsimovitch et al., 2005, "Allosteric modulation of the RNA polymerase catalytic reaction is an essential component of transcription control by rifamycins", Cell, 122:351-363.
Bacchi et al., 1998, "Comprehensive study on structure-activity relationships of rifamycins: discussion of molecular and crystal structure and spectroscopic and thermochemical properties of rifamycin O", J Med Chern, 41:2319-2332.
Barnard et al., 2008, "Rapid molecular screening for multidrug-resistant tuberculosis in a high-volume public health laboratory in South Africa", Am J Respir Crit Care Med, 177:787-792.
Bhullar et al., 2012, "Antibiotic resistance is prevalent in an isolated cave microbiome", PLoS One, 7:e34953.
Bihlmaier et al., 2006, "Biosynthetic gene cluster for the polyenoyltetramic acid alpha-lipomycin", Antimicrob Agents Chemother, 50:2113-2121.
Brady, 2007, "Construction of soil environmental DNA cosmid libraries and screening for clones that produce biologically active small molecules", Nat. Protoc., 2:1297-12305.
Brassier et al., 2006, "Performance of the genotype MTBDR line probe assay for detection of resistance to rifampin and isoniazid in strains of *Mycobacterium tuberculosis* with low- and high-level resistance", J Clin Microbiol, 44:3659-3664.
Campbell EA et al., 2001, "Structural mechanism for rifampicin inhibition of bacterial rna polymerase", Cell, 104:901-912.
Cavusoglu et al., 2002, "Characterization of rpoB mutations in rifampinresistant clinical isolates of *Mycobacterium tuberculosis* from Turkey by DNA sequencing and line probe assay", J Clin Microbiol, 40:4435-4438.
Charlop-Powers Z et al., 2015, "Global biogeographic sampling of bacterial secondary metabolism", Elife, 4:e05048.
D'Costa et al., 2006, "Sampling the antibiotic resistome", Science,311:374-377.
D'Costa et al., 2011, "Antibiotic resistance is ancient", Nature, 477:457-461.
Daniel, R, 2005, "The metagenomics of soil", Nat Rev Microbiol., 3:470-478.
Edgar et al., 2004, "MUSCLE: multiple sequence alignment with high accuracy and high throughput", Nucleic Acids Res., 32:1792-1797.
Edgar et al., 2010, "Search and clustering orders of magnitude faster than BLAST", Bioinformatics, 26:2460-2461.
Everest et al., 2011, "Evaluation of the antibiotic biosynthetic potential of the genus *Amycolatopsis* and description of *Amycolatopsis circi* sp. nov., *Amycolatopsis equina* sp. nov. and *Amycolatopsis hippodromi* sp. nov." J Appl Microbiol, 111:300-311.
Fernandez et al., 1998, "Identification of two genes from Streptomyces argillaceus encoding glycosyltransferases involved in transfer of a disaccharide during biosynthesis of the antitumor drug mithramycin", J. Bacteriol., 180:4929-4937.

(Continued)

*Primary Examiner* — Traviss C McIntosh, III
(74) *Attorney, Agent, or Firm* — Riverside Law LLP

(57) ABSTRACT

The present disclosure includes novel compounds useful as antimicrobial agents. The present disclosure further includes methods useful. The present disclosure further includes compositions and methods for treating or preventing a bacterial infection. The present disclosure further includes compositions and methods useful for preventing or reducing the growth or proliferation of microorganisms.

30 Claims, 7 Drawing Sheets

(56) References Cited

OTHER PUBLICATIONS

Floss et al., 2011, "The biosynthesis of 3-amino-5-hydroxybenzoic acid (AHBA), the precursor of mC7N units in ansamycin and mitomycin antibiotics: a review", J Antibiot (Tokyo), 64:35-44.
Gold et al., 2015, "Rapid, Semiquantitative Assay to Discriminate among Compounds with Activity against Replicating or Nonreplicating *Mycobacterium tuberculosis*", Antimicrob. Agents Chemother., 59:6521-6538.
Gonzalez-y-Merchand JA et al., 1996, "The rRNA operons of *Mycobacterium smegmatis* and *Mycobacterium tuberculosis*: comparison of promoter elements and of neighbouring upstream genes", Microbiology, 142:667-674.
He et al., 2017, "Identification of candidate genes involved in isoquinoline alkaloids biosynthesis in Dactylicapnos scandens by transcriptome analysis", Sci Rep, 7:9119.
Hubin et al., 2017, "Structure and function of the mycobacterial transcription initiation complex with the essential regulator RbpA", Elife, 6:e22520.
Huitu et al., 2009, "PCR screening of 3-amino-5-hydroxybenzoic acid synthase gene leads to identification of ansamycins and AHBA-related antibiotic producers in Actinomycetes", J Appl Microbiol, 106:755-763.
Ikezawa et al., 2003, "Molecular cloning and characterization of CYP719, a methylenedioxy bridge-forming enzyme that belongs to a novel P450 family, from cultured Coptis japonica cells", J Biol Chem, 278:38557-38565.
Jin et al. 'Synthesis and Structure-Activity Relationships of Novel Substituted 8-amino, 8-thio, and 1,8-Pyrazote Congeners of Antitubercular Rifamycin S and Rifampin', Bioorg Med Chem Lett. Oct. 15, 2011:21(20): 6049.
Johansen et al., 2003, "Direct detection of multidrug-resistant *Mycobacterium tuberculosis* in clinical specimens in low- and high-incidence countries by line probe assay", J Clin Microbiol, 41:4454-4456.
Kang HS et al., 2014, "Arixanthomycins A-C: Phylogeny-guided discovery of biologically active eDNA derived pentangular polyphenols", ACS Chem Biol, 9:1267-1272.
Kumar P et al., 2018, "Synergistic Lethality of a Binary Inhibitor of *Mycobacterium tuberculosis* KasA", mBio, 9:e02101-e02117.
Lee SH et al., 2016, "TarO-specific inhibitors of wall teichoic acid biosynthesis restore beta-lactam efficacy against methicillin-resistant staphylococci", Sci. Transl. Med., 8:329ra32.
Li J et al., 2007, "Preparation and in vitro anti-staphylococcal activity of novel 11-deoxy-11-hydroxyiminorifamycins", Bioorg. Med. Chem. Lett., 17:5510-5513.
Ma et al., 2006, "Antimycobacterium Agents. In Comprehensive Medicinal Chemistry II", Science, 7:699-739.
Moghazeh SL et al., 1996, "Comparative antimycobacterial activities of rifampin, rifapentine, and KRM-1648 against a collection of rifampin-resistant *Mycobacterium tuberculosis* isolates with known rpoB mutations", Antimicrob. Agents Chemother., 40:2655-2657.
Mosaei et al. "Mode of Action of Kanglemycin A, an Ansamycin Natural Product that is Active against Rifampicin-Resistant *Mycobacterium tuberculosis*", Molecular Cell. 2018. vol. 72, pp. 263-274.
Murphy CK et al., 2006, "In vitro activity of novel rifamycins against rifamycin-resistant *Staphylococcus aureus*", Antimicrob. Agents Chemother., 50:827-834.
Muthaiah et al., 2017, "Prevalence of mutations in genes associated with rifampicin and isoniazid resistance in *Mycobacterium tuberculosis* clinical isolates", Journal of Clinical Tuberculosis and Other Mycobacterial Diseases, 8:19-25.
Owen et al., 2013, "Mapping gene clusters within arrayed metagenomic libraries to expand the structural diversity of biomedically relevant natural products", Proc Nat Acad Sci USA, 110:11797-11802.
Owen et al., 2015, "Multiplexed metagenome mining using short DNA sequence tags facilitates targeted discovery of epoxyketone proteasome inhibitors", Proc Natl Acad Sci USA, 112:4221-4226.
Peek et al. "A Semisynthetic Kanglemycin Shows in Vivo Efficacy against High-Burden Rifampicin Resistant Pathogens", ACS Infect. Dis. 2020. vol. 6, pp. 2431-2440.
Peek et al. "Rifamycin Congeners Kanglemycins are Active Against Rifampicin-Resistant Bacteria via a Distinct Mechanism", Nature Communications. 2018. vol. 9:4147, 15 pages.
Perron et al., 2015, "Functional characterization of bacteria isolated from ancient arctic soil exposes diverse resistance mechanisms to modern antibiotics", PLoS One, 10:e0069533.
Price et al., 2010, "FastTree 2—Approximately Maximum-Likelihood Trees for Large Alignments", PLoS One, 5:e9490.
Pubchem Search for PCT/US21/34232, 2021.
Ramaswamy et al., 1998, "Molecular genetic basis of antimicrobial agent resistance in *Mycobacterium tuberculosis*", Tuber. Lung Dis., 79:3-29.
Rateb et al. 'Chaxamycins A-D, Bioactive Ansamycins from a Hyper-Arid Desert *Streptomyces* sp.', J. Nat. Prod., 2011, 74 (6), pp. 1491-1499.
Reddy et al., 2012, "Natural product biosynthetic gene diversity in geographically distinct soil microbiomes", Appl Environ Microbiol, 78:3744-3752.
Roesch et al., 2007, "Pyrosequencing enumerates and contrasts soil microbial diversity", ISME J, 1:283-290.
Rothstein DM et al., 2008, "Rifalazil retains activity against rifampin-resistant mutants of Chlamydia pneumoniae", J. Antibiot. (Tokyo), 61:489-495.
Saito H et al., 1991, "In vitro antimycobacterial activities of newly synthesized benzoxazinorifamycins", Antimicrob. Agents Chemother., 35:542-547.
Sajduda et al., 2004, "Molecular characterization of rifampin- and isoniazid-resistant *Mycobacterium tuberculosis* strains isolated in Poland", J Clin Microbiol, 42:2425-2431.
Sensi P, 1983, "History of the development of rifampin", Rev. Infect. Dis., 5:Suppl 3, S402-S406.
Singhal et al., 2017, "Frequency of multi-drug resistance and mutations in *Mycobacterium tuberculosis* isolates from Punjab state of India", J Epidemiol Glob Health, 7:175-180.
Srivastava, A. et al., 2012, Frequency, spectrum, and nonzero fitness costs of resistance to myxopyronin in *Staphylococcus aureus*. Antimicrob. Agents Chemother. 56, 6250-6255.
Standards NCfCL. Methods for Dilution-Antimicrobial Susceptibility Tests for Bacteria That Grow Aerobically; M7-A7; Broth Microdilution Method: CLSI, Wayne, PA, USA, 2018.
Tadesse et al., 2016, "Drug resistance-conferring mutations in *Mycobacterium tuberculosis* from pulmonary tuberculosis patients in Southwest Ethiopia", Int J Mycobacteriol, 5:185-191.
Thibodeaux et al., 2008, "Natural-product sugar biosynthesis and enzymatic glycodiversification", Angew Chem Int Ed Engl, 47:9814-9859.
Thirumurugan et al., 2015, "Molecular analysis of rpoB gene mutations in rifampicin resistant *Mycobacterium tuberculosis* isolates by multiple allele specific polymerase chain reaction in Puducherry, South India", J Infect Public Health, 8:619-625.
Wang et al. "Isolation and Structure of a New Ansamycin Antibiotic Kanglemycin A from a Nocardia", The Journal of Antibiotics. 1988. vol. XLI, No. 2, pp. 264-267.
Wang et al., 2013, "PCR screening reveals considerable unexploited biosynthetic potential of ansamycins and a mysterious family of AHBA-containing natural products in actinomycetes", J Appl Microbiol, 115:77-85.
Wood et al., 2007, "PCR screening reveals unexpected antibiotic biosynthetic potential in *Amycolatopsis* sp. strain UM16", J Appl Microbiol, 102:245-253.
Xia M et al., 2005, "Activities of rifamycin derivatives against wild-type and rpoB mutants of Chlamydia trachomatis", Antimicrob. Agents Chemother., 49:3974-3976.
Yamane T et al., 1993, "Synthesis and biological activity of 3'-hydroxy-5'-aminobenzoxazinorifamycin derivatives. Chem Pharm Bull (Tokyo)", Chem. Pharm. Bull. (Tokyo), 41:148-155.
Zhang et al., 2012, "BIGrat: a repeat resolver for pyrosequencing-based re-sequencing with Newbler", BMC Research Notes, 5:567.

(56) References Cited

OTHER PUBLICATIONS

Zhu et al., 2009, "Selective isolation and ansamycin-targeted screenings of commensal actinomycetes from the "maytansinoids-producing" arboreal Trewia nudiflora", Curr Microbiol, 58:87-94.
Zhu et al., 2010, "Ab initio gene identification in metagenomic sequences", Nucleic Acids Research, 38:e132.
Zumla et al., 2015, "The WHO 2014 global tuberculosis report-further to go", Lancet Glob Health, 3:e10-2.

* cited by examiner

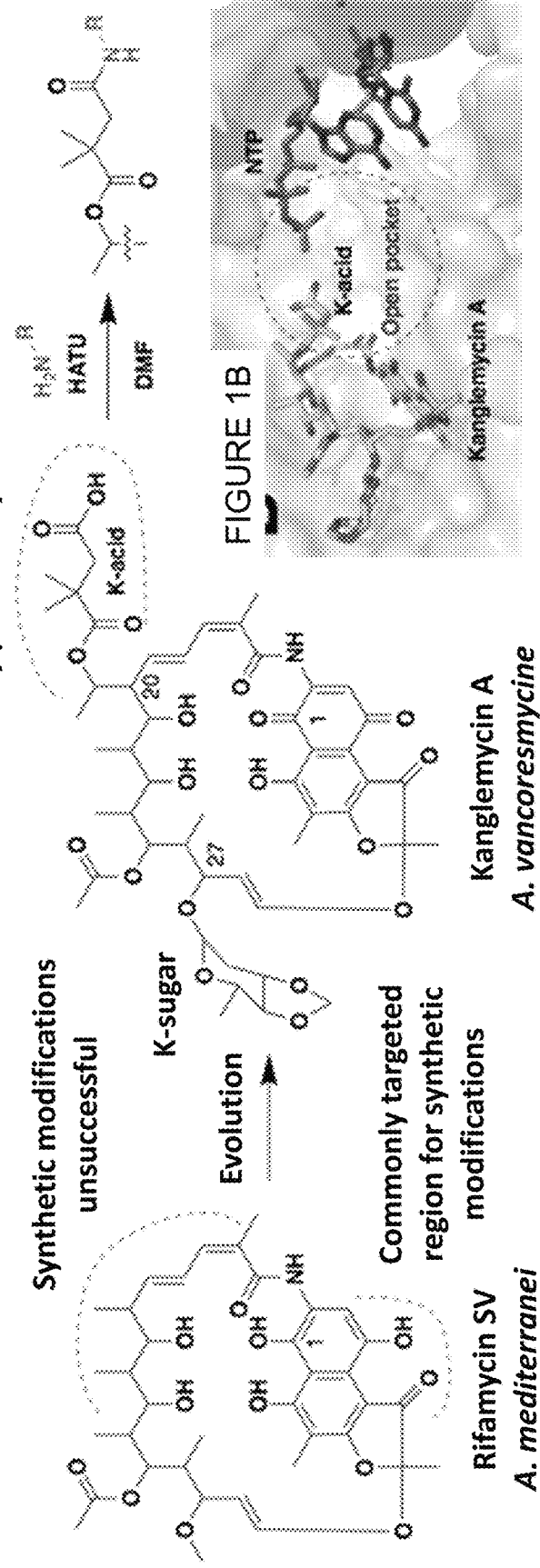
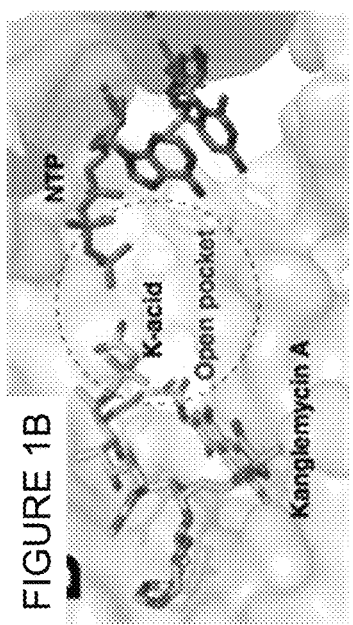
FIGURE 1

[Structure of compound 30 with OH and ester group]

| Amine Class | Hits/No. analogs |
|---|---|
| Aliphatic amines | 5/26 |
| Cyclic amines | 5/19 |
| Aromatic amines | 7/21 |
| Carboxylic acid amines | 0/13 |
| Phosphate mimics | 0/13 |
| Sugars | 0/3 |
| Phe/Trp/Tyr/His analogs | 0/10 |

FIGURE 5B

Reaction: compound + $H_2N-R$ → amide product, HATU, DMF

Aliphatic amines

| | Kang A | | | Rif |
|---|---|---|---|---|
| | C10 | D4 | E4 | N1 |
| WT | 0.0039 | 0.0039 | 0.016 | 0.0039 |
| H481Y | >64 | >64 | >64 | >64 |
| S486L | 16 | 4 | 0.25 | 16 |

Cyclic amines

| | J5 | B1 | N29 | C11 | J7 |
|---|---|---|---|---|---|
| WT | 0.000061 | 0.00098 | 0.00098 | 0.0039 | 0.0039 |
| H481Y | >64 | >64 | >64 | >64 | >64 |
| S486L | 16 | 16 | 4 | 64 | 16 |

FIGURE 5C

Aromatic amines

| | J4 | N4 | C13 | F1 | F2 | F5 | F6 |
|---|---|---|---|---|---|---|---|
| WT | 0.000061 | 0.000061 | 0.0039 | 0.0039 | 0.0039 | 0.0039 | 0.0039 |
| H481Y | >64 | >64 | >64 | >64 | >64 | >64 | 64 |
| S486L | 16 | 16 | 64 | 64 | 64 | 16 | 4 |

[Additional structures shown: C5 (cyclopropyl amine derivative) with values WT 0.00024, H481Y >64, S486L 16]

FIGURE 5

ANTIBACTERIAL COMPOUNDS, COMPOSITIONS THEREOF, AND METHODS USING SAME

RELATED APPLICATIONS

This application claims priority to, and the benefit of, the U.S. Provisional Application No. 62/877,417 filed Jul. 23, 2019 and the U.S. Provisional Application No. 63/050,288 filed Jul. 10, 2020, the contents of each of which are incorporated by reference in their entireties.

STATEMENT REGARDING FEDERALLY SPONSORED RESEARCH OR DEVELOPMENT

This invention was made with government support under NIH grant number 1U19AI142731 awarded by the National Institutes of Health (NIH). The government has certain rights in the invention.

BACKGROUND

Semisynthetic derivatives of the bacterial natural product rifamycin (e.g., rifampicin) have historically been used in the treatment of tuberculosis and other gram-positive bacterial infections. As with many antibiotics, the clinical utility of these therapeutics has declined due to the increased incidence of antibiotic resistant bacterial pathogens. Resistance to rifamycin family antibiotics commonly occurs in clinical isolates as a result of point mutations in the antibiotic's target, DNA-dependent RNA polymerase (RNAP). These mutations are unlikely to be unique to clinical isolates as many, if not all, clinically relevant antibiotic resistance mechanisms are present in natural environments where they would have evolved in response to antibiotics produced by other bacteria.

There is a continuing need in the art for novel antimicrobial agents. The present disclosure addresses this unmet need in the art.

SUMMARY

In some aspects, the present disclosure provides, inter alia, a compounds of Formula (I), (II), or (III):

Formula I

Formula II

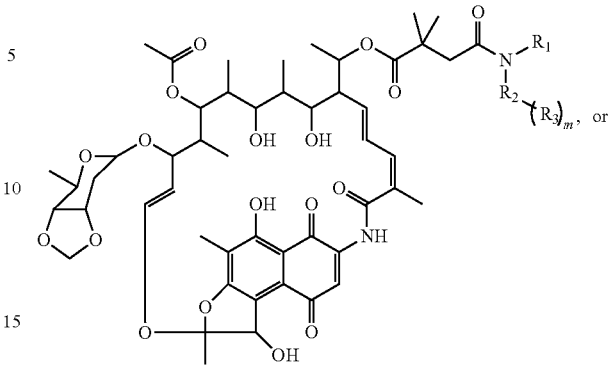

Formula III

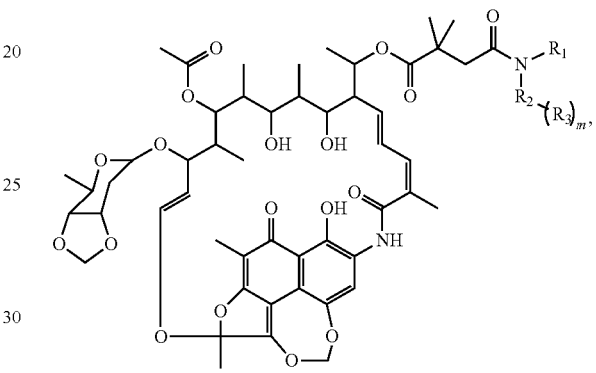

or a pharmaceutically acceptable salt, solvate, or tautomer, thereof, wherein:

$R_1$ is H, $C_{1-10}$ alkyl, $C_{2-10}$ alkenyl, or $C_{2-10}$ alkynyl;

$R_2$ is —$OR_4$, aryl, heteroaryl, aralkyl, aralkenyl, aralkynyl, heteroarylalkyl, heteroarylalkenyl, heteroarylalkynyl, cycloalkyl, cycloalkenyl, cycloalkynyl, heterocyclyl, cycloalkylalkyl, heterocycloalkyl or $C_{1-10}$ alkyl, or $R_1$ and $R_2$ together form a 3- to 10-membered heterocyclyl optionally substituted with one or more $R_5$;

each $R_3$ is independently H, oxo, halogen, —$OR_4$, —$N(R_4)(R_5)$, —$SR_4$, —$C(O)R_4$, —$C(O)OR_4$, —$C(O)NR_4R_5$, —$P(O)(OR_4)_2$, —$S(O)_2R_4$, —$S(O)_2OR_4$, —$NR_4C(O)R_5$, —$NR_4C(O)OR_5$, —$NC(O)NR_4R_5$, $C_{1-6}$ alkyl, $C_{1-6}$ haloalkyl, aryl, heteroaryl, $C_{3-10}$ cycloalkyl, or heterocyclyl, wherein the alkyl, aryl, heteroaryl, heterocyclyl, or $C_{3-10}$ cycloalkyl is optionally substituted with one or more $R_5$; or two $R_3$ together with the atoms to which they are attached form an aryl, heteroaryl, heterocyclyl, or $C_{3-10}$ cycloalkyl wherein the aryl, heteroaryl, heterocyclyl, or $C_{3-10}$ cycloalkyl is optionally substituted with one or more $R_5$;

$R_4$ is H or $C_{1-6}$ alkyl;

each $R_5$ is independently H, oxo, halogen, $C_{1-6}$ alkyl, $C_{2-6}$ alkenyl, $C_{2-6}$ alkynyl, $C_{1-6}$ alkoxy, $C_{1-6}$ haloalkyl, —$OR_6$, —$NH_2$, —$NH(C_{1-6}$ alkyl), —$NH(C_{1-6}$ alkyl)$_2$, —$C(O)OR_6$, —$P(O)(OR_6)_2$, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$;

$R_6$ is H, $C_{1-6}$ alkyl, $C_{2-6}$ alkenyl, or $C_{2-6}$ alkynyl;

each $R_7$ is independently oxo, —OH, —C(O)OH, —C(O)O($C_{1-6}$ alkyl), aryl, heteroaryl, heterocyclyl, or $C_{3-10}$ cycloalkyl wherein the aryl, heteroaryl, heterocyclyl, or $C_{3-10}$ cycloalkyl is optionally substituted with halogen, oxo, —OH, or —$NH_2$;

m is 1, 2, 3, or 4; and n is 1, 2, 3, or 4.

In some embodiments, the compounds of Formula (I), (II), and (III) are substantially pure. In some embodiments, the compounds of Formula (I), (II), and (III) are enantiomerically pure.

In some embodiments, the compounds of Formula (I), (II), and (III) have a lower MIC (μg/mL) against rifamycin-resistant bacteria than rifamycin.

In some embodiments, the disclosure provides for pharmaceutical compositions comprising a therapeutically effective amount of one or more compounds of Formula (I), (II), and (III) and a pharmaceutically acceptable excipient. In some embodiments, the pharmaceutical composition further comprises a pharmaceutical carrier.

In some embodiments, the present disclosure provides for a method of preventing or reducing the growth or proliferation of a microorganism, wherein the method comprises contacting the microorganism with a composition comprising a compound of Formula (I), (II), and (III). In some embodiments, the microorganism is a bacterium. In some embodiments, the bacterium is resistant to at least on antibiotic. In some embodiments, the bacterium is resistant to rifamycin. In some embodiments, the bacterium has at least one point mutation that confers antibiotic resistance. In some embodiments, the bacterium has one or more of the following mutations of one or more amino acids: (1) serine to leucine; (2) histidine to tyrosine; (3) or asparagine to tyrosine. In some embodiments, the method further comprises administering to the subject an additional therapeutic agent.

In some embodiments, the present disclosure provides for methods of treating or preventing a bacterial infection in a subject, wherein the method comprises administering to the subject a composition comprising a compound of Formula (I), (II), and (III). In some embodiments, the bacterial infection is an infection of *Staphylococcus aureus, Staphylococcus epidermidis, Listeria monocytogenes* and *M. tuberculosis*. In some embodiments, the bacterial infection is resistant to rifamycin. In some embodiments, the bacterial infection is caused by a bacterium that has at least one point mutation that confers antibiotic resistance. In some embodiments, the bacterium has one or more of the following mutations of one or more amino acids: (1) serine to leucine; (2) histidine to tyrosine; (3) or asparagine to tyrosine. In some embodiments, the method further comprises administering to the subject an additional therapeutic agent.

In some embodiments, the present disclosure provides for compounds of Formula (I), (II), and (III) for use in treating a bacterial infection. In some embodiments, the bacterial infection is an infection of *Staphylococcus aureus, Staphylococcus epidermidis, Listeria monocytogenes* and *M. tuberculosis*. In some embodiments, the bacterial infection is resistant to rifamycin. In some embodiments, the bacterial infection is caused by a bacterium that has at least one point mutation that confers antibiotic resistance. In some embodiments, the bacterium has one or more of the following mutations of one or more amino acids: (1) serine to leucine; (2) histidine to tyrosine; (3) or asparagine to tyrosine.

BRIEF DESCRIPTION OF THE DRAWINGS

The following detailed description of preferred embodiments of the disclosure will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities of the embodiments shown in the drawings.

FIG. 1, comprising FIG. 1A and FIG. 1B, depicts the semi-synthetic and evolved modifications of Rifamycin. FIG. 1A depicts a summary of the semi-synthetic modifications of rifamycin SW. FIG. 1B depicts the position of the K-acid relative to the nascent RNA transcript in the RNAP active site.

FIG. 2 depicts the synthesis and screening of Formula I-III analogs.

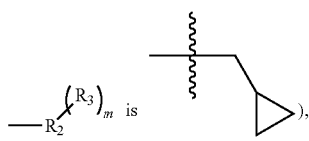

C5

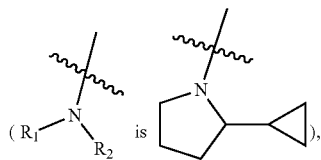

E4 ($R_1$ is H and

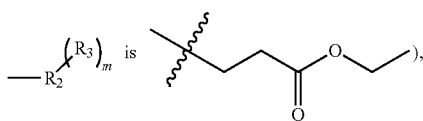

F6 ($R_1$ is H and

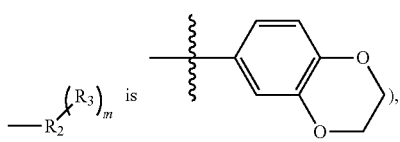

J4 ($R_1$ is H and

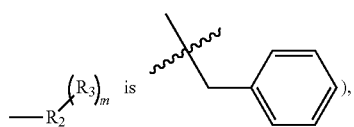

and J5 ($R_1$ is H and

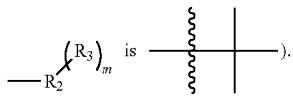

The curves shown represent data collected at 12 h (solid lines) and 24 hr (dashed lines).

Figure 4:
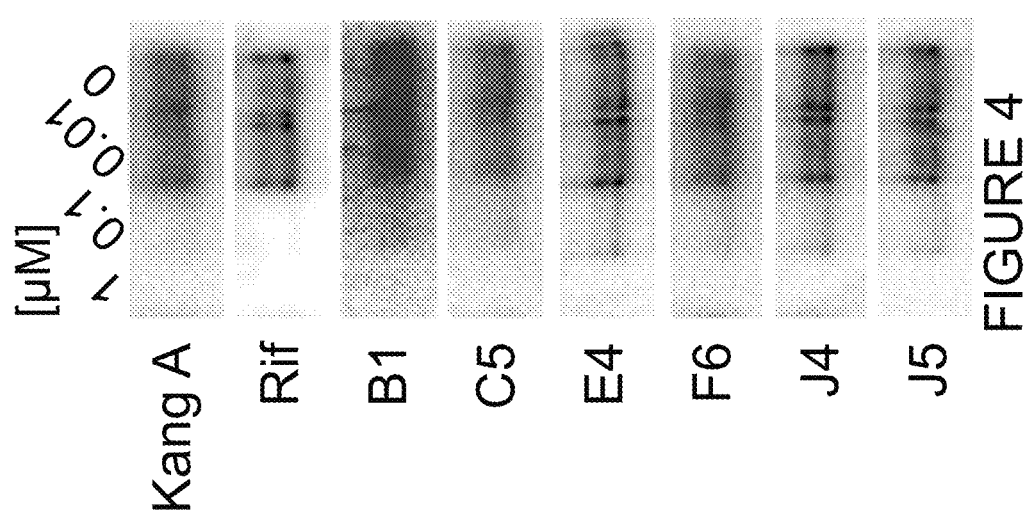

FIG. 4 depicts in vitro analysis of the RNAP inhibitory activity of Formula I and Formula III.

FIG. 5, comprising FIG. 5A through FIG. 5C, depicts activity of Kang amides against wild-type (WT) *S. aureus* compared to Kang A. FIG. 5A depicts the reaction used for the synthesis of Kang amides and summary of screening. FIG. 5B depicts MIC values (μg/mL) for Kang A and Rif against WT and RifR H481Y and S486L *S. aureus* strains. FIG. 5C depicts structural modifications and MIC values (μg/mL) of compounds of the present disclosure against WT and RifR *S. aureus* strains.

Figure 6:
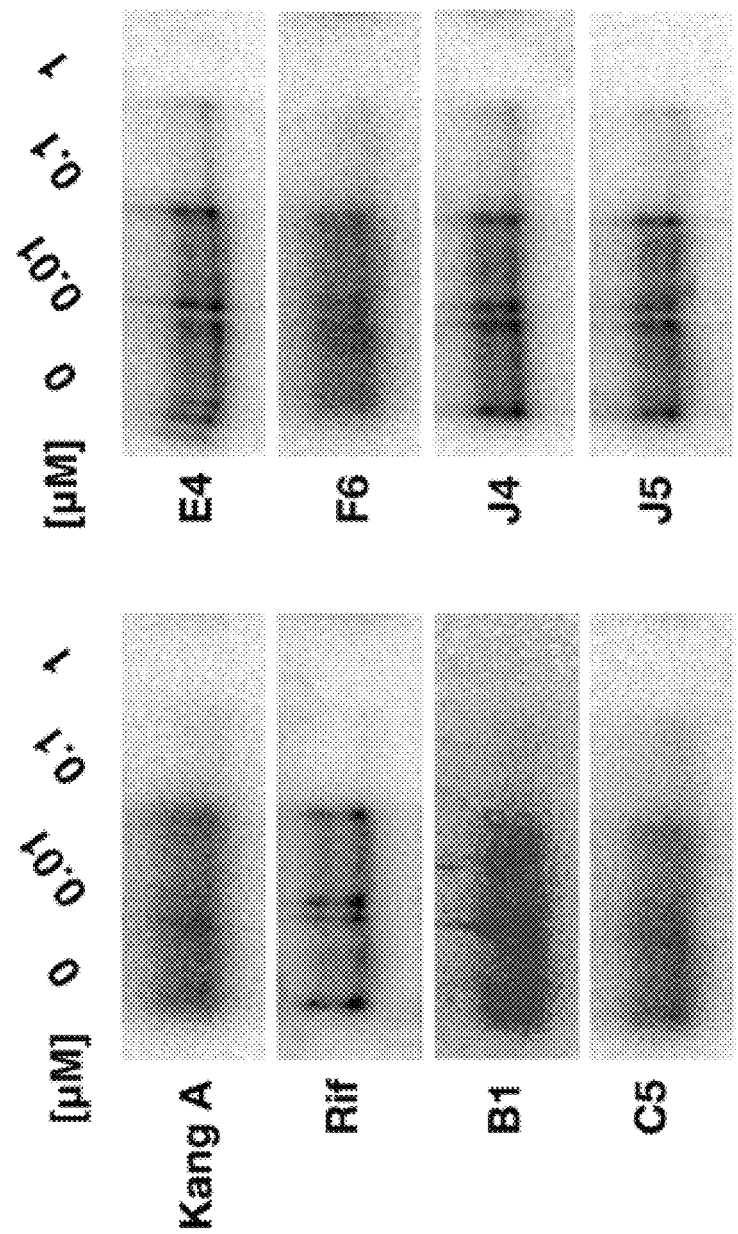

FIG. 6 depicts activity of B1, C5, E4, F6, J4, and J5 against WT and S456L RifR *M. tuberculosis*.

Figure 7:
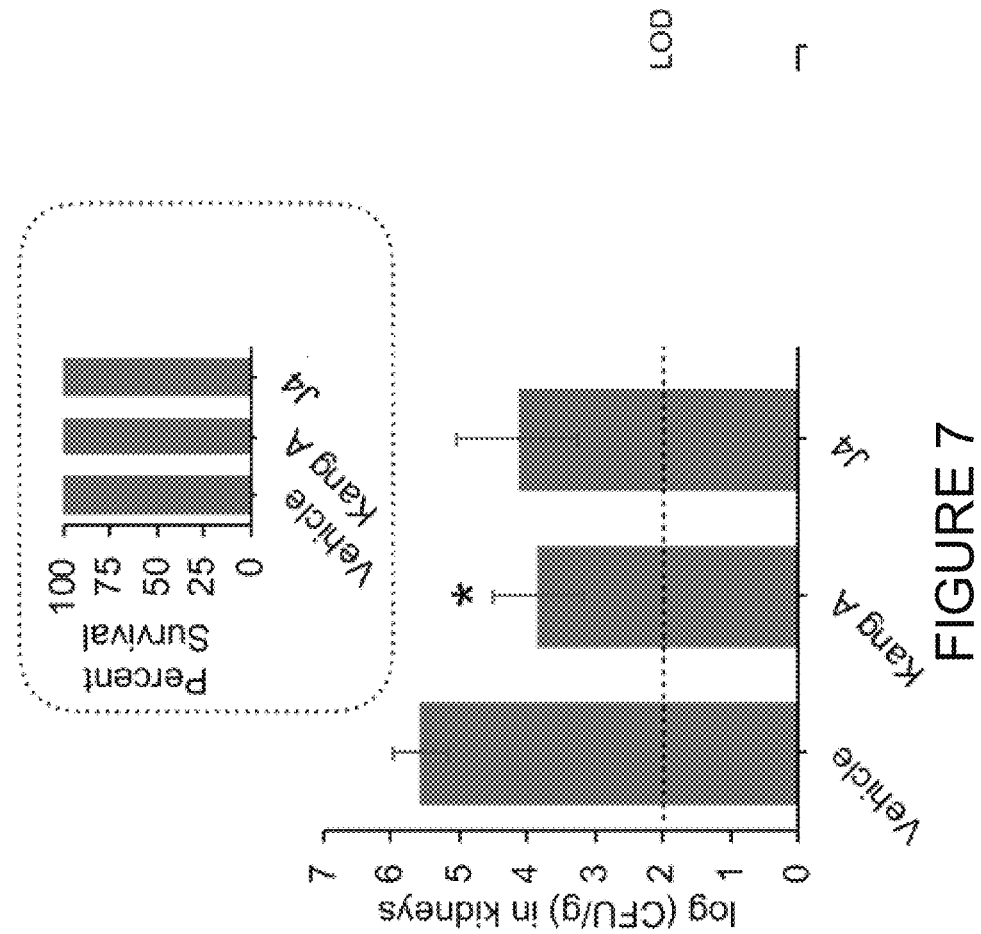

FIG. 7 depicts IP and PO bioavailability of J4 in comparison to Kang A in a neutropenic murine acute peritonitis/septicemia mouse model.

DETAILED DESCRIPTION

The present disclosure provides novel compounds that are useful as antibacterial agents. In some embodiments, the compounds are rifamycin congers. In some embodiments, the compounds exhibit antibacterial activity against strains resistant to antibacterial compounds, such as rifamycin. Thus, the present disclosure provides novel compounds, compositions comprising at least one compound of the disclosure, methods of making the compounds of the disclosure, and methods of using the compounds of the disclosure.

In some embodiments, the disclosure provides methods of treating a bacterial infection in a subject comprising administering a composition comprising a compound of the disclosure. The present disclosure also provides methods of preventing or reducing the growth or proliferation of microorganisms by contacting the microorganism with a composition comprising a compound of the disclosure.

In some embodiments, the present disclosure provides a method of overcoming antibacterial resistance. For example, In some embodiments, the method comprises introducing a methylenedioxy group into an antibacterial compound.

Definitions

Unless defined otherwise, all technical and scientific terms used herein have the same meaning as commonly understood by one of ordinary skill in the art to which this disclosure belongs. Although any methods, materials and components similar or equivalent to those described herein can be used in the practice or testing of the present disclosure, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element. As such, the terms "a" (or "an"), "one or more" and "at least one" are used interchangeably herein. In addition, reference to "a compound" by the indefinite article "a" or "an" does not exclude the possibility that more than one of the compounds is present, unless the context clearly requires that there is one and only one of the inhibitors.

"About" and/or "approximately" as used herein when referring to a measurable value, for example numerical values and/or ranges, such as an amount, a temporal duration, and the like, is meant to encompass variations of ±20%, ±10%, ±5%, ±1%, or ±0.1% from the specified value, as such variations are appropriate. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein, and all values within a given range may be an endpoint for the range encompassed thereby. Thus, the range "from 50 to 80" includes all possible ranges therein (e.g., 51-79, 52-78, 53-77, 54-76, 55-75, 60-70, etc.), as if each value and subrange were expressly disclosed. Accordingly, the description of a range should be considered to have disclosed all the possible subranges as well as individual numerical values within that range. For example, description of a range such as from 1 to 6 should be considered to have disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This definition applies regardless of the breadth of the range.

"Amino" refers to the —$NH_2$ group.
"Cyano" refers to the —CN group.
"Hydroxy" or "hydroxyl" refers to the —OH group.
"Imino" refers to the =NH group.
"Nitro" refers to the —$NO_2$ group.
"Oxo" refers to the =O group.
"Thioxo" refers to the =S group.

As used herein, the term "alkyl," or "alkyl group" by itself or as part of another substituent means, unless otherwise stated, a straight or branched chain hydrocarbon having from 1 to 12 carbon atoms. In some embodiments, the alkyl is a $C_1$-$C_{12}$ alkyl, a $C_1$-$C_{10}$ alkyl, a $C_1$-$C_8$ alkyl, a $C_1$-$C_6$ alkyl, a $C_1$-$C_4$ alkyl, or a $C_1$-$C_3$ alkyl. For example, an alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples include methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl, n-undecyl, n-dodecyl, and cyclopropylmethyl. Unless stated otherwise in the specification, an alkyl group can be optionally substituted.

"Alkylene" or "alkylene chain" refers to a fully saturated, straight or branched divalent hydrocarbon, and having from one to twelve carbon atoms, and which has two points of attachment to the rest of the molecule. In some embodiments, the alkylene is a $C_1$-$C_{12}$ alkylene, a $C_1$-$C_{10}$ alkylene, a $C_1$-$C_8$ alkylene, a $C_1$-$C_6$ alkylene, a $C_1$-$C_4$ alkylene, or a $C_1$-$C_3$ alkylene. Non-limiting examples of $C_1$-$C_{12}$ alkylene include methylene, ethylene, propylene, n-butylene, ethenylene, propenylene, n-butenylene, propynylene, n-butynylene, and the like. The points of attachment of the alkylene chain to the rest of the molecule can be through one carbon or any two carbons within the chain. Unless stated otherwise in the specification, an alkylene chain can be optionally substituted.

"Alkenyl" or "alkenyl group" refers to a straight or branched hydrocarbon chain having from two to twelve carbon atoms, and having one or more carbon-carbon double bonds. Each alkenyl group is attached to the rest of the molecule by a single bond. Alkenyl group comprising any number of carbon atoms from 2 to 12 are included. In some embodiments, the alkenyl is a $C_2$-$C_{12}$ alkenyl, a $C_2$-$C_{10}$ alkenyl, a $C_2$-$C_8$ alkenyl, a $C_2$-$C_6$ alkenyl, a $C_2$-$C_4$ alkenyl, or a $C_2$-$C_3$ alkenyl. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise in the specification, an alkenyl group can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. In some embodiments, the alkynyl is a $C_2$-$C_{12}$ alkynyl, a $C_2$-$C_{10}$ alkynyl, a $C_2$-$C_8$ alkynyl, a $C_2$-$C_6$ alkynyl, a $C_2$-$C_4$ alkynyl, or a $C_2$-$C_3$ alkynyl. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise in the specification, an alkynyl group can be optionally substituted.

As used herein, the term "alkoxy" employed alone or in combination with other terms means, unless otherwise stated, refers to a group of the formula —$OR_a$ where $R_a$ is an alkyl, alkenyl or alknyl group having from 1 to 12 carbon atoms, as defined above, connected to the rest of the molecule via an oxygen atom, such as, for example, methoxy, ethoxy, 1-propoxy, 2-propoxy (isopropoxy) and the higher homologs and isomers. Unless stated otherwise in the specification, an alkoxy group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise in the specification, a haloalkyl group can be optionally substituted.

As used herein, the term "heteroalkyl" by itself or in combination with another term means, unless otherwise stated, a stable straight or branched chain alkyl group consisting of from 1 to 12 carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$. Unless stated otherwise in the specification, an heteroalkyl group can be optionally substituted.

"Alkylamino" refers to a group of the formula —$NHR_a$ or —$NR_aR_a$ where each $R_a$ is, independently, an alkyl, alkenyl or alkynyl group as defined above containing one to twelve carbon atoms. Unless stated otherwise in the specification, an alkylamino group can be optionally substituted.

"Alkylcarbonyl" refers to the —C(=O)$R_a$ moiety, wherein $R_a$ is an alkyl, alkenyl or alkynyl group as defined above. A non-limiting example of an alkyl carbonyl is the methyl carbonyl ("acetal") moiety. Alkylcarbonyl groups can also be referred to as "$C_w$-$C_z$ acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl group as defined above. Unless stated otherwise in the specification, an alkyl carbonyl group can be optionally substituted.

As used herein, the term "halo" or "halogen" alone or as part of another substituent means, unless otherwise stated, a fluorine, chlorine, bromine, or iodine group.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. Unless stated otherwise in the specification, a carbocyclyl group can be optionally substituted.

As used herein, the term "cycloalkyl" refers to a stable mono cyclic or polycyclic non-aromatic group, wherein each of the atoms forming the ring (i.e. skeletal atoms) is a carbon atom, which can include fused or bridged ring systems, having from three to twenty carbon atoms (e.g., having from three to ten carbon atoms) and which is attached to the rest of the molecule by a single bond. In some embodiments, the cycloalkyl group is saturated or partially unsaturated. In some embodiments, the cycloalkyl group is fused with an aromatic ring. Cycloalkyl groups include groups having from 3 to 20 carbon ring atoms. Illustrative examples of cycloalkyl groups include, but are not limited to, the following moieties:

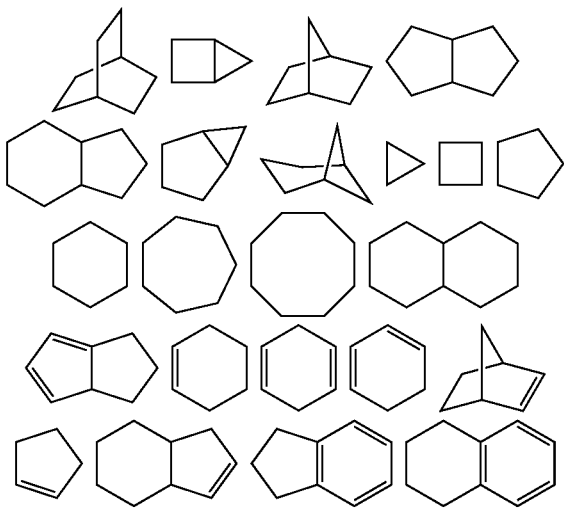

wherein any hydrogen atom in the above groups may be replaced by a bond to the molecule.

Monocyclic cycloalkyls include, but are not limited to, cyclopropyl, cyclobutyl, cyclopentyl, cyclohexyl, cycloheptyl, and cyclooctyl. Dicyclic or polycyclic cycloalkyls include, but are not limited to, tetrahydronaphthyl, indanyl, and tetrahydropentalenyl, adamantyl and norbornyl. The term cycloalkyl includes "unsaturated nonaromatic carbocyclyl," "carbocyclyl," "carbocyclic ring," "carbocycle," or "nonaromatic unsaturated carbocyclyl" groups, both of which refer to a nonaromatic carbocycle as defined herein, which contains at least one carbon double bond or one carbon triple bond.

"Cycloalkenyl" refers to a stable non aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyls include, for example, cyclopentenyl, cyclohexenyl, cycloheptenyl, cyclooctenyl, and the like. Polycyclic cycloalkenyls include, for example, bicyclo[2.2.1]hept-2-enyl and the like. Unless otherwise stated in the specification, a cycloalkenyl group can be optionally substituted.

"Cycloalkynyl" refers to a stable non aromatic monocyclic or polycyclic hydrocarbon consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyls include, for example, cycloheptynyl, cyclooctynyl, and the like. Unless otherwise stated in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise in the specification, a cycloalkylalkyl group can be optionally substituted.

The terms "heterocyclic ring", "heterocycle" and "heterocyclyl" are used interchangeably herein to refer to a 3- to 20-membered containing one to six heteroatoms each independently selected from the group consisting of O, S and N. In some embodiments, each heterocyclyl group has from 4- to 10-atoms in its ring system, and from one to three heteroatoms each independently selected from the group consisting of O, S and N. Unless stated otherwise in the specification, the heterocyclyl can be a monocyclic, bicyclic, tricyclic or tetracyclic ring system, which can include fused or bridged ring systems. In some embodiments, the nitrogen, carbon, or sulfur heteroatoms may be optionally oxidized, and the nitrogen atom may be optionally quaternized. The heterocyclic system may be attached, unless otherwise stated, at any heteroatom or carbon atom that affords a stable structure. The heterocyclyl can be partially or fully saturated. A heterocycle may be polycyclic, wherein the polycyclic ring may be non-aromatic or contain both aromatic and non-aromatic rings. Unless stated otherwise in the specification, a heterocyclyl group can be optionally substituted.

Examples of such heterocyclyls include, but are not limited to, aziridinyl, azetidinyl, beta lactamyl, dioxolanyl, oxazolidinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrrolinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxothiomorpholinyl, oxiranyl, thiiranyl, oxetanyl, thietanyl, sulfolanyl, 2,3-dihydrofuranyl, 2,5-dihydrofuranyl, thiophanyl, 1,2,3,6-tetrahydropyridinyl, 1,4-dihydropyridinyl, piperazinyl, thiomorpholinyl, pyranyl, 2,3-dihydropyranyl, tetrahydropyranyl, 1,4-dioxanyl, 1,3-dioxanyl, homopiperazinyl, homopiperidinyl, 1,3-dioxepanyl, 4,7-dihydro-1,3-dioxepinyl, and hexamethyleneoxidyl.

Other non-limiting examples of heterocyclyl groups are:

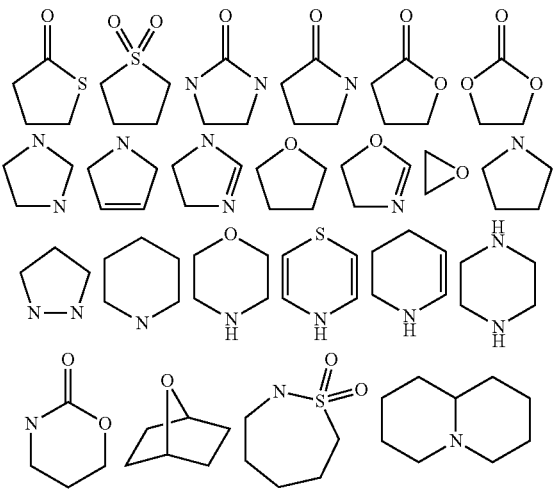

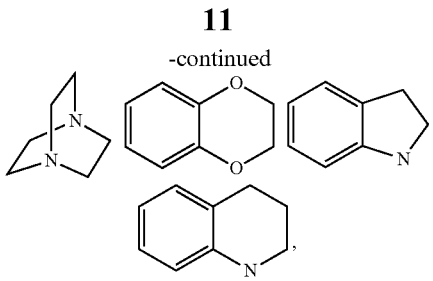

wherein any hydrogen atom in the above groups may be replaced by a bond to the molecule.

"Heterocycloalkyl" refers to a radical of the formula —$R_b$—$R_e$ where $R_b$ is an alkylene, alkenylene, or alkynylene group as defined above and $R_e$ is a heterocyclyl radical as defined above. Unless stated otherwise in the specification, a heterocycloalkylalkyl group can be optionally substituted.

"Thioalkyl" refers to a formula —$SR_a$ where $R_a$ is an alkyl, alkenyl, or alkynyl as defined above containing one to twelve carbon atoms. Unless stated otherwise in the specification, a thioalkyl group can be optionally substituted.

As used herein, the term "aromatic" refers to a carbocyclyl or heterocyclyl with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a hydrocarbon ring system, comprising hydrogen, 6 to 18 carbon atoms and at least one aromatic ring. For purposes of this disclosure, the aryl can be a monocyclic, bicyclic, tricyclic or tetracyclic ring system, which can include fused or bridged ring systems. For example, aryls include, but are not limited to, a biphenyl, or may be fused, such as naphthalene. Examples of aryl groups include benzyl, indacenyl, pyrenyl, triphenyl, phenyl, anthracyl, and naphthyl. Unless stated otherwise in the specification, the term "aryl" is meant to include aryl groups that are optionally substituted.

As used herein, the term "heteroaryl" or "heteroaromatic" refers to a 5 to 20 membered ring system comprising hydrogen atoms, one to fourteen carbon atoms, one to six heteroatoms selected from the group consisting of nitrogen, oxygen and sulfur, and at least one aromatic ring. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. A polycyclic heteroaryl may include one or more rings that are partially saturated. Examples include the following moieties:

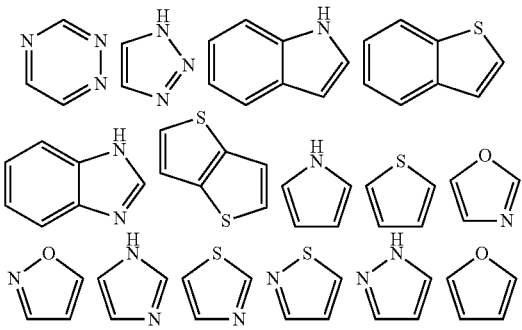

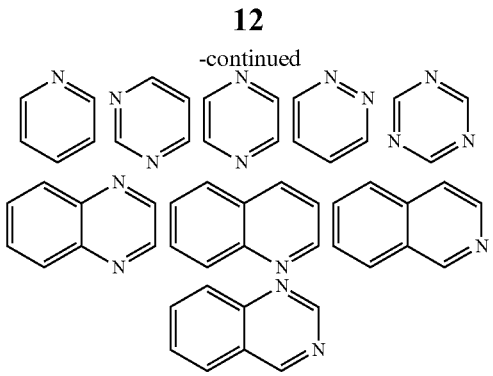

wherein any hydrogen atom in the above groups may be replaced by a bond to the molecule.

Examples of heteroaryl groups include, but are not limited to, pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl, 1,3,4-oxadiazolyl, indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl. Unless stated otherwise in the specification, a heteroaryl group can be optionally substituted.

"Aralkyl" or "arylalkyl" refers to a radical of the formula —$R_b$—$R_c$ where $R_b$ is an alkylene group as defined above and $R_c$ is one or more aryl radicals as defined above, for example, benzyl, diphenylmethyl and the like. Unless stated otherwise in the specification, an aralkyl group can be optionally substituted.

Aralkenyl" or "arylalkenyl" refers to a radical of the formula —$R_b$—$R_c$ where $R_b$ is an alkenylene o group as defined above and $R_c$ is one or more aryl radicals as defined above. Unless stated otherwise in the specification, an aralkenyl group can be optionally substituted.

"Aralkynyl" or "arylalkynyl" refers to a radical of the formula —$R_b$—$R_c$ where $R_b$ is an alkynylene group as defined above and $R_c$ is one or more aryl radicals as defined above. Unless stated otherwise in the specification, an aralkynyl group can be optionally substituted.

"Heteroarylalkyl" refers to a radical of the formula —$R_b$—$R_f$ where $R_b$ is an alkylene chain as defined above and $R_f$ is a heteroaryl radical as defined above. Unless stated otherwise in the specification, a heteroarylalkyl group can be optionally substituted.

"Heteroarylalkenyl" refers to a radical of the formula —$R_b$—$R_f$ where $R_b$ is an alkenylene, chain as defined above and $R_f$ is a heteroaryl radical as defined above. Unless stated otherwise in the specification, a heteroarylalkenyl group can be optionally substituted.

"Heteroarylalkynyl" refers to a radical of the formula —$R_b$—$R_f$ where $R_b$ is an alkynylene chain as defined above and $R_f$ is a heteroaryl radical as defined above. Unless stated otherwise in the specification, a heteroarylalkynyl group can be optionally substituted.

As used herein, the term "substituted" means any of the above groups (i.e., alkyl, alkylene, alkenyl, alkynyl, alkoxy, aryl, carbocyclyl, cycloalkyl, cycloalkenyl, cycloalkynyl, heterocyclyl, and/or heteroaryl) wherein at least hydrogen atom is replaced by a bond to a non-hydrogen atom or group of atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. The term "substituted" further refers to any level of substitution, namely mono-, di-, tri-, tetra-, or penta-substitution, where such substitution is permitted. The substituents are independently selected, and substitution may be at any chemically accessible position. In some embodiments, the substituents vary in number between one and four. In some embodiments, the substituents vary in number between one and three. In yet another embodiment, the substituents vary in number between one and two. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with, for example, $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with, for example, $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently selected from any of the above groups, including but not limited to: hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to any of the above groups, including but not limited to amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the term "optionally substituted" means that the referenced group may be substituted or unsubstituted. In some embodiments, the referenced group is optionally substituted with zero substituents, i.e., the referenced group is unsubstituted. In some embodiments, the referenced group is optionally substituted with one or more additional group(s) individually and independently selected from groups described herein.

As used herein, the term "antimicrobial" refers to an ability to kill or inhibit the growth of microorganisms, including but not limited to bacteria, viruses, yeast, fungi, and protozoa, or to attenuate the severity of a microbial infection. The antimicrobial compounds or compositions of the present disclosure are compounds or compositions that may be used for cleaning or sterilization, or may be used in the treatment of disease and infection. The applications may include both in vitro and in vivo antimicrobial uses. "Applying" an antimicrobial composition may include administrating a composition into a human or animal subject.

As used herein, the term "contacting" includes, but is not limited to, impregnating, compounding, mixing, integrating, coating, rubbing, painting, spraying, immersing, rolling, smearing and dipping.

As used herein, the term "treatment" or "treating," is defined as one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition. In some embodiments "treatment" or "treating," is defined as the application or administration of a therapeutic agent, i.e., a compound useful within the disclosure (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be tailored or modified, based on knowledge obtained from the field of medicine or pharmacology. In some embodiments, the condition is selected from the group consisting of a bacterial infection, fungal infection, mycobacterial infection, viral infection, and a combination thereof.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "pharmaceutical composition" refers to a mixture of at least one compound useful within the disclosure with a pharmaceutically acceptable carrier. The pharmaceutical composition facilitates administration of the compound to a patient or subject, or use of the compound within the methods of the disclosure. Multiple techniques of administering a compound exist in the art including, but not limited to, intravenous, oral, aerosol, parenteral, ophthalmic, pulmonary and topical administration.

As used herein, the terms "effective amount," "pharmaceutically effective amount" and "therapeutically effective amount" refer to a non-toxic but sufficient amount of an agent and/or formulation according to the disclosure that when administered to a patient for treating a state, disorder or condition is sufficient to provide the desired biological and/or clinical result. That result may be reduction and/or alleviation of the signs, symptoms, or causes of a disease, or any other desired alteration of a biological system. An appropriate therapeutic amount in any individual case may be determined by one of ordinary skill in the art using routine experimentation. The "effective amount" will vary depending on the active ingredient, the state, disorder, or condition to be treated and its severity, and the age, weight, physical condition and responsiveness of the mammal to be treated.

All weight percentages (i.e., "% by weight" and "wt. %" and "w/w") referenced herein, unless otherwise indicated, are measured relative to the total weight of the pharmaceutical composition.

As used herein, the term "potency" refers to the dose needed to produce half the maximal response ($ED_{50}$).

As used herein, the term "efficacy" refers to the maximal effect ($E_{max}$) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" embraces addition salts of free acids or free bases. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the disclosure include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. In some embodiments, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. Supplementary active compounds may also be incorporated into the compositions. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, Pa.), which is incorporated herein by reference.

As used herein, the term "minimum inhibitory concentration (MIC)" refers to the lowest concentration of an antimicrobial agent that will inhibit the visible growth of a microorganism after overnight incubation. MIC values against bacteria may be determined by standard methods. See also P. A. Wayne, Methods for Dilution Antimicrobial Tests for Bacteria that Grow Aerobically; Approved Standard, Ninth Edition, 2012, CLSI Document M07-A9, Vol. 32 No. 2, which is incorporated by reference herein in its entirety.

As used herein, the term "organic solvent" refers to solvents including, but not limited to, alcohols (e.g., methanol and ethanol), ketones (e.g., acetone and methylethylketone), ethers (e.g., tetrahydrofuran), aldehydes (e.g., formaldehyde), acetonitrile, carboxylic acids (e.g., formic acid and acetic acid), methylene chloride, chloroform, alkyl carbonates, and hydrocarbons (e.g., hexane and heptane, and xylene), esters (e.g., ethyl acetate, propyl acetate, butyl acetate, amyl acetate, and combination thereof) or similar solvents.

As used herein, the term "alkalinizing agent" refers to an organic and inorganic base, including sodium hydroxide, potassium hydroxide, alkyl hydroxides, ammonia in water (27% ammonium hydroxide), diethylamine and triethylamine.

As used herein, the term "high ionic strength salt" refers to a salt exhibiting high ionic strength, such as sodium chloride, potassium chloride, or ammonium acetate. These salts may act both as an alkalinizing agent and as a penetrating agent to enhance the reactivity of the surface. Therefore, in some embodiments, high ionic strength salts may also be used in the step of forming the biofilm-penetrating composition.

The following description includes information that may be useful in understanding the present disclosure. It is not an admission that any of the information provided herein is prior art or relevant to the presently claimed inventions, or that any publication or implicitly referenced is prior art.

Description

The present disclosure provides for antibacterial compounds. In some embodiments, these compounds have potent activity against the most common RNA polymerase point mutations that are known to confer antibacterial resistance in clinical isolates of pathogenic bacteria (*Nature Communications* (2018) 9, 4147, which is incorporated by reference herein in its entirety). For example, RNA polymerase point mutations may confer antibacterial resistance through one of one or more of the following amino acid mutations in bacteria: (1) serine to leucine; (2) histidine to tyrosine; (3) or asparagine to tyrosine. Other examples are known in the art, e.g., J Antibiot (Tokyo). 2014 September; 67(9):625-30. doi: 10.1038/ja.2014.107. Epub 2014 Aug. 13, which is incorporated by reference herein in its entirety. In some embodiments, the antibacterial compounds disclosed here are active against bacteria having one or more of these amino acid mutations. In some embodiments, the disclosure also provides a composition comprising at least one compound of the disclosure and methods of treating or preventing a bacterial infection in a subject.

Compounds of the Present Disclosure

In some aspects, the present disclosure provides, inter alia, a compounds of Formula (I), (II), or (III):

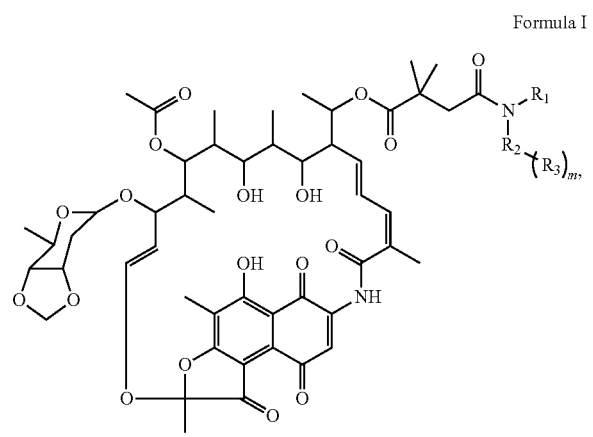

Formula I

Formula II

Formula III or a pharmaceutically acceptable salt, solvate, or tautomer, thereof, wherein:

$R_1$ is H, $C_{1-10}$ alkyl, $C_{2-10}$ alkenyl, or $C_{2-10}$ alkynyl;

$R_2$ is —$OR_4$, aryl, heteroaryl, aralkyl, aralkenyl, aralkynyl, heteroarylalkyl, heteroarylalkenyl, heteroarylalkynyl, cycloalkyl, cycloalkenyl, cycloalkynyl, heterocyclyl, cycloalkylalkyl, heterocycloalkyl or $C_{1-10}$ alkyl, or $R_1$ and $R_2$ together form a 3- to 10-membered heterocyclyl optionally substituted with one or more $R_5$;

each $R_3$ is independently H, oxo, halogen, —$OR_4$, —$N(R_4)(R_5)$, —$SR_4$, —$C(O)R_4$, —$C(O)OR_4$, —$C(O)NR_4R_5$, —$P(O)(OR_4)_2$, —$S(O)_2R_4$, —$S(O)_2OR_4$, —$NR_4C(O)R_5$, —$NR_4C(O)OR_5$, —$NC(O)NR_4R_5$, $C_{1-6}$ alkyl, $C_{1-6}$ haloalkyl, aryl, heteroaryl, $C_{3-10}$ cycloalkyl, or heterocyclyl, wherein the alkyl, aryl, heteroaryl, heterocyclyl, or $C_{3-10}$ cycloalkyl is optionally substituted with one or more $R_5$; or two $R_3$ together with the atoms to which they are attached form an aryl, heteroaryl, heterocyclyl, or $C_{3-10}$ cycloalkyl wherein the aryl, heteroaryl, heterocyclyl, or $C_{3-10}$ cycloalkyl is optionally substituted with one or more $R_5$;

$R_4$ is H or $C_{1-6}$ alkyl;

each $R_5$ is independently H, oxo, halogen, $C_{1-6}$ alkyl, $C_{2-6}$ alkenyl, $C_{2-6}$ alkynyl, $C_{1-6}$ alkoxy, $C_{1-6}$ haloalkyl, —$OR_6$, —$NH_2$, —$NH(C_{1-6}$ alkyl), —$NH(C_{1-6}$ alkyl)$_2$, —$C(O)OR_6$, —$P(O)(OR_6)_2$, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$;

$R_6$ is H, $C_{1-6}$ alkyl, $C_{2-6}$ alkenyl, or $C_{2-6}$ alkynyl;

each $R_7$ is independently oxo, —OH, —C(O)OH, —C(O)O($C_{1-6}$ alkyl), aryl, heteroaryl, heterocyclyl, or $C_{3-10}$ cycloalkyl wherein the aryl, heteroaryl, heterocyclyl, or $C_{3-10}$ cycloalkyl is optionally substituted with halogen, oxo, —OH, or —$NH_2$;

m is 1, 2, 3, or 4; and n is 1, 2, 3, or 4.

In some embodiments, the present disclosure provides, inter alia, a compound of Formula (I):

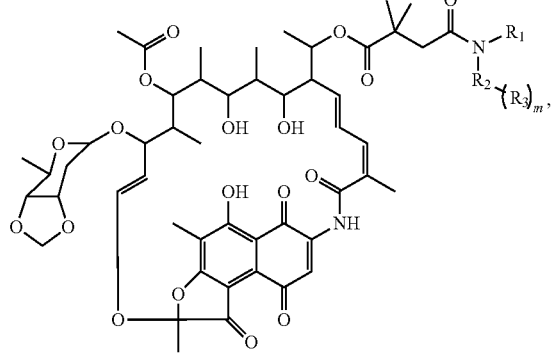

or a pharmaceutically acceptable salt, solvate, or tautomer, thereof, wherein:

$R_1$ is H, $C_{1-10}$ alkyl, $C_{2-10}$ alkenyl, or $C_{2-10}$ alkynyl;

$R_2$ is —$OR_4$, aryl, heteroaryl, aralkyl, aralkenyl, aralkynyl, heteroarylalkyl, heteroarylalkenyl, heteroarylalkynyl, cycloalkyl, cycloalkenyl, cycloalkynyl, heterocyclyl, cycloalkylalkyl, heterocycloalkyl or $C_{1-10}$ alkyl, or $R_1$ and $R_2$ together form a 3- to 10-membered heterocyclyl optionally substituted with one or more $R_5$;

each $R_3$ is independently H, oxo, halogen, —$OR_4$, —$N(R_4)(R_5)$, —$SR_4$, —$C(O)R_4$, —$C(O)OR_4$, —$C(O)NR_4R_5$, —$P(O)(OR_4)_2$, —$S(O)_2R_4$, —$S(O)_2OR_4$, —$NR_4C(O)R_5$, —$NR_4C(O)OR_5$, —$NC(O)NR_4R_5$, $C_{1-6}$ alkyl, $C_{1-6}$ haloalkyl, aryl, heteroaryl, $C_{3-10}$ cycloalkyl, or heterocyclyl, wherein the alkyl, aryl, heteroaryl, heterocyclyl, or $C_{3-10}$ cycloalkyl is optionally substituted with one or more $R_5$; or two $R_3$ together with the atoms to which they are attached form an aryl, heteroaryl, heterocyclyl, or $C_{3-10}$ cycloalkyl wherein the aryl, heteroaryl, heterocyclyl, or $C_{3-10}$ cycloalkyl is optionally substituted with one or more $R_5$;

$R_4$ is H or $C_{1-6}$ alkyl;

each $R_5$ is independently H, oxo, halogen, $C_{1-6}$ alkyl, $C_{2-6}$ alkenyl, $C_{2-6}$ alkynyl, $C_{1-6}$ alkoxy, $C_{1-6}$ haloalkyl, —$OR_6$, —$NH_2$, —$NH(C_{1-6}$ alkyl), —$NH(C_{1-6}$ alkyl)$_2$, —$C(O)OR_6$, —$P(O)(OR_6)_2$, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$;

$R_6$ is H, $C_{1-6}$ alkyl, $C_{2-6}$ alkenyl, or $C_{2-6}$ alkynyl;

each $R_7$ is independently oxo, —OH, —C(O)OH, —C(O)O($C_{1-6}$ alkyl), aryl, heteroaryl, heterocyclyl, or $C_{3-10}$ cycloalkyl wherein the aryl, heteroaryl, heterocyclyl, or $C_{3-10}$ cycloalkyl is optionally substituted with halogen, oxo, —OH, or —$NH_2$;

m is 1, 2, 3, or 4; and n is 1, 2, 3, or 4.

In some embodiments, the present disclosure provides, inter alia, a compound of Formula (II):

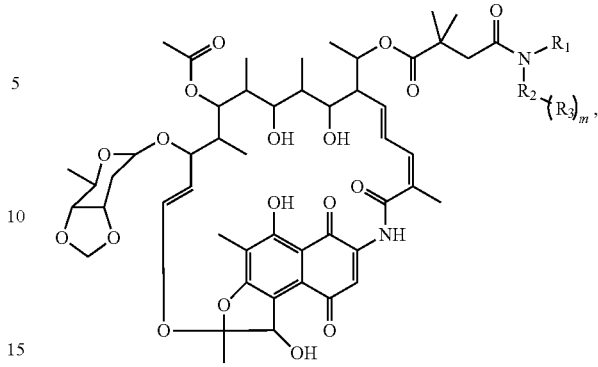

or a pharmaceutically acceptable salt, solvate, or tautomer, thereof, wherein:

$R_1$ is H, $C_{1-10}$ alkyl, $C_{2-10}$ alkenyl, or $C_{2-10}$ alkynyl;

$R_2$ is —$OR_4$, aryl, heteroaryl, aralkyl, aralkenyl, aralkynyl, heteroarylalkyl, heteroarylalkenyl, heteroarylalkynyl, cycloalkyl, cycloalkenyl, cycloalkynyl, heterocyclyl, cycloalkylalkyl, heterocycloalkyl or $C_{1-10}$ alkyl, or $R_1$ and $R_2$ together form a 3- to 10-membered heterocyclyl optionally substituted with one or more $R_5$;

each $R_3$ is independently H, oxo, halogen, —$OR_4$, —$N(R_4)(R_5)$, —$SR_4$, —$C(O)R_4$, —$C(O)OR_4$, —$C(O)NR_4R_5$, —$P(O)(OR_4)_2$, —$S(O)_2R_4$, —$S(O)_2OR_4$, —$NR_4C(O)R_5$, —$NR_4C(O)OR_5$, —$NC(O)NR_4R_5$, $C_{1-6}$ alkyl, $C_{1-6}$ haloalkyl, aryl, heteroaryl, $C_{3-10}$ cycloalkyl, or heterocyclyl, wherein the alkyl, aryl, heteroaryl, heterocyclyl, or $C_{3-10}$ cycloalkyl is optionally substituted with one or more $R_5$; or two $R_3$ together with the atoms to which they are attached form an aryl, heteroaryl, heterocyclyl, or $C_{3-10}$ cycloalkyl wherein the aryl, heteroaryl, heterocyclyl, or $C_{3-10}$ cycloalkyl is optionally substituted with one or more $R_5$;

$R_4$ is H or $C_{1-6}$ alkyl;

each $R_5$ is independently H, oxo, halogen, $C_{1-6}$ alkyl, $C_{2-6}$ alkenyl, $C_{2-6}$ alkynyl, $C_{1-6}$ alkoxy, $C_{1-6}$ haloalkyl, —$OR_6$, —$NH_2$, —$NH(C_{1-6}$ alkyl), —$NH(C_{1-6}$ alkyl)$_2$, —$C(O)OR_6$, —$P(O)(OR_6)_2$, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$;

$R_6$ is H, $C_{1-6}$ alkyl, $C_{2-6}$ alkenyl, or $C_{2-6}$ alkynyl;

each $R_7$ is independently oxo, —OH, —C(O)OH, —C(O)O($C_{1-6}$ alkyl), aryl, heteroaryl, heterocyclyl, or $C_{3-10}$ cycloalkyl wherein the aryl, heteroaryl, heterocyclyl, or $C_{3-10}$ cycloalkyl is optionally substituted with halogen, oxo, —OH, or —$NH_2$;

m is 1, 2, 3, or 4; and n is 1, 2, 3, or 4.

In some embodiments, the present disclosure provides, inter alia, a compound of Formula (III):

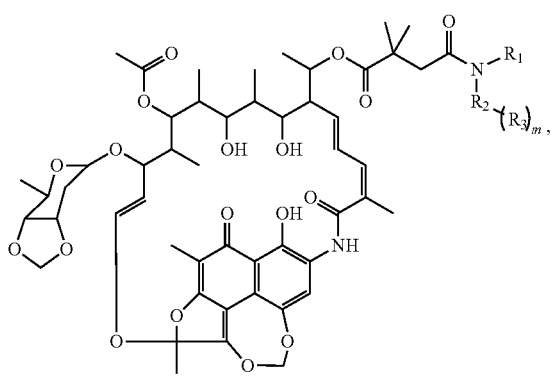

or a pharmaceutically acceptable salt, solvate, or tautomer, thereof, wherein:

$R_1$ is H, $C_{1-10}$ alkyl, $C_{2-10}$ alkenyl, or $C_{2-10}$ alkynyl;

$R_2$ is —$OR_4$, aryl, heteroaryl, aralkyl, aralkenyl, aralkynyl, heteroarylalkyl, heteroarylalkenyl, heteroarylalkynyl, cycloalkyl, cycloalkenyl, cycloalkynyl, heterocyclyl, cycloalkylalkyl, heterocycloalkyl or $C_{1-10}$ alkyl, or $R_1$ and $R_2$ together form a 3- to 10-membered heterocyclyl optionally substituted with one or more $R_5$;

each $R_3$ is independently H, oxo, halogen, —$OR_4$, —$N(R_4)(R_5)$, —$SR_4$, —$C(O)R_4$, —$C(O)OR_4$, —$C(O)NR_4R_5$, —$P(O)(OR_4)_2$, —$S(O)_2R_4$, —$S(O)_2OR_4$, —$NR_4C(O)R_5$, —$NR_4C(O)OR_5$, —$NC(O)NR_4R_5$, $C_{1-6}$ alkyl, $C_{1-6}$ haloalkyl, aryl, heteroaryl, $C_{3-10}$ cycloalkyl, or heterocyclyl, wherein the alkyl, aryl, heteroaryl, heterocyclyl, or $C_{3-10}$ cycloalkyl is optionally substituted with one or more $R_5$; or two $R_3$ together with the atoms to which they are attached form an aryl, heteroaryl, heterocyclyl, or $C_{3-10}$ cycloalkyl wherein the aryl, heteroaryl, heterocyclyl, or $C_{3-10}$ cycloalkyl is optionally substituted with one or more $R_5$;

$R_4$ is H or $C_{1-6}$ alkyl;

each $R_5$ is independently H, oxo, halogen, $C_{1-6}$ alkyl, $C_{2-6}$ alkenyl, $C_{2-6}$ alkynyl, $C_{1-6}$ alkoxy, $C_{1-6}$ haloalkyl, —$OR_6$, —$NH_2$, —$NH(C_{1-6}$ alkyl), —$NH(C_{1-6}$ alkyl)$_2$, —$C(O)OR_6$, —$P(O)(OR_6)_2$, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$;

$R_6$ is H, $C_{1-6}$ alkyl, $C_{2-6}$ alkenyl, or $C_{2-6}$ alkynyl;

each $R_7$ is independently oxo, —OH, —$C(O)OH$, —$C(O)O(C_{1-6}$ alkyl), aryl, heteroaryl, heterocyclyl, or $C_{3-10}$ cycloalkyl wherein the aryl, heteroaryl, heterocyclyl, or $C_{3-10}$ cycloalkyl is optionally substituted with halogen, oxo, —OH, or —$NH_2$;

m is 1, 2, 3, or 4; and n is 1, 2, 3, or 4.

It is understood that, for a compound of Formula (I), (II), or (III), $R_1$, $R_2$ $R_3$, $R_4$, $R_5$, $R_6$, and $R_7$ can each be, where applicable, selected from the groups described herein, and any group described herein for any of $R_1$, $R_2$ $R_3$, $R_4$, $R_5$, $R_6$, and $R_7$ can be combined, where applicable, with any group described herein for one or more of the remainder of $R_1$, $R_2$ $R_3$, $R_4$, $R_5$, $R_6$, and $R_7$.

In some embodiments $R_1$ is H, $C_{1-6}$ alkyl, $C_{2-6}$ alkenyl, or $C_{2-6}$ alkynyl.

In some embodiments $R_1$ is H.

In some embodiments $R_1$ is $C_{1-10}$ alkyl, $C_{2-10}$ alkenyl, or $C_{2-10}$ alkynyl.

In some embodiments $R_1$ is $C_{1-6}$ alkyl, $C_{2-6}$ alkenyl, or $C_{2-6}$ alkynyl.

In some embodiments $R_1$ is $C_{1-6}$ alkyl. In some embodiments $R_1$ is $C_1$ alkyl. In some embodiments $R_1$ is $C_2$ alkyl. In some embodiments $R_1$ is $C_3$ alkyl. In some embodiments $R_1$ is $C_4$ alkyl. In some embodiments $R_1$ is $C_5$ alkyl. In some embodiments $R_1$ is $C_6$ alkyl. In some embodiments $R_1$ is methyl. In some embodiments $R_1$ is ethyl. In some embodiments $R_1$ is propyl. In some embodiments $R_1$ is butyl. In some embodiments $R_1$ is pentyl. In some embodiments $R_1$ is hexyl. In some embodiments $R_1$ is isopropyl. In some embodiments $R_1$ is isobutyl. In some embodiments $R_1$ is isopentyl. In some embodiments $R_1$ is isohexyl. In some embodiments $R_1$ is secbutyl. In some embodiments $R_1$ is secpentyl. In some embodiments $R_1$ is sechexyl. In some embodiments $R_1$ is tertbutyl.

In some embodiments $R_1$ is $C_{2-6}$ alkenyl. In some embodiments $R_1$ is $C_2$ alkenyl. In some embodiments $R_1$ is $C_3$ alkenyl. In some embodiments $R_1$ is $C_4$ alkenyl. In some embodiments $R_1$ is $C_5$ alkenyl. In some embodiments $R_1$ is $C_6$ alkenyl.

In some embodiments $R_1$ is $C_{2-6}$ alkynyl. In some embodiments $R_1$ is $C_2$ alkynyl. In some embodiments $R_1$ is $C_3$ alkynyl. In some embodiments $R_1$ is $C_4$ alkynyl. In some embodiments $R_1$ is $C_5$ alkynyl. In some embodiments $R_1$ is $C_6$ alkynyl.

In some embodiments, $R_2$ is —$OR_4$, aryl, heteroaryl, aralkyl, aralkenyl, aralkynyl, heteroarylalkyl, heteroarylalkenyl, heteroarylalkynyl, cycloalkyl, cycloalkenyl, cycloalkynyl, heterocyclyl, cycloalkylalkyl, heterocycloalkyl or $C_{1-10}$ alkyl.

In some embodiments, $R_2$ is —$OR_4$, aryl, heteroaryl, aralkyl, heteroaralkyl, cycloalkyl, heterocyclyl, cycloalkylalkyl, heterocycloalkyl or $C_{1-10}$ alkyl.

In some embodiments, $R_2$ is —$OR_4$.

In some embodiments, $R_2$ is aryl, heteroaryl, aralkyl, heteroaralkyl, cycloalkyl, heterocyclyl, cycloalkylalkyl, heterocycloalkyl or $C_{1-10}$ alkyl.

In some embodiments, $R_2$ is aryl or heteroaryl. In some embodiments, $R_2$ is aryl. In some embodiments, the aryl is a $C_{6-14}$ aryl. In some embodiments, $R_2$ is heteroaryl. In some embodiments, the heteroaryl is a 5 to 14 membered heteroaryl ring having 1, 2, 3, 4, or 5 heteroatoms selected from the group consisting of nitrogen, oxygen and sulfur.

In some embodiments, $R_2$ is aralkyl, heteroaralkyl, cycloalkyl, heterocyclyl, cycloalkylalkyl, or heterocycloalkyl.

In some embodiments, $R_2$ is aralkyl or heteroaralkyl. In some embodiments, $R_2$ is aralkyl. In some embodiments, the aralkyl is a $C_{1-6}$ alkylene-$C_{6-14}$ aryl. In some embodiments, $R_2$ is heteroaralkyl. In some embodiments, the heteroaralkyl is a $C_{1-6}$ alkylene-5 to 14 membered heteroaryl ring having 1, 2, 3, 4, or 5 heteroatoms selected from the group consisting of nitrogen, oxygen and sulfur.

In some embodiments, $R_2$ is cycloalkyl, heterocyclyl, cycloalkylalkyl, or heterocycloalkyl.

In some embodiments, $R_2$ is aralkenyl, aralkynyl, heteroarylalkenyl, heteroarylalkynyl, cycloalkenyl, or cycloalkynyl.

In some embodiments, $R_2$ is aralkenyl, aralkynyl, heteroarylalkenyl, or heteroarylalkynyl.

In some embodiments, $R_2$ is aralkenyl or heteroarylalkenyl. In some embodiments, $R_2$ is aralkenyl. In some embodiments, the aralkenyl is a $C_{2-6}$ alkenylene-$C_{6-14}$ aryl. In some embodiments, $R_2$ is heteroarylalkenyl. In some embodiments, the heteroarylalkenyl is a $C_{2-6}$ alkenylene-5 to 14 membered heteroaryl ring having 1, 2, 3, 4, or 5 heteroatoms selected from the group consisting of nitrogen, oxygen and sulfur.

In some embodiments, $R_2$ is aralkynyl or heteroarylalkynyl. In some embodiments, $R_2$ is aralkynyl. In some embodiments, the aralkynyl is a $C_{2-6}$ alkynylene-$C_{6-14}$ aryl. In some embodiments, $R_2$ is heteroarylalkynyl. In some embodiments, the heteroarylalkynyl is a $C_{2-6}$ alkynylene-5 to 14 membered heteroaryl ring having 1, 2, 3, 4, or 5 heteroatoms selected from the group consisting of nitrogen, oxygen and sulfur.

In some embodiments, $R_2$ is cycloalkenyl, or cycloalkynyl.

In some embodiments, $R_2$ is cycloalkenyl or cycloalkynyl. In some embodiments, $R_2$ is cycloalkenyl. In some embodiments, $R_2$ is cycloalkynyl.

In some embodiments, $R_2$ is cycloalkyl or heterocyclyl. In some embodiments, $R_2$ is cycloalkyl. In some embodiments, the cycloalkyl is a $C_{3-10}$ cycloalkyl. In some embodiments, $R_2$ is heterocyclyl. In some embodiments, the heterocyclyl is a 3-10 membered heterocyclyl having 1, 2, or 3 heteroatoms selected from the group consisting of nitrogen, oxygen, and sulfur.

In some embodiments, $R_2$ is cycloalkylalkyl or heterocycloalkyl. In some embodiments, $R_2$ is cycloalkylalkyl. In some embodiments, the cycloalkylalkyl is a $C_{1-6}$ alkylene-$C_{3-10}$ cycloalkyl. In some embodiments, $R_2$ is heterocycloalkyl. In some embodiments, the heterocycloalkylalkyl is a $C_{1-6}$ alkylene-3- to -10 membered heterocyclyl having 1, 2, or 3 heteroatoms selected from the group consisting of nitrogen, oxygen, and sulfur.

In some embodiments, $R_2$ is $C_{1-10}$ alkyl. In some embodiments, $R_2$ is $C_1$ alkyl. In some embodiments, $R_2$ is $C_2$ alkyl. In some embodiments, $R_2$ is $C_3$ alkyl. In some embodiments, $R_2$ is $C_4$ alkyl. In some embodiments, $R_2$ is $C_5$ alkyl. In some embodiments, $R_2$ is $C_6$ alkyl. In some embodiments, $R_2$ is $C_7$ alkyl. In some embodiments, $R_2$ is $C_8$ alkyl. In some embodiments, $R_2$ is $C_9$ alkyl. In some embodiments, $R_2$ is $C_{10}$ alkyl.

In some embodiments, $R_1$ and $R_2$ together form a 3- to 10-membered heterocyclyl. In some embodiments, $R_1$ and $R_2$ together form a 3-membered heterocyclyl. In some embodiments, $R_1$ and $R_2$ together form a 4-membered heterocyclyl. In some embodiments, $R_1$ and $R_2$ together form a 5-membered heterocyclyl. In some embodiments, $R_1$ and $R_2$ together form a 6-membered heterocyclyl. In some embodiments, $R_1$ and $R_2$ together form a 7-membered heterocyclyl. In some embodiments, $R_1$ and $R_2$ together form a 8-membered heterocyclyl. In some embodiments, $R_1$ and $R_2$ together form a 9-membered heterocyclyl. In some embodiments, $R_1$ and $R_2$ together form a 10-membered heterocyclyl.

In some embodiments, $R_1$ and $R_2$ together form a 3- to 10-membered unsubstituted heterocyclyl. In some embodiments, $R_1$ and $R_2$ together form a 3- to 9-membered unsubstituted heterocyclyl. In some embodiments, $R_1$ and $R_2$ together form a 4- to 9-membered unsubstituted heterocyclyl. In some embodiments, $R_1$ and $R_2$ together form a 4- to 8-membered unsubstituted heterocyclyl. In some embodiments, $R_1$ and $R_2$ together form a 4- to 7-membered unsubstituted heterocyclyl. In some embodiments, $R_1$ and $R_2$ together form a 4- to 6-membered unsubstituted heterocyclyl. In some embodiments, $R_1$ and $R_2$ together form a 5- to 6-membered unsubstituted heterocyclyl.

In some embodiments, $R_1$ and $R_2$ together form a 3- to 10-membered heterocyclyl optionally substituted with one or more $R_5$. In some embodiments, $R_1$ and $R_2$ together form a 3-membered heterocyclyl optionally substituted with one or more $R_5$. In some embodiments, $R_1$ and $R_2$ together form a 4-membered heterocyclyl optionally substituted with one or more $R_5$. In some embodiments, $R_1$ and $R_2$ together form a 5-membered heterocyclyl optionally substituted with one or more $R_5$. In some embodiments, $R_1$ and $R_2$ together form a 6-membered heterocyclyl optionally substituted with one or more $R_5$. In some embodiments, $R_1$ and $R_2$ together form a 7-membered heterocyclyl optionally substituted with one or more $R_5$. In some embodiments, $R_1$ and $R_2$ together form a 8-membered heterocyclyl optionally substituted with one or more $R_5$. In some embodiments, $R_1$ and $R_2$ together form a 9-membered heterocyclyl optionally substituted with one or more $R_5$. In some embodiments, $R_1$ and $R_2$ together form a 10-membered heterocyclyl optionally substituted with one or more $R_5$.

In some embodiments, $R_1$ and $R_2$ together form a 3- to 10-membered heterocyclyl substituted with one or more $R_5$. In some embodiments, $R_1$ and $R_2$ together form a 3-membered heterocyclyl substituted with one or more $R_5$. In some embodiments, $R_1$ and $R_2$ together form a 4-membered heterocyclyl substituted with one or more $R_5$. In some embodiments, $R_1$ and $R_2$ together form a 5-membered heterocyclyl substituted with one or more $R_5$. In some embodiments, $R_1$ and $R_2$ together form a 6-membered heterocyclyl substituted with one or more $R_5$. In some embodiments, $R_1$ and $R_2$ together form a 7-membered heterocyclyl substituted with one or more $R_5$. In some embodiments, $R_1$ and $R_2$ together form a 8-membered heterocyclyl substituted with one or more $R_5$. In some embodiments, $R_1$ and $R_2$ together form a 9-membered heterocyclyl substituted with one or more $R_5$. In some embodiments, $R_1$ and $R_2$ together form a 10-membered heterocyclyl substituted with one or more $R_5$.

In some embodiments, $R_1$ and $R_2$ together form a 3- to 10-membered heterocyclyl substituted with one $R_5$. In some embodiments, $R_1$ and $R_2$ together form a 3- to 10-membered heterocyclyl substituted with two $R_5$. In some embodiments, $R_1$ and $R_2$ together form a 3- to 10-membered heterocyclyl substituted with three $R_5$. In some embodiments, $R_1$ and $R_2$ together form a 3- to 10-membered heterocyclyl substituted with four $R_5$.

In some embodiments, any of the groups $R_2$ disclosed herein are substituted with 1, 2, 3, 4, or 5 $R_3$. In some embodiments, each $R_3$ is independently H, halogen, —$OR_4$, —$N(R_4)(R_5)$, —$SR_4$, —$C(O)R_4$, —$C(O)OR_4$, —$C(O)NR_4R_5$, —$P(O)(OR_4)_2$, —$S(O)_2R_4$, —$S(O)_2OR_4$, —$NR_4C(O)R_5$, —$NR_4C(O)OR_5$, —$NC(O)NR_4R_5$, $C_{1-6}$ alkyl, $C_{1-6}$ haloalkyl, aryl, heteroaryl, $C_{3-10}$ cycloalkyl, or heterocyclyl.

In some embodiments, each $R_3$ is independently H, halogen, oxo, —$OR_4$, —$N(R_4)(R_5)$, —$SR_4$, —$C(O)R_4$, —$C(O)OR_4$, —$C(O)NR_4R_5$, —$P(O)(OR_4)_2$, —$S(O)_2R_4$, —$S(O)_2OR_4$, —$NR_4C(O)R_5$, —$NR_4C(O)OR_5$, —$NC(O)NR_4R_5$, $C_{1-6}$ alkyl, $C_{1-6}$ haloalkyl, aryl, heteroaryl, $C_{3-10}$ cycloalkyl, or heterocyclyl, wherein the aryl, heteroaryl, heterocyclyl, or $C_{3-10}$ cycloalkyl is optionally substituted with one or more $R_5$.

In some embodiments, each $R_3$ is independently H.

In some embodiments, each $R_3$ is independently halogen, oxo, —$OR_4$, —$N(R_4)(R_5)$, —$SR_4$, —$C(O)R_4$, —$C(O)OR_4$, —$C(O)NR_4R_5$, —$P(O)(OR_4)_2$, —$S(O)_2R_4$, —$S(O)_2OR_4$, —$NR_4C(O)R_5$, —$NR_4C(O)OR_5$, —$NC(O)NR_4R_5$, $C_{1-6}$ alkyl, $C_{1-6}$ haloalkyl, aryl, heteroaryl, $C_{3-10}$ cycloalkyl, or heterocyclyl.

In some embodiments, each $R_3$ is independently halogen.
In some embodiments, each $R_3$ is independently oxo.
In some embodiments, each $R_3$ is independently —$OR_4$, —$N(R_4)(R_5)$, or —$SR_4$.
In some embodiments, each $R_3$ is independently —$OR_4$.
In some embodiments, each $R_3$ is independently —$N(R_4)(R_5)$.

In some embodiments, each $R_3$ is independently —$SR_4$.

In some embodiments, each $R_3$ is independently —C(O)$R_4$, —C(O)O$R_4$, —C(O)N$R_4R_5$, —P(O)(O$R_4$)$_2$, —S(O)$_2R_4$, —S(O)$_2$O$R_4$, —N$R_4$C(O)$R_5$, —N$R_4$C(O)O$R_5$, or —NC(O)N$R_4R_5$.

In some embodiments, each $R_3$ is independently —C(O)$R_4$, —C(O)O$R_4$, or —C(O)N$R_4R_5$.

In some embodiments, each $R_3$ is independently —C(O)$R_4$. In some embodiments, each $R_3$ is independently —C(O)O$R_4$. In some embodiments, each $R_3$ is independently —C(O)N$R_4R_5$. In some embodiments, each $R_3$ is independently —P(O)(O$R_4$)$_2$.

In some embodiments, each $R_3$ is independently —S(O)$_2R_4$ or —S(O)$_2$O$R_4$.

In some embodiments, each $R_3$ is independently —S(O)$_2R_4$. In some embodiments, each $R_3$ is independently —S(O)$_2$O$R_4$.

In some embodiments, each $R_3$ is independently —N$R_4$C(O)$R_5$, —N$R_4$C(O)O$R_5$, or —NC(O)N$R_4R_5$.

In some embodiments, each $R_3$ is independently —N$R_4$C(O)$R_5$. In some embodiments, each $R_3$ is independently —N$R_4$C(O)O$R_5$. In some embodiments, each $R_3$ is independently —NC(O)N$R_4R_5$.

In some embodiments, each $R_3$ is independently $C_{1-6}$ alkyl or $C_{1-6}$ haloalkyl.

In some embodiments, each $R_3$ is independently $C_{1-6}$ alkyl. In some embodiments, each $R_3$ is independently $C_1$ alkyl. In some embodiments, each $R_3$ is independently $C_2$ alkyl. In some embodiments, each $R_3$ is independently $C_3$ alkyl. In some embodiments, each $R_3$ is independently $C_4$ alkyl. In some embodiments, each $R_3$ is independently $C_5$ alkyl. In some embodiments, each $R_3$ is independently $C_6$ alkyl. In some embodiments, each $R_3$ is independently methyl. In some embodiments, each $R_3$ is independently ethyl. In some embodiments, each $R_3$ is independently propyl. In some embodiments, each $R_3$ is independently butyl. In some embodiments, each $R_3$ is independently pentyl. In some embodiments, each $R_3$ is independently hexyl. In some embodiments, each $R_3$ is independently isopropyl. In some embodiments, each $R_3$ is independently isobutyl. In some embodiments, each $R_3$ is independently isopentyl. In some embodiments, each $R_3$ is independently isohexyl. In some embodiments, each $R_3$ is independently secbutyl. In some embodiments, each $R_3$ is independently secpentyl. In some embodiments, each $R_3$ is independently sechexyl. In some embodiments, each $R_3$ is independently tertbutyl.

In some embodiments, each $R_3$ is independently $C_{1-6}$ haloalkyl. In some embodiments, each $R_3$ is independently halomethyl. In some embodiments, each $R_3$ is independently haloethyl. In some embodiments, each $R_3$ is independently halopropyl. In some embodiments, each $R_3$ is independently halobutyl. In some embodiments, each $R_3$ is independently halopentyl. In some embodiments, each $R_3$ is independently halohexyl.

In some embodiments, each $R_3$ is independently —$CF_3$, —$CHF_2$, or —$CH_2F$. In some embodiments, each $R_3$ is independently —$CF_3$. In some embodiments, each $R_3$ is independently —$CHF_2$. In some embodiments, each $R_3$ is independently —$CH_2F$.

In some embodiments, each $R_3$ is independently aryl, heteroaryl, $C_{3-10}$ cycloalkyl, or heterocyclyl.

In some embodiments, each $R_3$ is independently aryl or heteroaryl.

In some embodiments, each $R_3$ is independently aryl.

In some embodiments, each $R_3$ is independently heteroaryl.

In some embodiments, each $R_3$ is independently $C_{3-10}$ cycloalkyl or heterocyclyl.

In some embodiments, each $R_3$ is independently $C_{3-10}$ cycloalkyl.

In some embodiments, each $R_3$ is independently heterocyclyl.

In some embodiments, each $R_3$ is independently $C_{1-6}$ alkyl, aryl, heteroaryl, $C_{3-10}$ cycloalkyl, or heterocyclyl, wherein the alkyl, aryl, heteroaryl, heterocyclyl, or $C_{3-10}$ cycloalkyl is optionally substituted with one or more $R_5$.

In some embodiments, each $R_3$ is independently $C_{1-6}$ alkyl optionally substituted with one or more $R_5$.

In some embodiments, each $R_3$ is independently aryl or heteroaryl, wherein the aryl or heteroaryl is optionally substituted with one or more $R_5$.

In some embodiments, each $R_3$ is independently aryl optionally substituted with one or more $R_5$.

In some embodiments, each $R_3$ is independently heteroaryl optionally substituted with one or more $R_5$.

In some embodiments, each $R_3$ is independently $C_{3-10}$ cycloalkyl or heterocyclyl, wherein the $C_{3-10}$ cycloalkyl or heterocyclyl is optionally substituted with one or more $R_5$.

In some embodiments, each $R_3$ is independently $C_{3-10}$ cycloalkyl, optionally substituted with one or more $R_5$.

In some embodiments, each $R_3$ is independently heterocyclyl, optionally substituted with one or more $R_5$.

In some embodiments, two $R_3$ together with the atoms to which they are attached form an aryl, heteroaryl, heterocyclyl, or $C_{3-10}$ cycloalkyl, each of which is optionally substituted with one or more $R_5$.

In some embodiments, two $R_3$ together with the atoms to which they are attached form an aryl or heteroaryl.

In some embodiments, two $R_3$ together with the atoms to which they are attached form an aryl. In some embodiments, the aryl is a $C_{6-14}$ aryl (e.g., $C_6$ aryl).

In some embodiments, two $R_3$ together with the atoms to which they are attached form a heteroaryl. In some embodiments, the heteroaryl is a 5 to 14 membered heteroaryl ring having 1, 2, 3, 4, or 5 heteroatoms selected from the group consisting of nitrogen, oxygen and sulfur (e.g., a 5 or 6 membered heteroaryle having 1 or 2 nitrogen atoms).

In some embodiments, two $R_3$ together with the atoms to which they are attached form a heterocyclyl or $C_{3-10}$ cycloalkyl.

In some embodiments, two $R_3$ together with the atoms to which they are attached form a heterocyclyl. In some embodiments, the heterocyclyl is a 3-10 membered heterocyclyl having 1, 2, or 3 heteroatoms selected from the group consisting of nitrogen, oxygen, and sulfur In some embodiments, two $R_3$ together with the atoms to which they are attached form a $C_{3-10}$ cycloalkyl.

In some embodiments, two $R_3$ together with the atoms to which they are attached form an aryl, heteroaryl, heterocyclyl, or $C_{3-10}$ cycloalkyl wherein the aryl, heteroaryl, heterocyclyl, or $C_{3-10}$ cycloalkyl is optionally substituted with one or more $R_5$.

In some embodiments, two $R_3$ together with the atoms to which they are attached form an aryl or heteroaryl, wherein the aryl or heteroaryl is optionally substituted with one or more $R_5$.

In some embodiments, two $R_3$ together with the atoms to which they are attached form an aryl optionally substituted with one or more $R_5$.

In some embodiments, two $R_3$ together with the atoms to which they are attached form a heteroaryl optionally substituted with one or more $R_5$.

In some embodiments, two $R_3$ together with the atoms to which they are attached form a heterocyclyl or $C_{3-10}$ cycloalkyl, wherein the heterocyclyl or $C_{3-10}$ cycloalkyl is optionally substituted with one or more $R_5$.

In some embodiments, two $R_3$ together with the atoms to which they are attached form a heterocyclyl optionally substituted with one or more $R_5$.

In some embodiments, two $R_3$ together with the atoms to which they are attached form a $C_{3-10}$ cycloalkyl optionally substituted with one or more $R_5$.

In some embodiments, two $R_3$ together with the atoms to which they are attached form an aryl, heteroaryl, heterocyclyl, or $C_{3-10}$ cycloalkyl wherein the aryl, heteroaryl, heterocyclyl, or $C_{3-10}$ cycloalkyl is substituted with one or more $R_5$.

In some embodiments, two $R_3$ together with the atoms to which they are attached form an aryl or heteroaryl, wherein the aryl or heteroaryl is substituted with one or more $R_5$.

In some embodiments, two $R_3$ together with the atoms to which they are attached form an aryl substituted with one or more $R_5$.

In some embodiments, two $R_3$ together with the atoms to which they are attached form a heteroaryl substituted with one or more $R_5$.

In some embodiments, two $R_3$ together with the atoms to which they are attached form a heterocyclyl or $C_{3-10}$ cycloalkyl, wherein the heterocyclyl or $C_{3-10}$ cycloalkyl is substituted with one or more $R_5$.

In some embodiments, two $R_3$ together with the atoms to which they are attached form a heterocyclyl substituted with one or more $R_5$.

In some embodiments, two $R_3$ together with the atoms to which they are attached form a $C_{3-10}$ cycloalkyl substituted with one or more $R_5$.

In some embodiments, $R_4$ is H or $C_{1-6}$ alkyl.

In some embodiments, $R_4$ is H.

In some embodiments, $R_4$ is $C_{1-6}$ alkyl. In some embodiments, $R_4$ is $C_1$ alkyl. In some embodiments, $R_4$ is $C_2$ alkyl. In some embodiments, $R_4$ is $C_3$ alkyl. In some embodiments, $R_4$ is $C_4$ alkyl. In some embodiments, $R_4$ is $C_5$ alkyl. In some embodiments, $R_4$ is $C_6$ alkyl. In some embodiments, $R_4$ is methyl. In some embodiments, $R_4$ is ethyl. In some embodiments, $R_4$ is propyl. In some embodiments, $R_4$ is butyl. In some embodiments, $R_4$ is pentyl. In some embodiments, $R_4$ is hexyl. In some embodiments, $R_4$ is isopropyl. In some embodiments, $R_4$ is isobutyl. In some embodiments, $R_4$ is isopentyl. In some embodiments, $R_4$ is isohexyl. In some embodiments, $R_4$ is secbutyl. In some embodiments, $R_4$ is secpentyl. In some embodiments, $R_4$ is sechexyl. In some embodiments, $R_4$ is tertbutyl.

In some embodiments, each $R_5$ is independently H, oxo, halogen, $C_{1-6}$ alkyl, $C_{2-6}$ alkenyl, $C_{2-6}$ alkynyl, $C_{1-6}$ alkoxy, $C_{1-6}$ haloalkyl, —$OR_6$, —$NH_2$, —$NH(C_{1-6}$ alkyl), —NH$(C_{1-6}$ alkyl)$_2$, —C(O)$OR_6$, —P(O)(OR$_6$)$_2$, aryl, heteroaryl, heterocyclyl, or $C_{3-10}$ cycloalkyl.

In some embodiments, each $R_5$ is independently H.

In some embodiments, each $R_5$ is independently oxo or halogen.

In some embodiments, each $R_5$ is independently oxo.

In some embodiments, each $R_5$ is independently halogen. In some embodiments, each $R_5$ is independently F, Cl, Br, or I. In some embodiments, each $R_5$ is independently F or Cl. In some embodiments, each $R_5$ is independently F. In some embodiments, each $R_5$ is independently Cl.

In some embodiments, each $R_5$ is independently $C_{1-6}$ alkyl, $C_{2-6}$ alkenyl, $C_{2-6}$ alkynyl, $C_{1-6}$ alkoxy, or $C_{1-6}$ haloalkyl.

In some embodiments, each $R_5$ is independently $C_{1-6}$ alkyl, $C_{2-6}$ alkenyl or $C_{2-6}$ alkynyl.

In some embodiments, each $R_5$ is independently $C_{1-6}$ alkyl. In some embodiments, each $R_5$ is independently $C_1$ alkyl. In some embodiments, each $R_5$ is independently $C_2$ alkyl. In some embodiments, each $R_5$ is independently $C_3$ alkyl. In some embodiments, each $R_5$ is independently $C_4$ alkyl. In some embodiments, each $R_5$ is independently $C_5$ alkyl. In some embodiments, each $R_5$ is independently $C_6$ alkyl. In some embodiments, each $R_5$ is independently methyl. In some embodiments, each $R_5$ is independently ethyl. In some embodiments, each $R_5$ is independently propyl. In some embodiments, each $R_5$ is independently butyl. In some embodiments, each $R_5$ is independently pentyl. In some embodiments, each $R_5$ is independently hexyl. In some embodiments, each $R_5$ is independently isopropyl. In some embodiments, each $R_5$ is independently isobutyl. In some embodiments, each $R_5$ is independently isopentyl. In some embodiments, each $R_5$ is independently isohexyl. In some embodiments, each $R_5$ is independently secbutyl. In some embodiments, each $R_5$ is independently secpentyl. In some embodiments, each $R_5$ is independently sechexyl. In some embodiments, each $R_5$ is independently tertbutyl.

In some embodiments, each $R_5$ is independently $C_{2-6}$ alkenyl.

In some embodiments, each $R_5$ is independently $C_{2-6}$ alkynyl.

In some embodiments, each $R_5$ is independently $C_{1-6}$ alkoxy or $C_{1-6}$ haloalkyl.

In some embodiments, each $R_5$ is independently $C_{1-6}$ alkoxy. In some embodiments, each $R_5$ is independently methoxy. In some embodiments, each $R_5$ is independently ethoxy. In some embodiments, each $R_5$ is independently propoxy. In some embodiments, each $R_5$ is independently butoxy. In some embodiments, each $R_5$ is independently pentoxy. In some embodiments, each $R_5$ is independently hexoxy.

In some embodiments, each $R_5$ is independently $C_{1-6}$ haloalkyl. In some embodiments, each $R_5$ is independently halomethyl. In some embodiments, each $R_5$ is independently haloethyl. In some embodiments, each $R_5$ is independently halopropyl. In some embodiments, each $R_5$ is independently halobutyl. In some embodiments, each $R_5$ is independently halopentyl. In some embodiments, each $R_5$ is independently halohexyl.

In some embodiments, each $R_5$ is independently —$CF_3$, —$CHF_2$, or —$CH_2F$. In some embodiments, each $R_5$ is independently —$CF_3$. In some embodiments, each $R_5$ is independently —$CHF_2$. In some embodiments, each $R_5$ is independently —$CH_2F$.

In some embodiments, each $R_5$ is independently —$OR_6$, —$NH_2$, —NH($C_{1-6}$ alkyl), —NH($C_{1-6}$ alkyl)$_2$, —C(O)$OR_6$, or —P(O)(OR$_6$)$_2$.

In some embodiments, each $R_5$ is independently —$OR_6$.

In some embodiments, each $R_5$ is independently —$NH_2$, —NH($C_{1-6}$ alkyl), or —NH($C_{1-6}$ alkyl)$_2$.

In some embodiments, each $R_5$ is independently —$NH_2$.

In some embodiments, each $R_5$ is independently —NH($C_{1-6}$ alkyl). In some embodiments, each $R_5$ is independently —NH(methyl). In some embodiments, each $R_5$ is independently —NH(ethyl). In some embodiments, each $R_5$ is independently —NH(propyl). In some embodiments, each $R_5$ is independently —NH(butyl). In some embodiments, each $R_5$ is independently —NH(pentyl). In some embodiments, each $R_5$ is independently —NH(hexyl).

In some embodiments, each $R_5$ is independently —NH($C_{1-6}$ alkyl)$_2$.

In some embodiments, each $R_5$ is independently —C(O)OR$_6$ or —P(O)(OR$_6$)$_2$.

In some embodiments, each $R_5$ is independently —C(O)OR$_6$.

In some embodiments, each $R_5$ is independently —P(O)(OR$_6$)$_2$.

In some embodiments, each $R_5$ is independently aryl, heteroaryl, heterocyclyl, or $C_{3-10}$ cycloalkyl.

In some embodiments, each $R_5$ is independently aryl. In some embodiments, each $R_5$ is independently phenyl.

In some embodiments, each $R_5$ is independently heteroaryl.

In some embodiments, each $R_5$ is independently heterocyclyl.

In some embodiments, each $R_5$ is independently $C_{3-10}$ cycloalkyl.

In some embodiments, each $R_5$ is independently H, oxo, halogen, $C_{1-6}$ alkyl, $C_{2-6}$ alkenyl, $C_{2-6}$ alkynyl, $C_{1-6}$ alkoxy, $C_{1-6}$ haloalkyl, —OR$_6$, —NH$_2$, —NH($C_{1-6}$ alkyl), —NH($C_{1-6}$ alkyl)$_2$, —C(O)OR$_6$, —P(O)(OR$_6$)$_2$, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$.

In some embodiments, each $R_5$ is independently $C_{1-6}$ alkyl, $C_{2-6}$ alkenyl, $C_{2-6}$ alkynyl, $C_{1-6}$ alkoxy, $C_{1-6}$ haloalkyl, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$.

In some embodiments, each $R_5$ is independently $C_{1-6}$ alkyl, $C_{2-6}$ alkenyl, $C_{2-6}$ alkynyl, $C_{1-6}$ alkoxy, or $C_{1-6}$ haloalkyl, wherein the alkyl, alkenyl, alkynyl, alkoxy, or haloalkyl is optionally substituted with one or more $R_7$.

In some embodiments, each $R_5$ is independently C1-6 alkyl, C2-6 alkenyl, or C2-6 alkynyl, wherein the alkyl, alkenyl, or alkynyl is optionally substituted with one or more $R_7$.

In some embodiments, each $R_5$ is independently $C_{1-6}$ alkyl optionally substituted with one or more $R_7$.

In some embodiments, each $R_5$ is independently $C_{2-6}$ alkenyl optionally substituted with one or more $R_7$.

In some embodiments, each $R_5$ is independently $C_{2-6}$ alkynyl optionally substituted with one or more $R_7$.

In some embodiments, each $R_5$ is independently $C_{1-6}$ alkyl substituted with one or more $R_7$.

In some embodiments, each $R_5$ is independently $C_{2-6}$ alkenyl substituted with one or more $R_7$.

In some embodiments, each $R_5$ is independently $C_{2-6}$ alkynyl substituted with one or more $R_7$.

In some embodiments, each $R_5$ is independently $C_{1-6}$ alkyl substituted with one $R_7$.

In some embodiments, each $R_5$ is independently $C_{2-6}$ alkenyl substituted with one $R_7$.

In some embodiments, each $R_5$ is independently $C_{2-6}$ alkynyl substituted with one $R_7$.

In some embodiments, each $R_5$ is independently $C_{1-6}$ alkyl substituted with two $R_7$.

In some embodiments, each $R_5$ is independently $C_{2-6}$ alkenyl substituted with two $R_7$.

In some embodiments, each $R_5$ is independently $C_{2-6}$ alkynyl substituted with two $R_7$.

In some embodiments, each $R_5$ is independently $C_{1-6}$ alkoxy or $C_{1-6}$ haloalkyl, wherein the alkoxy or haloalkyl is optionally substituted with one or more $R_7$.

In some embodiments, each $R_5$ is independently $C_{1-6}$ alkoxy optionally substituted with one or more $R_7$.

In some embodiments, each $R_5$ is independently $C_{1-6}$ haloalkyl optionally substituted with one or more $R_7$.

In some embodiments, each $R_5$ is independently $C_{1-6}$ alkoxy substituted with one or more $R_7$.

In some embodiments, each $R_5$ is independently $C_{1-6}$ haloalkyl substituted with one or more $R_7$.

In some embodiments, each $R_5$ is independently $C_{1-6}$ alkoxy substituted with one $R_7$.

In some embodiments, each $R_5$ is independently $C_{1-6}$ haloalkyl substituted with one $R_7$.

In some embodiments, each $R_5$ is independently $C_{1-6}$ alkoxy substituted with two $R_7$.

In some embodiments, each $R_5$ is independently $C_{1-6}$ haloalkyl substituted with two $R_7$.

In some embodiments, each $R_5$ is independently aryl, heteroaryl, heterocyclyl, or $C_{3-10}$ cycloalkyl, wherein the aryl, heteroaryl, heterocyclyl, or cycloalkyl is optionally substituted with one or more $R_7$.

In some embodiments, each $R_5$ is independently aryl or heteroaryl, wherein the aryl or heteroaryl is optionally substituted with one or more $R_7$.

In some embodiments, each $R_5$ is independently aryl optionally substituted with one or more $R_7$.

In some embodiments, each $R_5$ is independently heteroaryl optionally substituted with one or more $R_7$.

In some embodiments, each $R_5$ is independently heterocyclyl or $C_{3-10}$ cycloalkyl, wherein the heterocyclyl or cycloalkyl is optionally substituted with one or more $R_7$.

In some embodiments, each $R_5$ is independently heterocyclyl optionally substituted with one or more $R_7$.

In some embodiments, each $R_5$ is independently $C_{3-10}$ cycloalkyl optionally substituted with one or more $R_7$.

In some embodiments $R_6$ is H, $C_{1-6}$ alkyl, $C_{2-6}$ alkenyl, or $C_{2-6}$ alkynyl.

In some embodiments $R_6$ is H.

In some embodiments $R_6$ is $C_{1-6}$ alkyl, $C_{2-6}$ alkenyl, or $C_{2-6}$ alkynyl.

In some embodiments $R_6$ is $C_{1-6}$ alkyl. In some embodiments $R_6$ is $C_1$ alkyl. In some embodiments $R_6$ is $C_2$ alkyl. In some embodiments $R_6$ is $C_3$ alkyl. In some embodiments $R_6$ is $C_4$ alkyl. In some embodiments $R_6$ is $C_5$ alkyl. In some embodiments $R_6$ is $C_6$ alkyl. In some embodiments $R_6$ is methyl. In some embodiments $R_6$ is ethyl. In some embodiments $R_6$ is propyl. In some embodiments $R_6$ is butyl. In some embodiments $R_6$ is pentyl. In some embodiments $R_6$ is hexyl. In some embodiments $R_6$ is isopropyl. In some embodiments $R_6$ is isobutyl. In some embodiments $R_6$ is isopentyl. In some embodiments, $R_6$ is isohexyl. In some embodiments $R_6$ is secbutyl. In some embodiments $R_6$ is secpentyl. In some embodiments $R_6$ is sechexyl. In some embodiments $R_6$ is tertbutyl.

In some embodiments $R_6$ is $C_{2-6}$ alkenyl.

In some embodiments $R_6$ is $C_{2-6}$ alkynyl.

In some embodiments, each $R_7$ is independently oxo, —OH, —C(O)OH, —C(O)O($C_{1-6}$ alkyl), aryl, heteroaryl, heterocyclyl, or $C_{3-10}$ cycloalkyl.

In some embodiments, each $R_7$ is independently oxo.

In some embodiments, each $R_7$ is independently —OH, —C(O)OH, or —C(O)O($C_{1-6}$ alkyl).

In some embodiments, each $R_7$ is independently —OH.

In some embodiments, each $R_7$ is independently —C(O)OH or —C(O)O($C_{1-6}$ alkyl).

In some embodiments, each $R_7$ is independently —C(O)OH.

In some embodiments, each $R_7$ is independently —C(O)O($C_{1-6}$ alkyl).

In some embodiments, each $R_7$ is independently aryl, heteroaryl, heterocyclyl, or $C_{3-10}$ cycloalkyl.

In some embodiments, each $R_7$ is independently aryl or heteroaryl.

In some embodiments, each $R_7$ is independently aryl.

In some embodiments, each $R_7$ is independently heteroaryl.

In some embodiments, each $R_7$ is independently heterocyclyl or $C_{3-10}$ cycloalkyl.

In some embodiments, each $R_7$ is independently heterocyclyl.

In some embodiments, each $R_7$ is independently $C_{3-10}$ cycloalkyl.

In some embodiments, each $R_7$ is independently oxo, —OH, —C(O)OH, —C(O)O($C_{1-6}$ alkyl), aryl, heteroaryl, heterocyclyl, or $C_{3-10}$ cycloalkyl wherein the aryl, heteroaryl, heterocyclyl, or $C_{3-10}$ cycloalkyl is optionally substituted with halogen, oxo, —OH, or —NH$_2$.

In some embodiments, each $R_7$ is independently aryl, heteroaryl, heterocyclyl, or $C_{3-10}$ cycloalkyl wherein the aryl, heteroaryl, heterocyclyl, or $C_{3-10}$ cycloalkyl is optionally substituted with halogen, oxo, —OH, or —NH$_2$.

In some embodiments, each $R_7$ is independently aryl or heteroaryl optionally substituted with halogen, —OH, or —NH$_2$.

In some embodiments, each $R_7$ is independently aryl or heteroaryl optionally substituted with halogen.

In some embodiments, each $R_7$ is independently aryl or heteroaryl optionally substituted with —OH.

In some embodiments, each $R_7$ is independently aryl or heteroaryl optionally substituted with —NH$_2$.

In some embodiments, each $R_7$ is independently aryl or heteroaryl substituted with halogen, —OH, or —NH$_2$.

In some embodiments, each $R_7$ is independently aryl or heteroaryl substituted with halogen.

In some embodiments, each $R_7$ is independently aryl or heteroaryl substituted with —OH.

In some embodiments, each $R_7$ is independently aryl or heteroaryl substituted with —NH$_2$.

In some embodiments, each $R_7$ is independently aryl optionally substituted with halogen, —OH, or —NH$_2$.

In some embodiments, each $R_7$ is independently aryl optionally substituted with halogen.

In some embodiments, each $R_7$ is independently aryl optionally substituted with —OH.

In some embodiments, each $R_7$ is independently aryl optionally substituted with —NH$_2$.

In some embodiments, each $R_7$ is independently aryl substituted with halogen, —OH, or —NH$_2$.

In some embodiments, each $R_7$ is independently aryl substituted with halogen.

In some embodiments, each $R_7$ is independently aryl substituted with —OH.

In some embodiments, each $R_7$ is independently aryl substituted with —NH$_2$.

In some embodiments, each $R_7$ is independently heteroaryl optionally substituted with halogen, —OH, or —NH$_2$.

In some embodiments, each $R_7$ is independently heteroaryl optionally substituted with halogen.

In some embodiments, each $R_7$ is independently heteroaryl optionally substituted with —OH.

In some embodiments, each $R_7$ is independently heteroaryl optionally substituted with —NH$_2$.

In some embodiments, each $R_7$ is independently heteroaryl substituted with halogen, —OH, or —NH$_2$.

In some embodiments, each $R_7$ is independently heteroaryl substituted with halogen.

In some embodiments, each $R_7$ is independently heteroaryl substituted with —OH.

In some embodiments, each $R_7$ is independently heteroaryl substituted with —NH$_2$.

In some embodiments, each $R_7$ is independently heterocyclyl or $C_{3-10}$ cycloalkyl wherein the heterocyclyl or $C_{3-10}$ cycloalkyl is optionally substituted with halogen, oxo, —OH, or —NH$_2$.

In some embodiments, each $R_7$ is independently heterocyclyl or $C_{3-10}$ cycloalkyl wherein the heterocyclyl or $C_{3-10}$ cycloalkyl is substituted with halogen, oxo, —OH, or —NH$_2$.

In some embodiments, each $R_7$ is independently heterocyclyl optionally substituted with halogen, oxo, —OH, or —NH$_2$.

In some embodiments, each $R_7$ is independently heterocyclyl optionally substituted with halogen.

In some embodiments, each $R_7$ is independently heterocyclyl optionally substituted with oxo.

In some embodiments, each $R_7$ is independently heterocyclyl optionally substituted with —OH.

In some embodiments, each $R_7$ is independently heterocyclyl optionally substituted with —NH$_2$.

In some embodiments, each $R_7$ is independently heterocyclyl substituted with halogen, oxo, —OH, or —NH$_2$.

In some embodiments, each $R_7$ is independently heterocyclyl substituted with halogen.

In some embodiments, each $R_7$ is independently heterocyclyl substituted with oxo.

In some embodiments, each $R_7$ is independently heterocyclyl substituted with —OH.

In some embodiments, each $R_7$ is independently heterocyclyl substituted with —NH$_2$.

In some embodiments, each $R_7$ is independently $C_{3-10}$ cycloalkyl optionally substituted with halogen, oxo, —OH, or —NH$_2$.

In some embodiments, each $R_7$ is independently $C_{3-10}$ cycloalkyl optionally substituted with halogen.

In some embodiments, each $R_7$ is independently $C_{3-10}$ cycloalkyl optionally substituted with oxo.

In some embodiments, each $R_7$ is independently $C_{3-10}$ cycloalkyl optionally substituted with —OH.

In some embodiments, each $R_7$ is independently $C_{3-10}$ cycloalkyl optionally substituted with —NH$_2$.

In some embodiments, each $R_7$ is independently $C_{3-10}$ cycloalkyl substituted with halogen, oxo, —OH, or —NH$_2$.

In some embodiments, each $R_7$ is independently $C_{3-10}$ cycloalkyl substituted with halogen.

In some embodiments, each $R_7$ is independently $C_{3-10}$ cycloalkyl substituted with oxo.

In some embodiments, each $R_7$ is independently $C_{3-10}$ cycloalkyl substituted with —OH.

In some embodiments, each $R_7$ is independently $C_{3-10}$ cycloalkyl substituted with —NH$_2$.

In some embodiments, m is 1, 2, 3, or 4. In some embodiments, m is 1, 2, or 3. In some embodiments, m is 2, 3, or 4. In some embodiments, m is 1 or 2. In some embodiments, m is 1 or 3. In some embodiments, m is 1 or 4. In some embodiments, m is 2 or 3. In some embodiments, m is 2 or 4. In some embodiments, m is 1. In some embodiments, m is 2. In some embodiments, m is 3. In some embodiments, m is 4.

In some embodiments, n is 1, 2, 3, or 4. In some embodiments, n is 1, 2, or 3. In some embodiments, n is 2, 3, or 4. In some embodiments, n is 1 or 2. In some embodiments, n is 1 or 3. In some embodiments, n is 1 or 4. In some embodiments, n is 2 or 3. In some embodiments, n is 2 or 4. In some embodiments, n is 1. In some embodiments, n is 2. In some embodiments, n is 3. In some embodiments, n is 4.
In some embodiments,
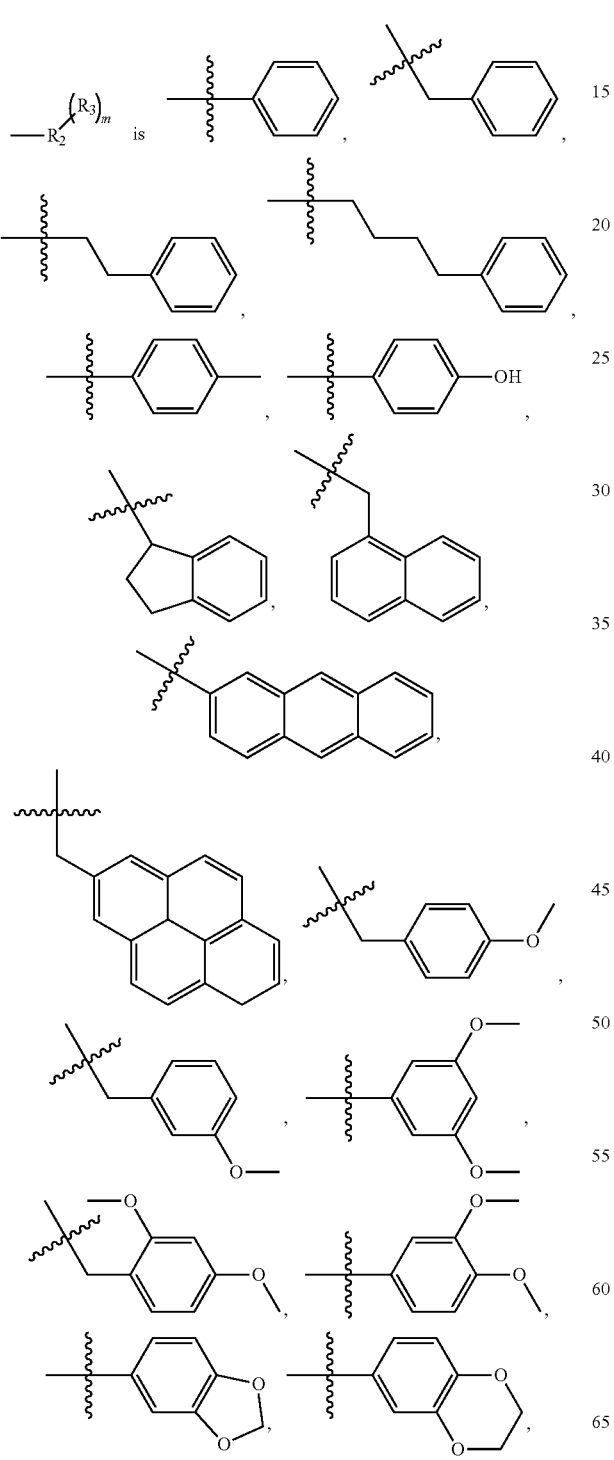
-continued
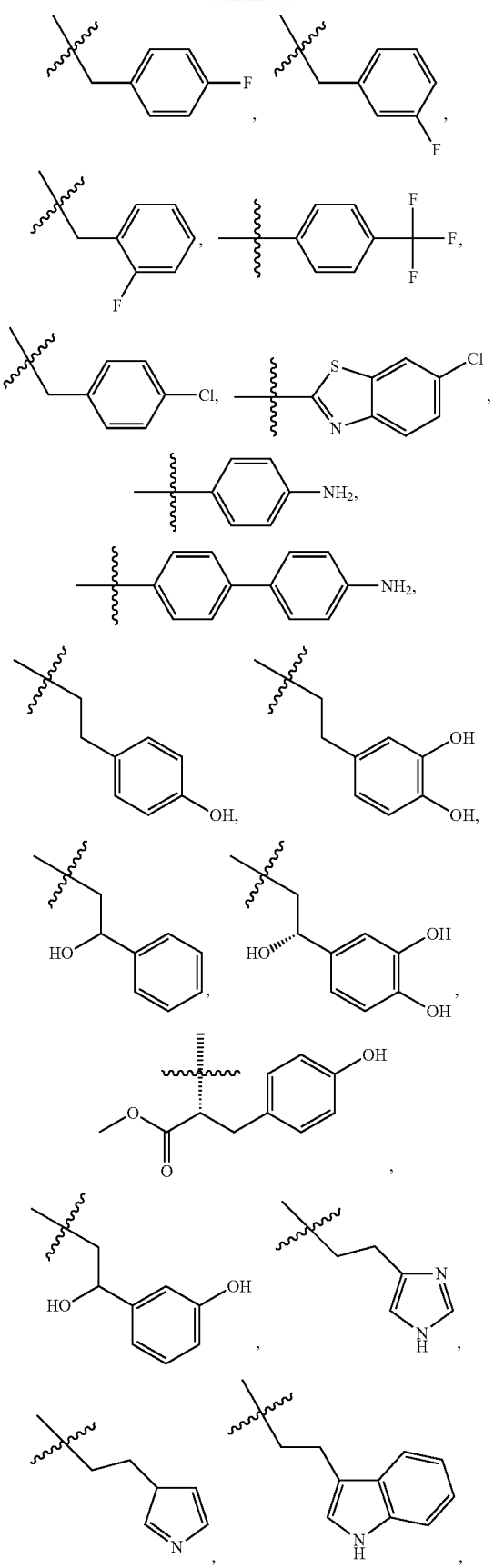

35
-continued
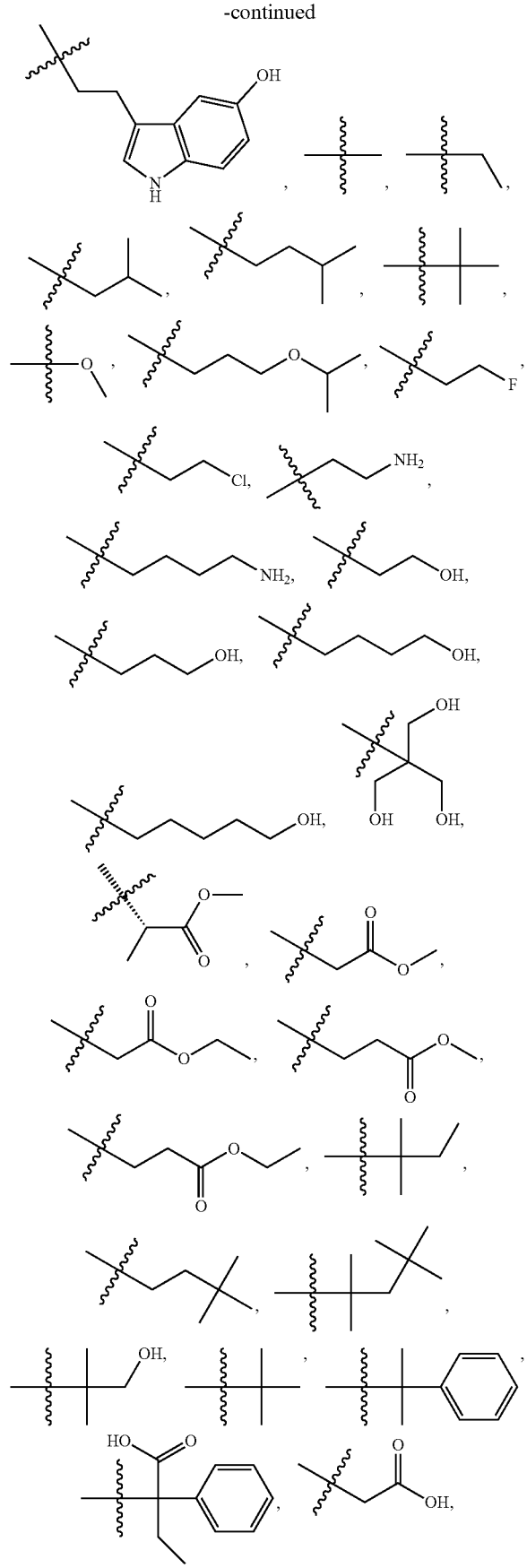
36
-continued
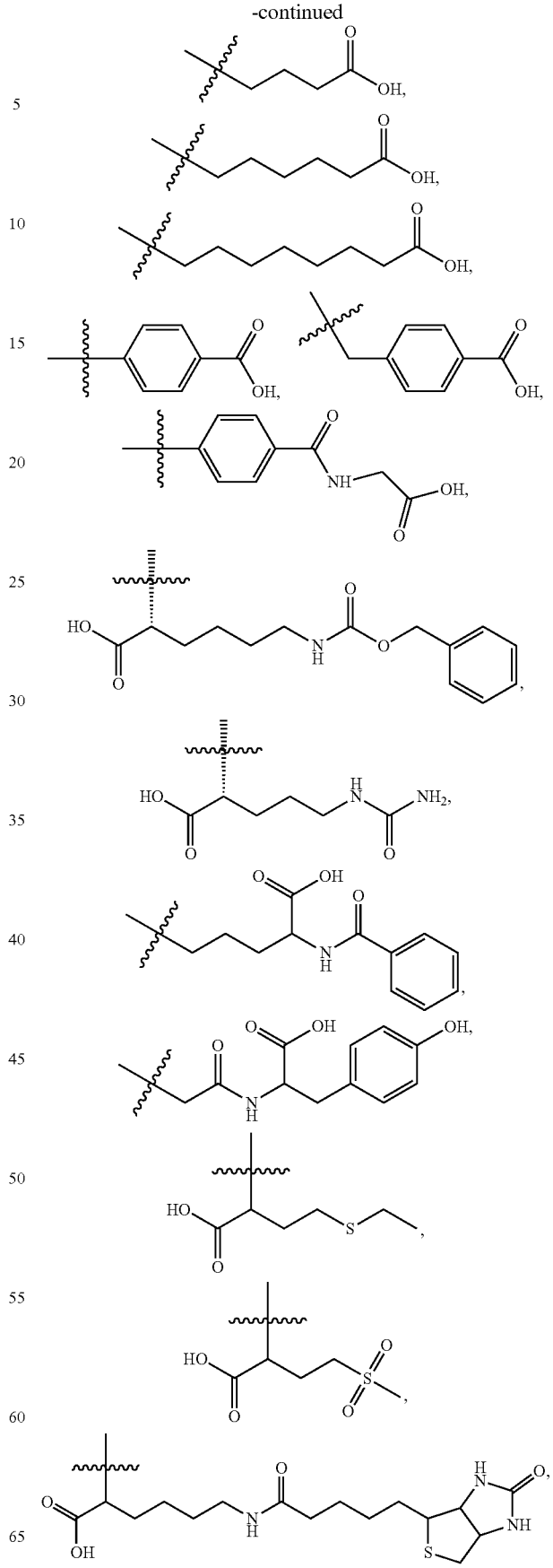

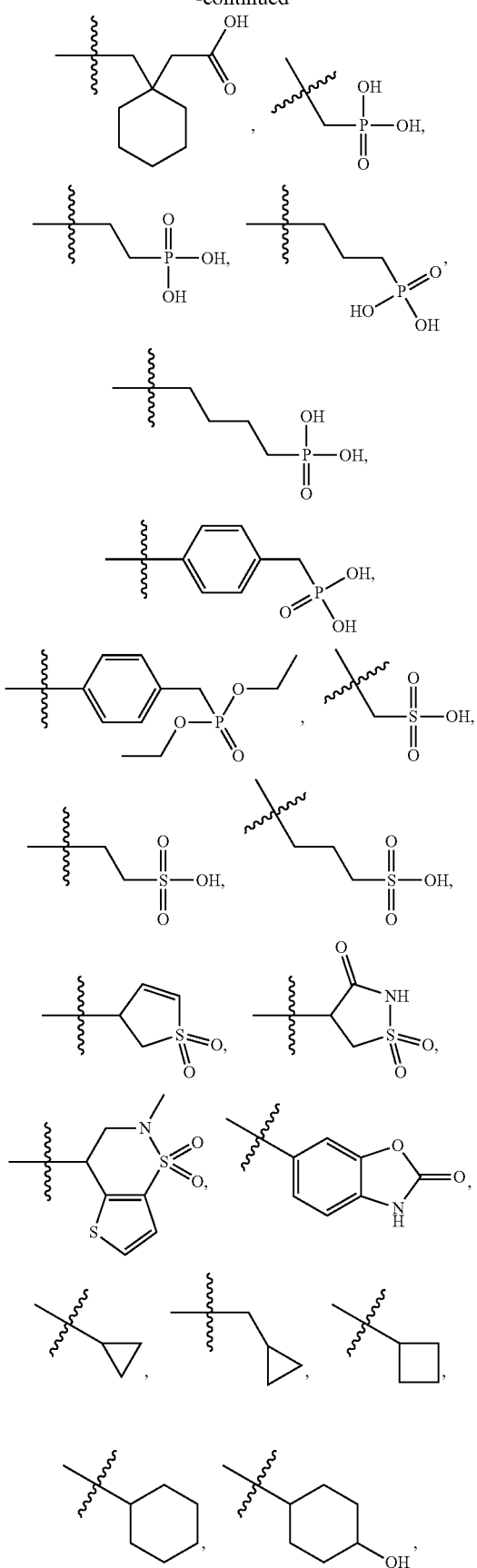
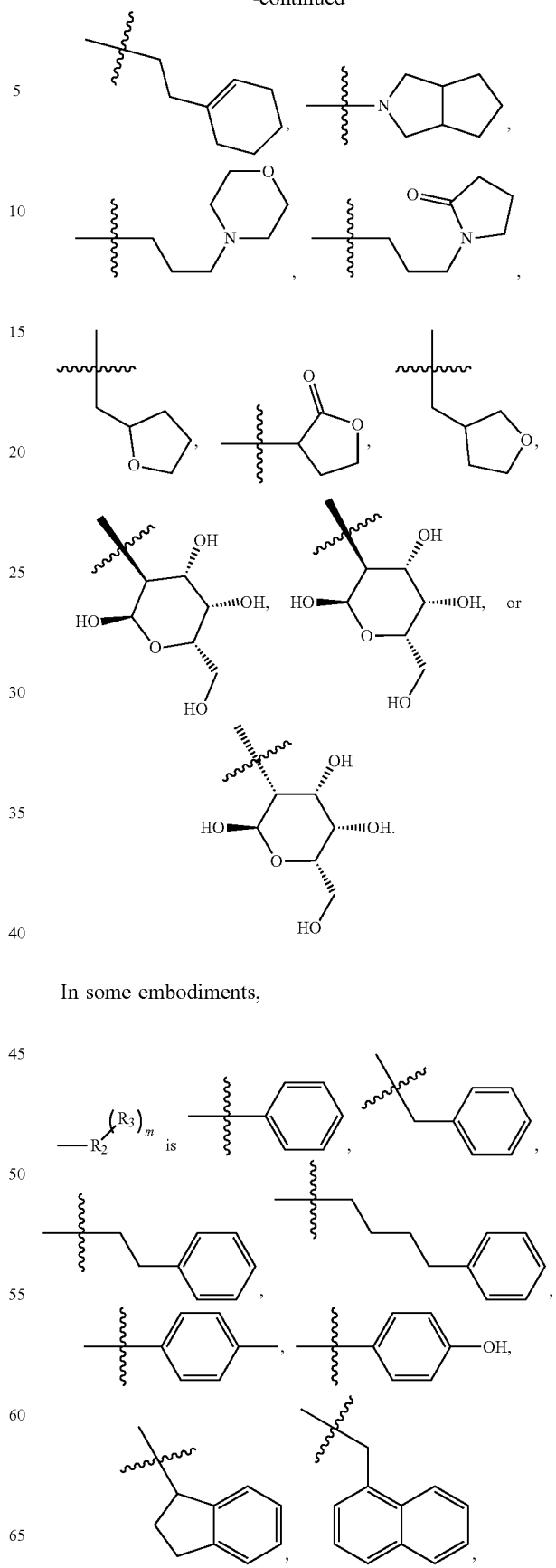
In some embodiments,

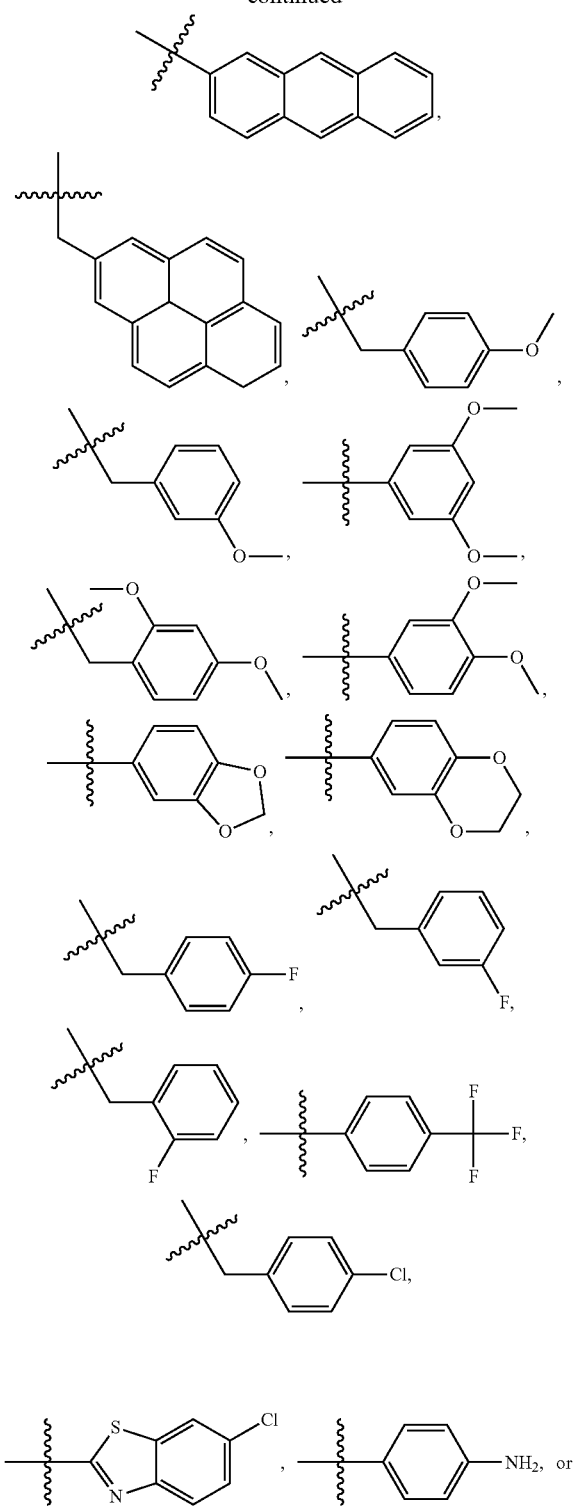
In some embodiments, —R₂(R₃)ₘ is
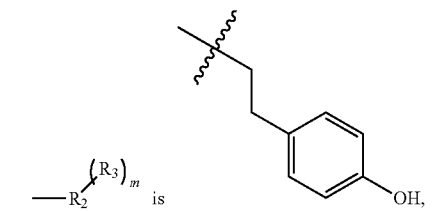
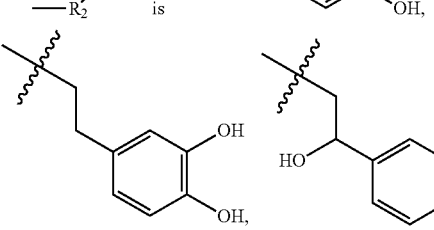
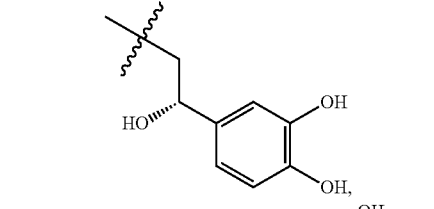
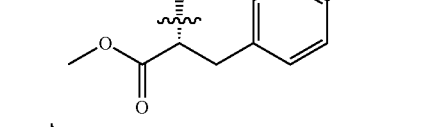
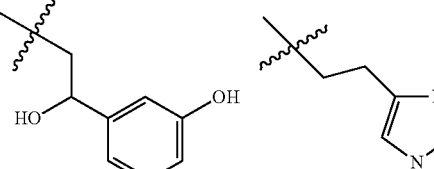
, or
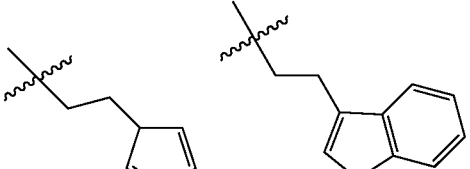
In some embodiments, —R₂(R₃)ₘ is
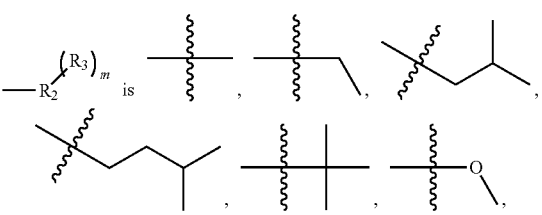

-continued
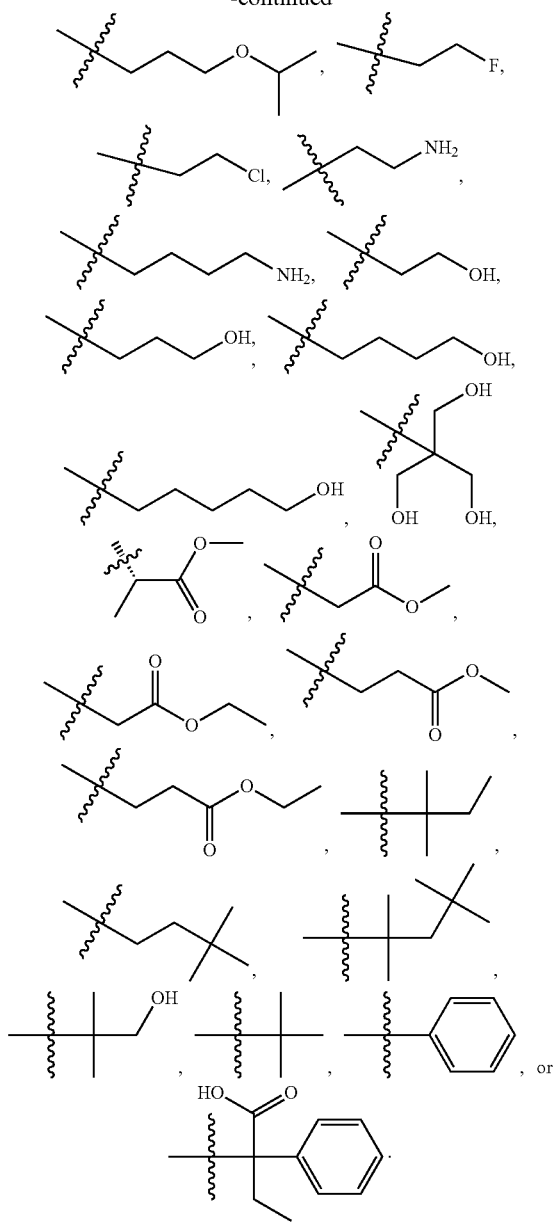
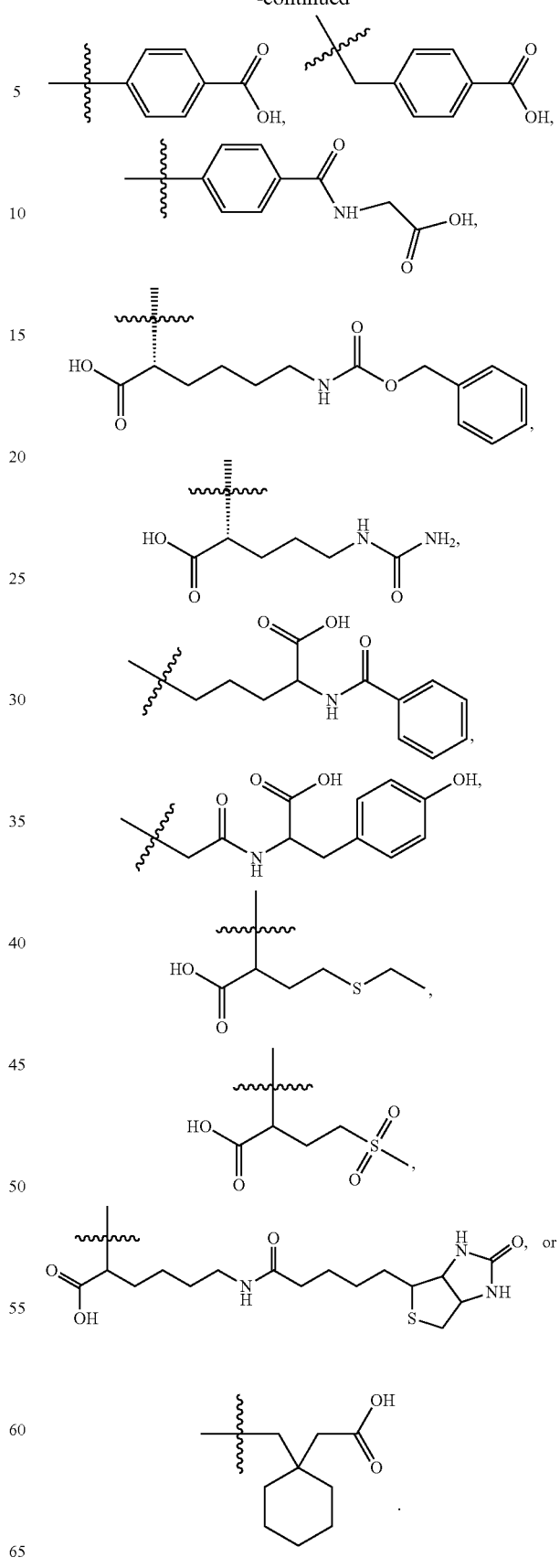
In some embodiments,
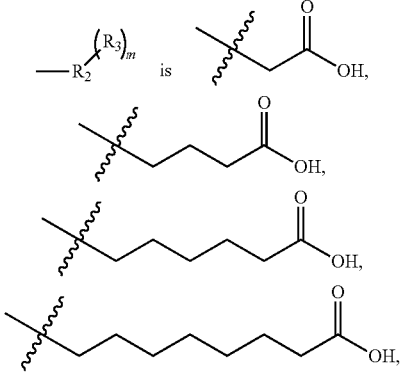

In some embodiments, —R$_2$(R$_3$)$_m$ is
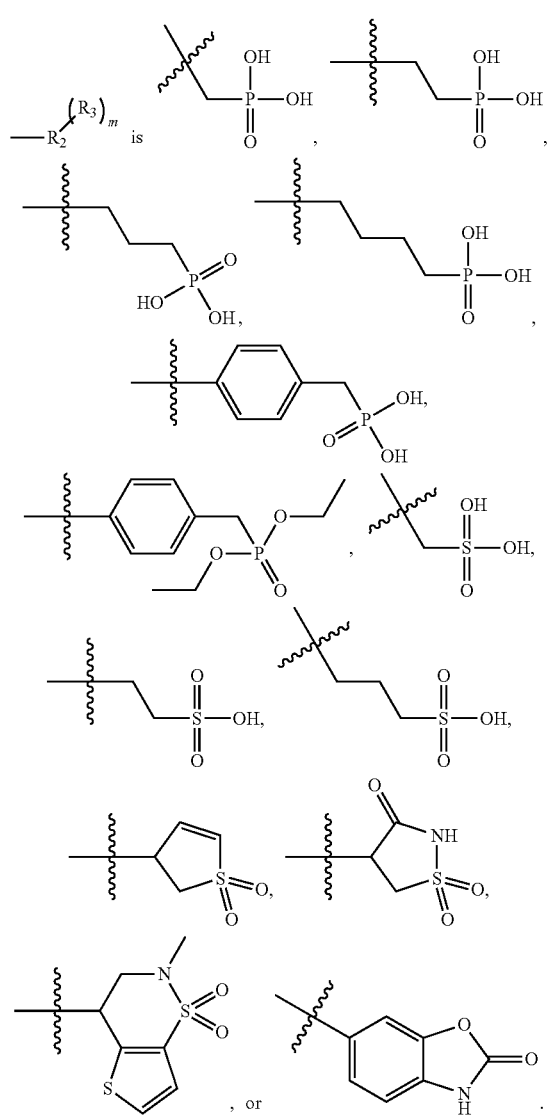
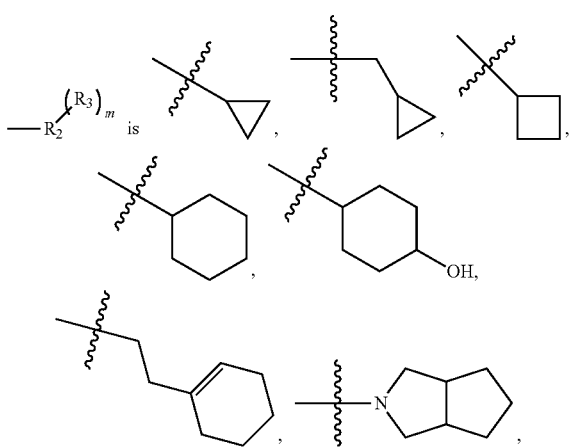
In some embodiments,
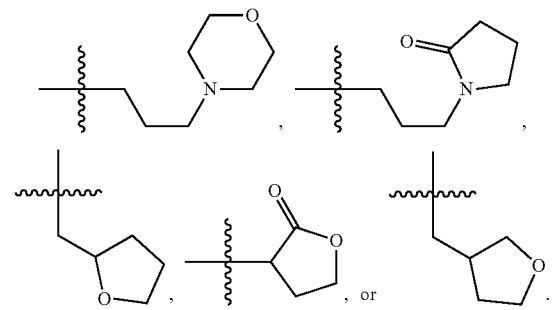
In some embodiments, —R$_2$(R$_3$)$_m$ is
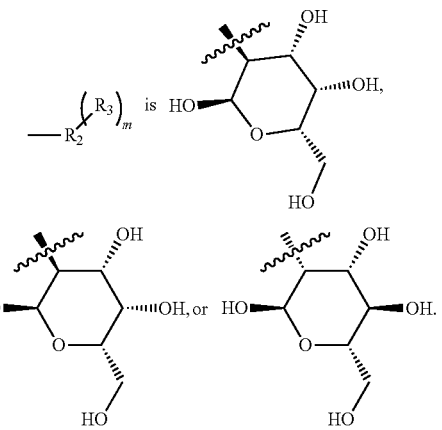
In some embodiments,
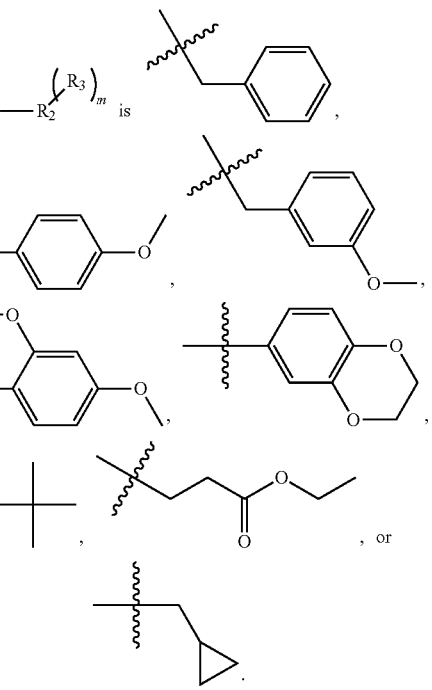

In some embodiments,
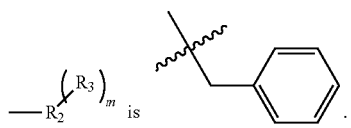
In some embodiments,
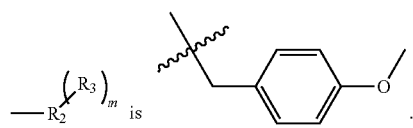
In some embodiments,
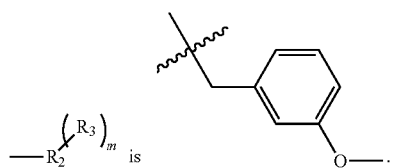
In some embodiments,
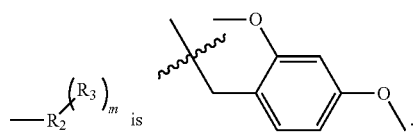
In some embodiments,
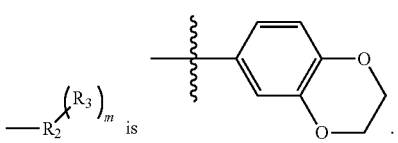
In some embodiments,
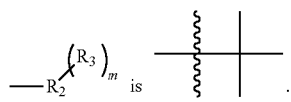
In some embodiments,
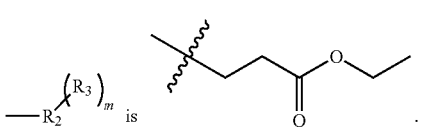
In some embodiments,
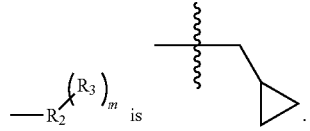
In some embodiments,
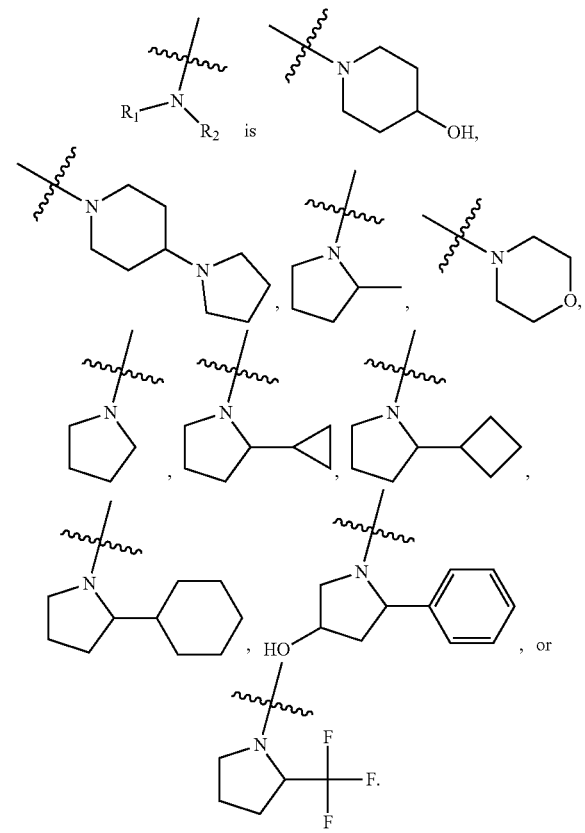
In some embodiments, In some embodiments,
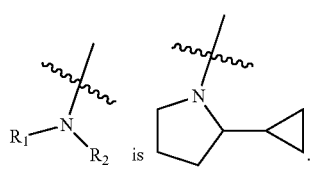 is
In some embodiments, the compound is of Formula (Ia), (Ib), or (Ic):
(Ia)
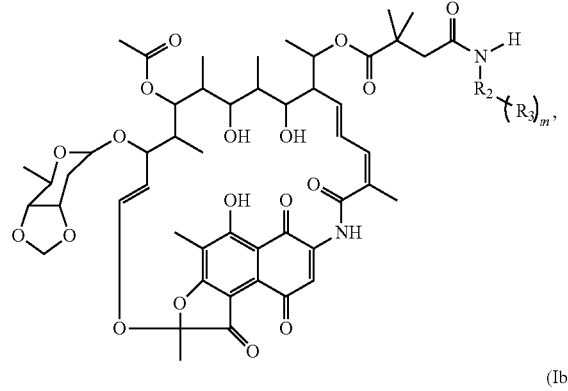
(Ib)
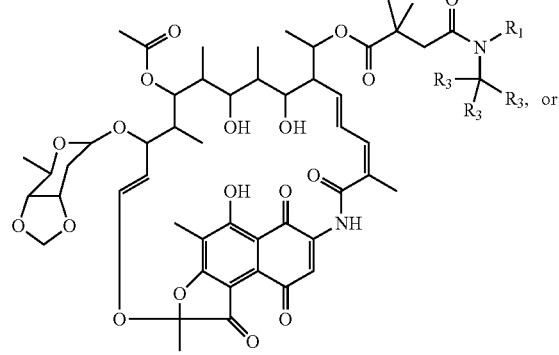
(Ic)
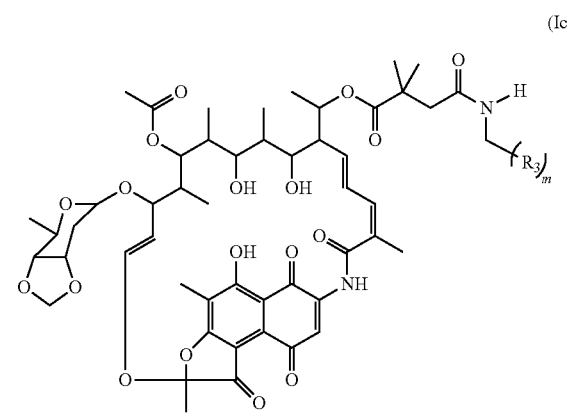
or a prodrug, solvate, or pharmaceutically acceptable salt thereof.
In some embodiments, the compound is of Formula (IIa), (IIb), or (IIc):
(IIa)
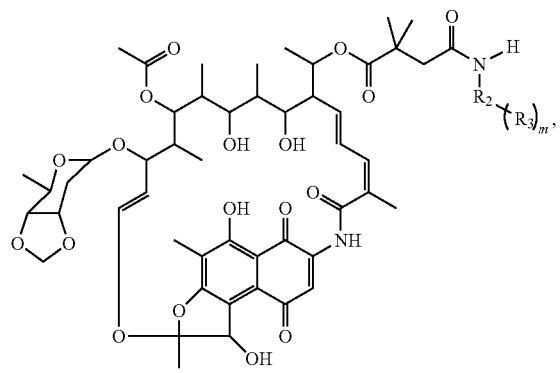
(IIb)
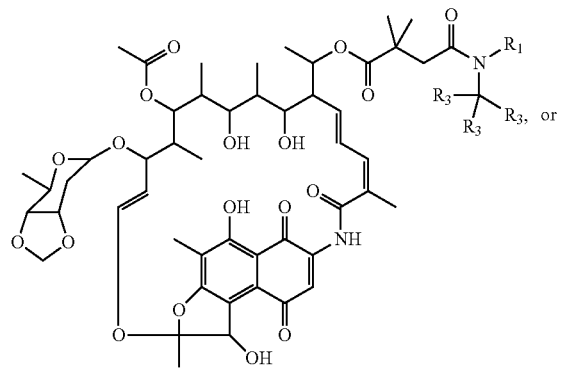
(IIc)
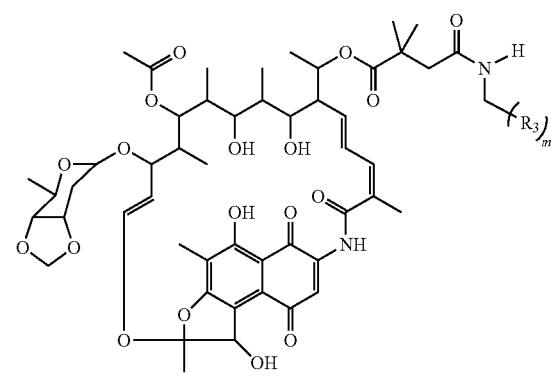
or a prodrug, solvate, or pharmaceutically acceptable salt thereof.

In some embodiments, the compound is of Formula (IIIa), (IIIb), or (IIIc):

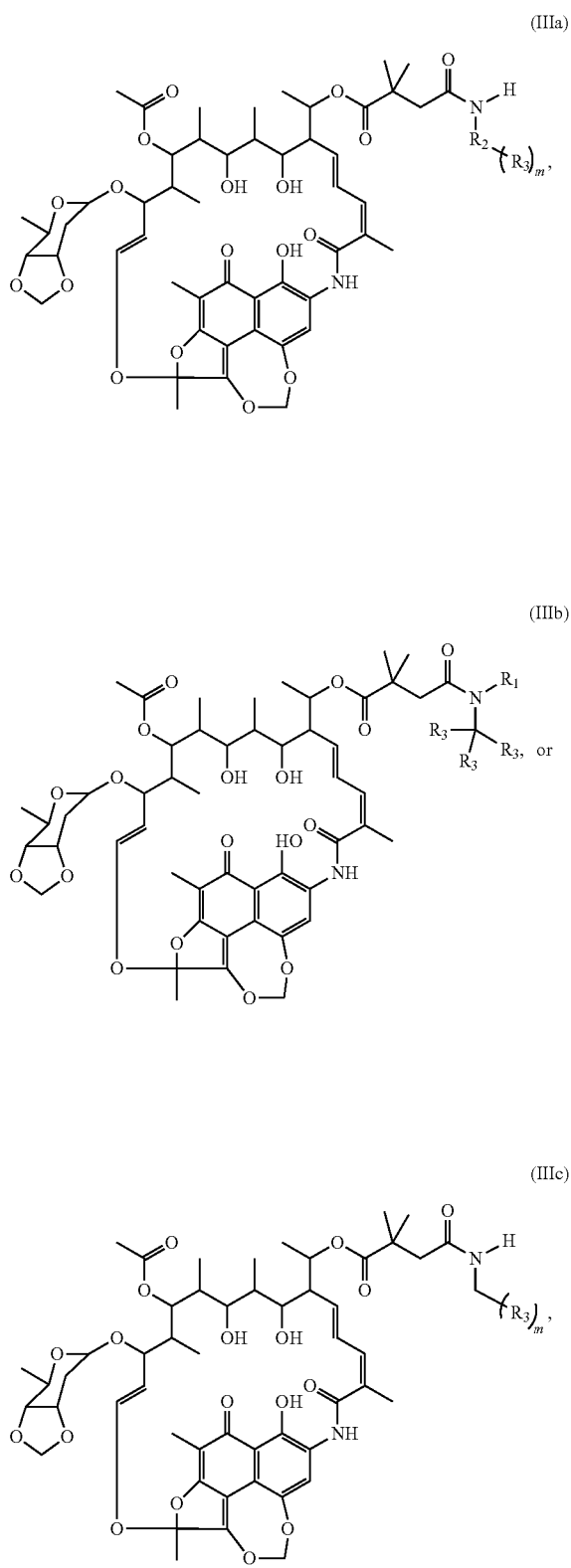

or a prodrug, solvate, or pharmaceutically acceptable salt thereof.

It is understood that, for a compound of any one of the formulae described herein, $R_1$, $R_2$, $R_3$, $R_4$, $R_5$, $R_6$, and $R_7$ can each be, where applicable, selected from the groups described herein, and any group described herein for any of $R_1$, $R_2$, $R_3$, $R_4$, $R_5$, $R_6$, and $R_7$ can be combined, where applicable, with any group described herein for one or more of the remainder of $R_1$, $R_2$, $R_3$, $R_4$, $R_5$, $R_6$, and $R_7$.

In some embodiments, the compound of Formula (I) is selected from Table A, or a prodrug, solvate, or pharmaceutically acceptable salt thereof.

In some embodiments, the compound of Formula (I) is selected from Table A, or a pharmaceutically acceptable salt thereof.

In some embodiments, the compound of Formula (I) is selected from Table A.

In some embodiments, the compound of Formula (I) is selected from Table B, or a prodrug, solvate, or pharmaceutically acceptable salt thereof.

In some embodiments, the compound of Formula (I) is selected from Table B, or a pharmaceutically acceptable salt thereof.

In some embodiments, the compound of Formula (I) is selected from Table B.

In some embodiments, the compound of Formula (II) is selected from Table C, or a prodrug, solvate, or pharmaceutically acceptable salt thereof.

In some embodiments, the compound of Formula (II) is selected from Table C, or a pharmaceutically acceptable salt thereof.

In some embodiments, the compound of Formula (II) is selected from Table C.

In some embodiments, the compound of Formula (II) is selected from Table D, or a prodrug, solvate, or pharmaceutically acceptable salt thereof.

In some embodiments, the compound of Formula (II) is selected from Table D, or a pharmaceutically acceptable salt thereof.

In some embodiments, the compound of Formula (II) is selected from Table D.

In some embodiments, the compound of Formula (III) is selected from Table E, or a prodrug, solvate, or pharmaceutically acceptable salt thereof.

In some embodiments, the compound of Formula (III) is selected from Table E, or a pharmaceutically acceptable salt thereof.

In some embodiments, the compound of Formula (III) is selected from Table E.

In some embodiments, the compound of Formula (III) is selected from Table F, or a prodrug, solvate, or pharmaceutically acceptable salt thereof.

In some embodiments, the compound of Formula (III) is selected from Table F, or a pharmaceutically acceptable salt thereof.

In some embodiments, the compound of Formula (III) is selected from Table F.

TABLE A

Compounds of Formula (I)

| Cmpnd Name | R₁ | -R₂-(R₃)ₘ |
|---|---|---|
| A1 | H | phenyl |
| J4 | H | benzyl (–CH₂–phenyl) |
| C22 | H | –CH₂CH₂–phenyl |
| N8 | H | –CH₂CH₂CH₂CH₂–phenyl |
| A2 | H | 4-methylphenyl |
| A3 | H | 4-hydroxyphenyl |
| N33 | H | indan-1-yl |
| C21 | H | (naphthalen-1-yl)methyl |
| N34 | H | anthracen-2-yl |

TABLE A-continued
Compounds of Formula (I)
| Cmpnd Name | R₁ | R₂–(R₃)ₘ |
|---|---|---|
| N35 | H | 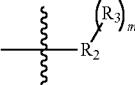 |
| F2 | H | 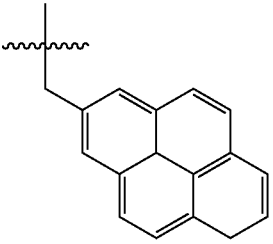 [SMILES: *CC1=CC2=CC=C3CC=CC4=C3C2C(=C1)C=C4] |
| F1 | H | 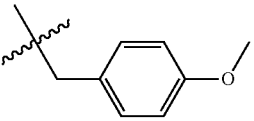 [SMILES: *Cc1ccc(OC)cc1] |
| F4 | H | 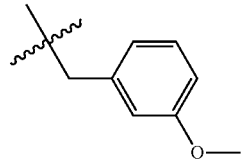 [SMILES: *Cc1cccc(OC)c1] |
| C13 | H | 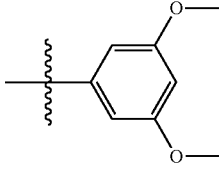 [SMILES: *c1cc(OC)cc(OC)c1] |
| F3 | H | 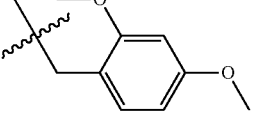 |
| F5 | H | 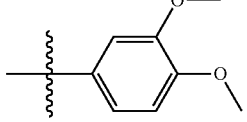 |
| F6 | H | 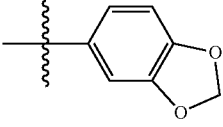 [SMILES: *c1ccc2c(c1)OCO2] |
| N4 | H | 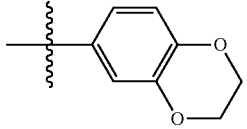 [SMILES: *c1ccc2c(c1)OCCO2] |

TABLE A-continued
Compounds of Formula (I)
| Cmpnd Name | R₁ | |
|---|---|---|
| N37 | H | 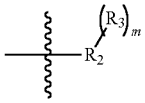 |
| N38 | H | 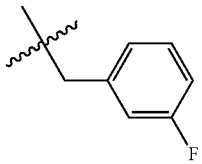 [SMILES: *Cc1cccc(F)c1] |
| N3 | H | 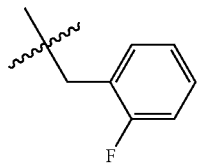 [SMILES: *Cc1ccccc1F] |
| N2 | H | 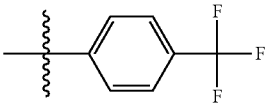 [SMILES: *c1ccc(C(F)(F)F)cc1] |
| N5 | H | 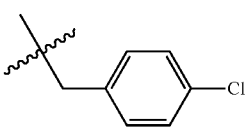 |
| N47 | H | 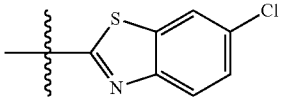 [SMILES: *c1nc2ccc(Cl)cc2s1] |
| N48 | H | 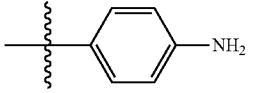 |
| A4 | H | 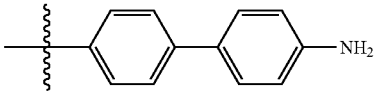 |
| A7 | H | 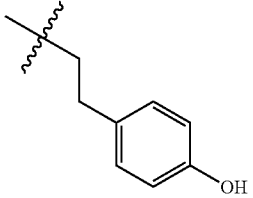 [SMILES: *CCc1ccc(O)cc1] |

TABLE A-continued
Compounds of Formula (I)
| Cmpnd Name | R₁ | -R₂(R₃)ₘ |
|---|---|---|
| C17 | H | 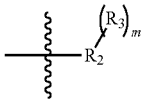 |
| C14 | H | 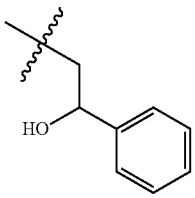 [SMILES: *CC(O)c1ccccc1] |
| J3 | H | 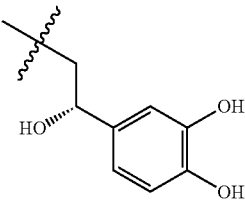 [SMILES: *C[C@@H](O)c1ccc(O)c(O)c1] |
| C15 | H | 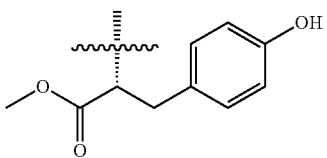 |
| P2 | H | 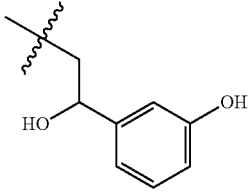 [SMILES: *CC(O)c1cccc(O)c1] |
| P1 | H | 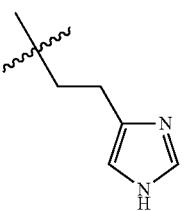 [SMILES: *CCc1c[nH]cn1] |
| A5 | H | 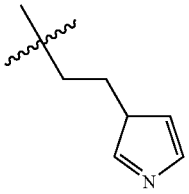 [SMILES: *CCC1C=CN=C1] |

TABLE A-continued
Compounds of Formula (I)
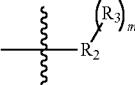
| Cmpnd Name | R₁ | |
|---|---|---|
| A6 | H | 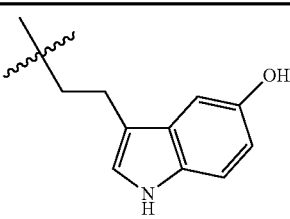 |
| C23 | H | —CH₃ |
| D4 | —CH₃ | —CH₃ |
| D1 | H |  |
| C10 | H |  |
| D2 | H | 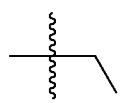 [SMILES: *CC] |
| J5 | H | 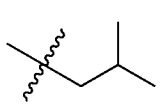 [SMILES: *CC(C)C] |
| E1 | H | 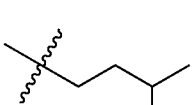 |
| N7 | H | 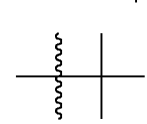 |
| N36 | H | 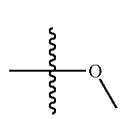 [SMILES: *OC] |
| N1 | H | 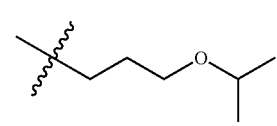 |
| N45 | H | 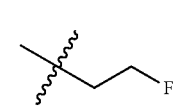 [SMILES: *CCF] |
| N46 | H | 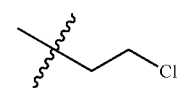 [SMILES: *CCCl] |
| J1 | H | 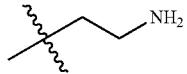 |

TABLE A-continued
Compounds of Formula (I)
| Cmpnd Name | R₁ | -R₂(R₃)ₘ |
|---|---|---|
| G1 | H | 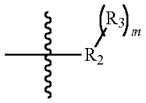 |
| G2 | H | 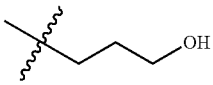 [SMILES: *CCCO] |
| G3 | H | 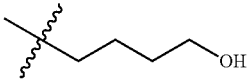 [SMILES: *CCCCO] |
| G5 | H | 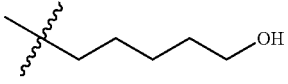 [SMILES: *CCCCCO] |
| J2 | H | 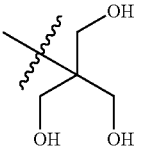 [SMILES: *C(CO)(CO)CO] |
| E2 | H | 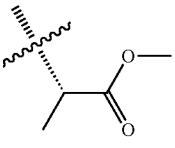 |
| J6 | H | 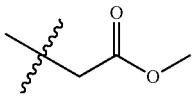 [SMILES: *CC(=O)OC] |
| E3 | H | 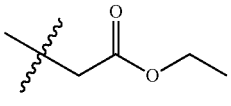 [SMILES: *CC(=O)OCC] |
| E4 | H | 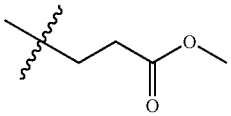 [SMILES: *CCC(=O)OC] |
| N39 | H | 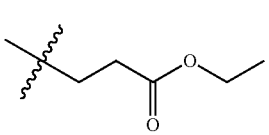 [SMILES: *CCC(=O)OCC] |
| N6 | H |  |

TABLE A-continued

Compounds of Formula (I)

| Cmpnd Name | R₁ | -R₂-(R₃)ₘ |
|---|---|---|
| N40 | H | -C(CH₃)₂-CH₂-C(CH₃)₃ |
| N42 | H | -C(CH₃)₂-CH₂OH |
| N41 | —OH | -C(CH₃)₃ |
| N43 | H | -C(CH₃)₂-phenyl |
| N44 | H | -C(CH₃)(CH₂CH₃)(phenyl)-COOH |
| N14 | H | -CH₂-COOH |
| N15 | H | -(CH₂)₃-COOH |
| N16 | H | -(CH₂)₅-COOH |
| N17 | H | -(CH₂)₇-COOH |
| N12 | H | -(4-carboxyphenyl) |
| N13 | H | -CH₂-(4-carboxyphenyl) |

TABLE A-continued

Compounds of Formula (I)

| Cmpnd Name | R₁ | −R₂−(R₃)ₘ |
|---|---|---|
| N20 | H | 4-carboxyphenyl group connected via NH to glycine (−C₆H₄−C(O)−NH−CH₂−COOH) |
| N22 | H | (S)-2-carboxy-5-(benzyloxycarbonylamino)pentyl group |
| N18 | H | (S)-2-carboxy-4-ureidobutyl group |
| N25 | H | 2-(benzoylamino)-5-carboxypentyl group |
| N23 | H | −CH₂−C(O)−NH−CH(COOH)−CH₂−(4-hydroxyphenyl) |
| N26 | H | 2-carboxy-4-(ethylthio)butyl group |
| N21 | H | 2-carboxy-4-(methylsulfonyl)butyl group |
| N24 | H | 2-carboxy-5-(biotinylamino)pentyl group |

TABLE A-continued
Compounds of Formula (I)
| Cmpnd Name | R₁ | ⸺R₂(R₃)ₘ |
|---|---|---|
| N27 | H | 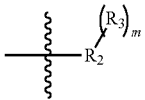 |
| P10 | H | 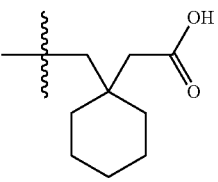 [SMILES: *CC1(CC(=O)O)CCCCC1] |
| P11 | H | 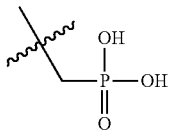 [SMILES: *CP(=O)(O)O] |
| P12 | H | 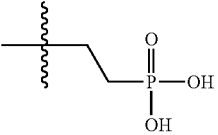 |
| P13 | H | 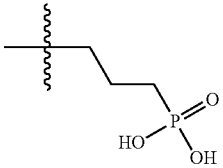 [SMILES: *CCCP(=O)(O)O] |
| P14 | H | 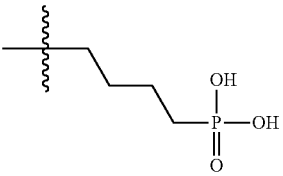 [SMILES: *CCCCP(=O)(O)O] |
| C16 | H | 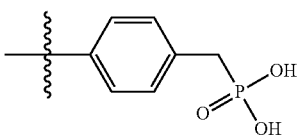 [SMILES: *c1ccc(CP(=O)(O)O)cc1] |
| P7 | H | 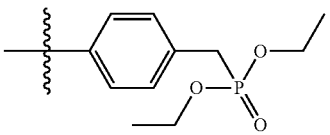 [SMILES: *c1ccc(CP(=O)(OCC)OCC)cc1] |
| P8 | H | 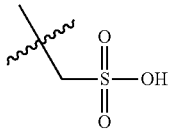 [SMILES: *CS(=O)(=O)O] |

TABLE A-continued
Compounds of Formula (I)
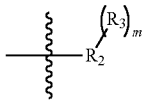
| Cmpnd Name | R₁ | |
|---|---|---|
| P9 | H | 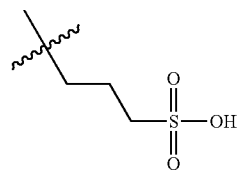 [SMILES: *CCCS(=O)(=O)O] |
| P6 | H | 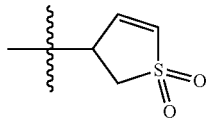 |
| P3 | H | 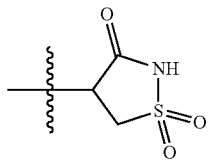 [SMILES: *C1CS(=O)(=O)NC1=O] |
| P4 | H | 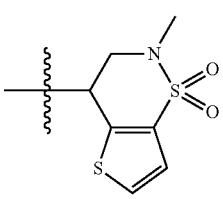 [SMILES: *C1CN(C)S(=O)(=O)c2ccsc21] |
| P5 | H | 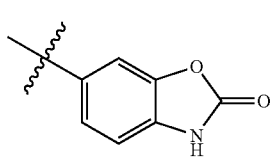 [SMILES: *c1ccc2[nH]c(=O)oc2c1] |
| C9 | H | 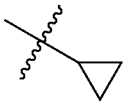 |
| B1 | H | 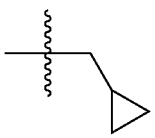 [SMILES: *CC1CC1] |
| J7 | H | 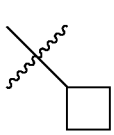 [SMILES: *C1CCC1] |
| C11 | H | 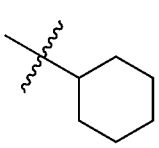 [SMILES: *C1CCCCC1] |

TABLE A-continued
Compounds of Formula (I)
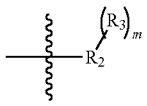
| Cmpnd Name | R₁ | |
|---|---|---|
| B2 | H | 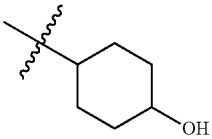 [SMILES: *C1CCC(O)CC1] |
| N9 | H | 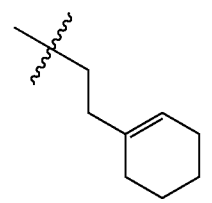 [SMILES: *CCC1=CCCCC1] |
| N32 | H | 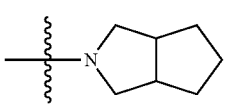 |
| N11 | H | 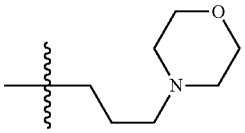 [SMILES: *CCCN1CCOCC1] |
| N10 | H | 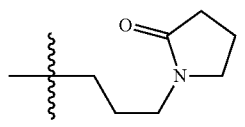 [SMILES: *CCCN1CCCC1=O] |
| B3 | H | 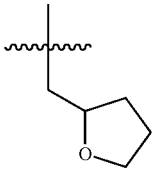 [SMILES: *CC1CCCO1] |
| C20 | H | 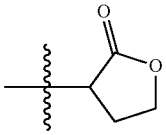 [SMILES: *C1CCOC1=O] |
| B4 | H | 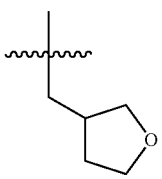 [SMILES: *CC1CCOC1] |

TABLE A-continued

Compounds of Formula (I)

| Cmpnd Name | R₁ | -R₂(R₃)ₘ |
|---|---|---|
| C18 | H | (sugar structure with OH, HO, HO, OH groups on pyranose ring) |
| C19 | H | (sugar structure with OH, HO, HO, OH groups on pyranose ring) |
| S1 | H | (sugar structure with OH, HO, HO, OH groups on pyranose ring) |

TABLE B

Compounds of Formula (I)

R₁—N(R₂)—

| Compound Name | Structure |
|---|---|
| C12 | N-piperidinyl with 4-OH |
| C5 | 2-cyclopropyl-pyrrolidinyl |

TABLE B-continued

Compounds of Formula (I)

R₁—N(R₂)—

| Compound Name | Structure |
|---|---|
| N31 | 4-(pyrrolidin-1-yl)piperidinyl |
| C6 | 2-cyclobutyl-pyrrolidinyl |

TABLE B-continued

Compounds of Formula (I)

| Compound Name | ![R1-N-R2 structure] |
|---|---|
| N29 | 2-methylpyrrolidin-1-yl |
| C7 | 2-cyclohexylpyrrolidin-1-yl |
| C4 | morpholin-4-yl |
| C8 | 4-hydroxy-2-phenylpyrrolidin-1-yl |
| N28 | pyrrolidin-1-yl |
| N30 | 2-(trifluoromethyl)pyrrolidin-1-yl |

TABLE C

Compounds of Formula (II)

| Cmpnd Name | $R_1$ | $-R_2-(R_3)_m$ |
|---|---|---|
| A1' | H | phenyl |
| J4' | H | benzyl |
| C22' | H | 2-phenylethyl |
| N8' | H | 4-phenylbutyl |
| A2' | H | 4-methylphenyl |
| A3' | H | 4-hydroxyphenyl |
| N33' | H | 2,3-dihydro-1H-inden-1-yl |
| C21' | H | (naphthalen-1-yl)methyl |
| N34' | H | anthracen-2-yl |
| N35' | H | (pyren-2-yl)methyl |

TABLE C-continued
Compounds of Formula (II)
| Cmpnd Name | R₁ | -R₂-(R₃)ₘ |
|---|---|---|
| F2' | H | 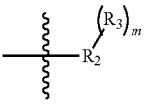 |
| F1' | H | 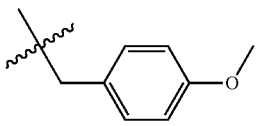 [SMILES: *Cc1ccc(OC)cc1] |
| F4' | H | 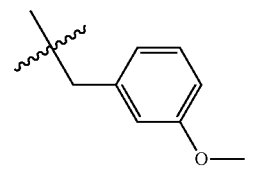 [SMILES: *Cc1cccc(OC)c1] |
| C13' | H | 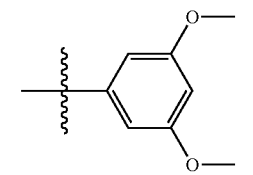 [SMILES: *c1cc(OC)cc(OC)c1] |
| F3' | H | 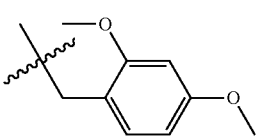 [SMILES: *Cc1ccc(OC)cc1OC] |
| F5' | H | 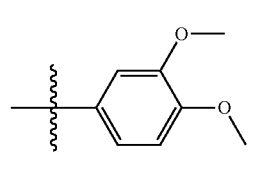 [SMILES: *c1ccc(OC)c(OC)c1] |
| F6' | H | 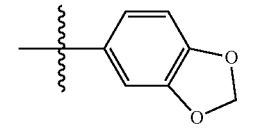 [SMILES: *c1ccc2c(c1)OCO2] |
| N4' | H | 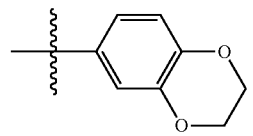 |
| N37' | H | 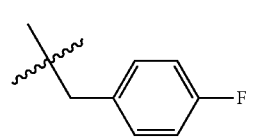 [SMILES: *Cc1ccc(F)cc1] |
| N38' | H | 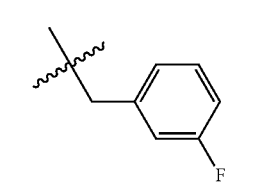 [SMILES: *Cc1cccc(F)c1] |
| N3' | H | 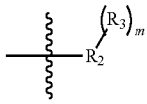 |
| N2' | H | 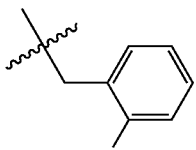 |
| N5' | H | 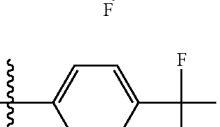 |
| N47' | H | 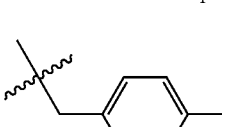 |
| N48' | H | 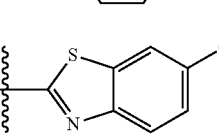 |
| A4' | H | 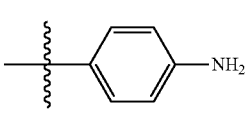 [SMILES: *c1ccc(N)cc1] |
| A7' | H | 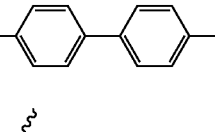 |
| C17' | H | 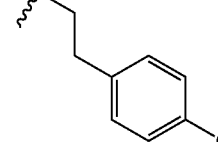 |

TABLE C-continued

Compounds of Formula (II)

| Cmpnd Name | R₁ | −R₂−(R₃)ₘ |
|---|---|---|
| C14' | H | (S)-3,4-dihydroxyphenyl-2-hydroxyethyl-CH₂- group |
| J3' | H | methyl 2-(4-hydroxybenzyl)propanoate group |
| C15' | H | 1-hydroxy-1-(3-hydroxyphenyl)ethyl-CH₂- group |
| P2' | H | 2-(1H-imidazol-4-yl)ethyl group |
| P1' | H | 2-(1H-pyrrol-3-yl)ethyl group |
| A5' | H | 2-(1H-indol-3-yl)ethyl group |
| A6' | H | 2-(5-hydroxy-1H-indol-3-yl)ethyl group |
| C23' | H | —CH₃ |
| D4' | —CH₃ | —CH₃ |
| D1' | H | —CH(CH₃)CH₂CH₃ |
| C10' | H | —CH₂CH(CH₃)₂ |
| D2' | H | —CH(CH₃)CH₂CH(CH₃)₂ |
| J5' | H | —C(CH₃)₃ |
| E1' | H | —CH(CH₃)OCH₃ |
| N7' | H | —(CH₂)₃OCH(CH₃)₂ |
| N36' | H | —(CH₂)₂CH₂F |
| N1' | H | —(CH₂)₂CH₂Cl |
| N45' | H | —(CH₂)₂NH₂ |
| N46' | H | —(CH₂)₄NH₂ |
| J1' | H | —(CH₂)₂OH |
| G1' | H | —(CH₂)₃OH |
| G2' | H | —(CH₂)₄OH |

TABLE C-continued

Compounds of Formula (II)

| Cmpnd Name | $R_1$ | $R_2$—$(R_3)_m$ |
|---|---|---|
| G3' | H | hexyl-OH chain |
| G5' | H | C(CH2OH)3 (pentaerythritol-like) |
| J2' | H | CH(CH3)C(=O)OCH3 |
| E2' | H | CH2C(=O)OCH3 |
| J6' | H | CH2C(=O)OEt |
| E3' | H | CH2CH2C(=O)OCH3 |
| E4' | H | CH2CH2C(=O)OEt |
| N39' | H | C(CH3)2CH2CH3 |
| N6' | H | CH2C(CH3)3 branched |
| N40' | H | extended branched alkyl |
| N42' | H | C(CH3)2CH2OH |
| N41' | —OH | C(CH3)3 |
| N43' | H | C(CH3)2-phenyl |
| N44' | H | C(CH3)(Et)(phenyl)COOH |
| N14' | H | CH2CH2COOH (with methyl) |
| N15' | H | (CH2)3COOH |
| N16' | H | (CH2)5COOH |
| N17' | H | (CH2)7COOH |
| N12' | H | 4-carboxyphenyl |
| N13' | H | CH2-(4-carboxyphenyl) |
| N20' | H | 4-(C(=O)NHCH2COOH)phenyl |
| N22' | H | HOOC-CH(NH-)-(CH2)4-NH-C(=O)O-CH2-phenyl |
| N18' | H | HOOC-CH(NH-)-(CH2)3-NH-C(=O)NH2 |

TABLE C-continued

Compounds of Formula (II)

| Cmpnd Name | R₁ | structure |
|---|---|---|
| N25' | H | 2-benzamido-hexanoic acid substituent |
| N23' | H | 2-acetamido-3-(4-hydroxyphenyl)propanoic acid substituent |
| N26' | H | 2-(2-(ethylthio)ethyl)-carboxylic acid substituent |
| N21' | H | 2-(2-(methylsulfonyl)ethyl)-carboxylic acid substituent |
| N24' | H | biotin-lysine conjugate |
| N27' | H | 1-(carboxymethyl)cyclohexyl methyl substituent |
| P10' | H | —CH₂—P(O)(OH)₂ |
| P11' | H | —CH₂CH₂—P(O)(OH)₂ |
| P12' | H | —(CH₂)₃—P(O)(OH)₂ |
| P13' | H | —(CH₂)₄—P(O)(OH)₂ |
| P14' | H | —(p-C₆H₄)—CH₂—P(O)(OH)₂ |
| C16' | H | —(p-C₆H₄)—CH₂—P(O)(OEt)₂ |
| P7' | H | —CH₂—SO₃H |
| P8' | H | —CH₂CH₂—SO₃H |
| P9' | H | —(CH₂)₃—SO₃H |
| P6' | H | 2,3-dihydrothiophene-1,1-dioxide substituent |
| P3' | H | isothiazolidinone-1,1-dioxide substituent |
| P4' | H | N-methyl thieno-fused sultam substituent |

TABLE C-continued

Compounds of Formula (II)

| Cmpnd Name | R₁ | -R₂-(R₃)ₘ |
|---|---|---|
| P5' | H | 6-oxo-2,3-dihydro-1,3-benzoxazol-5-yl (benzoxazolone attached) |
| C9' | H | cyclopropyl |
| B1' | H | cyclopropylmethyl (CH₂-cyclopropyl) |
| J7' | H | cyclobutyl |
| C11' | H | cyclohexyl |
| B2' | H | 4-hydroxycyclohexyl |
| N9' | H | 2-(cyclohex-1-en-1-yl)ethyl |
| N32' | H | octahydrocyclopenta[c]pyrrol-2-yl |
| N11' | H | 3-(morpholin-4-yl)propyl |
| N10' | H | 3-(2-oxopyrrolidin-1-yl)propyl |
| B3' | H | (tetrahydrofuran-2-yl)methyl |
| C20' | H | 2-oxotetrahydrofuran-3-yl |
| B4' | H | (tetrahydrofuran-3-yl)methyl |
| C18' | H | hexopyranosyl (sugar) |
| C19' | H | hexopyranosyl (sugar) |
| S1' | H | hexopyranosyl (sugar) |

TABLE D

Compounds of Formula (II)

| Compound Name | Structure |
|---|---|
| C12' | 1-substituted-4-hydroxypiperidine |
| C5' | 2-cyclopropylpyrrolidine (N-substituted) |
| N31' | 1-substituted-4-(pyrrolidin-1-yl)piperidine |
| C6' | 2-cyclobutylpyrrolidine (N-substituted) |
| N29' | 2-methylpyrrolidine (N-substituted) |

TABLE D-continued

Compounds of Formula (II)

| Compound Name | Structure |
|---|---|
| C7' | 2-cyclohexylpyrrolidine (N-substituted) |
| C4' | morpholine (N-substituted) |
| C8' | 4-hydroxy-2-phenylpyrrolidine (N-substituted) |
| N28' | pyrrolidine (N-substituted) |
| N30' | 2-(trifluoromethyl)pyrrolidine (N-substituted) |

TABLE E

Compounds of Formula (III)

| Cmpnd Name | R₁ | R₂–(R₃)ₘ |
|---|---|---|
| A1″ | H | phenyl |
| J4″ | H | benzyl |

TABLE E-continued
Compounds of Formula (III)
| Cmpnd Name | R₁ | —R₂(R₃)ₘ |
|---|---|---|
| C22″ | H | 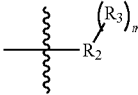 |
| N8″ | H | 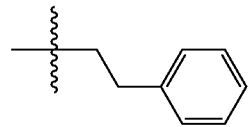 [SMILES: *CCc1ccccc1] |
| A2″ | H | 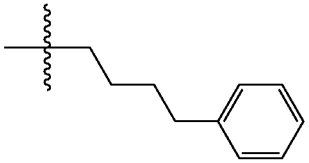 [SMILES: *CCCCc1ccccc1] |
| A3″ | H | 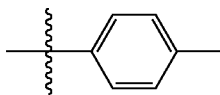 |
| N33″ | H | 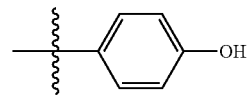 |
| C21″ | H | 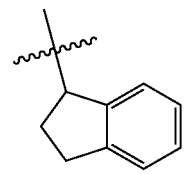 [SMILES: *C1CCc2ccccc21] |
| N34″ | H | 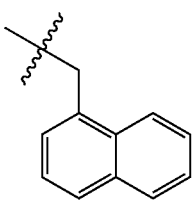 [SMILES: *Cc1cccc2ccccc12] |
| N35″ | H | 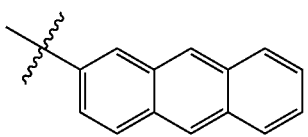 [SMILES: *c1ccc2cc3ccccc3cc2c1] |
| F2″ | H | 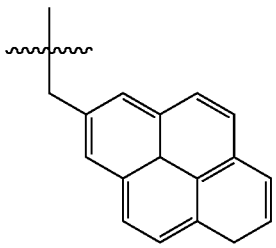 [SMILES: *CC1=CC2=CC=C3CC=CC4=C3C2C(=C1)C=C4] |

TABLE E-continued
Compounds of Formula (III)
| Cmpnd Name | R₁ | -R₂-(R₃)ₘ |
|---|---|---|
| F1" | H | 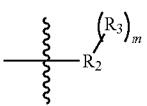 3-methoxybenzyl |
| F4" | H | 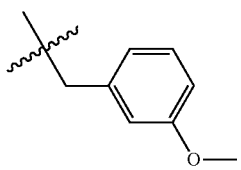 [SMILES: *Cc1cccc(OC)c1] 3,5-dimethoxybenzyl |
| C13" | H | 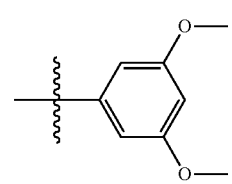 [SMILES: *c1cc(OC)cc(OC)c1] 2,4-dimethoxybenzyl |
| F3" | H | 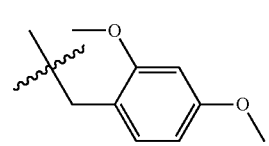 [SMILES: *Cc1ccc(OC)cc1OC] 3,4-dimethoxybenzyl |
| F5" | H | 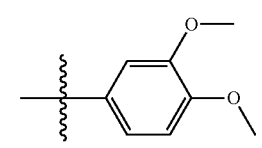 [SMILES: *c1ccc(OC)c(OC)c1] benzo[1,3]dioxol-5-ylmethyl |
| F6" | H | 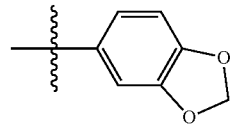 [SMILES: *c1ccc2c(c1)OCO2] 2,3-dihydrobenzo[1,4]dioxin-6-ylmethyl |
| N4" | H | 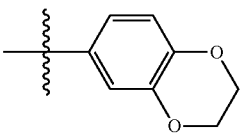 [SMILES: *c1ccc2c(c1)OCCO2] 4-fluorobenzyl |
| N37" | H | 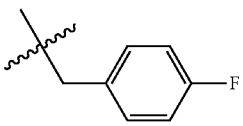 [SMILES: *Cc1ccc(F)cc1] 3-fluorobenzyl |
| N38" | H | 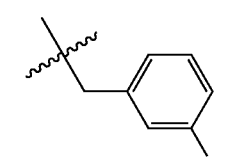 2-fluorobenzyl |

TABLE E-continued
Compounds of Formula (III)
| Cmpnd Name | R₁ | -R₂-(R₃)ₘ |
|---|---|---|
| N3" | H | 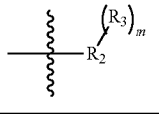 4-(trifluoromethyl)phenyl |
| N2" | H | 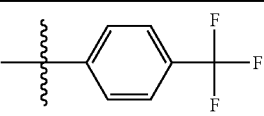 4-chlorobenzyl |
| N5" | H | 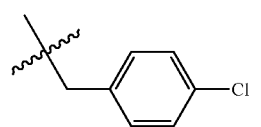 [SMILES: *Cc1ccc(Cl)cc1] 6-chlorobenzothiazol-2-yl |
| N47" | H | 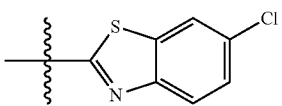 4-aminophenyl |
| N48" | H | 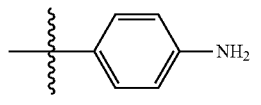 4'-amino-biphenyl-4-yl |
| A4" | H | 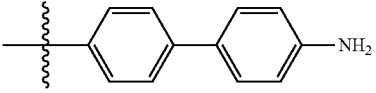 [SMILES: *c1ccc(-c2ccc(N)cc2)cc1] 2-(4-hydroxyphenyl)ethyl |
| A7" | H | 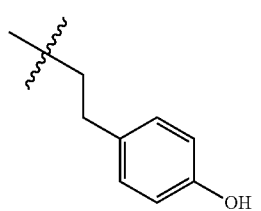 [SMILES: *CCc1ccc(O)cc1] 2-(3,4-dihydroxyphenyl)ethyl |
| C17" | H | 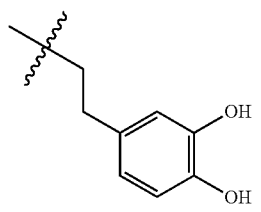 [SMILES: *CCc1ccc(O)c(O)c1] 2-hydroxy-2-phenylethyl |
| C14" | H | 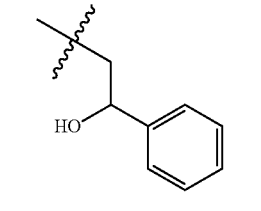 [SMILES: *CC(O)c1ccccc1] (S)-2-hydroxy-2-(3,4-dihydroxyphenyl)ethyl |

TABLE E-continued
Compounds of Formula (III)
| Cmpnd Name | R₁ | 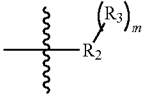 |
|---|---|---|
| J3" | H | 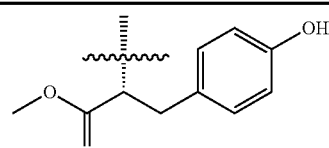 |
| C15" | H | 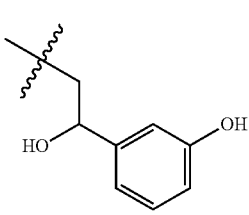 [SMILES: *CC(O)c1cccc(O)c1] |
| P2" | H | 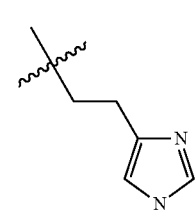 |
| P1" | H | 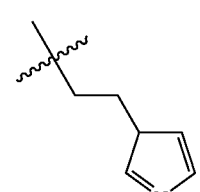 |
| A5" | H | 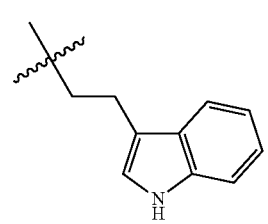 [SMILES: *CCc1c[nH]c2ccccc12] |
| A6" | H | 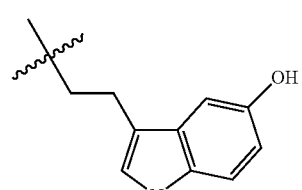 |
| C23" | H | —CH₃ |
| D4" | —CH₃ | —CH₃ |
| D1" | H | 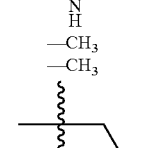 |
| C10" | H | 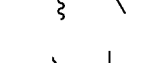 |

TABLE E-continued
Compounds of Formula (III)
| Cmpnd Name | R₁ | −R₂−(R₃)ₘ |
|---|---|---|
| D2" | H | 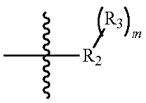 |
| J5" | H | 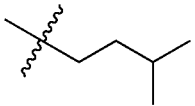 [SMILES: *CCC(C)C] |
| E1" | H |  |
| N7" | H | 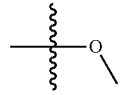 [SMILES: *OC] |
| N36" | H | 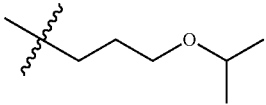 [SMILES: *CCCOC(C)C] |
| N1" | H | 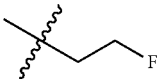 [SMILES: *CCF] |
| N45" | H | 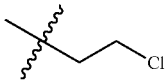 |
| N46" | H | 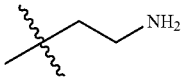 |
| J1" | H | 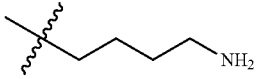 [SMILES: *CCCCN] |
| G1" | H | 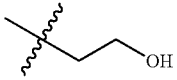 [SMILES: *CCO] |
| G2" | H | 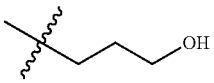 [SMILES: *CCCO] |
| G3" | H | 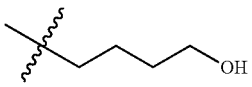 [SMILES: *CCCCO] |
| G5" | H | 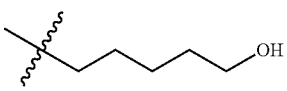 [SMILES: *CCCCCO] |

TABLE E-continued
Compounds of Formula (III)
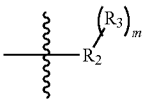

TABLE E-continued
Compounds of Formula (III)
| Cmpnd Name | R₁ | -R₂-(R₃)ₘ |
|---|---|---|
| N44″ | H | 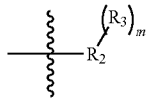 |
| N14″ | H | 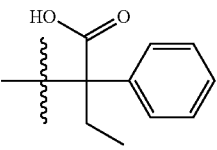 [SMILES: *C(CC)(C(=O)O)c1ccccc1] |
| N15″ | H | 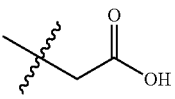 [SMILES: *CC(=O)O] |
| N16″ | H | 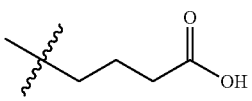 [SMILES: *CCCC(=O)O] |
| N17″ | H | 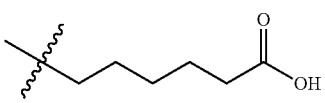 [SMILES: *CCCCCC(=O)O] |
| N12″ | H | 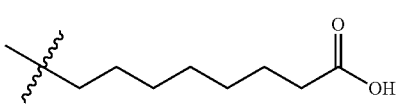 [SMILES: *CCCCCCCC(=O)O] |
| N13″ | H | 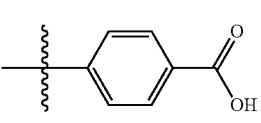 [SMILES: *c1ccc(C(=O)O)cc1] |
| N20″ | H | 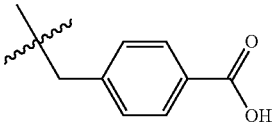 [SMILES: *Cc1ccc(C(=O)O)cc1] |
| N22″ | H | 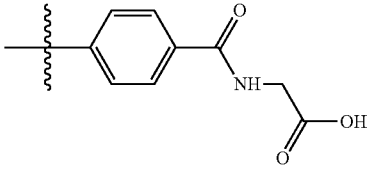 [SMILES: *c1ccc(C(=O)NCC(=O)O)cc1] |
| N18″ | H | 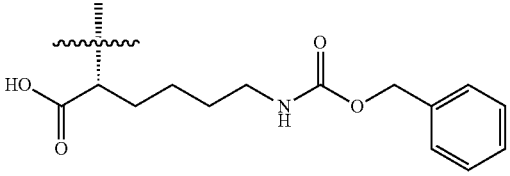 |

TABLE E-continued
Compounds of Formula (III)
| Cmpnd Name | R₁ | ⸺R₂⸺(R₃)ₘ |
|---|---|---|
| N25″ | H | 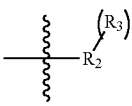 |
| N23″ | H | 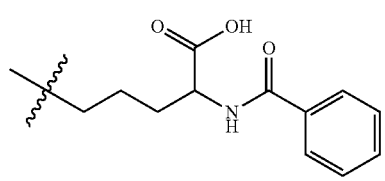 [SMILES: *CCCC(NC(=O)c1ccccc1)C(=O)O] |
| N26″ | H | 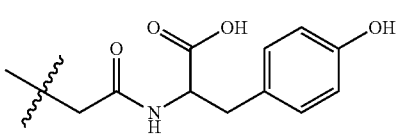 [SMILES: *CC(=O)NC(Cc1ccc(O)cc1)C(=O)O] |
| N21″ | H | 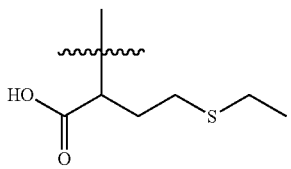 [SMILES: *C(CCSCC)C(=O)O] |
| N24″ | H | 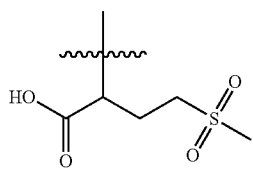 [SMILES: *C(CCS(C)(=O)=O)C(=O)O] |
| N27″ | H | 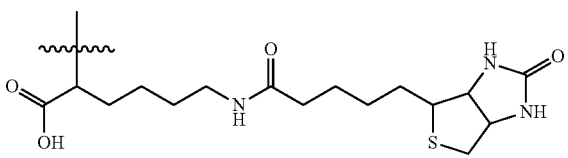 [SMILES: *C(CCCCNC(=O)CCCCC1SCC2NC(=O)NC21)C(=O)O] |
| P10″ | H | 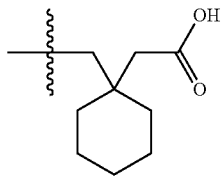 [SMILES: *CC1(CC(=O)O)CCCCC1] |
| P11″ | H | 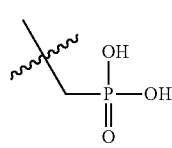 [SMILES: *CP(=O)(O)O] |

TABLE E-continued

Compounds of Formula (III)

| Cmpnd Name | R₁ | —R₂—(R₃)ₘ |
|---|---|---|
| P12" | H | —(CH₂)₃—P(=O)(OH)(OH) |
| P13" | H | —(CH₂)₄—P(=O)(OH)(OH) |
| P14" | H | —(p-C₆H₄)—CH₂—P(=O)(OH)(OH) |
| C16" | H | —(p-C₆H₄)—CH₂—P(=O)(OEt)(OEt) |
| P7" | H | —CH₂—S(=O)₂—OH |
| P8" | H | —(CH₂)₂—S(=O)₂—OH |
| P9" | H | —(CH₂)₃—S(=O)₂—OH |
| P6" | H | 3-yl-2,3-dihydrothiophene 1,1-dioxide |
| P3" | H | 4-yl-1,2-thiazolidin-3-one 1,1-dioxide |

TABLE E-continued
Compounds of Formula (III)
| Cmpnd Name | R₁ | —R₂—(R₃)ₘ |
|---|---|---|
| P4" | H | 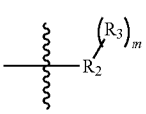 |
| P5" | H | 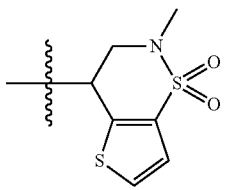 [SMILES: *C1CN(C)S(=O)(=O)c2ccsc21] |
| C9" | H | 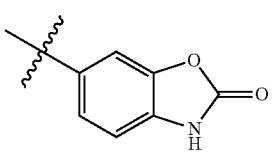 [SMILES: *c1ccc2[nH]c(=O)oc2c1] |
| B1" | H | 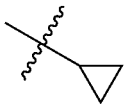 [SMILES: *C1CC1] |
| J7" | H | 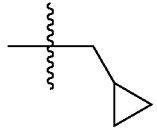 [SMILES: *CC1CC1] |
| C11" | H | 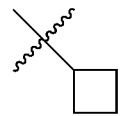 |
| B2" | H | 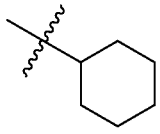 |
| N9" | H | 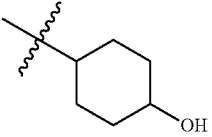 |
| N32" | H | 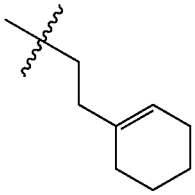 [SMILES: *CCC1=CCCCC1] |

TABLE E-continued
Compounds of Formula (III)
| Cmpnd Name | R₁ | $\underset{R_2}{\overset{(R_3)_m}{\xi}}$ |
|---|---|---|
| N11" | H | 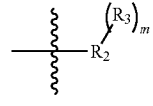 |
| N10" | H | 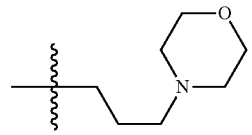 [SMILES: *CCCN1CCOCC1] |
| B3" | H | 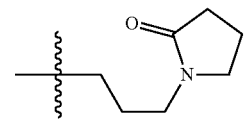 [SMILES: *CCCN1CCCC1=O] |
| C20" | H | 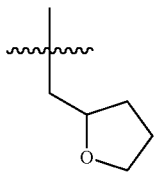 [SMILES: *CC1CCCO1] |
| B4" | H | 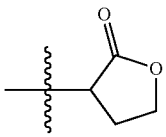 [SMILES: *C1CCOC1=O] |
| C18" | H | 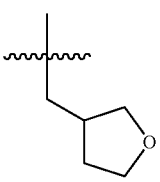 [SMILES: *CC1CCOC1] |
| C19" | H | |

TABLE E-continued
Compounds of Formula (III)
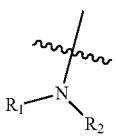
| Cmpnd Name | R₁ | |
|---|---|---|
| S1″ | H | 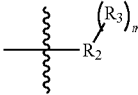 |
TABLE F
Compounds of Formula (III)
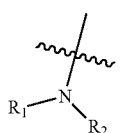
| Compound Name | |
|---|---|
| C12″ | 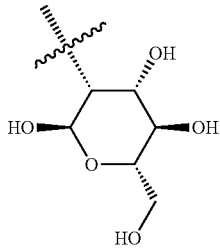 |
| C5″ | 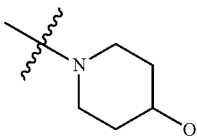 |
| N31″ | 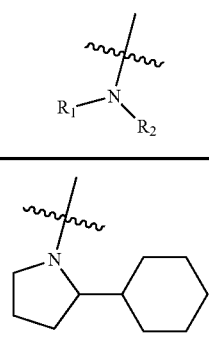 |
| C6″ | 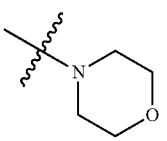 |
| N29″ | 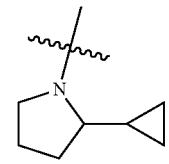 [SMILES: *N1CCCC1C1CC1] |
TABLE F-continued
Compounds of Formula (III)
| Compound Name | |
|---|---|
| C7″ | 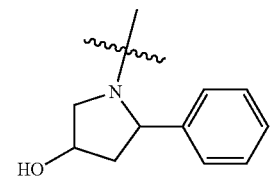 |
| C4″ | 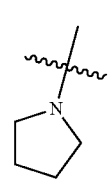 |
| C8″ | 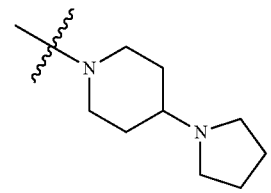 [SMILES: *N1CCC(N2CCCC2)CC1] |
| N28″ | 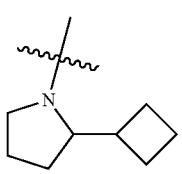 [SMILES: *N1CCCC1C1CCC1] |
| N30″ | 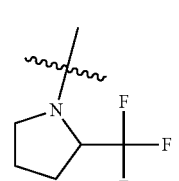 |

In some embodiments, the compound of the present disclosure is selected from J4, F2, F1, C13, F6, J5, E4, B1, N29, and C5, or a prodrug, solvate, or pharmaceutically acceptable salt thereof.

In some embodiments, the compound of the present disclosure is selected from J4, F2, F1, C13, F6, J5, E4, B1, N29, and C5, or a pharmaceutically acceptable salt thereof.

In some embodiments, the compound of the present disclosure is selected from J4, F2, F1, C13, F6, J5, E4, B1, N29, and C5.

In some embodiments, the compound of the present disclosure is selected from J4, F2, F1, C13, F6, J5, E4, or B1, or a prodrug, solvate, or pharmaceutically acceptable salt thereof.

In some embodiments, the compound of the present disclosure is selected from J4, F2, F1, C13, F6, J5, E4, or B1, or a pharmaceutically acceptable salt thereof.

In some embodiments, the compound of the present disclosure is selected from J4, F2, F1, C13, F6, J5, E4, or B1.

In some embodiments, the compound of the present disclosure is selected from N29 and C5, or a prodrug, solvate, or pharmaceutically acceptable salt thereof.

In some embodiments, the compound of the present disclosure is selected from N29 and C5, or a pharmaceutically acceptable salt thereof.

In some embodiments, the compound of the present disclosure is selected from N29 and C5.

In some embodiments, the compound of the present disclosure is J4, or a prodrug, solvate, or pharmaceutically acceptable salt thereof.

In some embodiments, the compound of the present disclosure is J4, or a pharmaceutically acceptable salt thereof.

In some embodiments, the compound of the present disclosure is J4.

As discussed herein, the compounds of Formula (I), (II), and (III) are potent antibiotics. In some embodiments, the compounds of Formula (I), (II), and (III) activity against rifamycin-resistant bacteria (e.g., as described herein). In some embodiments, a bacteria is considered to be rifamycin-resistant if the prescribed dose of rifamycin (e.g., as indicated on the FDA approved label for the indication being treated) is no longer therapeutically effective. In some embodiments, the compounds have an MIC ($\mu$g/mL) that is at least about 0.01 fold lower than the MIC of rifamycin measured for the rifamycin-resistant bacteria, e.g., about 0.01 fold, about 0.05 fold, about 0.10 fold, about 0.25 fold, about 0.50 fold, about 0.75 fold, about 1.0 fold, about 1.25 fold, 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 11 fold, about 12 fold, about 13 fold, about 14 fold, about 15 fold, about 16 fold, about 17 fold, about 18 fold, about 19 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 150 fold, about 200 fold, about 250 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, about 1000 fold or more, including all values and ranges inbetween. Methods of determining MIC are well known in the art.

In some embodiments, the compounds of formula (1) and (2) have an MIC value for any of the bacteria disclosed herein of less than about 1000 $\mu$g/mL, about 900 $\mu$g/mL, about 800 $\mu$g/mL, about 700 $\mu$g/mL, about 600 $\mu$g/mL, about 500 $\mu$g/mL, about 400 $\mu$g/mL, about 300 $\mu$g/mL, about 200 $\mu$g/mL, about 100 $\mu$g/mL, about 95 $\mu$g/mL, about 90 $\mu$g/mL, about 85 $\mu$g/mL, about 80 $\mu$g/mL, about 75 $\mu$g/mL, about 70 $\mu$g/mL, about 65 $\mu$g/mL, about 60 $\mu$g/mL, about 55 $\mu$g/mL, about 50 $\mu$g/mL, about 45 $\mu$g/mL, about 40 $\mu$g/mL, about 35 $\mu$g/mL, about 30 $\mu$g/mL, about 25 $\mu$g/mL, about 20 $\mu$g/mL, about 15 $\mu$g/mL, about 10 $\mu$g/mL, about 9 $\mu$g/mL, about 8 $\mu$g/mL, about 7 $\mu$g/mL, about 6 $\mu$g/mL, about 5 $\mu$g/mL, about 4 $\mu$g/mL, about 3 $\mu$g/mL, about 2 $\mu$g/mL, about 1 $\mu$g/mL, about 0.5 $\mu$g/mL, about 0.1 $\mu$g/mL, about 0.05 $\mu$g/mL, about 0.01 $\mu$g/mL, about 0.005 $\mu$g/mL, about 0.001 $\mu$g/mL, about 0.0005 $\mu$g/mL, about 0.0001 $\mu$g/mL, about 0.05 ng/mL, about 0.01 ng/mL, about 0.005 ng/mL, or about 0.001 ng/mL, or lower, including all values and ranges therebetween.

In some embodiments, the compounds of the disclosure when measured in vitro transcription assay (e.g., as described herein) inhibit RNA polymerase (RNAP) activity at a concentration that is at least about 0.01 fold lower than rifamycin, e.g., about 0.01 fold, about 0.05 fold, about 0.10 fold, about 0.25 fold, about 0.50 fold, about 0.75 fold, about 1.0 fold, about 1.25 fold, 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 11 fold, about 12 fold, about 13 fold, about 14 fold, about 15 fold, about 16 fold, about 17 fold, about 18 fold, about 19 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 150 fold, about 200 fold, about 250 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, about 1000 fold or more, including all values and ranges in between. In vitro transcription assays are well known in the art (See, e.g., J Vis Exp. 2016; (115): 54256; and *Nature Communications*. 2019; 9: 4147, each of which is herein incorporated by reference in its entirety for all purposes).

In some embodiments, the compounds of the disclosure inhibit RNAP activity as measured in an in vitro transcription assay (e.g., as described herein) a concentration of about 1000 $\mu$M or less, e.g., about 1000 $\mu$M, about 950 $\mu$M, about 900 $\mu$M, about 850 $\mu$M, about 800 $\mu$M, about 750 $\mu$M, about 700 $\mu$M, about 650 $\mu$M, about 600 $\mu$M, about 550 $\mu$M, about 500 $\mu$M, about 450 $\mu$M, about 400 $\mu$M, about 350 $\mu$M, about 300 $\mu$M, about 250 $\mu$M, about 200 $\mu$M, about 150 $\mu$M, about 100 $\mu$M, about 50 $\mu$M, about 45 $\mu$M, about 40 $\mu$M, about 35 $\mu$M, about 30 $\mu$M, about 25 $\mu$M, about 20 $\mu$M, about 15 $\mu$M, about 10 $\mu$M, about 9 $\mu$M, about 8 $\mu$M, about 7 $\mu$M, about 6 $\mu$M, about 5 $\mu$M, about 4 $\mu$M, about 3 $\mu$M, about 2 $\mu$M, about 1 $\mu$M, about 0.5 $\mu$M, about 0.1 $\mu$M, about 0.05 $\mu$M, about 0.01 $\mu$M, about 0.005 $\mu$M, about 0.001 $\mu$M, about 0.0005 $\mu$M, about 0.0001 $\mu$M, or lower, including all values and ranges therebetween.

Preparation of the Compounds of the Disclosure

The compounds of the disclosure may possess one or more stereocenters, and each stereocenter may exist independently in either the R or S configuration. In some embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In some embodiments, a mixture of one or more isomer is utilized as the therapeutic compound described herein. In some embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the disclosure, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In some embodiments, the compounds described herein exist in solvated forms with pharmaceutically acceptable solvents such as water, and ethanol. In some embodiments, the compounds described herein exist in unsolvated form.

In some embodiments, the compounds of the disclosure may exist as tautomers. All tautomers are included within the scope of the compounds presented herein.

In some embodiments, compounds described herein are prepared as prodrugs. A "prodrug" refers to an agent that is converted into the parent drug in vivo. In some embodiments, upon in vivo administration, a prodrug is chemically converted to the biologically, pharmaceutically or therapeutically active form of the compound. In some embodiments, a prodrug is enzymatically metabolized by one or more steps or processes to the biologically, pharmaceutically or therapeutically active form of the compound.

In some embodiments, sites on, for example, the aromatic ring portion of compounds of the disclosure are susceptible to various metabolic reactions. Incorporation of appropriate substituents on the aromatic ring structures may reduce, minimize or eliminate this metabolic pathway. In some embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In some embodiments, isotopically-labeled compounds are useful in drug and/or substrate tissue distribution studies. In some embodiments, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In some embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference in their entireties). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In some embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed.

In some embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In some embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

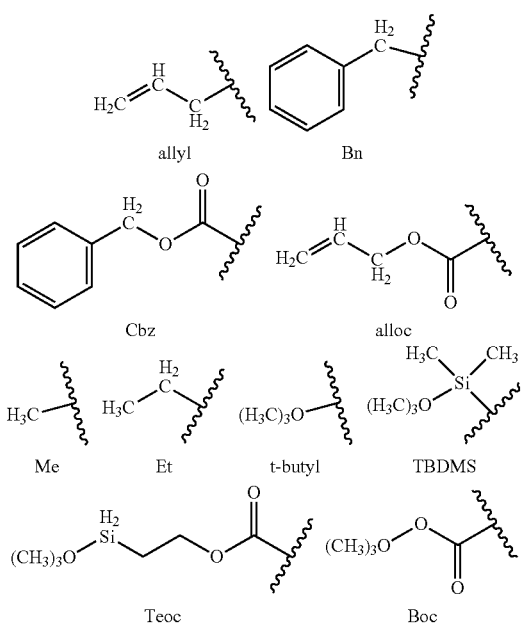

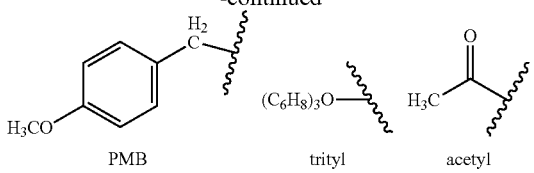

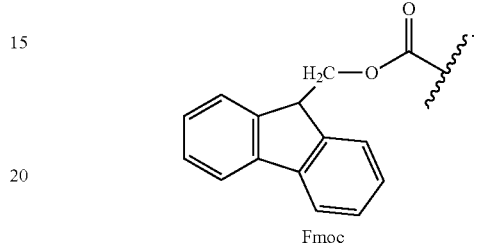

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In some embodiments, the compounds of the disclosure are synthesized using a semi-synthetic approach. In some embodiments, the compounds of the disclosure are synthesized using a biosynthetic approach. For example, In some embodiments, the compound is cyclized through an amide synthase reaction.

General routes for the preparation of a compound of the application are described in Scheme 1 herein.

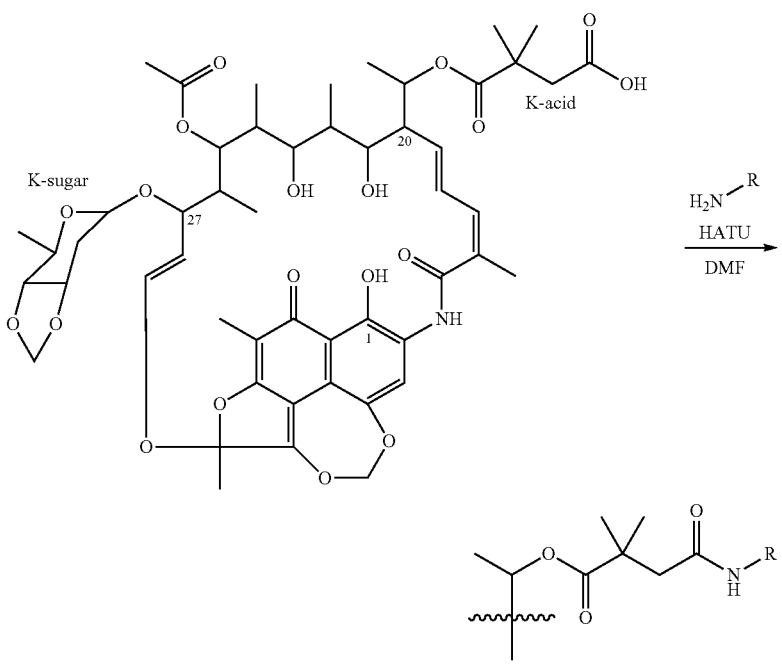

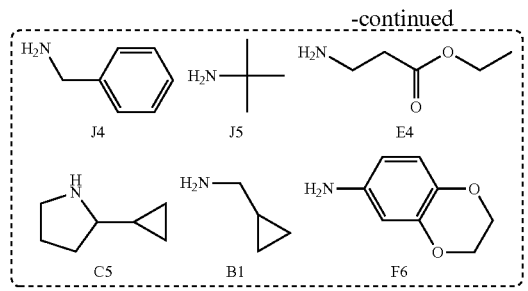

Pharmaceutical Compositions and Formulations

The disclosure also encompasses a pharmaceutical composition comprising a compound of the disclosure. In some embodiments, the pharmaceutical composition is useful for inhibiting bacterial infections. In some embodiments, the pharmaceutical composition is useful for overcoming antibacterial resistance. Such a pharmaceutical composition may consist of a compound of the disclosure in a form suitable for administration to a subject. The compound of the disclosure may be present in the pharmaceutical composition in the form of a physiologically acceptable salt, such as in combination with a physiologically acceptable cation, as is well known in the art.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

In some embodiments, the pharmaceutical compositions useful for practicing the method of the disclosure may be administered to deliver a dose of between 1 ng/kg/day and 100 mg/kg/day (e.g., about 1 ng/kg/day, about 10 ng/kg/day, 100 ng/kg/day, about 500 ng/kg/day, about 1000 ng/kg/day, about 5000 ng/kg/day, about 10000 ng/kg/day, about 50000 ng/kg/day, about 1 mg/kg/day, about 10 mg/kg/day, about 100 mg/kg/day, inclusive of all value sand ranges therebetween). In some embodiments, the pharmaceutical compositions useful for practicing the disclosure may be administered to deliver a dose of between 1 ng/kg/day and 500 mg/kg/day (e.g., about 1 ng/kg/day, about 10 ng/kg/day, 100 ng/kg/day, about 500 ng/kg/day, about 1000 ng/kg/day, about 5000 ng/kg/day, about 10000 ng/kg/day, about 50000 ng/kg/day, about 1 mg/kg/day, about 10 mg/kg/day, about 100 mg/kg/day, about 200 mg/kg/day, about 300 mg/kg/day, about 400 mg/kg/day, or about 500 mg/kg/day inclusive of all value sand ranges therebetween).

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient (e.g., about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, inclusive of all values and subranges therebetween).

Pharmaceutical compositions of the disclosure may be formulated for any suitable route of administration, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as cattle, pigs, horses, sheep, cats, and dogs.

In some embodiments, the compositions of the disclosure are formulated using one or more pharmaceutically acceptable excipients or carriers. In some embodiments, the pharmaceutical compositions of the disclosure comprise a therapeutically effective amount of a compound of the disclosure and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention or reduction of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; antiseptics; antiviral agents; anticoagulants; stabilizing agents; and pharmaceutically acceptable polymeric or hydrophobic materials. Other "additional ingredients" which may be included in the pharmaceutical compositions of the disclosure are known in the art and described, for example in Genaro, ed. (1985, Remington's Pharmaceutical Sciences, Mack Publishing Co., Easton, Pa.), which is incorporated herein by reference.

The composition of the disclosure may comprise a preservative from about 0.005% to 2.0% by total weight of the composition. The preservative is used to prevent spoilage in the case of exposure to contaminants in the environment. Examples of preservatives useful in accordance with the disclosure include but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

In some embodiments, the pharmaceutical compositions of the present disclosure (e.g., containing therapeutically effective amounts of one or more compounds of Formula (I), (II), and (III), may be formulated as immediate release formulation, a delayed release formulation, or a sustained release formulation, and may comprise at least one pharmaceutically acceptable carrier, diluent, and/or excipient. Pharmaceutically acceptable carriers, diluents or excipients include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier.

In some embodiments, suitable pharmaceutically acceptable carriers include, but are not limited to, inert solid fillers or diluents and sterile aqueous or organic solutions. Pharmaceutically acceptable carriers are well known to those skilled in the art and include, but are not limited to, aqueous and non-aqueous solutions. Pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate. Aqueous carriers suitable for use in the present application include, but are not limited to, water, ethanol, alcoholic/aqueous solutions, glycerol, emulsions or suspensions, including saline and buffered media.

Liquid carriers suitable for use in the present application include, but are not limited to, water (partially containing additives, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil).

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

The compositions useful within the disclosure comprise at least one compound of Formula (I), (II), and (III). The compositions of the disclosure may be used in aqueous emulsions such as latexes, water-based paints and coatings, caulks and adhesives, tape joint compounds, mineral slurries, water-cooling systems, personal care products, soaps and detergents, disinfectants, cleaners, and sanitizers, pesticide products, oilfield water and water-based fluids used in oilfield applications including drilling muds, fracturing fluids, and hydrotest fluids, and the like. In some embodiments, the composition is an antimicrobial composition. In some embodiments, the composition is an antiseptic.

Solid carriers suitable for use in the present application include, but are not limited to, inactive substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets may contain up to 99% of the active compound. Suitable solid carriers include, for example, calcium phosphate, magnesium stearate, talc, sugars, lactose, dextrin, starch, gelatin, cellulose, polyvinylpyrrolidone, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide delayed or controlled release of the active ingredient therein using, for example, hydroxypropyl methylcellulose in varying proportions to provide the desired release profile. Tablets may optionally be provided with an enteric coating, to provide release in parts of the gut other than the stomach.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations described herein. Diluents increase the bulk of a solid pharmaceutical composition and/or combination, and may make a pharmaceutical dosage form containing the composition and/or combination easier for the patient and care giver to handle. In various embodiments, diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT(r)), potassium chloride, powdered cellulose, sodium chloride, sorbitol, and talc, and/or mixtures of any of the foregoing. Some examples of: microcrystalline cellulose include those sold under the Trademark Avicel (FMC Corp., Philadelphia, Pa.), for example, Avicel™ pH101, Avicel™ pH102 and Avicel™ pH112; lactose include lactose monohydrate, lactose anhydrous and Pharmatose DCL21; dibasic calcium phosphate includes Emcompress.

Lubricants are used to facilitate tablet manufacture, promoting powder flow and preventing particle capping (i.e., particle breakage) when pressure is relieved. Useful lubricants are magnesium stearate, calcium stearate, stearic acid, glyceryl behenate, talc, colloidal silicon dioxide such as Aerosil™ 200, mineral oil (in PEG), hydrogenated vegetable oil (e.g., comprised of hydrogenated and refined triglycerides of stearic and palmitic acids), combinations thereof.

Binders are used to impart cohesive qualities to a tablet, and thus ensure that the tablet or tablet layer remains intact after compression. Suitable binder materials include, but are not limited to, starch (including corn starch and pregelatinized starch), gelatin, sugars (including sucrose, glucose, dextrose and lactose), polyethylene glycol, polyvinyl alcohol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum, and combinations thereof. Examples of polyvinylpyrrolidone include povidone, copovidone and crospovidone.

Fillers include, for example, materials such as silicon dioxide, titanium dioxide, alumina, talc, kaolin, powdered cellulose, microcrystalline cellulose, urea, sodium chloride, as well as saccharides, or combinations thereof. Any suitable saccharide may be used in the composition of the present disclosure. As used herein, the "saccharides" used in the disclosure include sugar alcohols, monosaccharides, disaccharides, and oligosaccharides. Exemplary sugar alcohols include, but not limited to, xylitol, mannitol, sorbitol, erythritol, lactitol, pentitol, and hexitol. Exemplary monosaccharides include, but are not limited to, glucose, fructose, aldose and ketose. Exemplary disaccharides include, but are not limited to, sucrose, isomalt, lactose, trehalose, and maltose. Exemplary oligosaccharides include, but are not limited to, fructo-oligosaccharides, inulin, galacto-ologosaccharides, and mannan-oligosaccharides. In some embodiments, the saccharide is sorbitol, mannitol, or xylitol. In some embodiments, the saccharide is sorbitol. In some embodiments, the saccharide is sucrose.

Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Other non-limiting examples of suitable disintegrants include, for example, lightly crosslinked polyvinyl pyrrolidone, corn starch, potato starch, maize starch and modified starches, croscarmellose sodium, crospovidone, sodium starch glycolate, and combinations and mixtures thereof.

In some embodiments of the present disclosure, the pharmaceutical composition may be prepared in an oral formulation. For oral administration, the compounds can be formulated readily by combining the active compounds with pharmaceutically acceptable carriers known in the art. Such carriers enable the compounds disclosed herein to be formulated as tablets, pills, dragees, capsules, liquids, gels, syrups, slurries, suspensions and the like, for oral ingestion by a subject. Pharmaceutical compositions for oral use may be obtained as solid excipients, optionally grinding a resulting mixture, and processing the mixture of granules, after adding suitable adjuvants, if desired, to obtain tablets or dragee cores. Such oral pharmaceutical compositions may also be prepared by milling or melt extrusion. Suitable excipients may be any of those disclosed herein and, in particular, fillers such as sugars, including lactose, sucrose, mannitol, or sorbitol; cellulose formulation such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP) formulation. Also, disintegrating agents may be employed, such as cross-linked polyvinylpyrrolidone, agar, or alginic acid or a salt thereof such as sodium alginate. Wetting agents, such as sodium dodecyl sulfate and the like, may be added.

In some embodiments, one or more of the compounds of Formula (I), (II), and/or (III) are combined with excipients to form a core comprising an active (an active core), thereby forming a solid dosage form. In some embodiments, the active core may comprise an inert particle such as a sugar sphere with an appropriate mean particle size. In some embodiments, the inactive core may be a sugar sphere, a cellulose sphere, a spheroidal silicon dioxide bead, a buffer crystal or an encapsulated buffer crystal, such as calcium carbonate, sodium bicarbonate, fumaric acid, tartaric acid, etc. Buffer crystals are useful to alter the microenvironment. Alternatively in accordance with other embodiments, drug-containing microgranules or pellets may be prepared by rotogranulation, high-shear granulation and extrusion-spheronization or compression of the drug (as mini-tablets, e.g., having a diameter of about 2 mm or more), a polymeric binder and optionally fillers/diluents.

In some embodiments, dragee cores may be provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds doses.

In some embodiments, pharmaceutical compositions described herein comprise one or more delayed release components. In some embodiments, delayed release is achieved by appropriately coating a drug-containing component with one or more suitable delayed-release polymers (also referred to as a controlled release polymer or rate-controlling polymer) or embedding the drug in a matrix comprising one or more suitable delayed-release polymers. Suitable delayed-release polymers include pharmaceutically acceptable water-insoluble polymers (also referred to as hydrophobic polymers), pharmaceutically acceptable water-soluble polymers (also referred to as hydrophilic polymers), pharmaceutically acceptable gastrosoluble polymers, pharmaceutically acceptable enteric polymers, and combinations thereof.

Non-limiting examples of pharmaceutically acceptable water-insoluble polymers include acrylic polymers, methacrylic acid polymers, acrylic copolymers, such as a methacrylic acid-ethyl acrylate copolymer available under the trade name of EUDRAGIT® (type L, RL, RS and NE30D), and their respective esters, zein, waxes, shellac and hydrogenated vegetable oil, cellulose derivatives, such as ethyl cellulose, cellulose acetate, cellulose acetate butyrate, and the like.

Non-limiting examples of pharmaceutically acceptable water-soluble polymers include homopolymers and copolymers of N-vinyl lactams, including homopolymers and copolymers of N-vinyl pyrrolidone, e.g. polyvinylpyrrolidone (PVP), copolymers of N-vinyl pyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, and hydroxypropylmethylcellulose, cellulose phthalates, succinates, butyrates, or trimellitates, in particular cellulose acetate phthalate, hydroxypropylmethylcellulose phthalate, hydroxypropylmethylcellulose succinate, and hydroxypropylmethylcellulose acetate succinate; high molecular polyalkylene oxides such as polyethylene oxide and polypropylene oxide and copolymers of ethylene oxide and propylene oxide, polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, polyethylene glycol oligo- and polysaccharides such as carrageenans, galactomannans and xanthan gum, or mixtures of one or more thereof.

Non-limiting examples of gastrosoluble polymers include maltrin, an aminoalkyl methacrylate copolymer available under the trade name of EUDRAGIT® (type E100 or EPO), polyvinylacetal diethylaminoacetate e.g., AEA® available from Sankyo Company Limited, Tokyo (Japan), and the like.

Non-limiting examples of such enteric polymers include carboxymethylethylcellulose, cellulose acetate phthalate (CAP), cellulose acetate succinate, methylcellulose phthalate, hydroxymethylethylcellulose phthalate, hydroxypropylmethylcellulose phthalate (HPMCP), hydroxypropylmethylcellulose acetate succinate (HPMCAS), polyvinyl alcohol phthalate, polyvinyl butyrate phthalate, polyvinyl acetal phthalate (PVAP), a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, cellulose acetate hexahydrophthalate, hydroxypropyl methylcellulose hexahydrophthalate, hydroxypropyl methylcellulose phthalate, cellulose propionate phthalate, cellulose acetate maleate, cellulose acetate trimellitate, cellulose acetate butyrate, cellulose acetate propionate, methacrylic acid/methacrylate polymer (acid number 300 to 330 and also known as EUDRAGIT L), methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SANDARAC, copal collophorium, and combinations comprising one or more of the foregoing polymers. Yet other examples of enteric polymers include synthetic resin bearing carboxyl groups. The term "enteric polymer" as used herein is defined to mean a polymeric substance that when used in an enteric coat formulation, is substantially insoluble and/or substantially stable under acidic conditions at a pH of less than about 5 and which are substantially soluble or can decompose under conditions exhibiting a pH of about 5 or more.

Non-limiting examples of hydrophilic polymers include hydroxypropyl celluloses (HPC), hydroxypropyl methylcelluloses, methylcelluloses, polyethylene oxides, sodium carboxymethyl celluloses, and the like, or combinations thereof.

In some embodiments, the delayed release component is a matrix. As used herein, the term "matrix" means a composition in which the drug is embedded or dispersed in water soluble, water insoluble, or hydrophilic polymers, or lipophilic maters, in order to achieve delayed release of the drug. The mechanisms of the drug release generally involve drug diffusion through a viscous gel layer or tortuous channels; and/or drug dissolution via gradual erosion or degradation of the polymer(s). In some embodiments, the matrix comprises swellable/erodable polymers, for example hydrophilic polymers which in contact with the water form a gel of high viscosity. In other embodiments, the matrix comprises water-insoluble polymers or lipophilic polymers.

For example, the matrix may be prepared using one or more hydrophilic polymers (e.g., hydroxypropyl cellulose, hydroxypropyl methylcellulose, polyethylene oxide), one or more lipophilic materials (e.g., carnauba wax, hardened castor oil, hardened rape seed oil, polyglycerin fatty acid ester), and/or coating tablets or granules with one or more delayed release polymers (e.g., cellulose polymers such as ethylcellulose; acrylic acid copolymer such as aminoalkyl methacrylate copolymer RS [Eudragit RS (trade name, Degussa Co.)], ethyl acrylate-methyl methacrylate copolymer suspension [Eudragit NE (trade name, Degussa Co.)]).

The hydrophilic matrix may further contain a pH-dependent polymer. The term "pH-dependent" refers to a polymer which releases the active at a certain pH. Non-limiting examples of suitable pH-dependent polymers include hydroxypropyl methylcellulose phthalate, cellulose acetate phthalate, carboxymethyl ethyl cellulose, methyl methacrylate-methacrylic acid copolymer, methacrylic acid-ethyl acrylate copolymer, ethyl acrylate-methyl methacrylate-trimethylammoniumethyl methacrylate chloride copolymer, methyl methacrylate-ethyl acrylate copolymer, methacrylic acid-methyl acrylate-methyl methacrylate copolymer, hydroxypropyl cellulose acetate succinate, polyvinyl acetate phthalate and the like, and combinations thereof.

In some embodiments, the pharmaceutical composition is formulated as a sustained release formulations, e.g., by appropriately integrating additional polymers into the composition, or as coatings over the core (e.g., pellet or granule). The polymers useful for this purpose can be, but are not limited to, ethylcellulose; hydroxypropylmethylcellulose; hydroxypropylcellulose; hydroxyethylcellulose; carboxymethylcellulose; methylcellulose; nitrocellulose; Eudragit R; Eudragit RS; and Eudragit RL; Carbopol; polyethyleneoxide or polyethylene glycols with molecular weights in excess of 8,000 daltons. In some embodiments, these polymers are present concentrations from about 4-20 w/w % (e.g., about 4, about 5, about 6, about 7, about 8, about 9, about 10, about 11, about 12, about 13, about 14, about 15, about 16, about 17, about 18, about 19, or about 20% w/w %). The sustained release polymers may be combined with the delayed release components described above.

The compositions useful within the disclosure may further comprise at least one additional antimicrobial agent. Non-limiting examples of the at least one additional antimicrobial agent are levofloxacin, doxycycline, neomycin, clindamycin, minocycline, gentamycin, rifampin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, lipopeptides, ketolides, polyenes, azoles, echinocandines, and any combination thereof.

In some embodiments, the compound of the disclosure and the at least one additional antimicrobial agent act synergistically in preventing, reducing or treating bacterial infections. A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The pharmaceutical compositions may be prepared by any suitable method, such as mixing, dissolving, granulating, dragee-making, levigating, emulsifying, encapsulating, entrapping, or lyophilizing processes.

Granulating techniques are well known in the pharmaceutical art for modifying starting powders or other particulate materials of an active ingredient. The powders may be mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

Methods of Use

In one aspect, the disclosure provides a method of preventing or reducing the growth or proliferation of microorganisms.

In some embodiments, the disclosure provides a method of preventing or reducing the growth of, or preventing or reducing the proliferation of a microorganism comprising administering to a subject in need thereof a therapeutically effective amount of a compound of Formula (I), Formula (II), or Formula (III).

In some embodiments, the disclosure provides a method of reducing the growth of or reducing the proliferation of a microorganism comprising administering to a subject in need thereof a therapeutically effective amount of a compound of Formula (I), Formula (II), or Formula (III).

In some embodiments, the disclosure provides a method of reducing the proliferation of a microorganism comprising administering to a subject in need thereof a therapeutically effective amount of a compound of Formula (I), Formula (II), or Formula (III).

In some embodiments, the disclosure provides a method of reducing the growth of a microorganism comprising administering to a subject in need thereof a therapeutically effective amount of a compound of Formula (I), Formula (II), or Formula (III).

In some embodiments, the disclosure provides use of a compound of Formula (I), Formula (II), or Formula (III) for the prevention or reduction of the growth of, or prevention or reduction of the proliferation of a microorganism.

In some embodiments, the disclosure provides use of a compound of Formula (I), Formula (II), or Formula (III) for the reduction of the growth of or reduction of the proliferation of a microorganism.

In some embodiments, the disclosure provides use of a compound of Formula (I), Formula (II), or Formula (III) for the reduction of the growth of a microorganism.

In some embodiments, the disclosure provides use of a compound of Formula (I), Formula (II), or Formula (III) for the reduction of the proliferation of a microorganism.

In some embodiments, the disclosure provides use of a compound of Formula (I), Formula (II), or Formula (III), for the manufacture of a medicament, for the prevention or reduction of the growth of, or prevention or reduction of the proliferation of a microorganism.

In some embodiments, the disclosure provides use of a compound of Formula (I), Formula (II), or Formula (III), for the manufacture of a medicament, for the reduction of the growth of or reduction of the proliferation of a microorganism.

In some embodiments, the disclosure provides use of a compound of Formula (I), Formula (II), or Formula (III), for the manufacture of a medicament, for the reduction of the growth of a microorganism.

In some embodiments, the disclosure provides use of a compound of Formula (I), Formula (II), or Formula (III), for the manufacture of a medicament, for the reduction of the proliferation of a microorganism.

In some embodiments, the disclosure provides a compound of Formula (I), Formula (II), or Formula (III) for use in preventing or reducing the growth of, or preventing or reducing the proliferation of a microorganism.

In some embodiments, the disclosure provides a compound of Formula (I), Formula (II), or Formula (III) for use in reducing the growth of or reducing the proliferation of a microorganism.

In some embodiments, the disclosure provides a compound of Formula (I), Formula (II), or Formula (III) for use in reducing the growth of a microorganism.

In some embodiments, the disclosure provides a compound of Formula (I), Formula (II), or Formula (III) for use in reducing the proliferation of a microorganism.

In some embodiments, the disclosure provides a method of preventing or reducing the growth of, or preventing or reducing the proliferation of a microorganism comprising administering to a subject in need thereof a therapeutically effective amount of Compound J4.

In some embodiments, the disclosure provides a method of reducing the growth of or reducing the proliferation of a microorganism comprising administering to a subject in need thereof a therapeutically effective amount of Compound J4.

In some embodiments, the disclosure provides a method of reducing the proliferation of a microorganism comprising administering to a subject in need thereof a therapeutically effective amount of Compound J4.

In some embodiments, the disclosure provides a method of reducing the growth of a microorganism comprising administering to a subject in need thereof a therapeutically effective amount of Compound J4.

In some embodiments, the disclosure provides use of Compound J4 for the prevention or reduction of the growth of, or prevention or reduction of the proliferation of a microorganism.

In some embodiments, the disclosure provides use of Compound J4 for the reduction of the growth of or reduction of the proliferation of a microorganism.

In some embodiments, the disclosure provides use of Compound J4 for the reduction of the growth of a microorganism.

In some embodiments, the disclosure provides use of Compound J4 for the reduction of the proliferation of a microorganism.

In some embodiments, the disclosure provides use of Compound J4, for the manufacture of a medicament, for the prevention or reduction of the growth of, or prevention or reduction of the proliferation of a microorganism.

In some embodiments, the disclosure provides use of Compound J4, for the manufacture of a medicament, for the reduction of the growth of or reduction of the proliferation of a microorganism.

In some embodiments, the disclosure provides use of Compound J4, for the manufacture of a medicament, for the reduction of the growth of a microorganism.

In some embodiments, the disclosure provides use of Compound J4, for the manufacture of a medicament, for the reduction of the proliferation of a microorganism.

In some embodiments, the disclosure provides Compound J4 for use in preventing or reducing the growth of, or preventing or reducing the proliferation of a microorganism.

In some embodiments, the disclosure provides Compound J4 for use in reducing the growth of or reducing the proliferation of a microorganism.

In some embodiments, the disclosure provides Compound J4 for use in reducing the growth of a microorganism.

In some embodiments, the disclosure provides Compound J4 for use in reducing the proliferation of a microorganism.

In some embodiments, the method comprises, contacting the microorganism with a composition comprising a compound of the disclosure.

In some embodiments, the microorganism is a bacterium. In some embodiments the bacteria include at least eleven distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green non-sulfur bacteria (also anaerobic phototrophs); (10) Radioresistant micrococci and relatives; (11) Thermotoga and Thermosipho thermophiles.

In some embodiments, the bacteria include cocci, nonenteric rods, enteric rods, nonsporulating rods, and sporulating rods. In some embodiments, bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, Fusobacterium, Brachyspira, Legionella, Helicobacter, Actinomyces, Bacillus, Clostridium, Corynebacterium, Erysipelothrix, Lactobacillus, Listeria, Mycobacterium, Myxococcus, Nocardia, Staphylococcus, Streptococcus, Streptomyces, Firmicutes, Borrelia, Campylobacter, Cryptosporidium, Entamoeba, Enterobacter, Gardnerella, Leishmania, Moraxella, Mycoplasma, Providencia, Serpulina, Toxoplasmosis, Tubercle, Acinetobacter, Enterococcus.*

In some embodiments, the genus of bacteria include *Mycobacterium*.

In some embodiments, the genera of bacteria include, for example, *Neisseria, Haemophilus, Bacteroides, Chlamydia, Brachyspira pilosicoli, Legionella*, and *Helicobacter*.

In some embodiments, the genera of bacteria include, for example, *Clostridium, Listeria, Staphylococcus*, and *Firmicutes*

In some embodiments, the bacterium is resistant to at least one antibiotic. In some embodiments, bacterium that has at least one point mutation that confers antibiotic resistance. In some embodiments, the bacterium has one or more of the following mutations of one or more amino acids: (1) serine to leucine; (2) histidine to tyrosine; (3) or asparagine to tyrosine. In some embodiments, the bacterium is resistant to rifamycin. In some embodiments, the bacterium is *Staphylococcus aureus, Staphylococcus epidermidis, Listeria monocytogenes Salmonella enterica, Pseudomonas aeruginosa, Proteus mirabills, Enterococcus faecium, Acinetobacter baumannii*, and *Mycobacterium tuberculosis*. In some embodiments, the *S. aureus* carries a mutation in its RNA polymerase (RNAP). In some embodiments, the *S. aureus* RNAP mutation is S447L, H481Y, or D471Y.

In one aspect, the disclosure provides a method of treating or preventing a bacterial infection in a subject.

In some embodiments, the disclosure provides a method of treating or preventing a bacterial infection comprising administering to a subject in need thereof a therapeutically effective amount of a compound of Formula (I), Formula (II), or Formula (III).

In some embodiments, the disclosure provides a method of treating a bacterial infection comprising administering to a subject in need thereof a therapeutically effective amount of a compound of Formula (I), Formula (II), or Formula (III).

In some embodiments, the disclosure provides use of a compound of Formula (I), Formula (II), or Formula (III) for the treatment or prevention of a bacterial infection.

In some embodiments, the disclosure provides use of a compound of Formula (I), Formula (II), or Formula (III) for the treatment of a bacterial infection.

In some embodiments, the disclosure provides use of a compound of Formula (I), Formula (II), or Formula (III), for the manufacture of a medicament, for the treatment or prevention of a bacterial infection.

In some embodiments, the disclosure provides use of a compound of Formula (I), Formula (II), or Formula (III), for the manufacture of a medicament, for the treatment of a bacterial infection.

In some embodiments, the present disclosure provides a compound of Formula (I), Formula (II), or Formula (III) for use in treating or preventing a bacterial infection.

In some embodiments, the present disclosure provides a compound of Formula (I), Formula (II), or Formula (III) for use in treating a bacterial infection.

In some embodiments, the disclosure provides a method of treating or preventing a bacterial infection comprising administering to a subject in need thereof a therapeutically effective amount of Compound J4.

In some embodiments, the disclosure provides a method of treating a bacterial infection comprising administering to a subject in need thereof a therapeutically effective amount of Compound J4.

In some embodiments, the disclosure provides use of Compound J4 for the treatment or prevention of a bacterial infection.

In some embodiments, the disclosure provides use of Compound J4 for the treatment of a bacterial infection.

In some embodiments, the disclosure provides use of Compound J4, for the manufacture of a medicament, for the treatment or prevention of a bacterial infection.

In some embodiments, the disclosure provides use of Compound J4, for the manufacture of a medicament, for the treatment of a bacterial infection.

In some embodiments, the present disclosure provides Compound J4 for use in treating or preventing a bacterial infection.

In some embodiments, the present disclosure provides Compound J4 for use in treating a bacterial infection.

In some embodiments, the method comprises, administering to the subject a composition comprising a compound of the disclosure.

In some embodiments, the subject has a bacterial infection.

In some embodiments, the bacterial infection is resistant to at least one antibiotic treatment. In some embodiments, the bacterial infection is caused by a bacterium that has at least one point mutation that confers antibiotic resistance. In some embodiments, the bacterium has one or more of the following mutations of one or more amino acids: (1) serine to leucine; (2) histidine to tyrosine; (3) or asparagine to tyrosine.

In some embodiments, the bacterial infection is resistant to rifamycin. Examples of rifamycin-resistance can be found in J Antibiot (Tokyo). 2014 September; 67(9):625-30. doi: 10.1038/ja.2014.107. Epub 2014 Aug. 13, which is herein incorporated by reference in its entirety. Examples of methods to identify rifamycin-resistant bacteria include Polymerase chain reaction (e.g., Lancet. 1993 Mar. 13; 341 (8846):647-50, which is herein incorporated by reference in its entirety).

In some embodiments, the bacterial infection is an infection of *Staphylococcus aureus, Staphylococcus epidermidis, Listeria monocytogenes* and *M. tuberculosis*. In some embodiments, the *S. aureus* carries a mutation in its RNA polymerase (RNAP). In some embodiments, the *S. aureus* RNAP mutation is S447L, H481Y, or D471Y.

In some embodiments, the disclosure provides a method of treating or preventing a disease or condition comprising administering to a subject in need thereof a therapeutically effective amount of a compound of Formula (I), Formula (II), or Formula (III).

In some embodiments, the disclosure provides a method of treating a disease or condition comprising administering to a subject in need thereof a therapeutically effective amount of a compound of Formula (I), Formula (II), or Formula (III).

In some embodiments, the disclosure provides use of a compound of Formula (I), Formula (II), or Formula (III) for the treatment or prevention of a disease or condition.

In some embodiments, the disclosure provides use of a compound of Formula (I), Formula (II), or Formula (III) for the treatment of a disease or condition.

In some embodiments, the disclosure provides use of a compound of Formula (I), Formula (II), or Formula (III), for the manufacture of a medicament, for the treatment or prevention of a disease or condition.

In some embodiments, the disclosure provides use of a compound of Formula (I), Formula (II), or Formula (III), for the manufacture of a medicament, for the treatment of a disease or condition.

In some embodiments, the disclosure provides a compound of Formula (I), Formula (II), or Formula (III) for use in treating or preventing a disease or condition.

In some embodiments, the disclosure provides a compound of Formula (I), Formula (II), or Formula (III) for use in treating a disease or condition.

In some embodiments, the disclosure provides a method of treating or preventing a disease or condition comprising administering to a subject in need thereof a therapeutically effective amount of Compound J4.

In some embodiments, the disclosure provides a method of treating a disease or condition comprising administering to a subject in need thereof a therapeutically effective amount of Compound J4.

In some embodiments, the disclosure provides use of Compound J4 for the treatment or prevention of a disease or condition.

In some embodiments, the disclosure provides use of Compound J4 for the treatment of a disease or condition.

In some embodiments, the disclosure provides use of Compound J4, for the manufacture of a medicament, for the treatment or prevention of a disease or condition.

In some embodiments, the disclosure provides use of Compound J4, for the manufacture of a medicament, for the treatment of a disease or condition.

In some embodiments, the disclosure provides Compound J4 for use in treating or preventing a disease or condition.

In some embodiments, the disclosure provides Compound J4 for use in treating a disease or condition.

In some embodiments, the disease or the condition is selected from the group consisting of tuberculosis, *Mycobacterium avium* complex, *Myobacterium leprae*, leprosy, and Legionnaires' disease, methicillin-resistant *Staphylococcus aureus* (MRSA), *Staphylococcus epidermidis, Neisseria meningitidis* (meningococcal) infections, tick-borne pathogens, including *Borrelia burgdorferi* and *Anaplasma phagocytophilum*, infections by *Listeria* species, such as *Neisseria gonorrhoeae, Haemophilus influenzae, Haemophilus influenzae* type b, and *Legionella pneumophila*, primary amoebic meningoencephalitis caused by Naegleria fowleri, *Mycobacterium kansasii*, Pruritus biliary cholangitis, *Chlamydophila pneumonia*, irritable bowel syndrome (IBS), Travelers' Diarrhea caused by *E. coli*, hepatic encephalopathy, infectious diarrhea, small intestinal bacterial overgrowth, diverticular disease, *Chlamydia* infection, *Clostridium difficile* associated diarrhea (CDAD), trachoma, buruli ulcer caused by *Mycobacterium ulcerans*, and gastric ulcer disease caused by *Helicobacter pylori*.

In some embodiments, the bacterium treated with compounds disclosed herein has one or more of the following mutations of one or more amino acids: (1) serine to leucine; (2) histidine to tyrosine; (3) asparagine to tyrosine; (4) aspartic acid to valine; (5) histidine to aspartic acid; (6) aspartic acid to glutamic acid; (7) histidine to asparagine; or (8) serine to tryptophan. Other mutations and mutated bacteria suitable for treatment with the present includes are disclosed in, e.g., "Resistance to rifampicin: a review" (*J Antibiot* (2014), 67(9), 625-30), MUBII-TB-DB: a database of mutations associated with antibiotic resistance in *Mycobacterium tuberculosis* (*BMC Bioinformatics* (2014) 15, 107), and the Comprehensive Antibiotic Resistance Database, which are herein incorporated by reference in their entireties for all purposes.

In some embodiments, the point mutation is Ser531Leu. In some embodiments, the point mutation is His526Asn. In some embodiments, the point mutation is Asp516Val. In some embodiments, the point mutation is His526Tyr. In some embodiments, the point mutation is His526Asp. In some embodiments, the point mutation is Asp516Glu. In some embodiments, the point mutation is Ser531Trp.

In some embodiments, the method further comprises administering to the subject an additional therapeutic agent. In some embodiments, the compound of the disclosure and the therapeutic agent are co-administered to the subject. In some embodiments, the compound of the disclosure and the therapeutic agent are co-formulated and co-administered to the subject. In some embodiments, the therapeutic agent is an antibacterial agent or an antiviral agent.

In some embodiments, the subject is a mammal. In some embodiments, the mammal is a human.

Methods of determining antibiotic resistance (e.g., resistance to rifamycin) are known in the art. For example, in Brock Biology of Microorganisms, $11^{th}$ edition (Pearson, 2006) which is herein incorporated by reference in its entirety for all purposes. In some embodiments, the method includes antimicrobial susceptibility testing. In some embodiments, the method is an agar diffusion method. In some embodiments, the method is a tube dilution technique to determine the minimum inhibitory concentration (MIC). In some embodiments, the method includes an antibiotic dilution assay in culture. In some embodiments, the method includes an antibiotic dilution assay in tubes. In some embodiments, the method includes the Kirby-Bauer method.

The "minimum inhibitory concentration" or "MIC" refers to the lowest concentration of an antimicrobial agent that will inhibit the visible growth of a microorganism after overnight (in vitro) incubation. Minimum inhibitory concentrations are important in diagnostic laboratories to confirm resistance of microorganisms to an antimicrobial agent and also to monitor the activity of new antimicrobial agents. The MIC is generally regarded as the most basic laboratory measurement of the activity of an antimicrobial agent against a bacterial organism. Thus, in some embodiments, the one or more antibacterial agents described herein have a minimum inhibitory concentration (MIC) against the bacteria or bacterium that is reduced by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to rifamycin. In some embodiments, the oligomer reduces the minimum inhibitory concentration (MIC) of an antimicrobial agent against the bacteria or bacterium by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to the antimicrobial agent alone. In some embodiments, the bacterium is *Staphylococcus aureus, Staphylococcus epidermidis, Listeria monocytogenes* or *M. tuberculosis*. In some embodiments, the bacterium is *Mycobacterium tuberculosis*.

In some embodiments, a bacterium is considered to be resistant to rifamycin if the MIC of rifamycin is greater than or equal to about 50 μm/mL, e.g., about 60 μm/mL, about 70 μm/mL, about 80 μm/mL, about 90 μm/mL, about 100 μm/mL, about 150 μm/mL, about 200 μm/mL, about 250 μm/mL, about 300 μm/mL, about 350 μm/mL, about 400 μm/mL, about 450 μm/mL, about 500 μm/mL, or more.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses, and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection may be also monitored using diagnostic techniques used to monitor the particular type of bacterial infection under treatment.

The therapeutic formulations may be administered to the patient either prior to or after the onset of pathogenic colonization, biofilm formation, and/or infection in a patient. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient, preferably a mammal, more preferably a human, may be carried out using known procedures, at dosages and for periods of time effective to prevent, reduce or disrupt pathogenic colonization, biofilm formation, and/or infection in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of breathing control disorders in a patient.

The therapeutically effective amount or dose of a compound of the present disclosure depends on the age, sex and weight of the patient, the current medical condition of the patient and the severity of the disease or infection in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the disclosure for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, a compound of the disclosure is administered at an amount of about 1 mg to about 2,500 mg. In some embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In some embodiments, the compound of the disclosure is administered at an amount of about 0.1 mg/kg to about 100 mg/kg. In some embodiments, a compound of the disclosure is administered at an amount of about 0.2 mg/kg to about 100 mg/kg. In some embodiments, a compound of the disclosure is administered at an amount of about 0.3 mg/kg to about 100 mg/kg. In some embodiments, a compound of the disclosure is administered at an amount of about 0.4 mg/kg to about 100 mg/kg. In some embodiments, a compound of the disclosure is administered at an amount of about 0.5 mg/kg to about 100 mg/kg. In some embodiments, a compound of the disclosure is administered at an amount of about 0.6 mg/kg to about 100 mg/kg. In some embodiments, a compound of the disclosure is administered at an amount of about 0.7 mg/kg to about 100 mg/kg. In some embodiments, a compound of the disclosure is administered at an amount of about 0.8 mg/kg to about 100 mg/kg. In some embodiments, a compound of the disclosure is administered at an amount of about 0.9 mg/kg to about 100 mg/kg. In some embodiments, a compound of the disclosure is administered at an amount of about 1 mg/kg to about 100 mg/kg. In some embodiments, a compound of the disclosure is administered at an amount of about 2 mg/kg to about 100 mg/kg. In some embodiments, a compound of the disclosure is administered at an amount of about 3 mg/kg to about 100 mg/kg. In some embodiments, a compound of the disclosure is administered at an amount of about 4 mg/kg to about 100 mg/kg. In some embodiments, a compound of the disclosure is administered at an amount of about 5 mg/kg to about 100 mg/kg. In some embodiments, a compound of the disclosure is administered at an amount of about 6 mg/kg to about 100 mg/kg. In some embodiments, a compound of the disclosure is administered at an amount of about 7 mg/kg to about 100 mg/kg. In some embodiments, a compound of the disclosure is administered at an amount of about 8 mg/kg to about 100 mg/kg. In some embodiments, a compound of the disclosure is administered at an amount of about 9 mg/kg to about 100 mg/kg. In some embodiments, a compound of the disclosure is administered at an amount of about 10 mg/kg to about 100 mg/kg. In some embodiments, a compound of the disclosure is administered at an amount of about 15 mg/kg to about 100 mg/kg. In some embodiments, a compound of the disclosure is administered at an amount of about 20 mg/kg to about 100 mg/kg. In some embodiments, a compound of the disclosure is administered at an amount of about 25 mg/kg to about 100 mg/kg. In some embodiments, a compound of the disclosure is administered at an amount of about 30 mg/kg to about 100 mg/kg. In some embodiments, a compound of the disclosure is administered at an amount of about 35 mg/kg to about 100 mg/kg. In some embodiments, a compound of the disclosure is administered at an amount of about 40 mg/kg to about 100 mg/kg. In some embodiments, a compound of the disclosure is administered at an amount of about 45 mg/kg to about 100 mg/kg. In some embodiments, a compound of the disclosure is administered at an amount of about 50 mg/kg to about 100 mg/kg. In some embodiments, a compound of the disclosure is administered at an amount of about 55 mg/kg to about 100 mg/kg. In some embodiments, a compound of the disclosure is administered at an amount of about 60 mg/kg to about 100 mg/kg. In some embodiments, a compound of the disclosure is administered at an amount of about 65 mg/kg to about 100 mg/kg. In some embodiments, a compound of the disclosure is administered at an amount of about 70 mg/kg to about 100 mg/kg. In some embodiments, a compound of the disclosure is administered at an amount of about 75 mg/kg to about 100 mg/kg. In some embodiments, a compound of the disclosure is administered at an amount of about 80 mg/kg to about 100 mg/kg. In some embodiments, a compound of the disclosure is administered at an amount of about 85 mg/kg to about 100 mg/kg. In some embodiments, a compound of the disclosure is administered at an amount of about 90 mg/kg to about 100 mg/kg. In some embodiments, a compound of the disclosure is administered at an amount of about 95 mg/kg to about 100 mg/kg.

In some embodiments, a compound of the disclosure is administered at an amount of about 0.1 mg/kg to about 95 mg/kg. In some embodiments, a compound of the disclosure is administered at an amount of about 0.1 mg/kg to about 90 mg/kg. In some embodiments, a compound of the disclosure is administered at an amount of about 0.1 mg/kg to about 85 mg/kg. In some embodiments, a compound of the disclosure is administered at an amount of about 0.1 mg/kg to about 80 mg/kg. In some embodiments, a compound of the disclosure is administered at an amount of about 0.1 mg/kg to about 75 mg/kg. In some embodiments, a compound of the disclosure is administered at an amount of about 0.1 mg/kg to about 70 mg/kg. In some embodiments, a compound of the disclosure is administered at an amount of about 0.1 mg/kg to about 65 mg/kg. In some embodiments, a compound of the disclosure is administered at an amount of about 0.1 mg/kg to about 60 mg/kg. In some embodiments, a compound of the disclosure is administered at an amount of about 0.1 mg/kg to about 55 mg/kg. In some embodiments, a compound of the disclosure is administered at an amount of about 0.1 mg/kg to about 50 mg/kg. In some embodiments, a compound of the disclosure is administered at an amount of about 0.1 mg/kg to about 45 mg/kg. In some embodiments, a compound of the disclosure is administered at an amount of about 0.1 mg/kg to about 40 mg/kg. In some embodiments, a compound of the disclosure is administered at an amount of about 0.1 mg/kg to about 35 mg/kg. In some embodiments, a compound of the disclosure is administered at an amount of about 0.1 mg/kg to about 30 mg/kg. In some embodiments, a compound of the disclosure is administered at an amount of about 0.1 mg/kg to about 25 mg/kg. In some embodiments, a compound of the disclosure is administered at an amount of about 0.1 mg/kg to about 20 mg/kg. In some embodiments, a compound of the disclosure is administered at an amount of about 0.1 mg/kg to about 15 mg/kg. In some embodiments, a compound of the disclosure is administered at an amount of about 0.1 mg/kg to about 10 mg/kg. In some embodiments, a compound of the disclosure is administered at an amount of about 0.1 mg/kg to about 9 mg/kg. In some embodiments, a compound of the disclosure is administered at an amount of about 0.1 mg/kg to about 8 mg/kg. In some embodiments, a compound of the disclosure is administered at an amount of about 0.1 mg/kg to about 7 mg/kg. In some embodiments, a compound of the disclosure is administered at an amount of about 0.1 mg/kg to about 6 mg/kg. In some embodiments, a compound of the disclosure is administered at an amount of about 0.1 mg/kg to about 5 mg/kg. In some embodiments, a compound of the disclosure is administered at an amount of about 0.1 mg/kg to about 4 mg/kg. In some embodiments, a compound of the disclosure is administered at an amount of about 0.1 mg/kg to about 3 mg/kg. In some embodiments, a compound of the disclosure is administered at an amount of about 0.1 mg/kg to about 2 mg/kg. In some embodiments, a compound of the disclosure is administered at an amount of about 0.1 mg/kg to about 1 mg/kg. In some embodiments, a compound of the disclosure is administered at an amount of about 0.1 mg/kg to about 0.9 mg/kg. In some embodiments, a compound of the disclosure is administered at an amount of about 0.1 mg/kg to about 0.8 mg/kg. In some embodiments, a compound of the disclosure is administered at an amount of about 0.1 mg/kg to about 0.7 mg/kg. In some embodiments, a compound of the disclosure is administered at an amount of about 0.1 mg/kg to about 0.6 mg/kg. In some embodiments, a compound of the disclosure is administered at an amount of about 0.1 mg/kg to about 0.5 mg/kg. In some embodiments, a compound of the disclosure is administered at an amount of about 0.1 mg/kg to about 0.4 mg/kg. In some embodiments, a compound of the disclosure is administered at an amount of about 0.1 mg/kg to about 0.3 mg/kg. In some embodiments, a compound of the disclosure is administered at an amount of about 0.1 mg/kg to about 0.2 mg/kg.

In some embodiments, a compound of the disclosure is administered at an amount of about 0.1 mg/kg. In some embodiments, a compound of the disclosure is administered at an amount of about 0.2 mg/kg. In some embodiments, the compound of the disclosure is administered at an amount of about 0.3 mg/kg. In some embodiments, a compound of the disclosure is administered at an amount of about 0.4 mg/kg. In some embodiments, a compound of the disclosure is administered at an amount of about 0.5 mg/kg. In some embodiments, a compound of the disclosure is administered at an amount of about 0.6 mg/kg. In some embodiments, a compound of the disclosure is administered at an amount of about 0.7 mg/kg. In some embodiments, a compound of the disclosure is administered at an amount of about 0.8 mg/kg. In some embodiments, a compound of the disclosure is administered at an amount of about 0.9 mg/kg. In some embodiments, a compound of the disclosure is administered at an amount of about 1 mg/kg. In some embodiments, a compound of the disclosure is administered at an amount of about 2 mg/kg. In some embodiments, a compound of the disclosure is administered at an amount of about 3 mg/kg. In some embodiments, a compound of the disclosure is administered at an amount of about 4 mg/kg. In some embodiments, a compound of the disclosure is administered at an amount of about 5 mg/kg. In some embodiments, a compound of the disclosure is administered at an amount of about 6 mg/kg. In some embodiments, a compound of the disclosure is administered at an amount of about 7 mg/kg. In some embodiments, a compound of the disclosure is administered at an amount of about 8 mg/kg. In some embodiments, a compound of the disclosure is administered at an amount of about 9 mg/kg. In some embodiments, a compound of the disclosure is administered at an amount of about 10 mg/kg. In some embodiments, a compound of the disclosure is administered at an amount of about 15 mg/kg. In some embodiments, a compound of the disclosure is administered at an amount of about 20 mg/kg. In some embodiments, a compound of the disclosure is administered at an amount of about 25 mg/kg. In some embodiments, a compound of the disclosure is administered at an amount of about 30 mg/kg. In some embodiments, a compound of the disclosure is administered at an amount of about 35 mg/kg.

In some embodiments, a compound of the disclosure is administered at an amount of about 40 mg/kg. In some embodiments, a compound of the disclosure is administered at an amount of about 45 mg/kg. In some embodiments, a compound of the disclosure is administered at an amount of about 50 mg/kg. In some embodiments, a compound of the disclosure is administered at an amount of about 55 mg/kg. In some embodiments, a compound of the disclosure is administered at an amount of about 60 mg/kg. In some embodiments, a compound of the disclosure is administered at an amount of about 65 mg/kg. In some embodiments, a compound of the disclosure is administered at an amount of about 70 mg/kg. In some embodiments, a compound of the disclosure is administered at an amount of about 75 mg/kg. In some embodiments, a compound of the disclosure is administered at an amount of about 80 mg/kg. In some embodiments, a compound of the disclosure is administered at an amount of about 85 mg/kg. In some embodiments, a compound of the disclosure is administered at an amount of about 90 mg/kg. In some embodiments, a compound of the disclosure is administered at an amount of about 95 mg/kg. In some embodiments, a compound of the disclosure is administered at an amount of about 100 mg/kg.

The compounds for use in the method of the disclosure may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In some embodiments, the compositions of the disclosure are administered to the patient from about one to about five times per day or more. In various embodiments, the compositions of the disclosure are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the disclosure will vary from individual to individual depending on many factors including, but not limited to, age, the disease or disorder to be treated, the severity of the disease or disorder to be treated, gender, overall health, and other factors. Thus, the disclosure should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the disclosure is optionally given continuously; alternatively, the dose of drug being administered is temporarily reduced or temporarily suspended for a length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In some embodiments, the present disclosure is directed to a packaged pharmaceutical composition comprising a container holding a therapeutically effective amount of a compound of the disclosure, alone or in combination with a second pharmaceutical agent; and instructions for using the compound to treat or prevent a disease or infection in a patient.

Medical Devices

The disclosure contemplates applying to or coating medical devices with the compositions useful within the disclosure. Non-limiting examples of medical devices include disposable or permanent catheters, (e.g., central venous catheters, dialysis catheters, long-term tunneled central venous catheters, short-term central venous catheters, arterial catheters, peripherally inserted central catheters, peripheral venous catheters, pulmonary artery Swan-Ganz catheters, urinary catheters, and peritoneal catheters, drainage catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings (e.g., intravenous tubes, breathing tubes, dental water lines, dental drain tubes, and feeding tubes), fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field.

Medical devices also include any device that may be inserted or implanted into a human being or other animal, or placed at the insertion or implantation site such as the skin near the insertion or implantation site, and that include at least one surface which is susceptible to colonization by microorganisms and/or biofilm-embedded microorganisms. Also contemplated within the disclosure is any other surface that may be desired or necessary to prevent microorganisms and/or biofilm-embedded microorganisms from growing or proliferating on at least one surface of the medical device, or to remove or clean microorganisms and/or biofilm-embedded microorganisms from the at least one surface of the medical device, such as the surfaces of equipment in operating rooms, emergency rooms, hospital rooms, clinics, and bathrooms. In some embodiments, the composition is integrated into an adhesive, such as tape, thereby providing an adhesive that may prevent or reduce growth or proliferation of microorganisms and/or biofilm embedded-microorganisms on at least one surface of the adhesive.

Implantable medical devices include orthopedic implants that may be inspected for contamination or infection by microorganisms and/or biofilm-embedded microorganisms using endoscopy. Insertable medical devices include catheters and shunts that can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex® (polytetrafluoroethylene), Dacron® (polyethylene tetraphthalate), Teflon® (polytetrafluoroethylene), latex, elastomers and Dacron® sealed with gelatin, collagen or albumin, and derivatives or combinations thereof. The medical devices include at least one surface for applying the biofilm-penetrating composition. In some embodiments, the biofilm-penetrating composition is applied to the entire medical device.

Those skilled in the art will recognize, or be able to ascertain using no more than routine experimentation, numerous equivalents to the exemplified procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present disclosure and practice the claimed methods. The following working examples therefore are not to be construed as limiting in any way the remainder of the disclosure.

Example 1. Isolation of Kang A

Kang A was isolated from fermentations of *Amycolatopsis vancoresmycina* (NRRL B-24208). 5 µL of a frozen glycerol spore stock of *A. vancoresmycina* was used to inoculate 50 mL of TSB media (Oxiod) in a 125 mL baffled flask. The culture was grown for 48 hr with shaking at 30° C. and 200 rpm. 200 µL of the saturated culture was used to inoculate 72×50 mL RSA media (100 g $L^{-1}$ sucrose, 0.25 g $L^{-1}$ $K_2SO_4$, 10.12 g $L^{-1}$ $MgCl_2*6H_2O$, 10 g $L^{-1}$ glucose, 0.1 g $L^{-1}$ casamino acids, 20.5 g $L^{-1}$ MOPS, 5 g $L^{-1}$ yeast extract, and 2 g $L^{-1}$ NaOH) containing 1.5 g Diaion HP-20 resin (Sigma) and a 1"×1" stainless steel metal mesh (for increased aeration) in 125 mL baffled flasks. The cultures were incubated at 30° C. with shaking at 200 rpm. After 10 days, HP-20 resin was removed from the cultures by filtration and washed with 2×500 mL water. Material bound to the resin was eluted using 2×500 mL methanol. The resulting crude extract was fractionated by flash chromatography (RediSep Rf, High Performance Gold 50 g HP C18 resin) using a linear gradient of 30-100% acetonitrile:water with 0.1% acetic acid over 30 min. A small portion of each fraction was analyzed by LC-MS (Waters xxx). Fractions containing Kang A were further purified by HPLC on a 10 mm×150 mm $C_{18}$ column (Waters) using an isocratic method of 42% acetonitrile with 0.1% formic acid at a flow rate of 3.5 mL $min^{-1}$. Purified Kang A was isolated with a yield of approximately 5 mg per liter of culture.

Example 2. Synthesis of Amide Analogs

The crystal structure of a mycobacterial RNAP in complex with kanglemycin A revealed that the acid moiety of kanglemycin A is positioned in a large opening in the active site adjacent to the nucleotide binding site. To explore the structure-activity-relationship (SAR), 1-[bis(dimethylamino)methylene]-1H-1,2,3-triazolo[4,5-b]pyridinium 3-oxid hexafluorophosphate (HATU) was used to couple the kanglemycin A acid to a collection of structurally diverse of amines. These amines fell into seven general structural classes: carboxylic acids, sugars, simple aromatic structures, aromatic amino acid and histidine analogs, as well as larger sets of simple aliphatic amines, cyclic amines, and phosphate analogs. The latter group was intended to mimic interactions between the phosphate tail of a nucleotide and the RNAP active site. The product of each 0.4 mg scale amide coupling reaction was purified by HPLC and its identity was verified by LC/MS. The concentration of each new analog was determined based on UV absorbance (395 nm) and comparison to standard curve generated with known quantities of kanglemycin A. The vast majority of amide side chains added do not absorb at 395 nm. Exceptions were the aromatic amines N34 and N35, which were instead produced in larger scale reactions (1 mg) and quantified by mass. The antibacterial of activity of each amide analog was then evaluated against *S. aureus* strain ATCC 12600 using a broth microdilution assay. Antibacterial minimal inhibitory concentrations (MIC) ranged from >64 ug/mL to about 0.0000153 ug/mL.

For synthesis of Kang amides, a 0.2 M stock of Kang A was prepared in dimethylformamide (DMF). 0.4 M stocks (in DMF) were prepared for each of the following: 1-[Bis (dimethylamino)methylene]-1H-1,2,3-triazolo[4,5-b]pyridinium 3-oxid hexafluorophosphate (HATU), triethylamine (TEA), and each amine to be coupled to the Kang A acid. As the amines containing carboxylic acid, phophonate and sulfonate moieties generally had poor solubility in DMF, solutions of these amines were instead prepared in water. 2 µL of each reagent were transferred to a 1.5 mL Eppendorf tube in the order: Kang A, TEA, HATU, and amine. Reactions were allowed proceed overnight with gentle agitation on a vortexer. The following day, reactions were diluted with 100 µL of DMF and purified by HPLC with a 10 mm×150 mm C18 column (Waters) and a linear gradient of 30-95% acetonitrile:water with 0.1% formic over 30 min at a flow rate of 3.5 mL min−1. The identity of each purified Kang amides was verified by mass analysis. Kang V2 amides were synthesized and purified in an identical manner at a 0.2 µg scale.

Example 3. Minimum Inhibitory Concentration (MIC) and Minimal Bactericidal Concentration (MBC) Assays The MIC was measured by the microdilution method of the Clinical and Laboratory Standards Institute (see, e.g., Standards NCfCL. *Methods for Dilution-Antimicrobial Susceptibility Tests for Bacteria That Grow Aerobically; M7-A7*; Broth Microdilution Method: CLSI, Wayne, Pa., USA, 2006 which is incorporated by reference herein in its entirety). Overnight cultures in an appropriate broth (e.g., Luria Bertani, Mueller-Hinton II) were diluted to 5×10$^5$ cfu/mL and used to fill wells of a 96-well plate. Rifamycin was added to the first well of each row, and a 2-fold dilution series was made by transferring 100 µl from one well to the next. The plates were incubated on a shaker (200 rpm) at 35-37° C. for 18-20 hours, and then the optical density was measured at 595 nm on a microplate reader. Samples of each well without visible growth were diluted and spread on LB agar petri dishes. The petri dishes were incubated overnight at 37° C., and the colonies were counted.

The MIC values of compounds of the present disclosure are shown in Table 1 and 2 below ("*" means ≤0.0625 µg/mL; "" means >0.0625 µg/mL and ≤1 µg/mL; "*" means >1 µg/mL).

TABLE 1

MIC values for Compounds of Formula (I)

| Compound Name | MIC | Compound Name | MIC |
|---|---|---|---|
| A1 | *** | A2 | *** |
| J4 | *** | A3 | ** |
| C22 | ** | N33 | *** |
| N8 | ** | C21 | ** |
| N34 | * | J6 | *** |
| N35 | * | E3 | *** |
| F2 | *** | E4 | *** |
| F1 | *** | N39 | *** |
| F4 | *** | N6 | ** |
| C13 | *** | N40 | ** |
| F3 | ** | N42 | ** |
| F5 | *** | N41 | *** |
| F6 | *** | N43 | ** |
| N4 | *** | N44 | ** |
| N37 | *** | N14 | * |
| N38 | *** | N15 | * |
| N3 | ** | N16 | * |
| N2 | *** | N17 | ** |
| N5 | ** | N12 | ** |
| N47 | — | N13 | * |
| N48 | — | N20 | * |

TABLE 1-continued

MIC values for Compounds of Formula (I)

| Compound Name | MIC | Compound Name | MIC |
|---|---|---|---|
| A4 | ** | N22 | ** |
| A7 | ** | N18 | * |
| C17 | *** | N25 | * |
| C14 | ** | N23 | * |
| J3 | *** | N26 | * |
| C15 | ** | N21 | * |
| P2 | * | N24 | * |
| P1 | ** | N27 | * |
| A5 | ** | P10 | * |
| A6 | * | P11 | ** |
| C23 | *** | P12 | * |
| D4 | *** | P13 | * |
| D1 | — | P14 | * |
| C10 | *** | C16 | ** |
| D2 | *** | P7 | * |
| J5 | *** | P8 | * |
| E1 | *** | P9 | * |
| N7 | *** | P6 | ** |
| N36 | *** | P3 | * |
| N1 | *** | P4 | *** |
| N45 | — | P5 | *** |
| N46 | — | C9 | *** |
| J1 | ** | B1 | *** |
| G1 | ** | J7 | *** |
| G2 | ** | C11 | *** |
| G3 | ** | B2 | ** |
| G5 | * | N9 | ** |
| J2 | *** | N32 | — |
| E2 | *** | N11 | ** |
| N10 | ** | C18 | * |
| B3 | *** | C19 | * |
| C20 | *** | S1 | * |
| B4 | *** | | |

TABLE 2

MIC for compounds of Formula (I)

| Compound Name | MIC |
|---|---|
| C12 | ** |
| N31 | * |
| N29 | *** |
| C4 | *** |
| N28 | *** |
| C5 | *** |
| C6 | *** |
| C7 | ** |
| C8 | ** |
| N30 | — |

Several of the modifications showed improved activity.

In a second round of synthesis, additional differentially modified benzylethylamines, as well as amines containing a tert-butyl substructure, and amines with a pyrrolidine core were synthesized. The benzylethylamines showed improved activity compared to Kang A. From the group of pyrrolidine-containing amides, a variant with a cyclopropyl moiety (C5) was identified which had improvement in activity. The combined results of our two rounds of screening demonstrate that the Kang A acid tolerates modification with a variety of substituents (in particular small hydrophobic and simple aromatic moieties) while still retaining antibiotic activity which in some cases exceeds that of the parent compound.

Example 4. Analysis of Growth Inhibition by Kang Amides/Growth Curves

Figure 3:
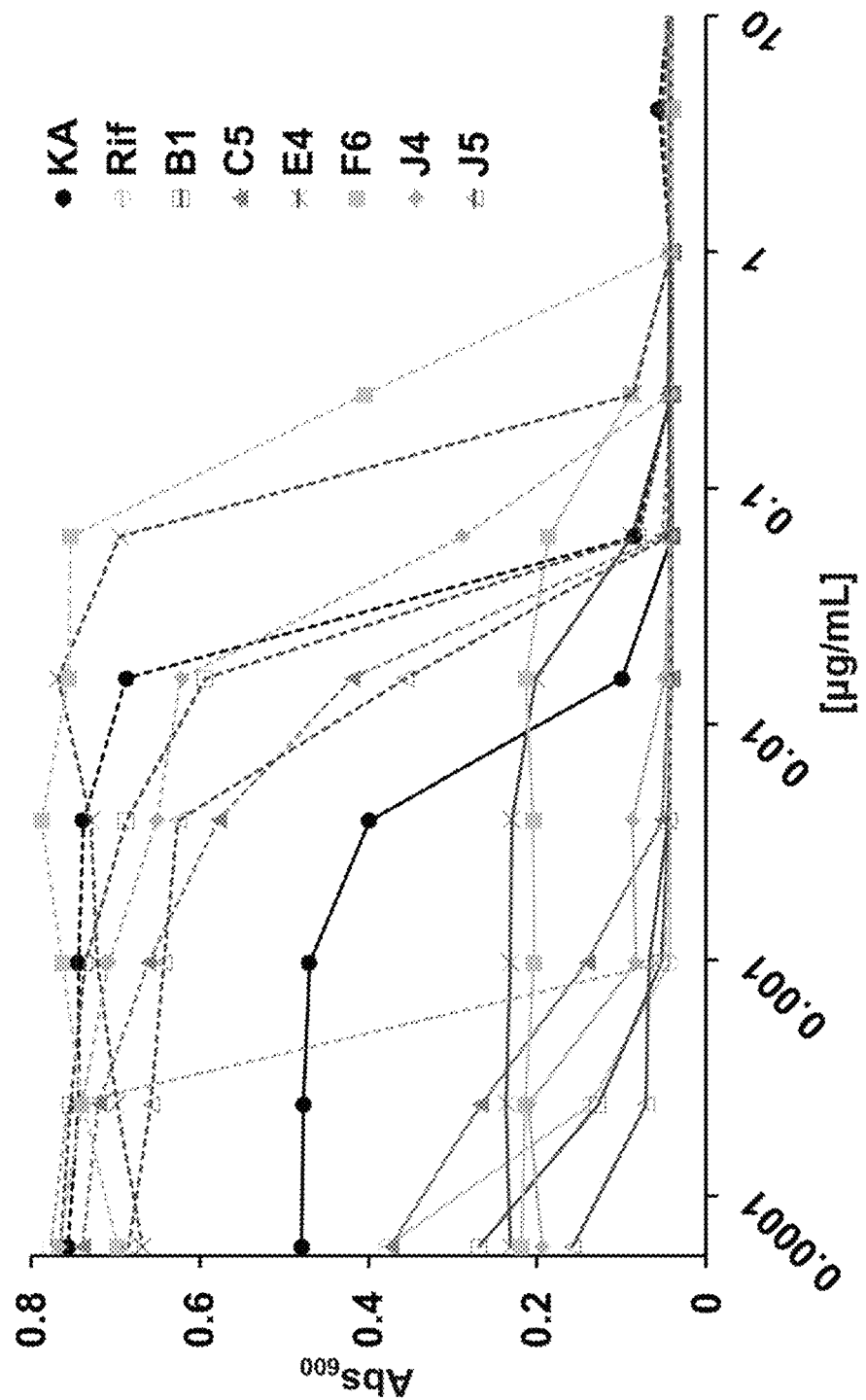
FIG. 3 depicts the dose-response curves for six derivates of Formula I, including B1 ($R_1$ is H.

During the initial activity screening, a strong time-dependent effect of some of the compounds on bacterial growth was observed. To explore this effect in more detail, the growth of S. aureus in the presence of the Kang amides described herein was monitored over 24 hr. Dose-response curves generated at 12 hr intervals confirmed amide activity, FIG. 3. The increased potency of the amides observed during initial screening appears to result from a strong bacteriostatic effect on bacterial growth at the 12 hr timepoint used in the screen.

Example 5. Spectrum of Activity

Representatives from Formula I (J4, J5, C5, B1, E4, and F6) were selected for additional analyses. Their activity was tested against a collection of Gram-positive and Gram-negative bacteria. Several of the amides showed improved activity compared to Kang A against different S. aureus strains and S. epidermidis, as well as against the Gram-negative bacterium, Legionella pneumophila. The compounds were also tested against a panel of mycobacteria. Although most several of the mycobacterial strains tested were resistant to both the Kang amides and Kang A, the Kang amides exhibited at least a two-fold improvement against M. tuberculosis H37rv. While the amides J4 and J5 were two of the most potent antibiotics against S. aureus, the amide C5 had the strongest activity against M. tuberculosis.

Antibiotic Assays Against Staphylococcus aureus

Minimum inhibitory concentration (MIC) assays were performed by incubating cells against a serial 1:3 dilution of compounds starting at 50 µg/mL. Briefly, a single colony of wild type S. aureus ATCC 12600 or S. aureus ATCC 12600 carrying either a D471Y, H481Y, or S486L mutation (FIG. 27; Srivastava et al, 2012, Antimicrob. Agents, 56:6250-6255, which is incorporated by reference herein in its entirety) was used to inoculate 7 mL of Luria-Bertani (LB) broth and the culture was grown overnight to saturation. The following day, 10 µL of overnight culture were diluted into 50 mL of LB broth and 80 µL aliquots were distributed to each well of a 96-well plate. 250 µg of dried test compound was re-suspended in 50 µL of methanol and diluted to 250 µg/mL with LB. Starting with 250 µg/mL of antibiotic in the first well, a 1:3 serial dilution of the was performed in LB across the plate. No compound was added to the final well in each row. 20 µL of diluted test compound were transferred, in triplicate, to the wells of a plate containing an assay strain. This yielded the final volume of 100 µL in assay wells, with the initial concentration of compound being 50 µg/mL. Plates were sealed with air permeable membranes (BreathEasy) and incubated at 30° C., with shaking at 200 rpm for 24 hrs. The $OD_{600}$ of each plate was read at 24 hr using an Epoch Microplate Spectrophotometer (BioTek Instrumetns) and MIC values were reported as the lowest concentration of the compound that inhibited the growth of the test strain.

Example 6. Activity Against Rifamycin Resistant M. tuberculosis Strains

In addition to the wild-type M. tuberculosis strain, the amides were tested against several rifampicin resistant strains containing point mutations in RNAP. The J4 and J5 amides had the strongest activity against S. aureus and the C5 amide showed the most potent activity against MTB.

Antibiotic Assays Against Mycobacterium tuberculosis

M. tuberculosis H37Rv was passaged in Middlebrook 7H9 media (BD Biosciences) supplemented with oleic acid-albumin-dextrose-catalase (OADC; BD Biosciences) and 0.02% tyloxapol (hereafter called 7H9 complete). Replicating conditions were prepared as previously described (Gold et al, 2015, Antimicrob. Agents Chemother., 59:6521-6538, which is incorporated by reference herein in its entirety). All compounds were reconstituted in dimethyl sulfoxide (DMSO) and serial dilutions were created in 96-well microplates. Mid-log phase M. tuberculosis was diluted to an $OD_{580}$ of 0.01 with 7H9 complete and 198 µL were distributed in 96-well microplates. 2 µL of the compound dilutions were added to the culture wells in triplicate rows, keeping the DMSO concentration at 1%. DMSO and rifampin controls were included in every experiment. Plates were incubated at 37° C. with room air oxygen and 5% $CO_2$. $IC_{90}$ values were determined using an M5 SpectraMax Microplate reader (Molecular Devices) at $OD_{580}$ between day 10 and 14 after thorough mixing of the wells.

Example 7. Parallel Modifications of Kang V2

The J4 and J5 modifications exhibited activities against Staph and the C5 modification exhibited activity against MTB.

Example 8. In Vitro Analysis of RNAP Inhibition by Kang Amides

Amides J4, J5, C5, B1, E4, and F6 were analyzed in an in vitro assay. The M. smegmatis polymerase exhibits a very high level of sequence identity with M. tuberculosis RNAP, including the complete conservation of amino acids in the Kang A/rifampicin binding site. All of the amides tested against the M. smegmatis polymerase inhibited the enzyme to the same extent as Kang A, with transcriptional significantly reduced at a concentration of 0.1 uM and completely inhibited at 1 uM. These results confirm that the open pocket in the RNAP active site adjacent to the Kang A binding site is sufficiently large to accept modifications made to the Kang A acid moiety without significantly impairing targeting of the enzyme by the modified compounds. Based on the similar in vitro activity of each of the compounds compared to Kang A, the improved antibiotic activity of the amides may be due to enhanced passage of these compounds into the bacterial cells.

Example 9. Assessment of Cytochrome P450 Induction and Cytotoxicity

A major disadvantage associated with the clinical use of rifampicin is that it is a potent cytochrome P450 (CYP) which can result in significant interactions with co-administered drugs. The kanglemycins and the J4 and C5 amides were tested to induce CYP3A, the main CYP induced by rifampicin, using a luciferin-based reported of CYP activity in HepaRG cells. The cytotoxicity of the kanglemycin A and the J4 and C5 amides was also tested against VERO cells. No indication of cytotoxicity for the compounds at concentrations up to 25 μg/mL was found.

Example 10. In Vivo Analysis of the J4 Kang Amide

To determine whether the improved potency of the Kang A amides observed in the MIC assays translates to improved in vivo activity, the activity of J4 is tested in a sepsis model in mice. For this assay, mice are infected with *S. aureus*. J4 (or Kang A or rifampicin) was administered by injection at a relevant concentration over a set number of hours and the efficacy of the compound is determined by survival of the mice.

Example 11. Antibiotic Assays Against Sau

Minimum inhibitory concentration (MIC) assays were performed by incubating cells against a serial 1:3 dilution of compounds starting at 50 μg mL$^{-1}$. Briefly, a single colony of wild type Sau ATCC 12600 or Sau ATCC 12600 carrying either a D471Y, H481Y, or S486L mutation[30] was used to inoculate 7 mL of Luria-Bertani (LB) broth and the culture was grown overnight to saturation. The following day, 10 μL of overnight culture were diluted into 50 mL of LB broth and 80 μL aliquots were distributed to each well of a 96-well plate. 250 μg of dried test compound was re-suspended in 50 μL of methanol and diluted to 250 μg mL$^{-1}$ with LB. Starting with 250 μg mL$^{-1}$ of antibiotic in the first well, a 1:3 serial dilution of the compounds was performed in LB across a separate plate. No compound was added to the final well in each row. 20 μL of diluted test compound were transferred, in triplicate, to the wells of the plate containing the assay strain. This yielded the final volume of 100 μL in assay wells, with the initial concentration of compound being 50 μg mL$^{-1}$. Plates were sealed with air permeable membrane (BreathEasy) and incubated at 30° C. with shaking at 200 rpm for 24 hrs. The OD$_{600}$ of each plate was read at 24 hrs using an Epoch Microplate Spectrophotometer (BioTek Instruments) and MIC values were reported as the lowest concentration of the compound that inhibited the growth of the test strain.

TABLE 3

Formula I derivatives MIC

| | B1 | C5 | E4 | F6 | J4 | J5 | KA | Rif |
|---|---|---|---|---|---|---|---|---|
| *M. tuberculosis* H37rv | 0.391 | <0.195 | 0.781 | 0.391 | 0.781 | 0.781 | 1.563 | <0.195 |
| Trial 2 | 0.63 | 0.63 | 2.5 | 1.25 | 1.25 | 1.25 | 3.13 | 0.31 |
| Trial 3 | 0.63 | 0.63 | 1.25 | 1.25 | 1.25 | 0.63 | 1.56 | 0.31 |
| Trial 4 | 1.25 | 0.63 | 2.5 | 1.25 | 1.25 | 1.25 | 1.56 | 0.31 |
| Rif$^R$ Mtb panel | | | | | | | | |
| RpoB D516V | TBD | TBD | TBD | TBD | TBD | TBD | TBD | TBD |
| RpoB S531L | 1.25 | 0.63 | 2.5 | >2.5 | 2.5 | >2.5 | 25 | >25 |
| RpoB H526R | >2.5 | 2.5 | >2.5 | >2.5 | >2.5 | >2.5 | >25 | >25 |
| RpoB H526Y | TBD | TBD | TBD | TBD | TBD | TBD | TBD | TBD |
| Other mycobacteria | | | | | | | | |
| *M. abscessus* | >25 | >25 | >25 | >25 | >25 | >25 | >25 | >25 |
| *M. avium* | 25 | 12.5 | 12.5 | 6.25 | 25 | 25/>25 | 25 | <0.195 |
| *M. marinum* | >25 | >25 | >25 | >25 | >25 | >25 | >25 | >25 |
| *M. smegmatis* | >25 | >25 | >25 | >25 | >25 | >25 | >25 | >25 |

TABLE 4

Formula III derivatives MIC

| | V2-B1 | V2-05 | V2-E4 | V2-F6 | V2-J4 | V2-J5 | V2 | KA | Rif |
|---|---|---|---|---|---|---|---|---|---|
| *M. tuberculosis* H37rv | 0.04 | <0.04 | 0.08 | 0.08 | 0.04 | 0.04 | 0.08 | 0.63-1.25 | <0.02 |
| Rif$^R$ Mtb panel | | | | | | | | | |
| RpoB D516V | TBD | TBD | TBD | TBD | TBD | TBD | | TBD | TBD |
| RpoB S531L | TBD | TBD | TBD | TBD | TBD | TBD | | TBD | TBD |
| RpoB H526R | TBD | TBD | TBD | TBD | TBD | TBD | | TBD | TBD |
| RpoB H526Y | TBD | TBD | TBD | TBD | TBD | TBD | | TBD | TBD |

TBD = To be determined

Example 12. Antibiotic Assays Against Mtb

The minimum concentrations of antibiotic that result in 90% inhibition of bacterial growth (MIC90) and 50% inhibition (MIC50) are identified for each compound against *Mycobacterium tuberculosis* (Mtb). In some embodiments, any MIC study known in the art can be used to show the activity of the Kang amides described herein. The MIC studies show that the Kang amides described herein inhibit growth of Mtb.

Example 13. Antibacterial Activity

Kanglemycins A, V1 and V2 are active as antibiotics against Gram-positive bacteria, including *Staphylococcus aureus, Staphylococcus epidermidis, Listeria monocytogenes* and *M. tuberculosis* (Table 5). Interestingly, kanglemycin V1 and V2 both show improved activity against *M. tuberculosis* (H37Rv; $IC_{90}$ 3.12 and 1.56 µM, respectively) compared to kanglemycin A (12.5 µM). Therefore, we determined the activity of the disclosed compounds against mutations in RNAP that confer resistance to rifampicin. Substitutions at just three RNAP amino acid positions, S531, H526 and D516, account for the vast majority of mutations observed in rifampicin resistant *M. tuberculosis* clinical isolates (Ramaswamy et al., 1998, Tuber. Lung Dis., 79:3-29, which is incorporated by reference herein in its entirety). The antibacterial activity of the kanglemycins against rifampicin resistant RNAP mutants was assessed in vivo using a collection of *S. aureus* strains carrying various RNAP point mutations and in vitro using purified wild-type and mutant (S477L) *Mycobacterium smegmatis* RNAP (Srivastava et al., 2012, Antimicrob. Agents, 56:6250-6255; Hubin et al., 2017, Elife, 6:e22520, which are incorporated by reference herein in their entireties).

Example 14. In Vitro Transcription Assay

Recombinantly produced wild-type and S447L mutant DNA-dependent RNAP were purified from *M. smegmatis* MGM6029 strain expressing a chromosomal copy of rpoC with a C-terminal ppx-$His_{10}$-tag, and either wild-type rpoB gene or rpoB mutant allele (S447L). *M. smegmatis* cells were grown to late exponential phase and collected at the Bioexpression and Fermentation Facility at the University of Georgia. Cells were lysed in a French press (Avestin) in 50 mM Tris-HCl, pH 8, 1 mM EDTA, 5% (v/v) glycerol, 5 mM DTT, 1 mM protease inhibitor cocktail, and 1 mM phenylmethylsulfonyl fluoride, and RNAP was precipitated from the cleared lysate by polyethyleneimine (PEI) precipitation (0.35%). The PEI pellet was washed three times with 10 mM Tris-HCl, pH 8, 0.5 M NaCl, 0.1 mM EDTA, 5 mM DTT, and 5% (v/v) glycerol, then eluted three times with the same buffer but with 1 M NaCl. Protein was precipitated overnight with 35% (w/v) ammonium sulfate and resuspended in 20 mM Tris-HCl, pH 8, 5% (v/v) glycerol, 1 M NaCl, and 1 mM β-mercaptoethanol. Protein was loaded on a $Ni^{2+}$-affinity column (HiTrap IMAC HP, GE Healthcare Life Sciences) and eluted in 20 mM Tris-HCl, pH 8, 5% (v/v) glycerol, 0.5 M NaCl, and 0.25 M imidazole. Protein was diluted in 10 mM Tris-HCl, pH 8, 5% (v/v) glycerol, 0.1 mM EDTA, and 5 mM DTT to a final salt concentration of 0.1 M NaCl, loaded on a Biorex (BioRad, Hercules, Calif.) ion exchange column, and eluted with a salt gradient (0.1 M-0.8 M). To generate the holoenzyme, the RNAP core was incubated with 5.0 molar excess of $γ^4$/$RbpA^{31}$ for 15 min at 4° C. and the resulting complex was purified by size exclusion chromatography (Superdex-200, GE Healthcare Life Sciences) in 20 mM Tris-HCl, pH 8, 5% (v/v) glycerol, and 0.5 M NaCl. The purified complex was dialyzed into 20 mM Tris-HCl, pH 8, 100 mM K-glutamate, 10 mM $MgCl_2$, and 1 mM DTT and stored at −80° C.

The transcription assay was performed in 20 µL volumes. 50 nM of the wild-type or mutant RNAP holoenzyme in transcription buffer [10 mM Tris HCl, pH 7.9, 50 mM KCl, 10 mM, $MgCl_2$, 1 mM DTT, 5 µg $mL^{-1}$ bovine serum albumin (BSA) and 0.1 mM EDTA] was mixed with Kang A, V1, or V2, or with Rif, at different concentrations of antibiotic. To allow binding of the antibiotics to the RNAP, the mixtures were incubated at 37° C. for 5 min. Following incubation, 10 nM of AP3 promoter[68] was added to each tube and the samples were incubated for an additional 15 min at 37° C. to allow formation of the RNAP open complex. Transcription was initiated by the addition of a nucleotide mixture consisting of 200 µM ATP, 200 µM CTP, 200 µM GTP, 50 µM unlabeled UTP and 1.25 µCi (0.3 µM) γ-$P^{32}$-UTP. Each reaction was allowed to proceed for 15 min at 37° C. before the addition of 20 µL of stop buffer (0.5×TBE, pH 8.3, 8 M urea, 30 mM EDTA, 0.05% bromophenol blue, and 0.05% xylene cyanol). Reactions were then heated to 95° C. for 10 min and loaded onto a polyacrylamide gel [23% Acrylamide/Bis acrylamide (19:1), 6M urea, and 1×TBE, pH 8.3]. Gels were run for 3 hours at 500 V, then exposed on a phosphoroimaging plate (GE Healthcare) for 12 hrs before being imaged using a Typhoon 9400 Variable Imager (Amersham Biosciences).

Example 15. In Vivo Mouse Studies

In vivo mouse studies were performed to assess compound efficacy. In some embodiments, any antibacterial mouse study known in the art can be used to show the activity of the Kang amides described herein. The in vivo mouse studies show that the Kang amides described herein are efficacious.

Example 16. Activity Screening of K-Acid Derivatives

The antibacterial activity of each amide analog was evaluated against Rif sensitive *S. aureus* and *S. aureus* strains carrying either an H481Y or an S486L RNAP mutation. H481Y or an S486L RNAP mutations correspond to the two most common $Rif^R$ mutations found in *M. tuberculosis* clinical isolates (*M. tuberculosis* RNAP H451Y and S456L). While Kang A shows strong activity against the S486L mutant, it is not active against the H481Y variant (FIG. 5B). Rif is inactive against both mutants.

Figure 2:
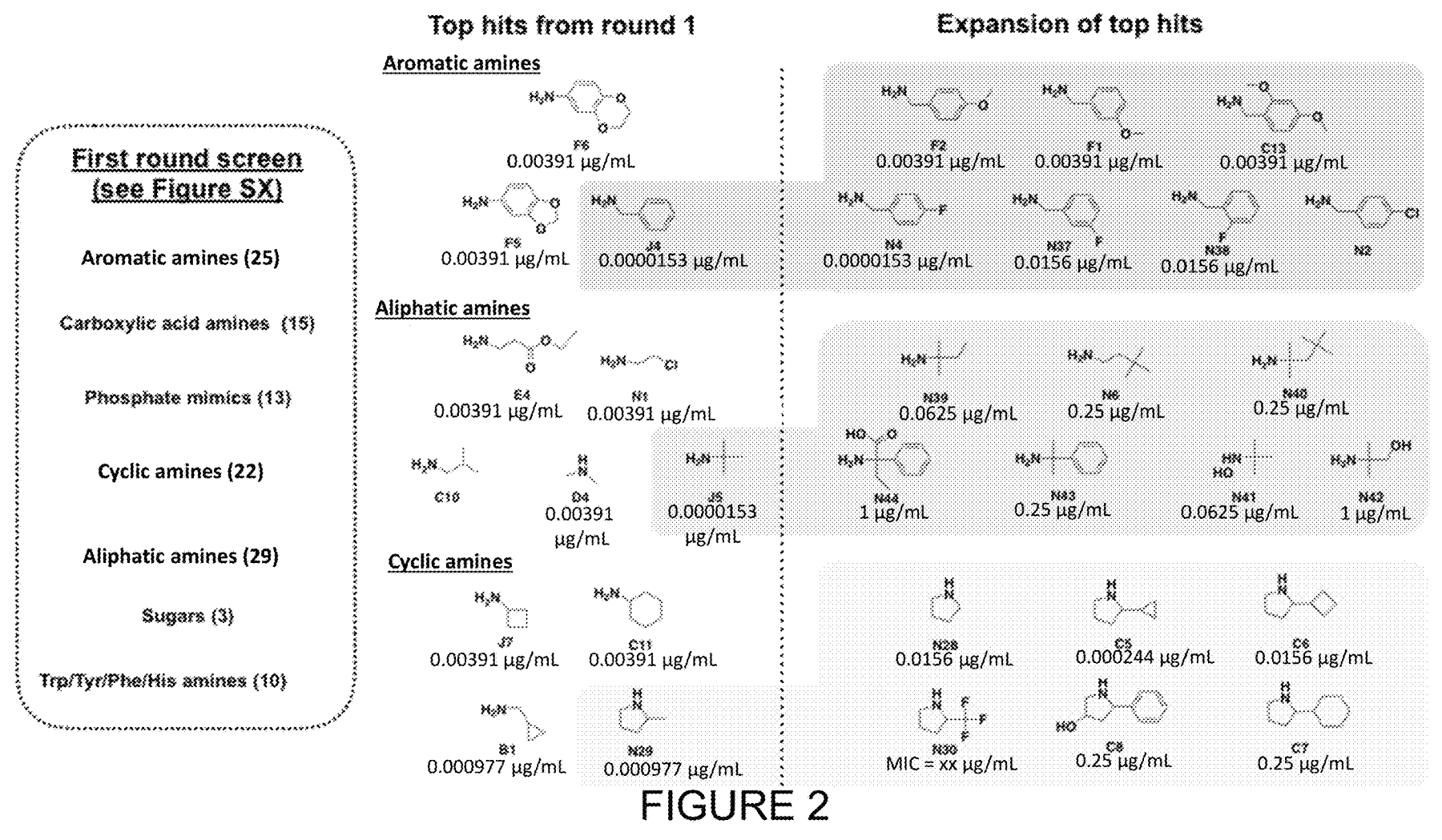

Amide analogs of the present disclosure exhibited a time-dependent improvement in inhibition of *S. aureus* growth, with the highest levels of inhibition relative to Kang A occurring after 12 hours with smaller differences in growth inhibition occurring at later timepoints. MICs for all amides were monitored at a 12 h timepoint to ensure detection of analogs that had an effect on the early growth of *S. aureus*. Amides with increased potency against wild-type *S. aureus* generally fell into three structural classes: aliphatic amides, cyclic amides, and aromatic amides (FIG. 5A and FIG. 5C). J5, synthesized from tert-butylamine, exhibited an MIC of 0.000061 µg/mL, J4, synthesized from benzylethylamine exhibited an MIC of 0.000061 µg/mL, B1, synthesized from cyclopropanemethylamine exhibited an MIC of 0.00098 µg/mL, and N29; synthesized from 2-methylpyrrolidine, exhibited an MIC of 0.00098 µg/mL (FIG. 2C). At least a 16-fold reduction in activity against the S486L strain was seen with K-acid modification. Most amide derivatives were inactive against the H481Y strain, with the exception of the amide of F6, which weakly inhibited the growth of this strain (MIC=64 µg/mL; FIG. 2C).

Five to seven additional Kang A amides were synthesized using primary and secondary amines related to J4, J5, and N29. Amides with improved potency included the methoxy-containing aromatic amides, C13, F1, and F2, which showed 4-fold increases in activity relative to Kang A, and a fluorinated aromatic amine, N4, exhibited an MIC of 0.000061 μg/mL (FIG. 2C). Pyrrolidine-comprising amides with a cyclopropyl moiety (C5) exhibited an MIC of 0.00024 μg/mL against wild-type *S. aureus*, a 4-fold increase in activity as compared to N29. The amides generated with primary and secondary amines, exhibited reduced activity against the S486L mutant and were inactive against the H481Y mutant.

Example 17. Activity of Derivatives Against Mycobacteria

B1, C5, E4, F6, J4, and J5 were tested against wild-type and Rif$^R$ strains of *M. tuberculosis* H37rv and in an in vitro assay against purified mycobacterial RNAP from *M. smegmatis* (FIG. 6). The *M. smegmatis* enzyme exhibits a high level of sequence identity with *M. tuberculosis* RNAP, including all amino acids that directly interact with Kang A/Rif. The amides had similar activity to Kang A against the wild-type *M. tuberculosis* strain, with the C5 and F6 amides showing 4-fold improvements in activity compared to Kang A (Table 5).

TABLE 5

Formula I derivatives MIC against wild-type (WT) and S456L Rif$^R$ *M. tuberculosis*

|  | Kang A | Rif | B1 | C5 | E4 | F6 | J4 | J5 |
|---|---|---|---|---|---|---|---|---|
| WT | 3.13 | 0.05 | 1.56 | 0.78 | 3.13 | 0.78 | 1.56 | 1.56 |
| S456L | 25 | >25 | 25 | 12.5 | >25 | >25 | >25 | >25 |

In vitro, the amides inhibited the purified mycobacterial RNAP, with transcription reduced at a concentration of 0.1 μM of antibiotic and strongly inhibited at 1 μM.

Example 18. In Vivo Efficacy of J4 in a Mouse Model

J4 amide, which showed potent activity against wild-type *S. aureus*, led to an improvement in bioavailability compared to Kang A (Table 6).

TABLE 6

Kang A and J4 IP and PO bioavailability

|  | IP | PO |
|---|---|---|
| Kang A | 6.84% | BLQ |
| J4 | 38.7% | 0.63% |

*BLQ = below limit of quanitation

The in vivo efficacy of J4 was evaluated with a murine neutropenic peritonitis/sepsis model as was used for Kang A using MRSA. As with Kang A, there was no overt morbidity or mortality observed upon treatment with J4 at an 15 mg/kg IP dose. The dose used in the mouse model can be converted to the human equivalent dose by multiplying the dose by 12.3. J4 caused a reduction in bacterial burden in the kidneys of infected mice (FIG. 7).

Equivalents

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (I), (II), or (III):

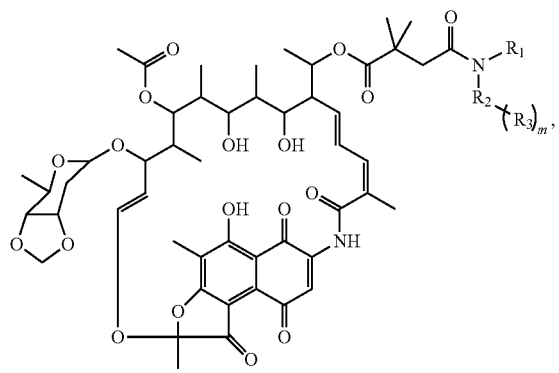

(I)

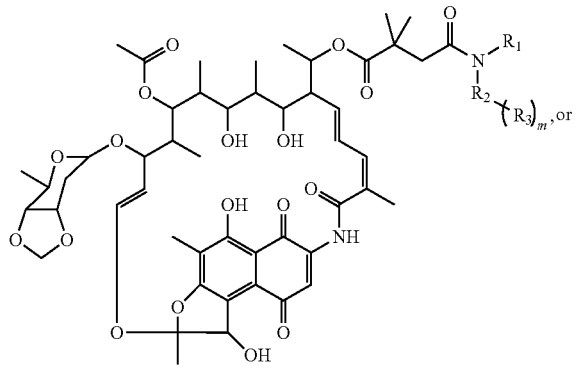

(II)

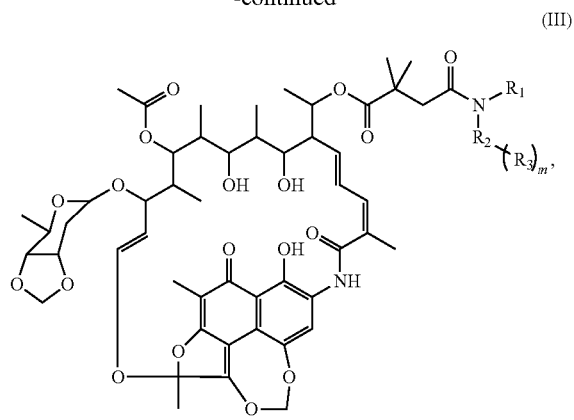
(III)
or a pharmaceutically acceptable salt, solvate, or tautomer, thereof, wherein:
R$_1$ is H, C$_1$ alkyl, C$_{3-10}$ alkyl, C$_{2-10}$ alkenyl, or C$_{2-10}$ alkynyl;
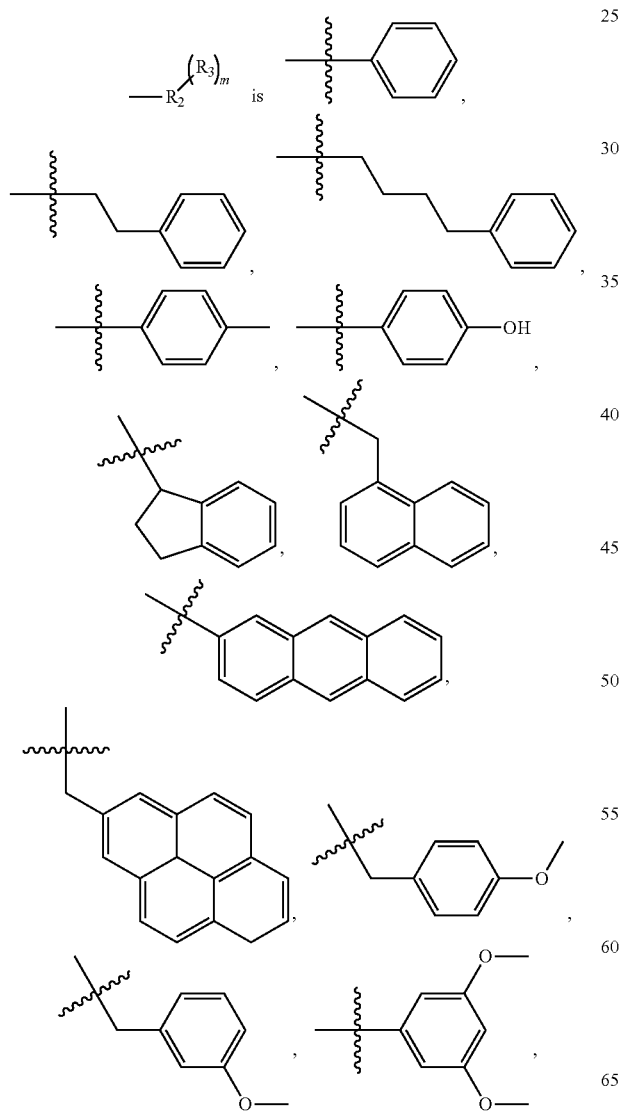
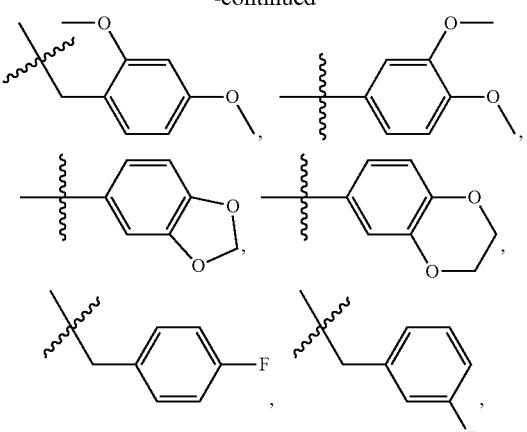
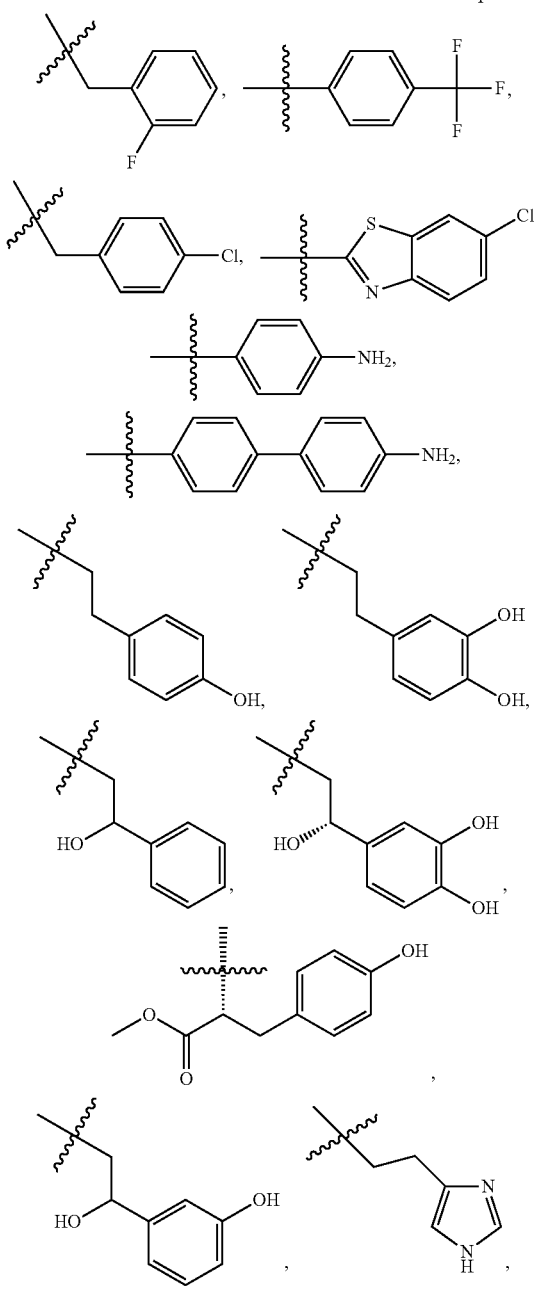

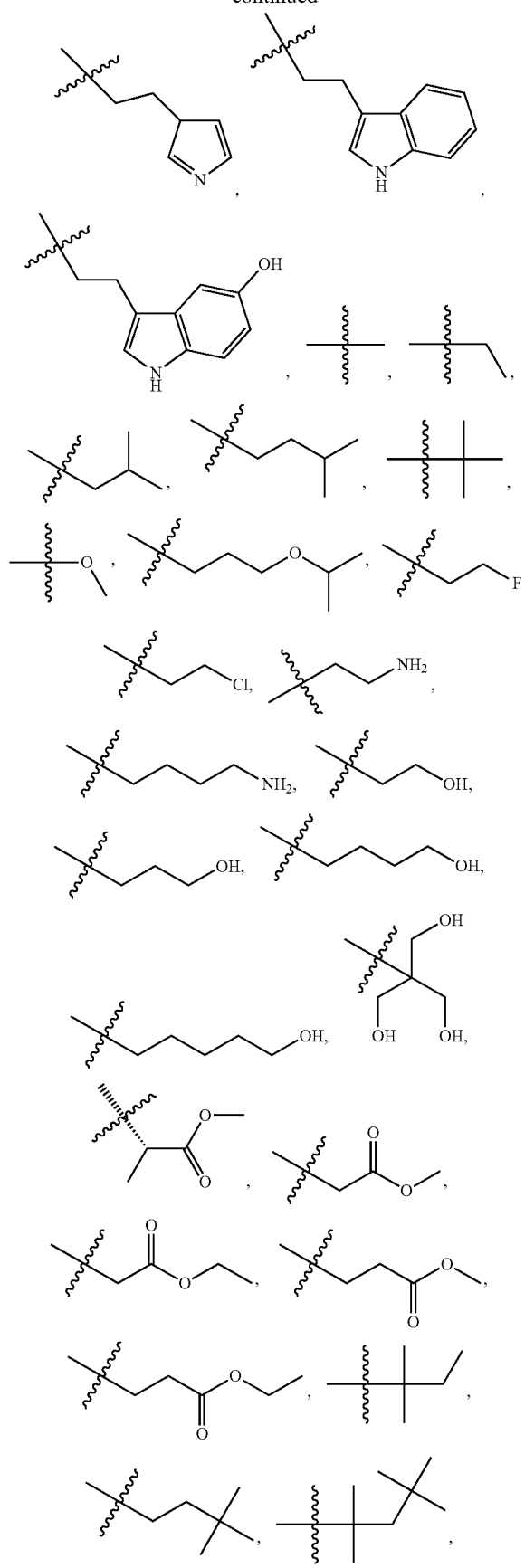
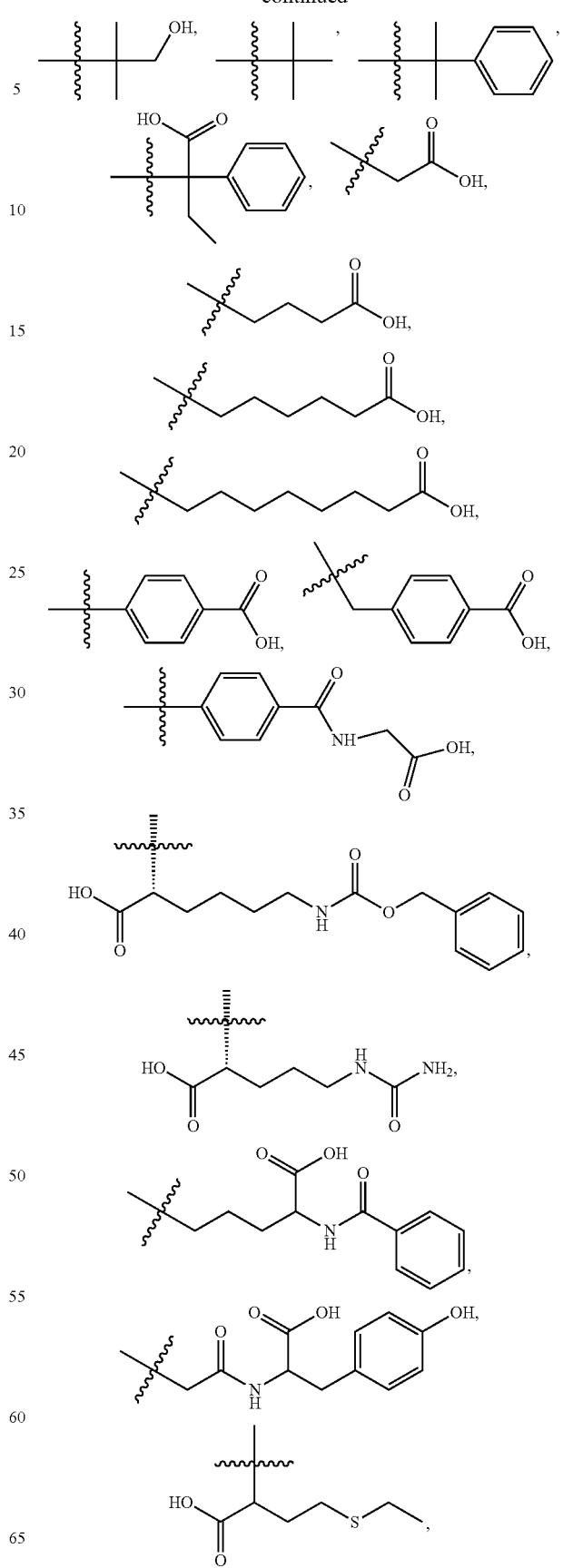

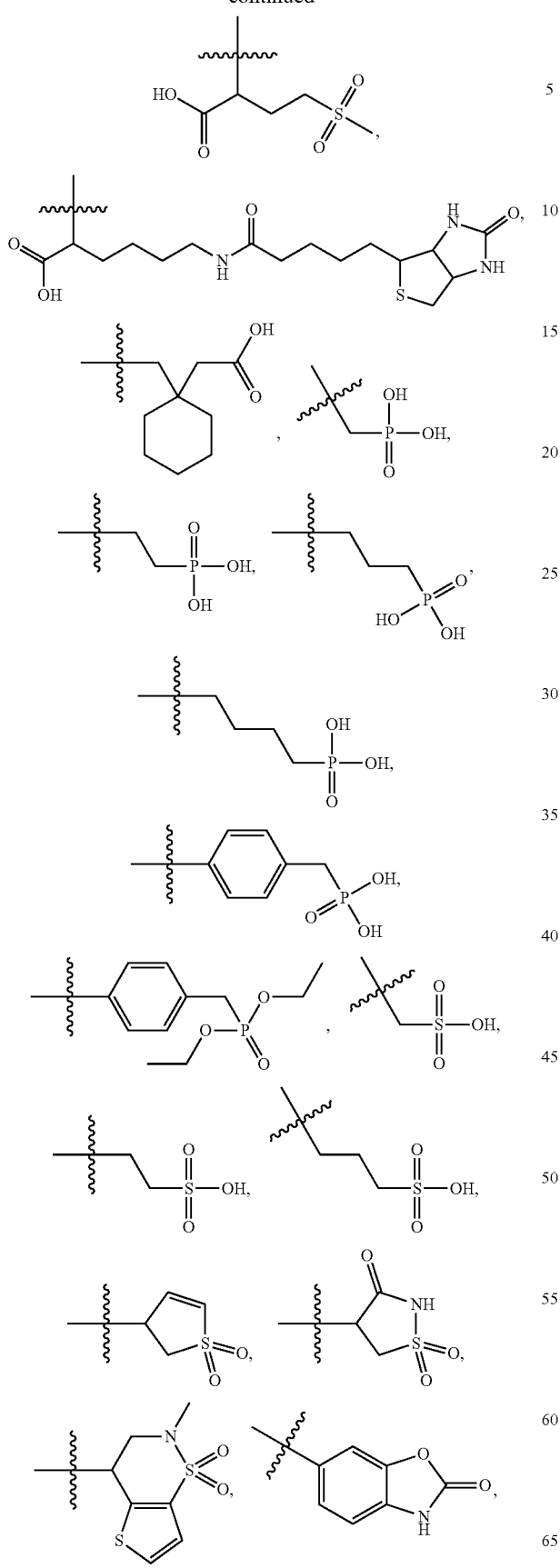
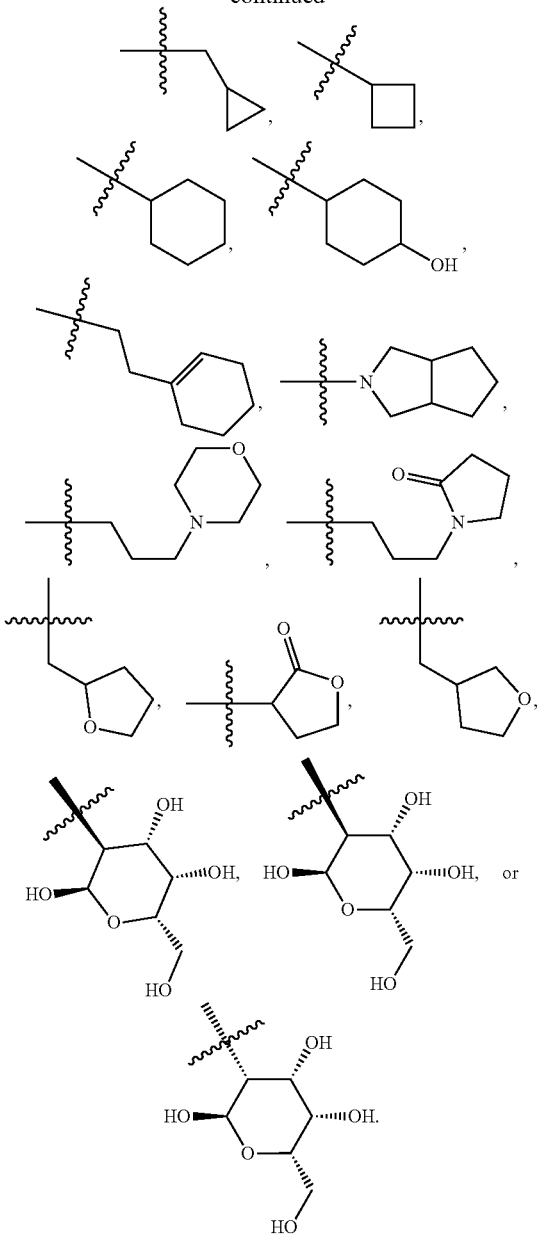

R₁ and R₂ together form a 3- to 10-membered heterocyclyl optionally substituted with one or more $R_5$;

each $R_5$ is independently H, oxo, halogen, $C_{1-6}$ alkyl, $C_{2-6}$ alkenyl, $C_{2-6}$ alkynyl, $C_{1-6}$ alkoxy, $C_{1-6}$ haloalkyl, —$OR_6$, —$NH_2$, —NH($C_{1-6}$ alkyl), —NH($C_{1-6}$ alkyl)₂, —C(O)$OR_6$, —P(O)(O$R_6$)₂, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$;

$R_6$ is H, $C_{1-6}$ alkyl, $C_{2-6}$ alkenyl, or $C_{2-6}$ alkynyl;

each $R_7$ is independently oxo, —OH, —C(O)OH, —C(O)O($C_{1-6}$ alkyl), aryl, heteroaryl, heterocyclyl, or $C_{3-10}$ cycloalkyl wherein the aryl, heteroaryl, heterocyclyl, or $C_{3-10}$ cycloalkyl is optionally substituted with halogen, oxo, —OH, or —$NH_2$;

and n is 1, 2, 3, or 4.

2. The compound of claim 1, wherein $R_1$ is H or methyl.

3. The compound of claim 1, wherein $R_2$ is —$OR_4$.

4. The compound of claim 1, wherein $R_1$ and $R_2$ together form a 4- to 8-membered heterocyclyl.

5. The compound of claim 1, wherein $R_1$ is H.

6. The compound of claim 1, wherein $R_1$ is $C_{1-6}$ alkyl.

7. The compound of claim 1, wherein each $R_5$ is independently H, oxo, or halogen.

8. The compound of claim 1, wherein each $R_5$ is independently $C_{1-6}$ alkyl, $C_{2-6}$ alkenyl, $C_{2-6}$ alkynyl, $C_{1-6}$ alkoxy, $C_{1-6}$ haloalkyl, aryl, heteroaryl, heterocyclyl, or $C_{3-10}$ cycloalkyl, wherein the alkyl, alkenyl, alkynyl, alkoxy, haloalkyl, aryl, heteroaryl, heterocyclyl, or cycloalkyl is optionally substituted with one or more $R_7$.

9. The compound of claim 1, wherein $R_6$ is H or $C_{1-6}$ alkyl.

10. The compound of claim 1, wherein each $R_7$ is independently aryl, heteroaryl, heterocyclyl or $C_{3-10}$ cycloalkyl, wherein the aryl, heteroaryl, heterocyclyl, or cycloalkyl is optionally substituted with halogen, —OH, or —$NH_2$.

11. The compound of claim 1, wherein

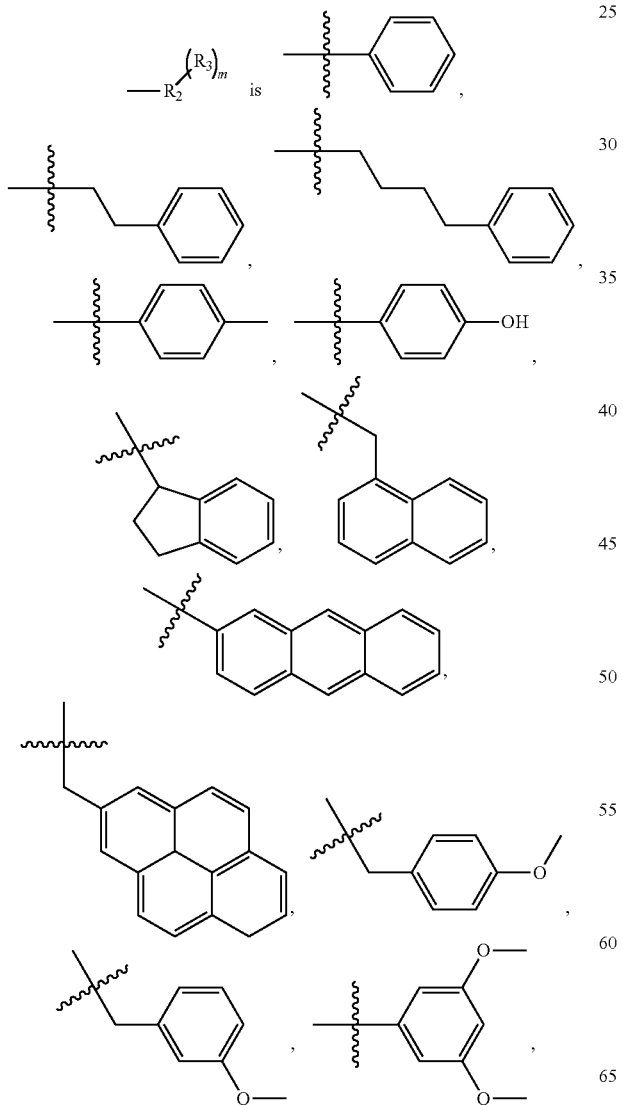
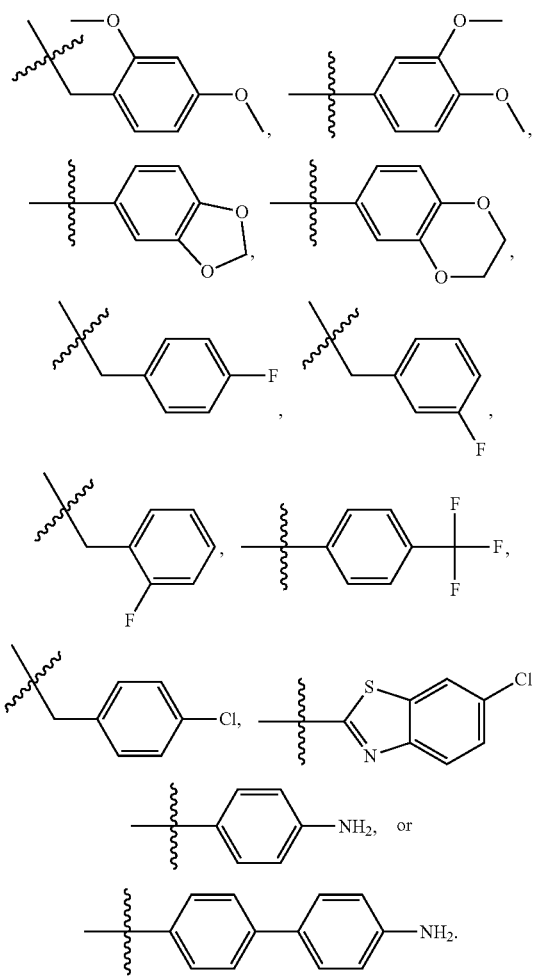

12. The compound of claim 1, wherein

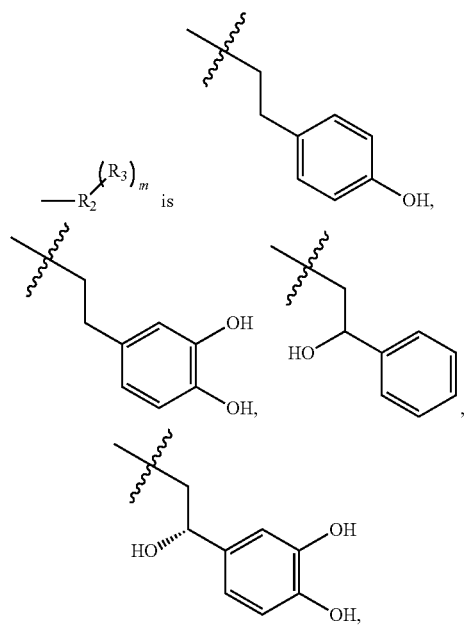

-continued
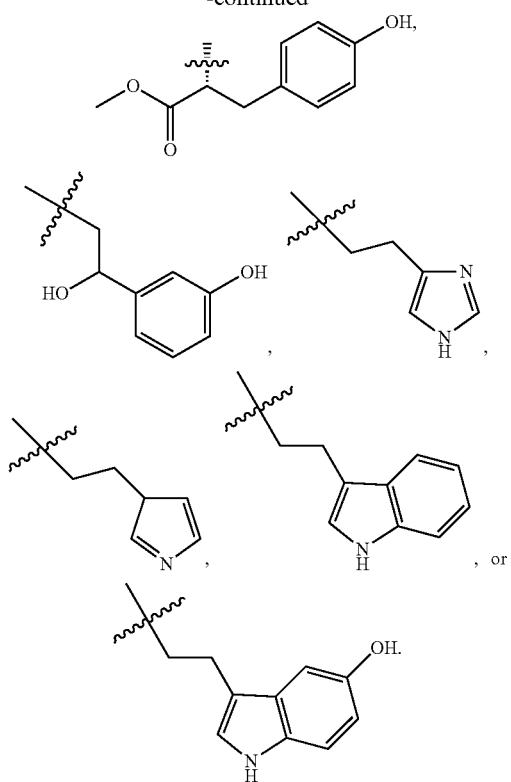
13. The compound of claim 1, wherein
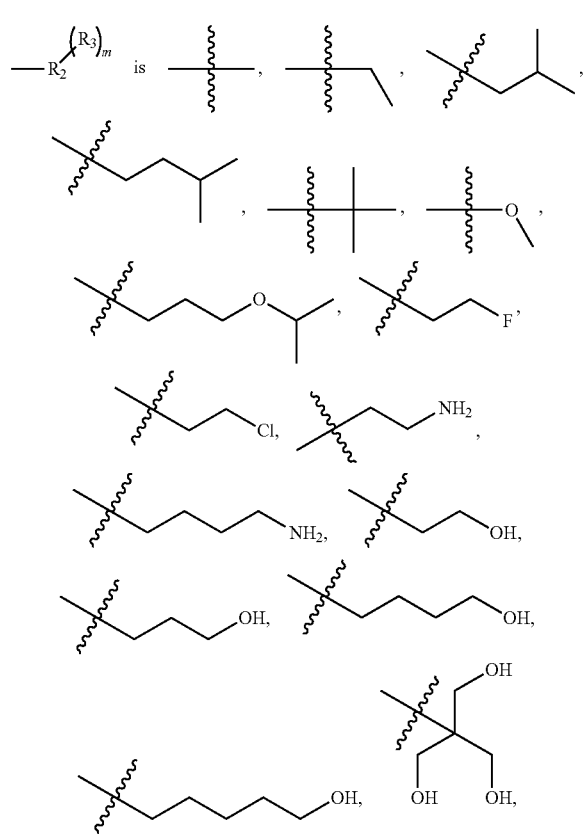
-continued
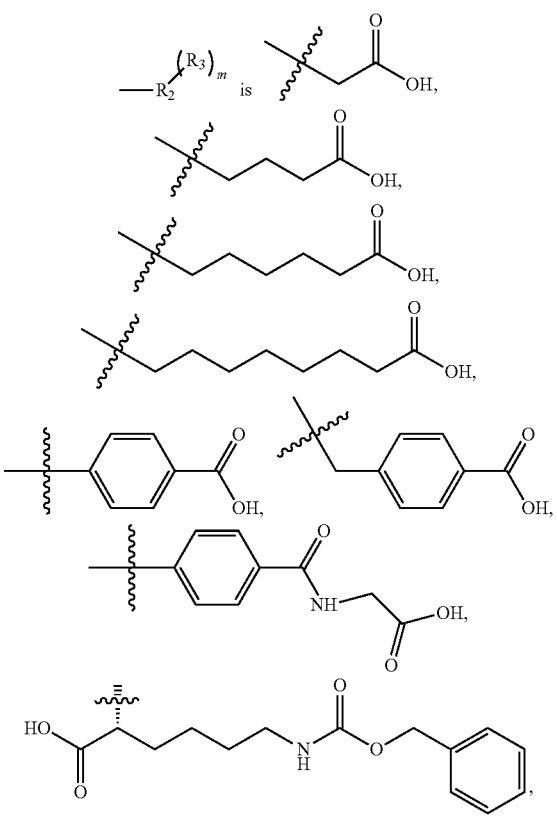
14. The compound of claim 1, wherein

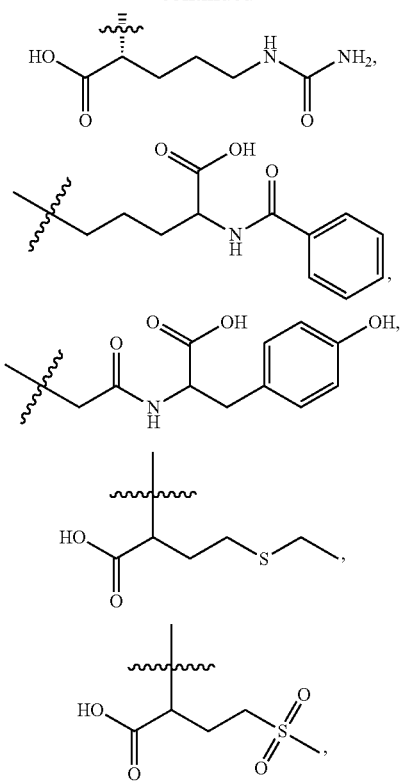
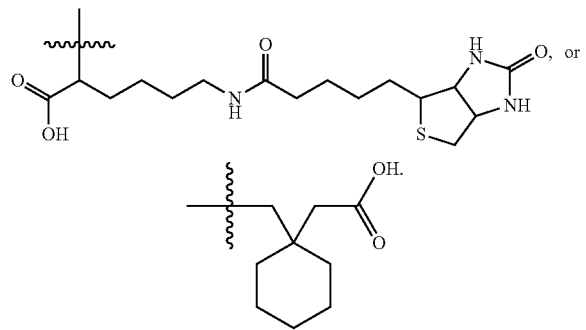
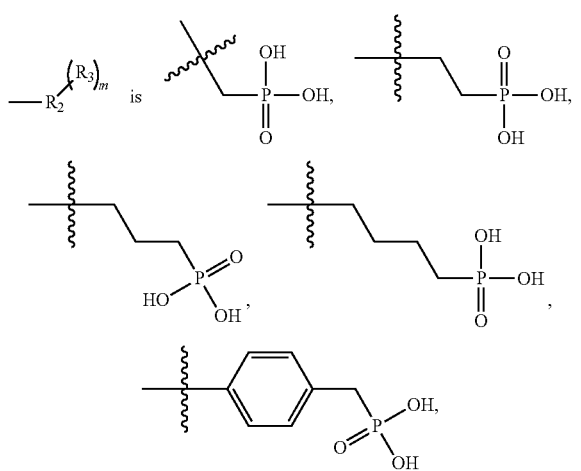
15. The compound of claim 1, wherein
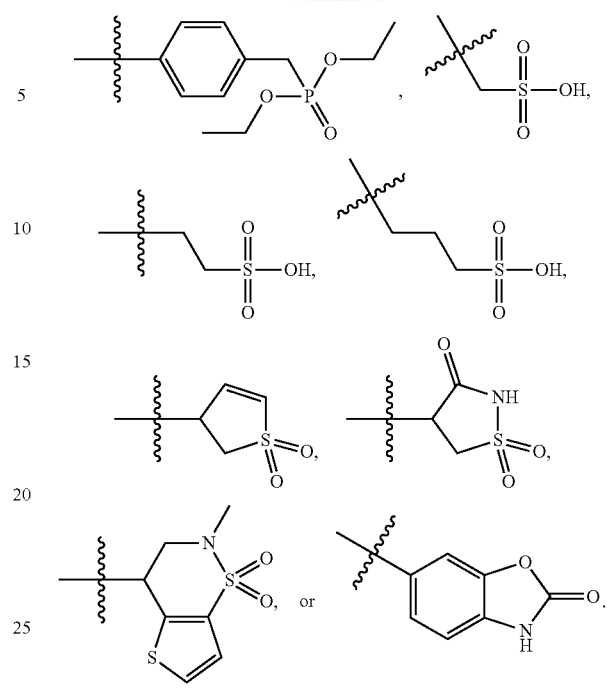
16. The compound of claim 1, wherein
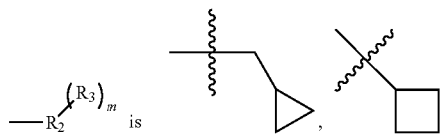
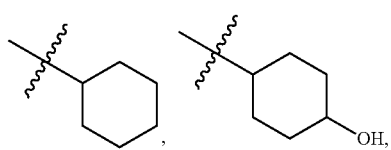
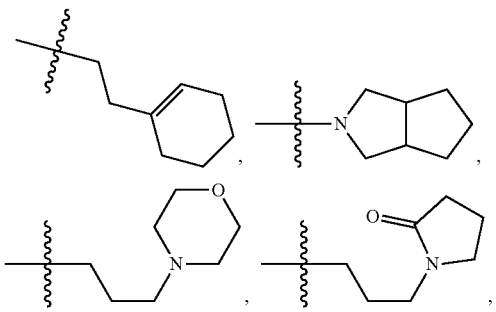
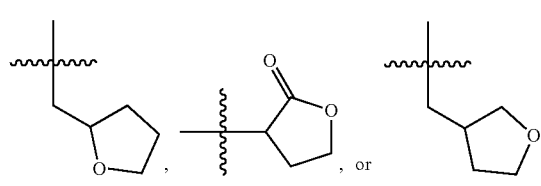

17. The compound of claim 1, wherein
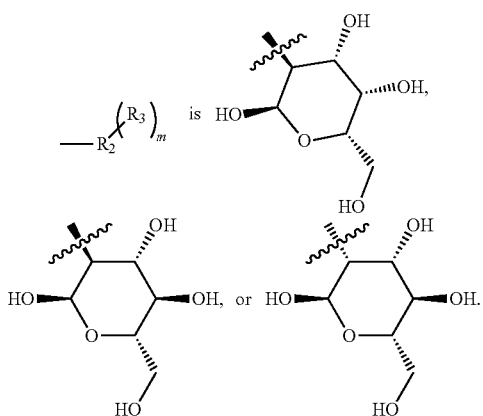
18. The compound of claim 1, wherein
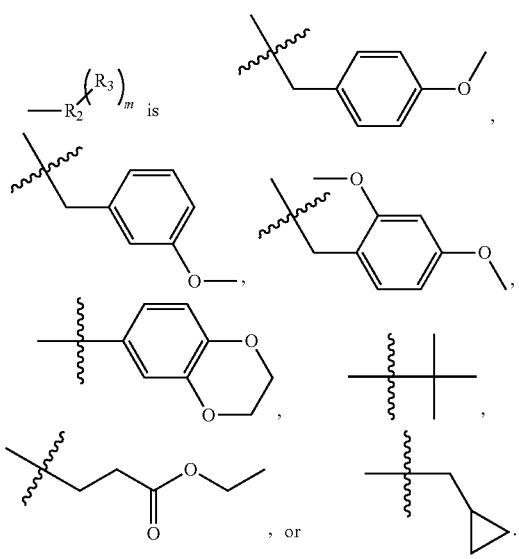
19. The compound of claim 1, wherein
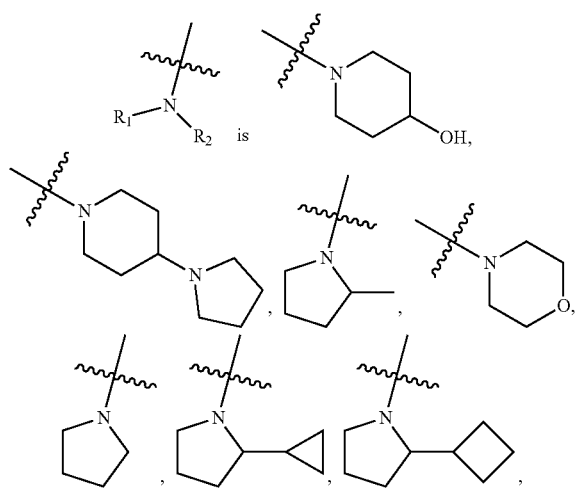
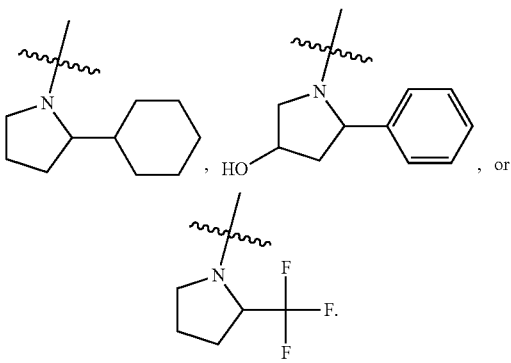
20. The compound of claim 1, wherein
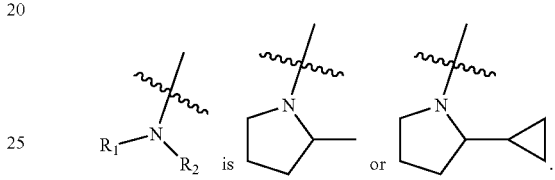
21. The compound of claim 1, wherein the compound is of Formula (Ia), (IIa), or (IIIa):
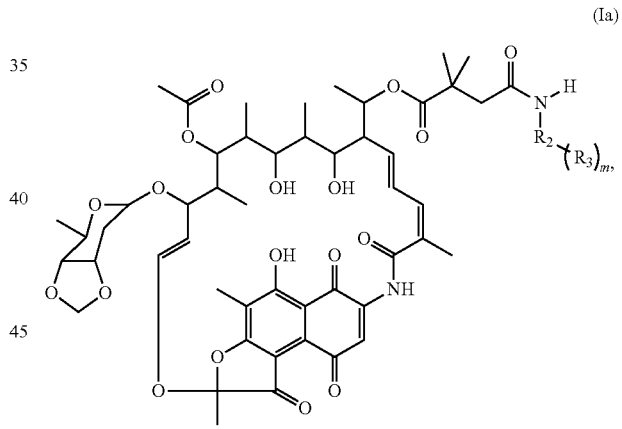
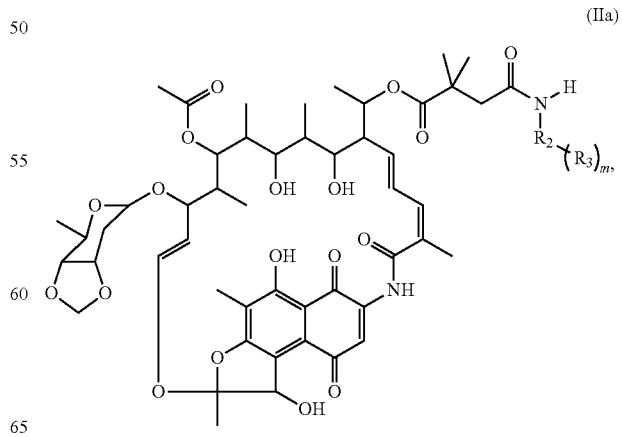

-continued
(IIIa)
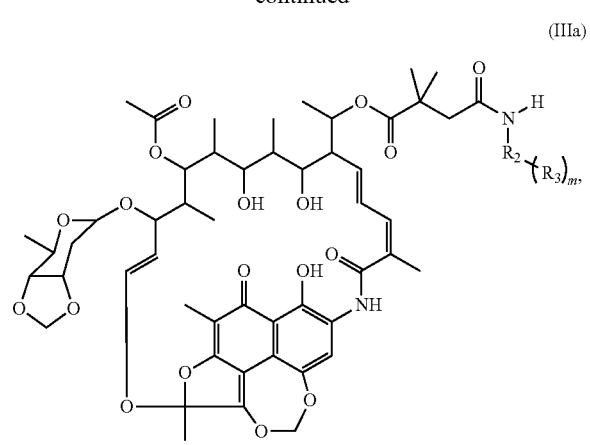
or a solvate, or pharmaceutically acceptable salt thereof.
22. The compound of claim 1, wherein the compound is of Formula (I), or a pharmaceutically acceptable salt thereof, wherein $R_1$ and
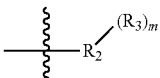
are selected from the group consisting of:
| $R_1$ | 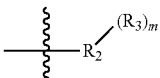 |
|---|---|
| H | 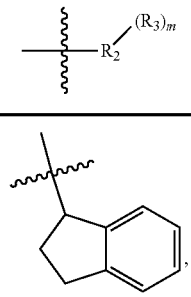 |
| H | |
| H | |
| H | |
| H | |
-continued
| $R_1$ | 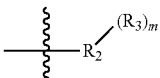 |
|---|---|
| H | 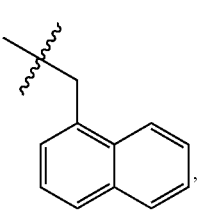 [SMILES: *Cc1cccc2ccccc12] |
| H | 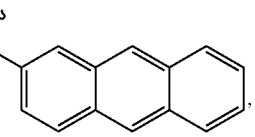 |
| H | 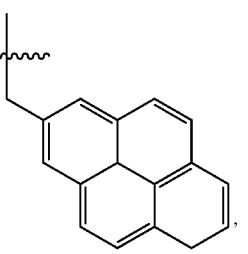 |
| H | 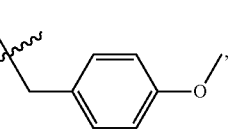 |
| H | 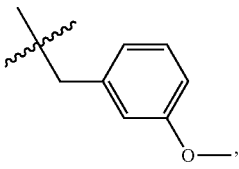 [SMILES: *Cc1cccc(OC)c1] |
| H | 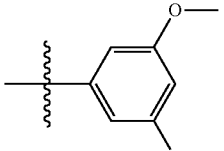 |
| H | 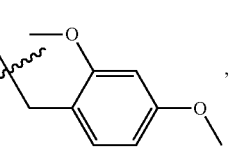 |

171
-continued
| R₁ | 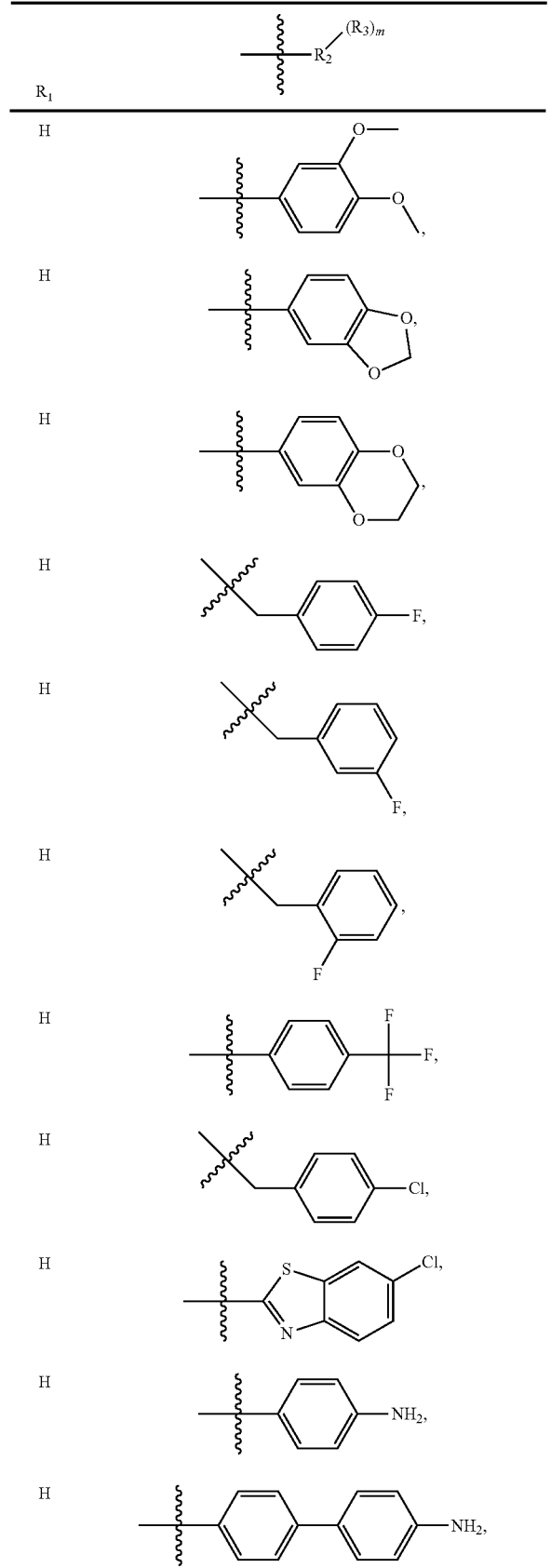 |
|---|---|
| H | |
| H | |
| H | |
| H | |
| H | |
| H | |
| H | |
| H | |
| H | |
| H | |
| H | |
172
-continued
| R₁ | 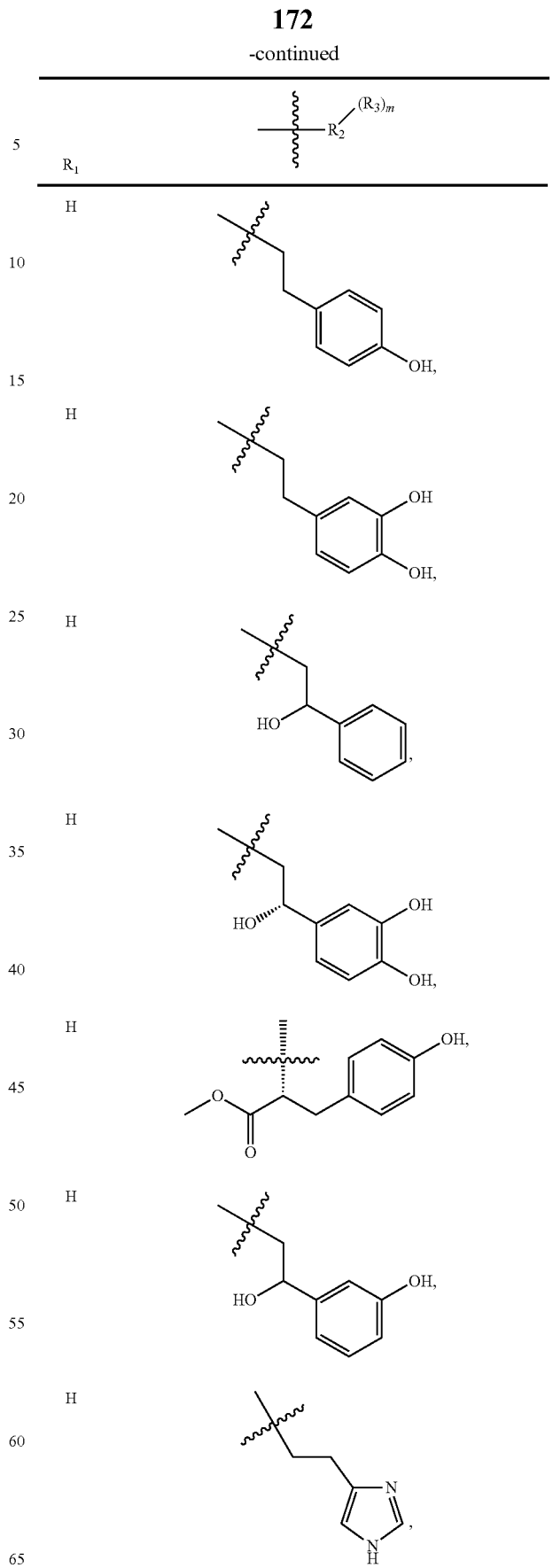 |
|---|---|
| H | |
| H | |
| H | |
| H | |
| H | |
| H | |
| H | |

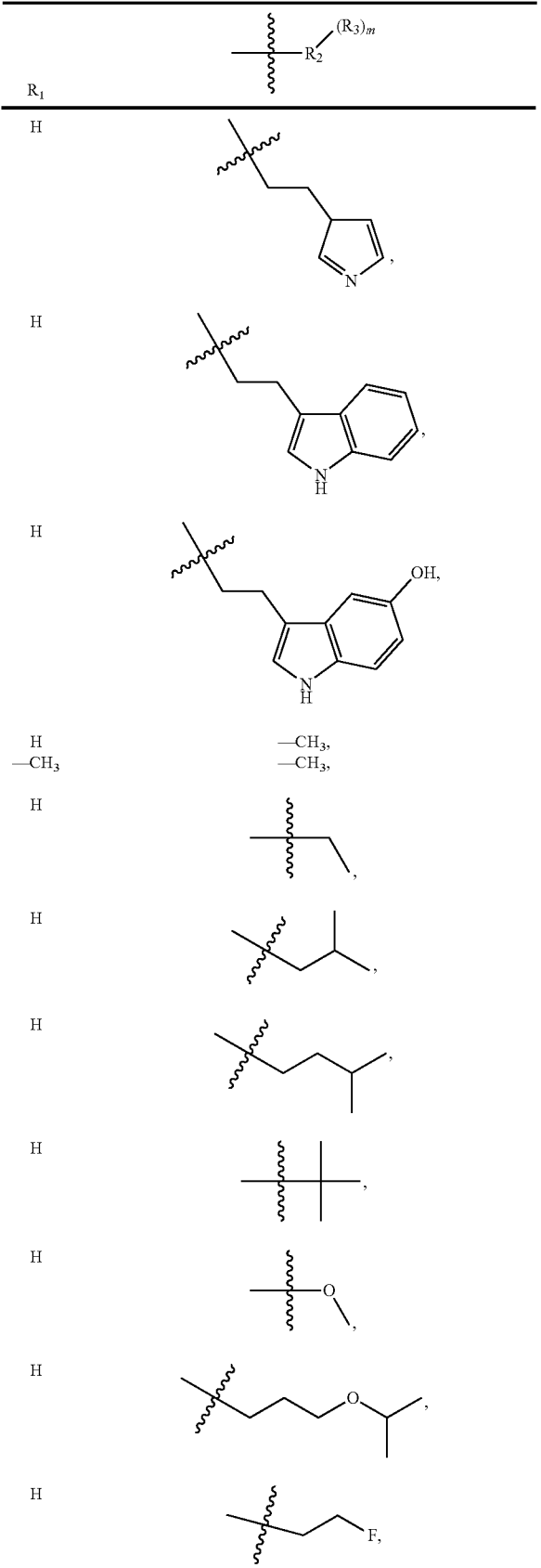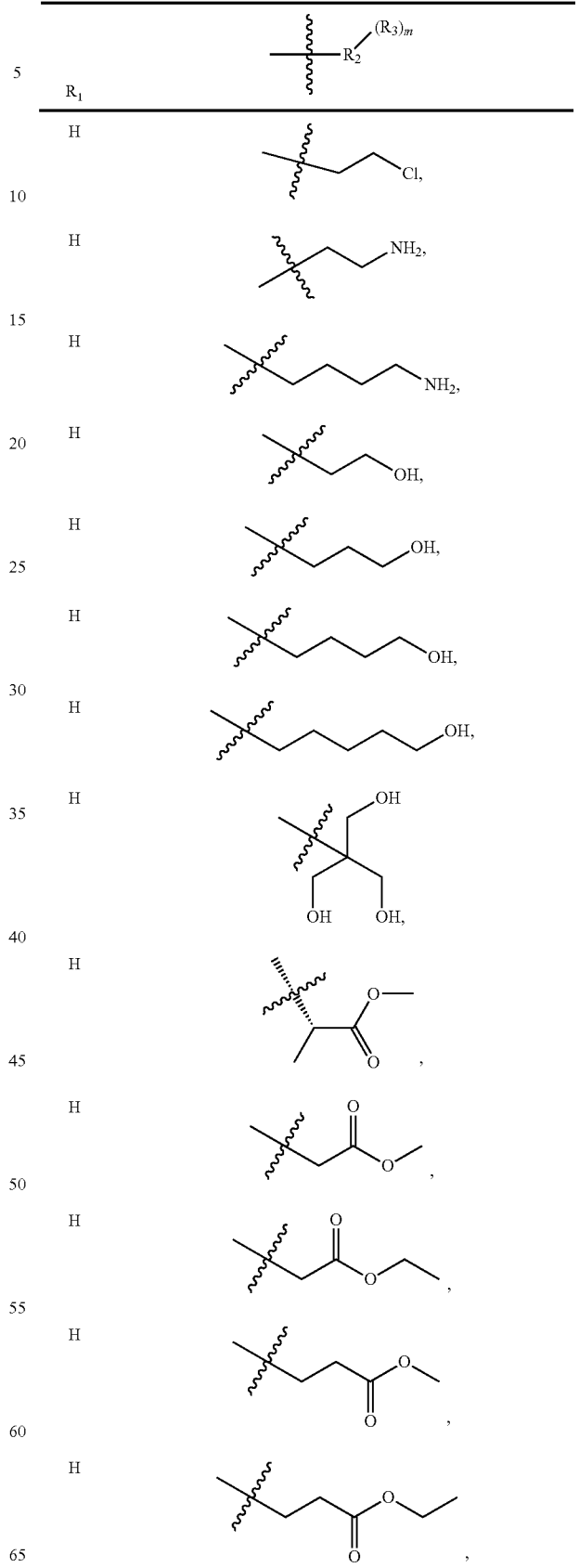

| 175 | | 176 | |
|---|---|---|---|
| -continued | | -continued | |
| $R_1$ | $R_2$-(R_3)_m$ | $R_1$ | $R_2$-(R_3)_m$ |
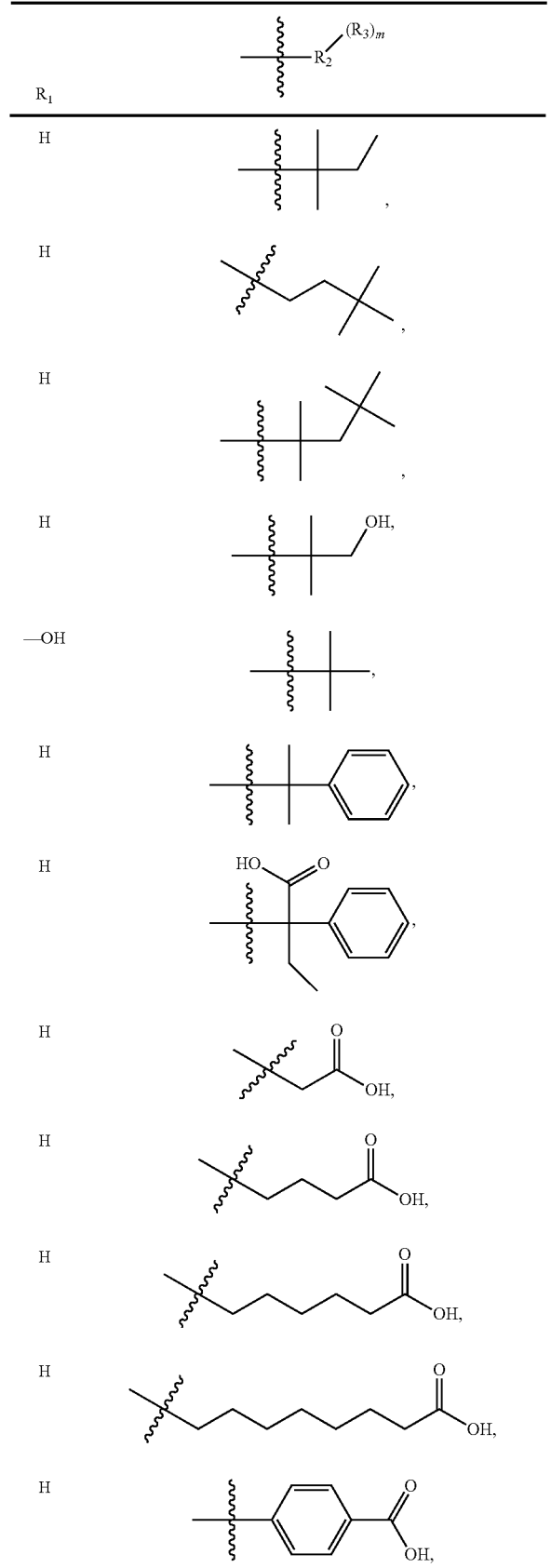
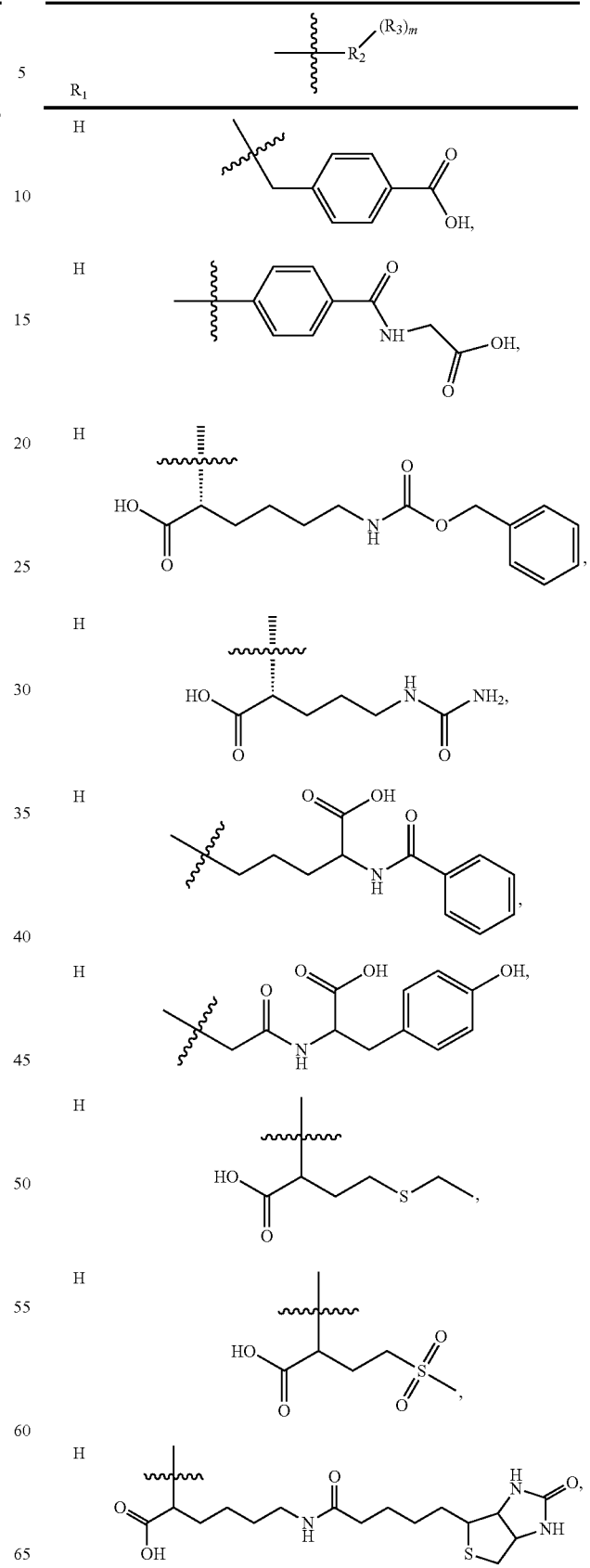

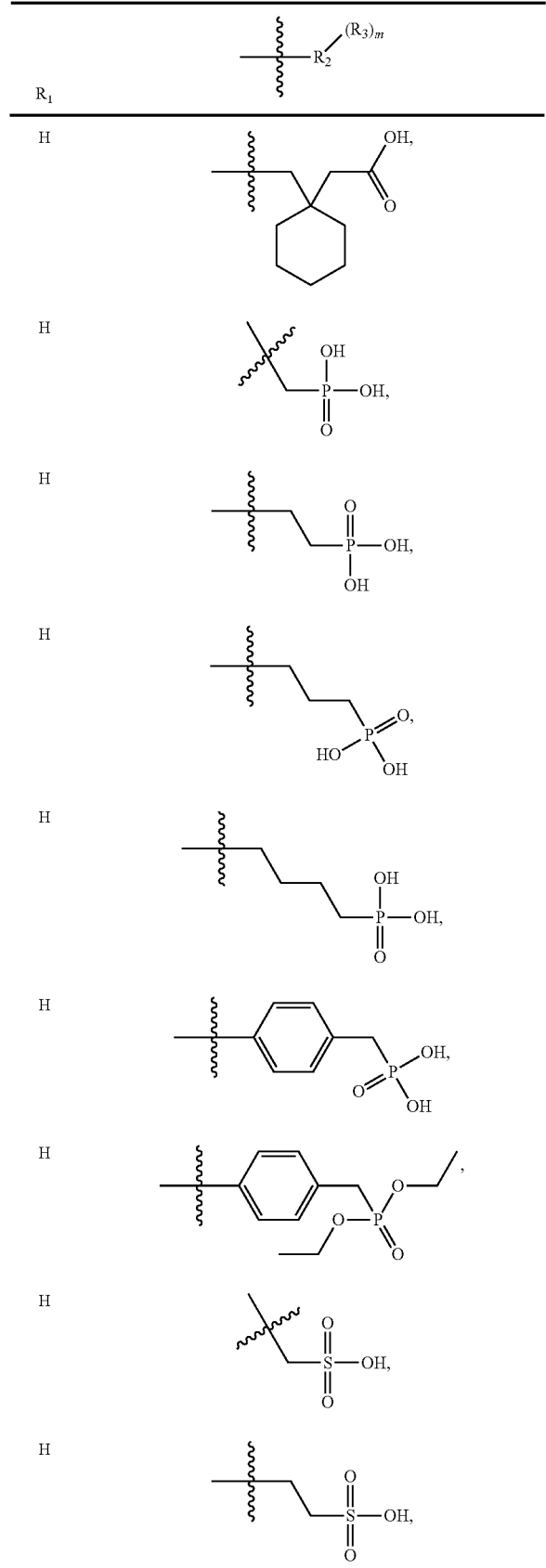
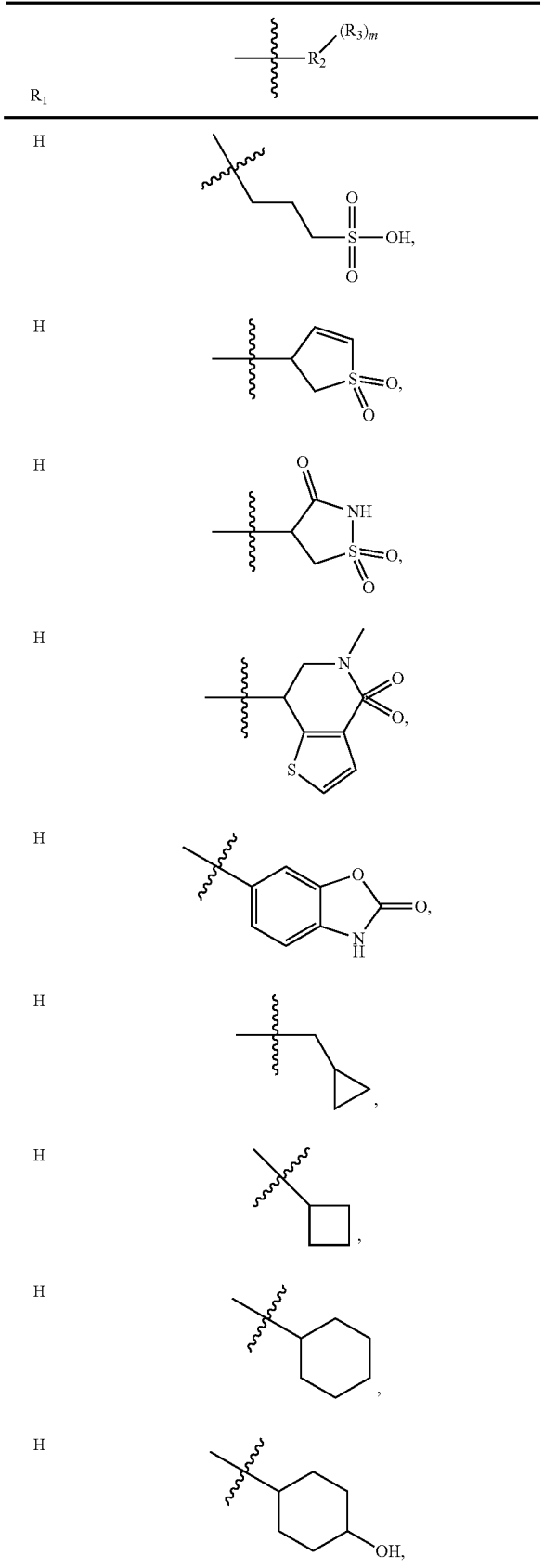

-continued

| $R_1$ | m) |
|---|---|
| H | 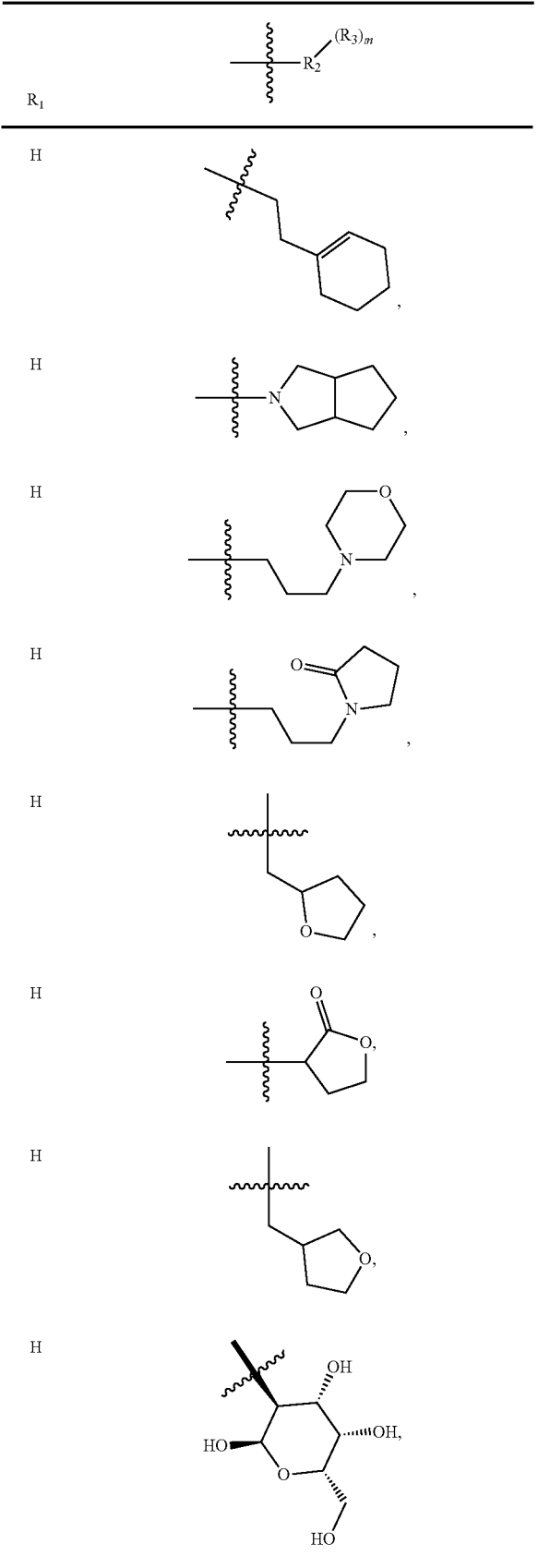 |

-continued

| $R_1$ | m) |
|---|---|
| H | 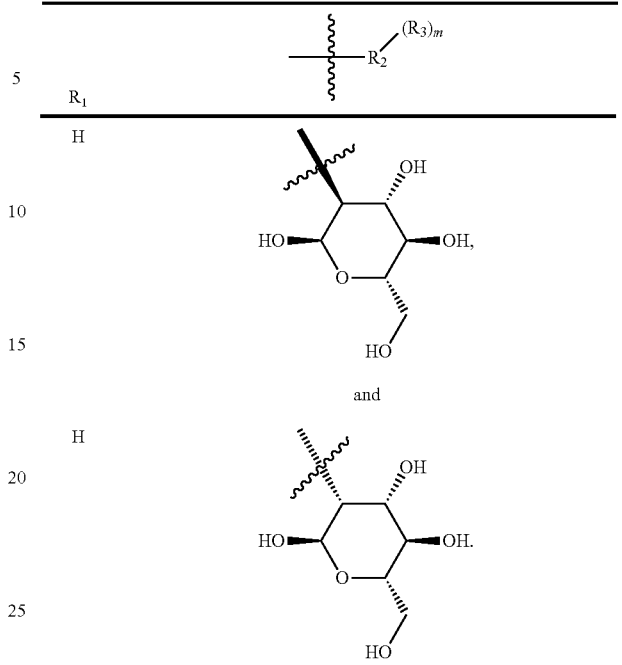 |
| | and |
| H | |

23. A pharmaceutical composition comprising the compound of claim 1 and a pharmaceutically acceptable excipient.

24. A method of reducing the growth or proliferation of a microorganism, wherein the method comprises contacting the microorganism with a composition comprising a compound of claim 1.

25. A method of treating a bacterial infection in a subject, wherein the method comprises administering to the subject a composition comprising a compound of claim 1.

26. The compound of claim 1, wherein the compound is of Formula (I), or a pharmaceutically acceptable salt thereof, wherein

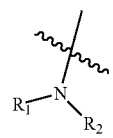

is selected from the group consisting of:

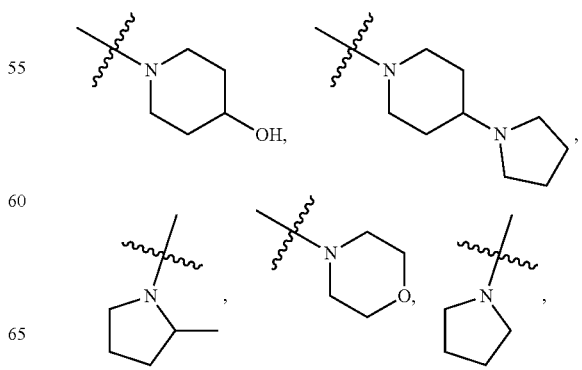

-continued
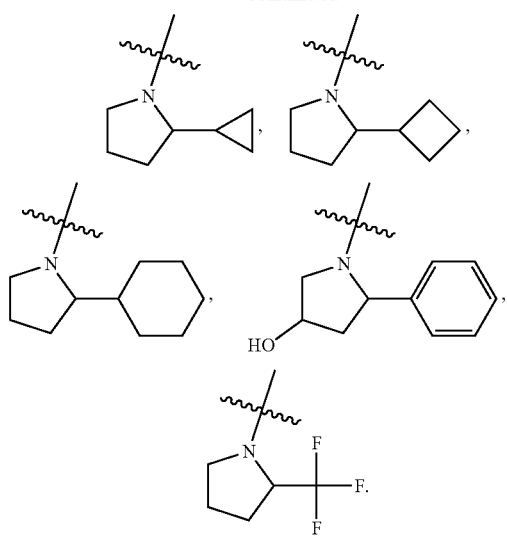
27. The compound of claim 1, wherein the compound is of Formula (II), or a pharmaceutically acceptable salt thereof, wherein R₁ and
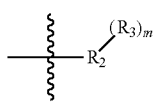
are selected from the group consisting of:
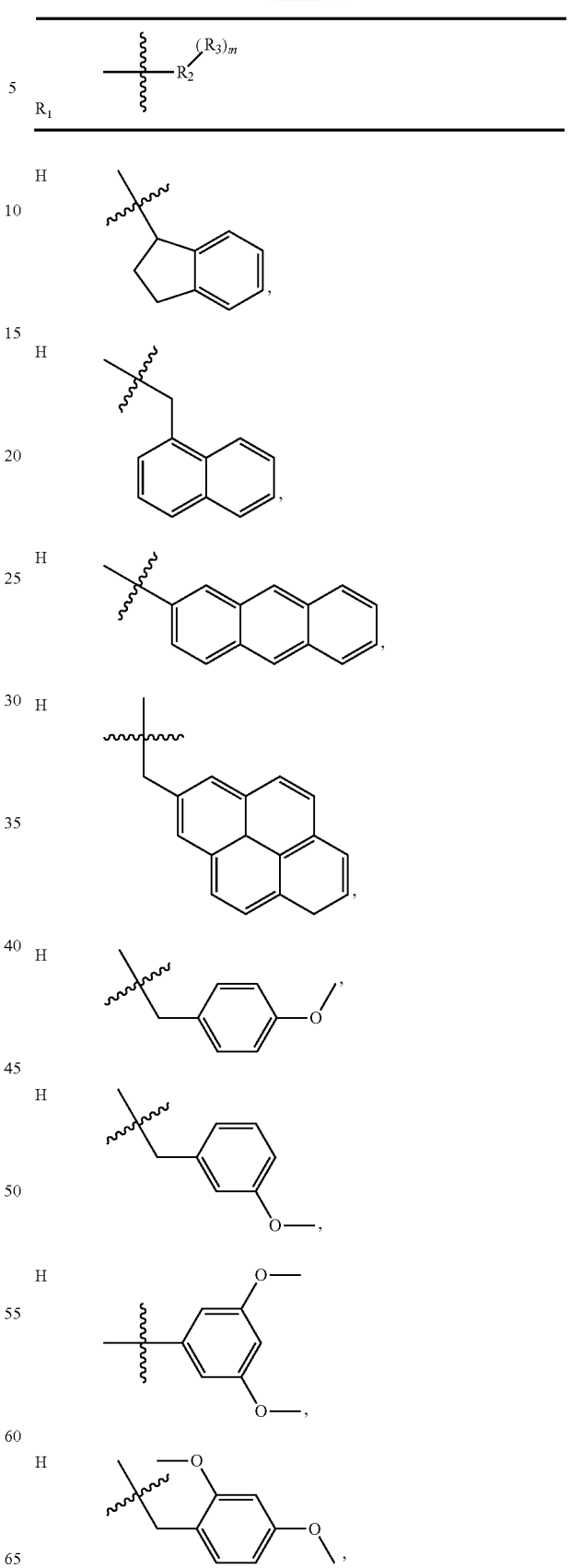

183
-continued
| R₁ | |
|---|---|
| H | 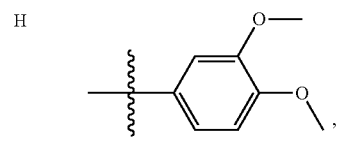 |
| H | 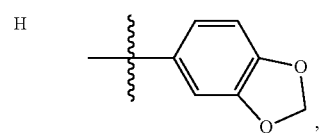 |
| H | 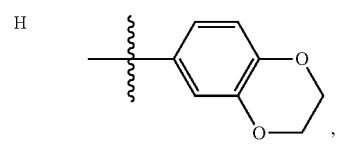 |
| H | 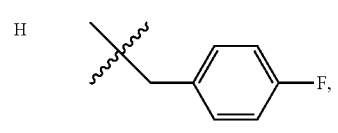 |
| H | 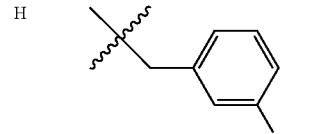 |
| H | 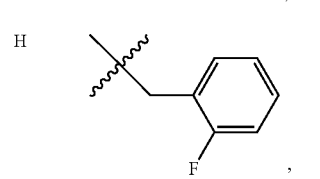 |
| H | 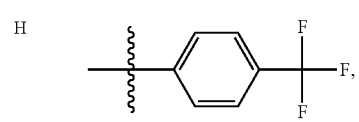 |
| H | 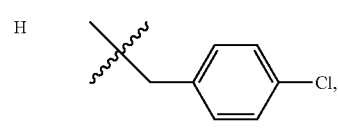 |
| H | 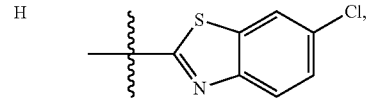 |
| H | 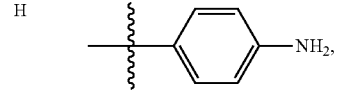 |
| H | 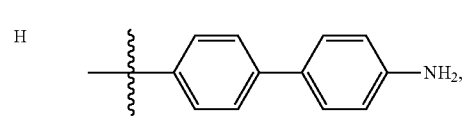 |
184
-continued
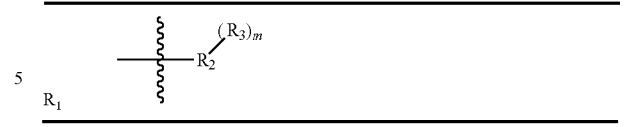
| R₁ | |
|---|---|
| H | 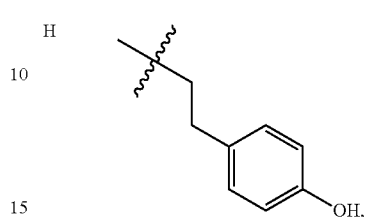 |
| H | 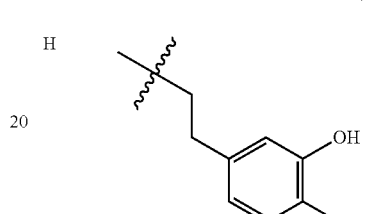 |
| H | 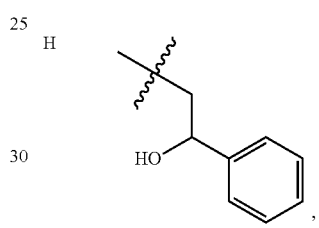 |
| H | 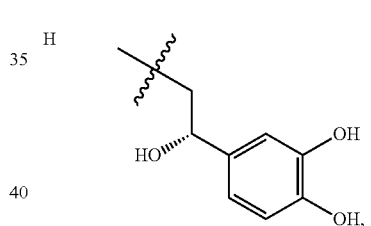 |
| H | 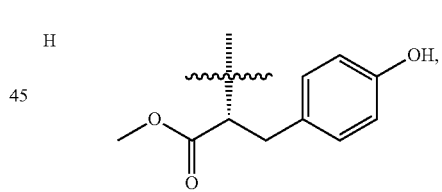 |
| H | 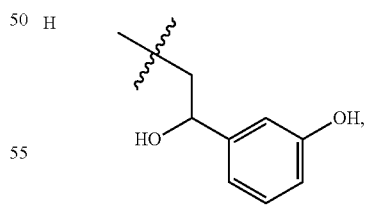 |
| H | 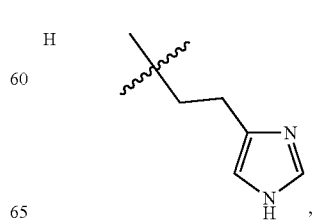 |

| R₁ |  |
|---|---|
| H | 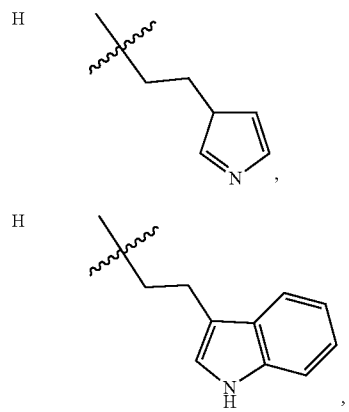 |
| H | |
| H | |
| H<br>—CH₃ | —CH₃,<br>—CH₃, |
| H | 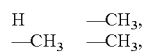 |
| H | 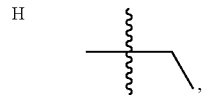 |
| H | 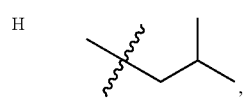 |
| H | 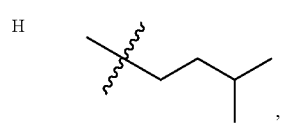 |
| H | 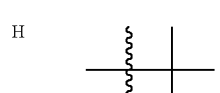 |
| H | 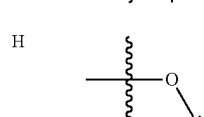 |
| H | 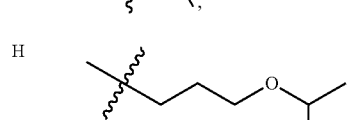 |
| H | 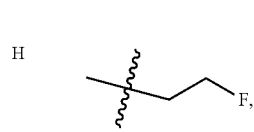 |
| R₁ | 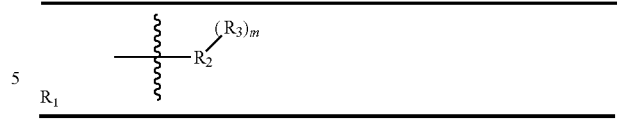 |
|---|---|
| H | 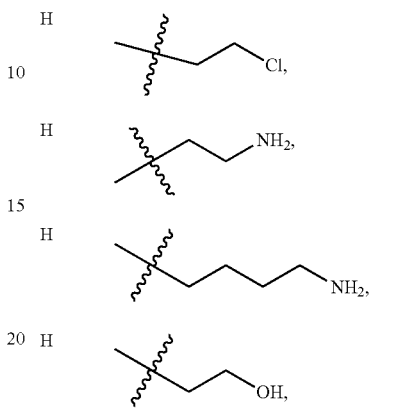 |
| H | |
| H | |
| H | |
| H | |
| H | |
| H | |
| H | 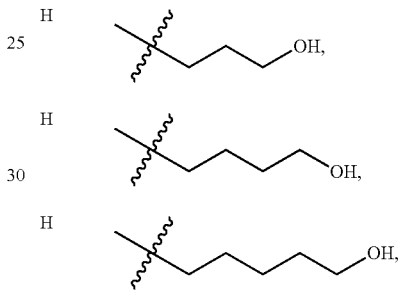 |
| H | 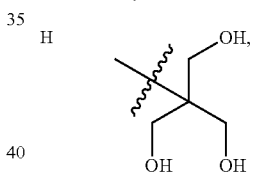 |
| H | 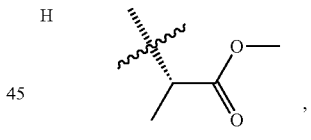 |
| H | 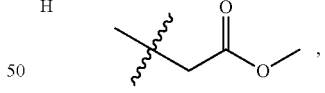 |
| H | 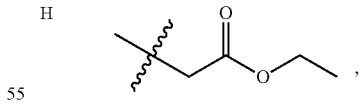 |
| H | 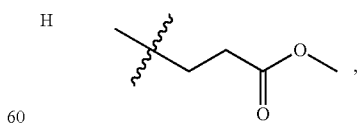 |
| H | 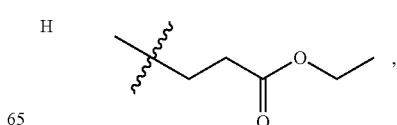 |

187
-continued
188
-continued
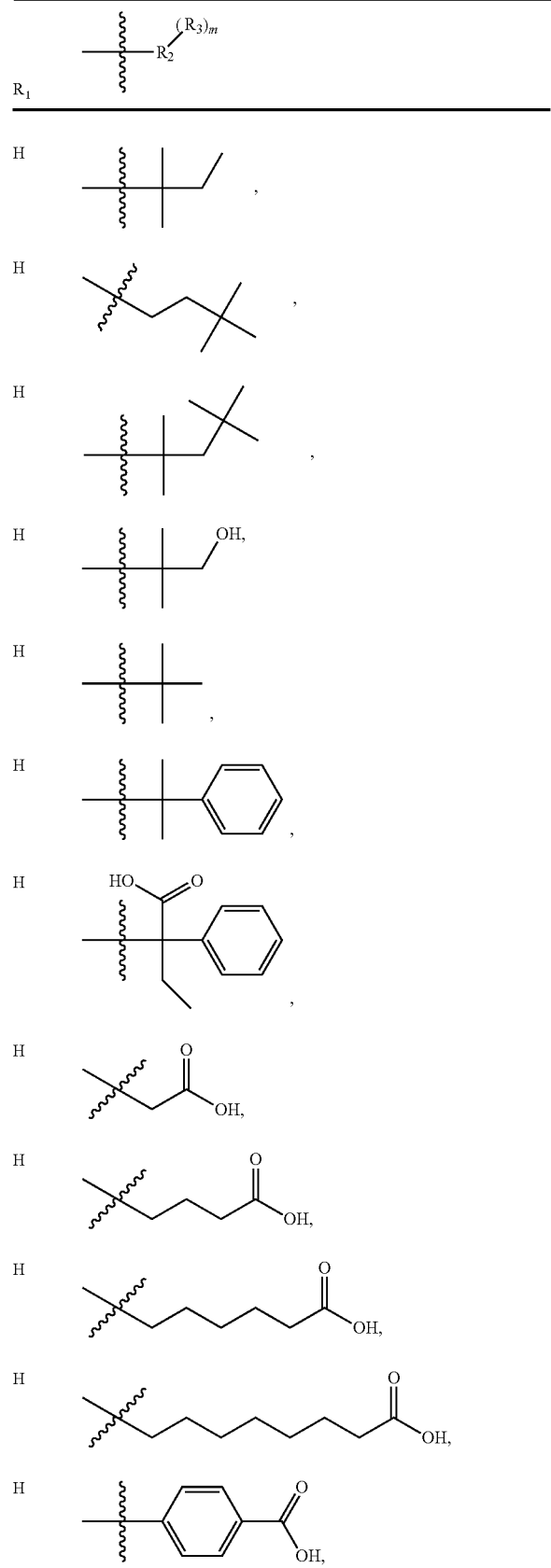
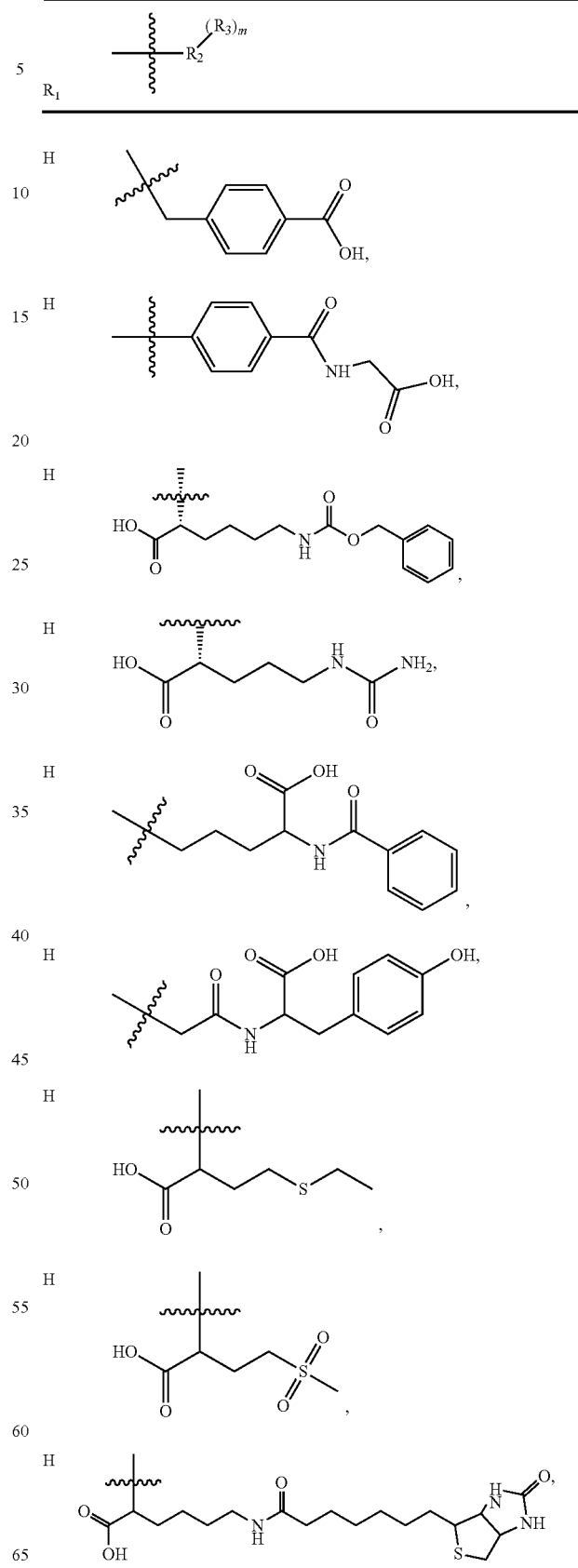

| R₁ | -R₂-(R₃)ₘ |
|---|---|
| H |  |
| H | 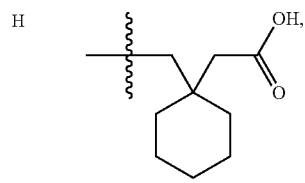 |
| H | 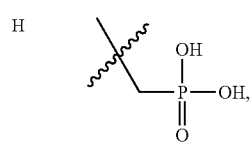 |
| H | 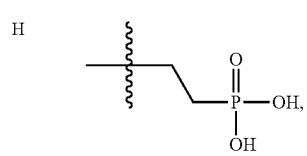 |
| H | 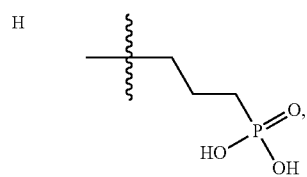 |
| H | 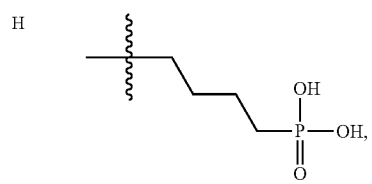 |
| H | 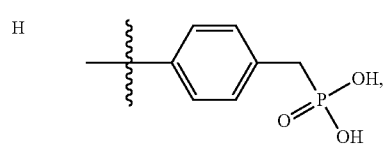 |
| H | 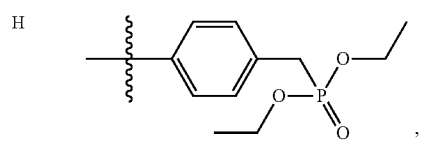, |
| H | 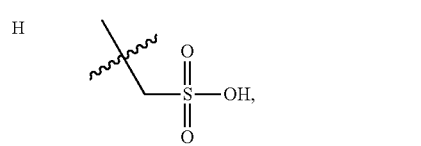 |
| H | 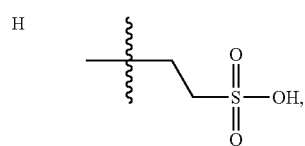 |
| R₁ | -R₂-(R₃)ₘ |
|---|---|
| H |  |
| H | 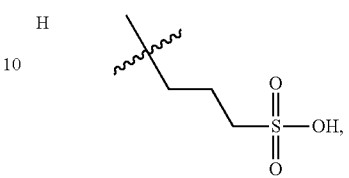 |
| H | 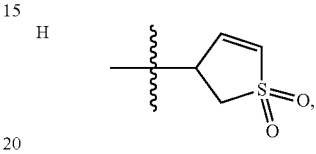 |
| H | 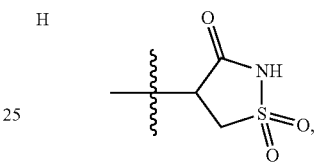 |
| H | 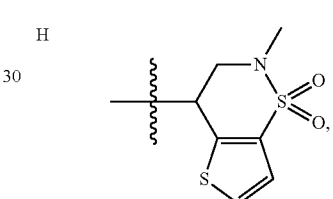 |
| H | 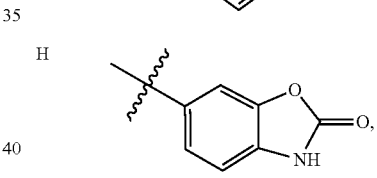 |
| H | 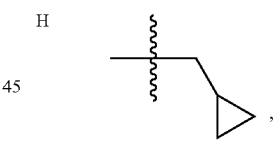, |
| H | 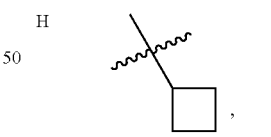, |
| H | 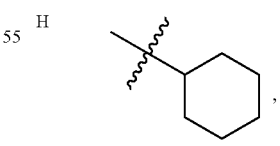, |
| H | 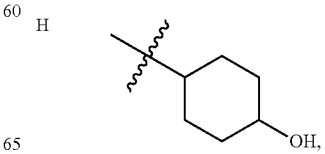 |

| $R_1$ | |
|---|---|
| H | 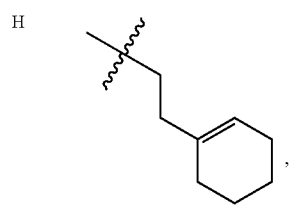 |
| H | 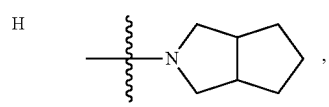 |
| H | 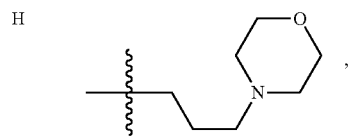 |
| H | 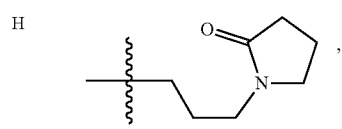 |
| H | 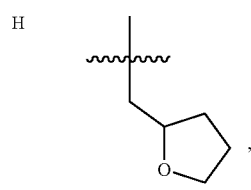 |
| H | 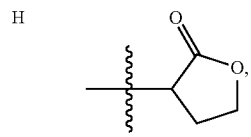 |
| H | 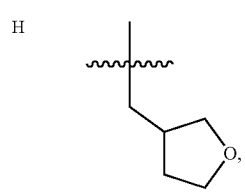 |
| H | 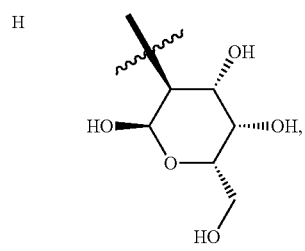 |
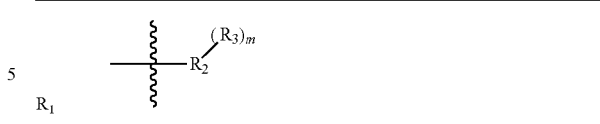
| $R_1$ | |
|---|---|
| H | 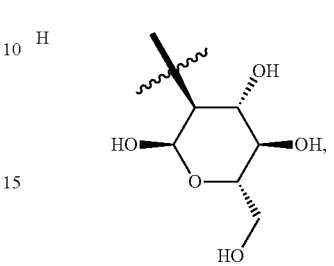 |
| H | 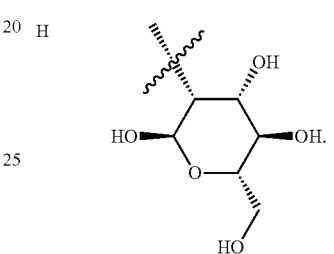 |
28. The compound of claim 1, wherein the compound is of Formula (II), or a pharmaceutically acceptable salt thereof, wherein
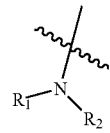
is selected from the group consisting of:
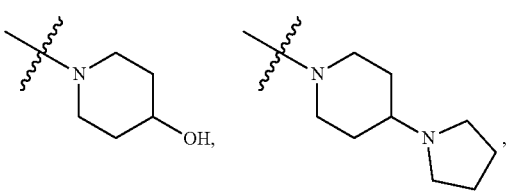
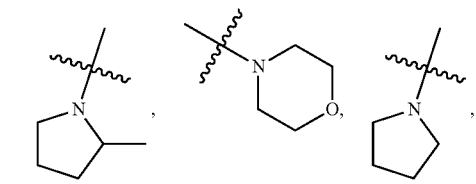
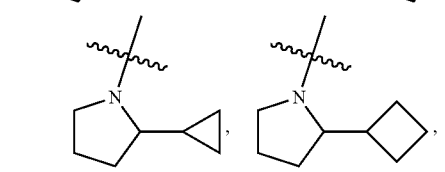

29. The compound of claim 1, wherein the compound is of Formula (III), or a pharmaceutically acceptable salt thereof, wherein R₁ and

[structure: $-R_2-(R_3)_m$]

are selected from the group consisting of:

| $R_1$ |  |
|---|---|
| H | 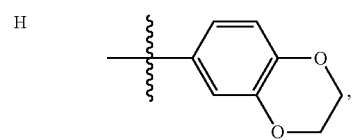 |
| H | 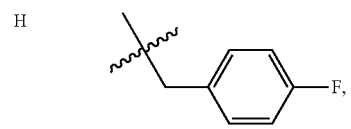 |
| H | 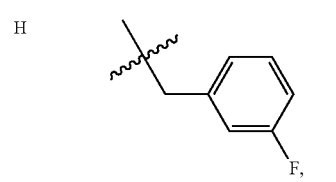 |
| H | 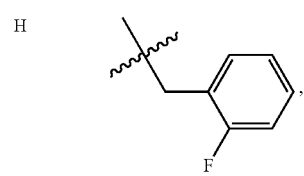 |
| H | 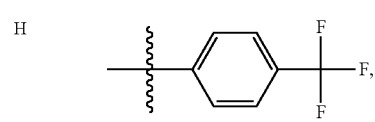 |
| H | 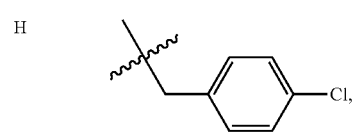 |
| H | 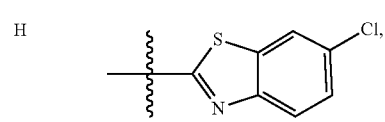 |
| H | 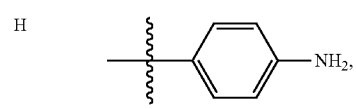 |
| H | 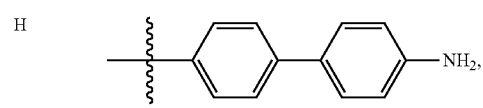 |
| H | 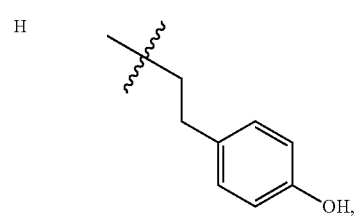 |
| $R_1$ | 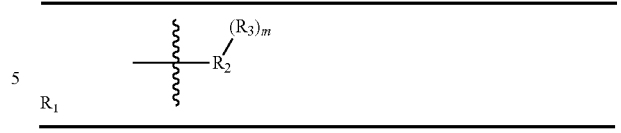 |
|---|---|
| H | 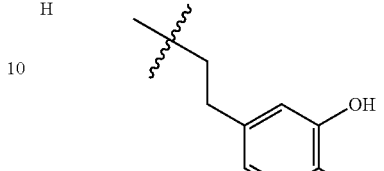 |
| H | 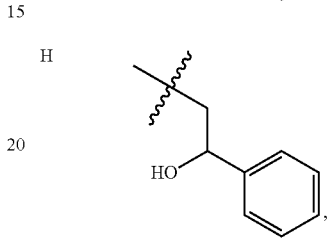 |
| H | 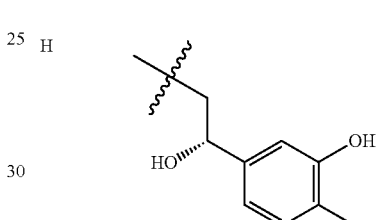 |
| H | 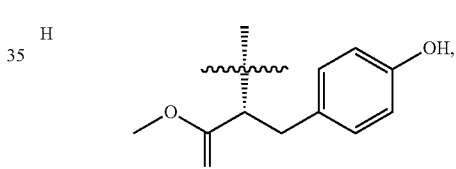 |
| H | 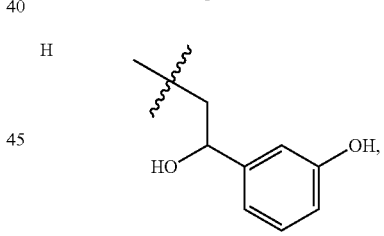 |
| H | 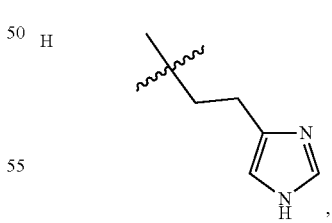 |
| H | 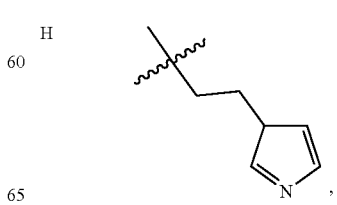 |

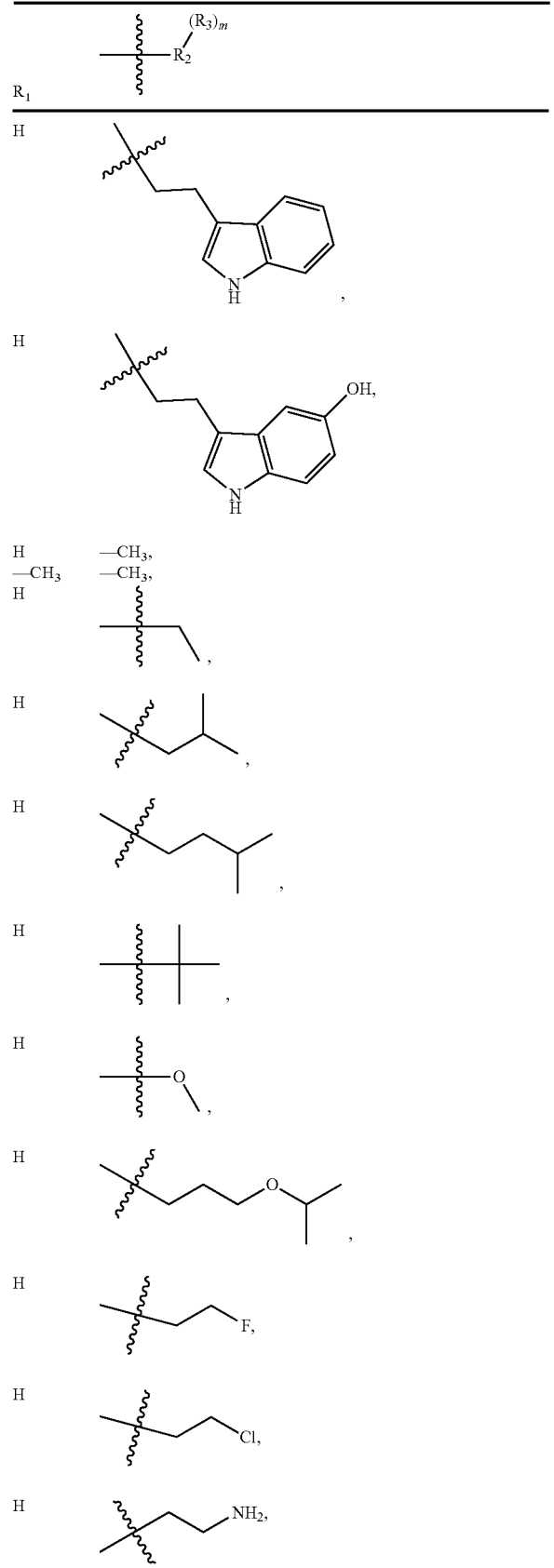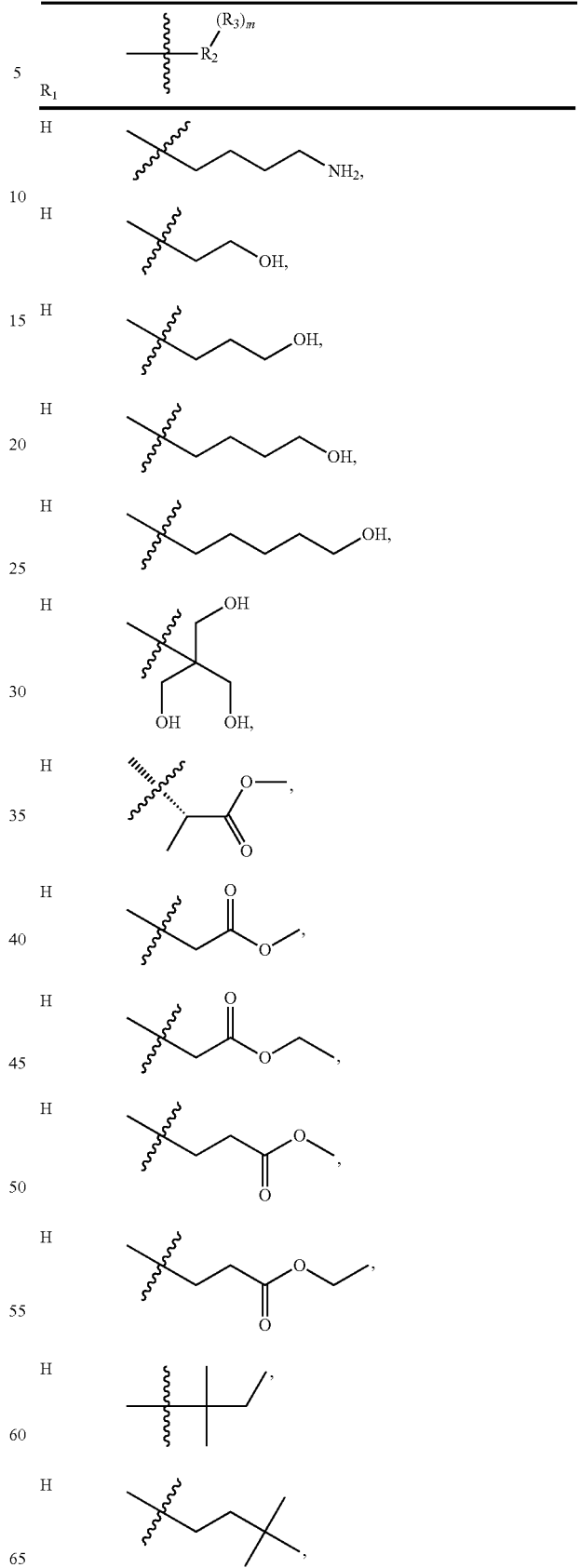

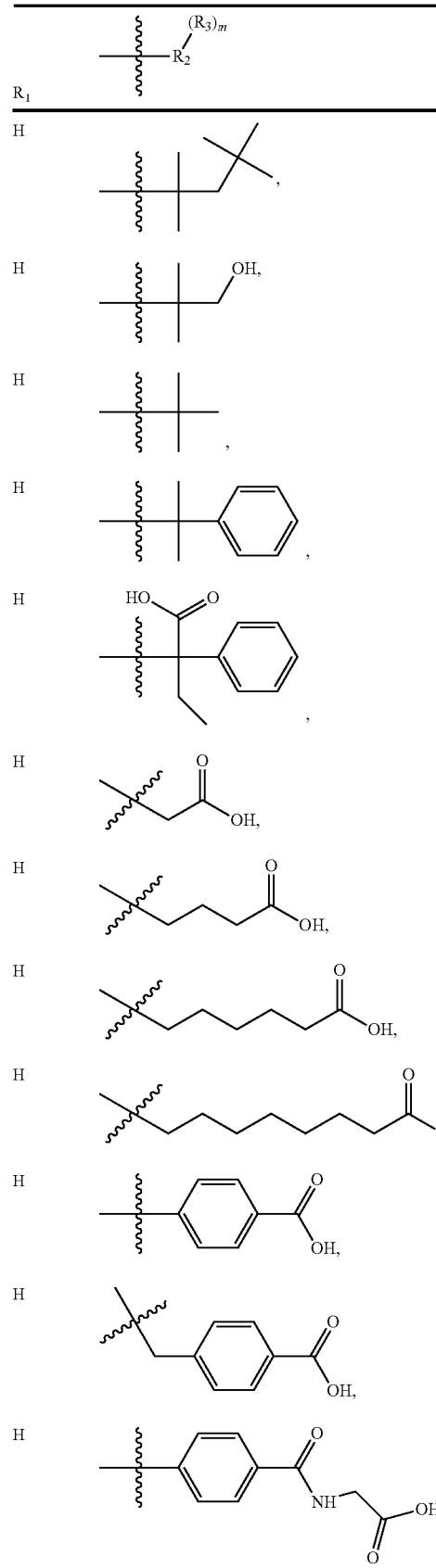

| $R_1$ | 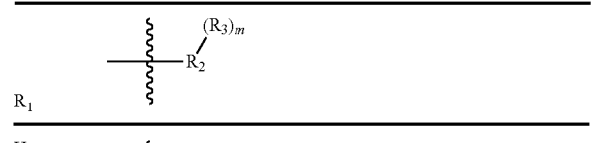 |
|---|---|
| H | 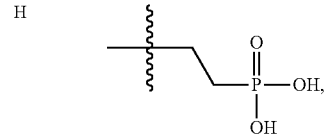 |
| H | 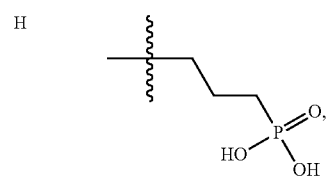 |
| H | 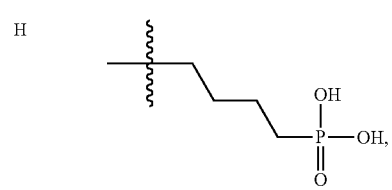 |
| H | 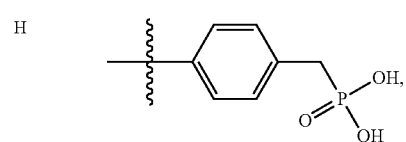 |
| H | 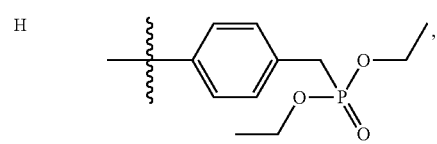 |
| H | 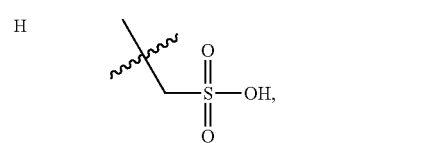 |
| H | 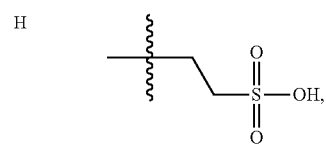 |
| H | 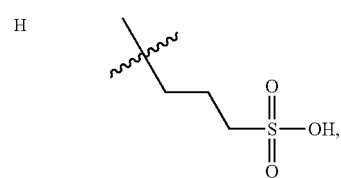 |
| H | 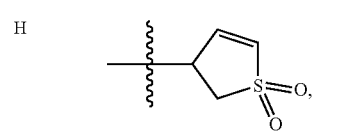 |
| $R_1$ | 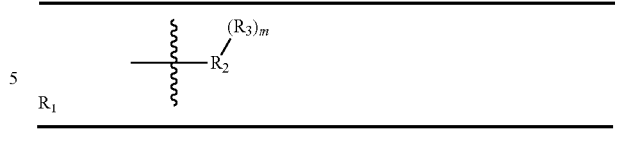 |
|---|---|
| H | 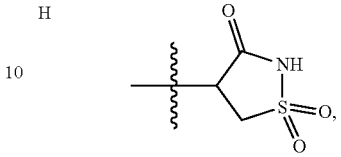 |
| H | 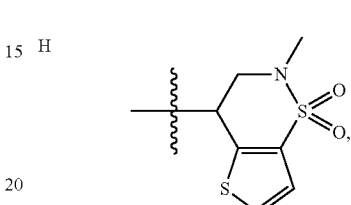 |
| H | 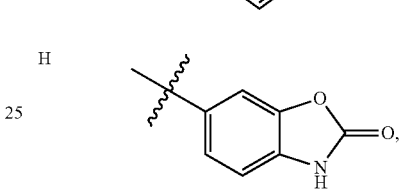 |
| H | 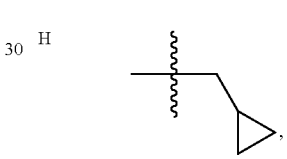 |
| H | 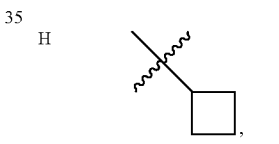 |
| H | 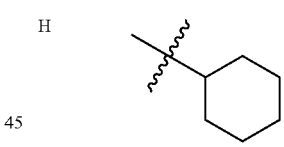 |
| H | 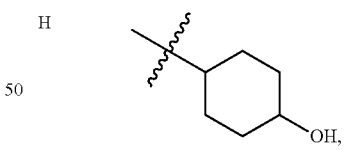 |
| H | 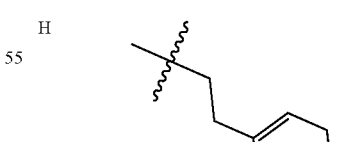 |
| H | 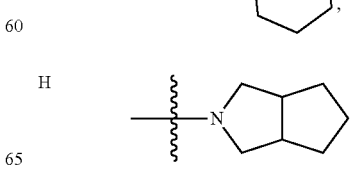 |

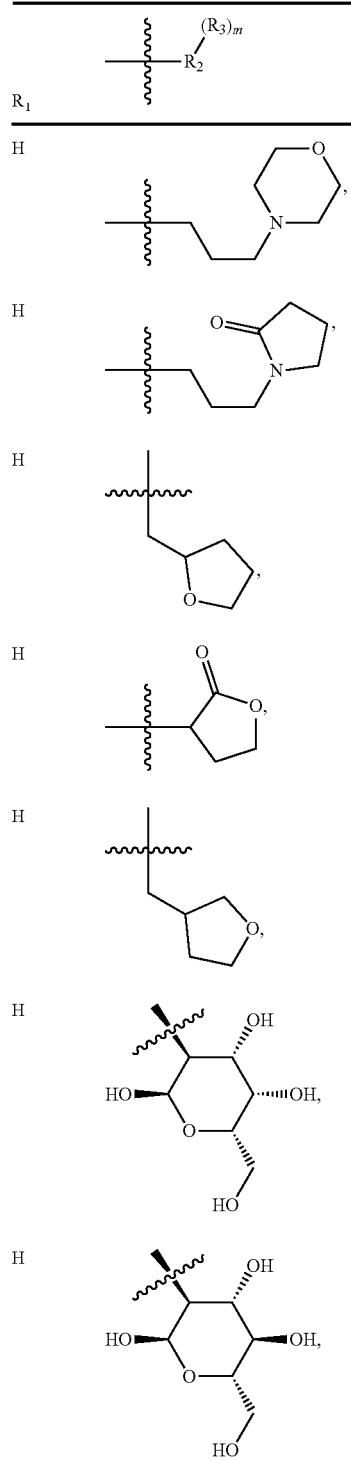
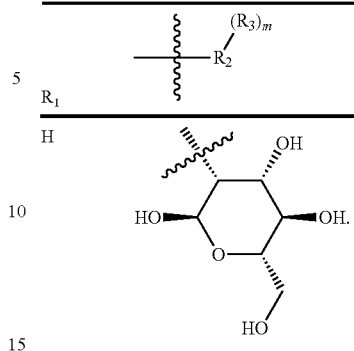
30. The compound of claim 1, wherein the compound is of Formula (III), or a pharmaceutically acceptable salt thereof, wherein
is selected from the group consisting of:
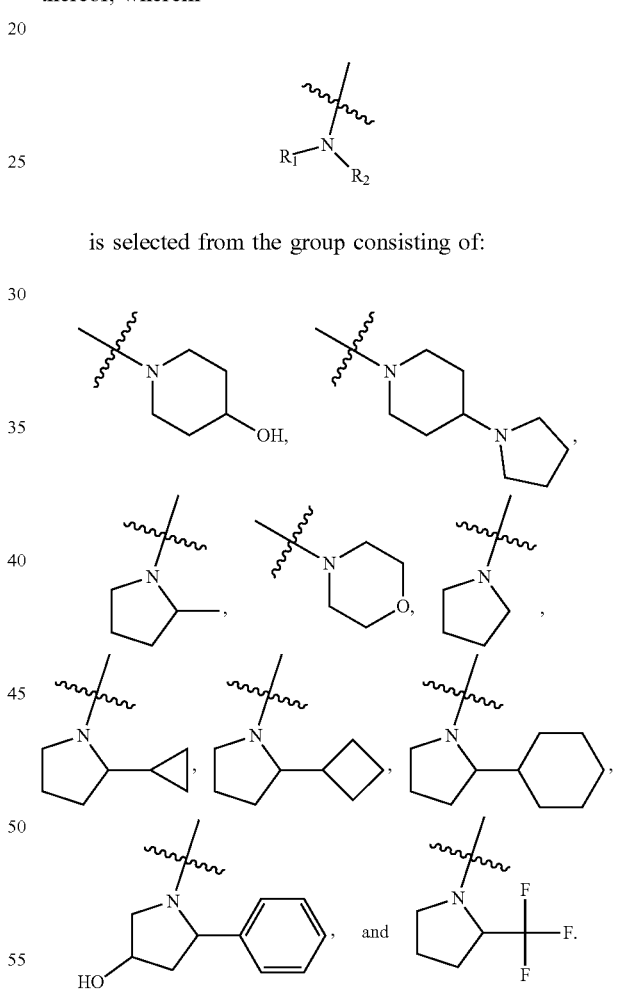
* * * * *